US011453914B2

(12) United States Patent
Hicks et al.

(10) Patent No.: US 11,453,914 B2
(45) Date of Patent: Sep. 27, 2022

(54) ANALYSIS AND PREDICTION OF TRAUMATIC BRAIN INJURY AND CONCUSSION SYMPTOMS

(71) Applicants: QUADRANT BIOSCIENCES INC., Syracuse, NY (US); THE RESEARCH FOUNDATION FOR THE STATE UNIVERSITY OF NEW YORK, Syracuse, NY (US); PENN STATE RESEARCH FOUNDATION, University Park, PA (US)

(72) Inventors: Steven D. Hicks, Hershey, PA (US); Frank A. Middleton, Fayetteville, NY (US); Richard Uhlig, Ithaca, NY (US)

(73) Assignees: QUADRANT BIOSCIENCES INC., Syracuse, NY (US); THE RESEARCH FOUNDATION FOR THE STATE UNIVERSITY OF NEW YORK, Syracuse, NY (US); PENN STATE RESEARCH FOUNDATION, University Park, PA (US)

( * ) Notice: Subject to any disclaimer, the term of this patent is extended or adjusted under 35 U.S.C. 154(b) by 274 days.

(21) Appl. No.: 16/496,154

(22) PCT Filed: Mar. 23, 2018

(86) PCT No.: PCT/US2018/024111
§ 371 (c)(1),
(2) Date: Sep. 20, 2019

(87) PCT Pub. No.: WO2018/175941
PCT Pub. Date: Sep. 27, 2018

(65) Prior Publication Data
US 2020/0277676 A1 Sep. 3, 2020

Related U.S. Application Data

(60) Provisional application No. 62/623,145, filed on Jan. 29, 2018, provisional application No. 62/502,107, filed on May 5, 2017, provisional application No. 62/480,079, filed on Mar. 31, 2017, provisional application No. 62/475,698, filed on Mar. 23, 2017.

(51) Int. Cl.
*C12Q 1/68* (2018.01)
*C12P 19/34* (2006.01)
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
CPC .. C12Q 1/6883; C12Q 2600/178; C12Q 1/68; C12Q 2600/158
See application file for complete search history.

(56) References Cited

U.S. PATENT DOCUMENTS

| | | | |
|---|---|---|---|
| 2015/0344954 A1* | 12/2015 | Patel | A61P 25/28 424/94.4 |
| 2017/0268058 A1 | 9/2017 | Patel et al. | |
| 2018/0127828 A1 | 5/2018 | Belli et al. | |
| 2018/0258483 A1 | 9/2018 | Van Keuren-Jensen et al. | |
| 2019/0085395 A1 | 3/2019 | Belli et al. | |
| 2019/0352716 A1 | 11/2019 | Patel et al. | |

FOREIGN PATENT DOCUMENTS

| | | | |
|---|---|---|---|
| JP | 2019-509044 A | 4/2019 | |
| WO | WO 2016/118662 A1 | 7/2016 | |
| WO | WO 2016/153549 A1 | 9/2016 | |
| WO | WO 2017/044750 A1 | 3/2017 | |
| WO | WO-2017044650 A1 * | 3/2017 | ........... C12Q 1/6876 |
| WO | WO 2017/153710 A1 | 9/2017 | |

OTHER PUBLICATIONS

Maffioletti et al. J. of Affective Disorder, vol. 200, pp. 2540-258, 2016 (Year: 2016).*
Qiagen product information sheet "miScript™ miRNA PCR Array Human Inflammatory Response & Autoimmunity", document 1070012, Oct. 2011, from https://www.qiagen.eom/~/media/genetable/mi/hs/10/mihs-105za. (Year: 2011).*
Hoshikawa, Y. et al., "Hypoxia induces different genes in the lungs of rats compared with mice" Physiol Genomics 12: 209-219, 2003 (Year: 2003).*
Cheung, V.G. et al., "Natural variation in human gene expression assessed in lymphoblastoid cells" Nature Genetic, vol. 33, p. 422-425, Mar. 2003. (Year: 2003).*
Extended European Search Report dated Nov. 26, 2020 in European Patent Application No. 18771563.6, 9 pages.
"MicroRNA Profiling on Automated Biochip Platform Reveals Biomarker Signatures from Blood Samples" Nature Methods, XP055751045, Feb. 1, 2020, 3 pages.
Douglas D. Taylor, et al., "Exosome Platform for Diagnosis and Monitoring of Traumatic Brain Injury" Philosophical Transactions of The Royal Society B, vol. 369, No. 1652, XP055419501, Aug. 18, 2014, pp. 1-10.
Steven D. Hicks, et al., "Overlapping MicroRNA Expression in Saliva and Cerebrospinal Fluid Accurately Identifies Pediatric Traumatic Brain Injury" Journal of Neurotrauma, vol. 35, No. 1, XP055702702, Jan. 1, 2018, pp. 64-72.
Valentina Di Pietro, et al., "Salivary MicroRNAs: Diagnostic Markers of Mild Traumatic Brain Injury in Contact-Sport" Frontiers in Molecular Neuroscience, vol. 11, XP055750500, Aug. 20, 2018, pp. 1-13 and cover page.

(Continued)

*Primary Examiner* — Stephen T Kapushoc
(74) *Attorney, Agent, or Firm* — Oblon, McClelland, Maier & Neustadt, L.L.P.

(57) ABSTRACT

Provided are methods for detecting or diagnosing a traumatic brain injury or TBI by detecting concentration levels miRNAs associated with TBI in saliva. Methods for controlled and normalized comparisons of salivary miRNA concentration levels are further provided. Assay kits comprising salivary miRNAs, probes and/or primers for detecting salivary miRNAs are also provided.

20 Claims, 60 Drawing Sheets

(56) References Cited

OTHER PUBLICATIONS

International Search Report and Written Opinion dated Aug. 24, 2018 in PCT/US2018/024111 filed Mar. 23, 2018.
Zhang, R. et al., "A circadian gene expression atlas in mammals: Implication for biology and medicine," Proceedings of the National Academy of Science of the United States of America, Nov. 11, 2014, vol. 111, No. 45 pp. 1-6.
Notification of Reason for Rejection dated Mar. 29, 2022 in Japanese Patent Application No. 2020-501432 (with English language translation), 10 pages.
Bergold et al, "Treatment of traumatic brain injury with anti-inflammatory drugs", *Experimental Neurology*, 2016, vol. 275, pp. 367-380.
Corps et al, "Inflammation and Neuroprotection in Traumatic Brain Injury", *JAMA Neurol.*, 2015, vol. 72, No. 3, pp. 355-362 (15 pages).
Centers for Disease Control and Prevention, (2015), Report to Congress on Traumatic Brain Injury in the United States: Epidemiology and Rehabilitation, National Center for Injury Prevention and Control; Division of Unintentional Injury Prevention. Atlanta, GA—72 pages.

\* cited by examiner

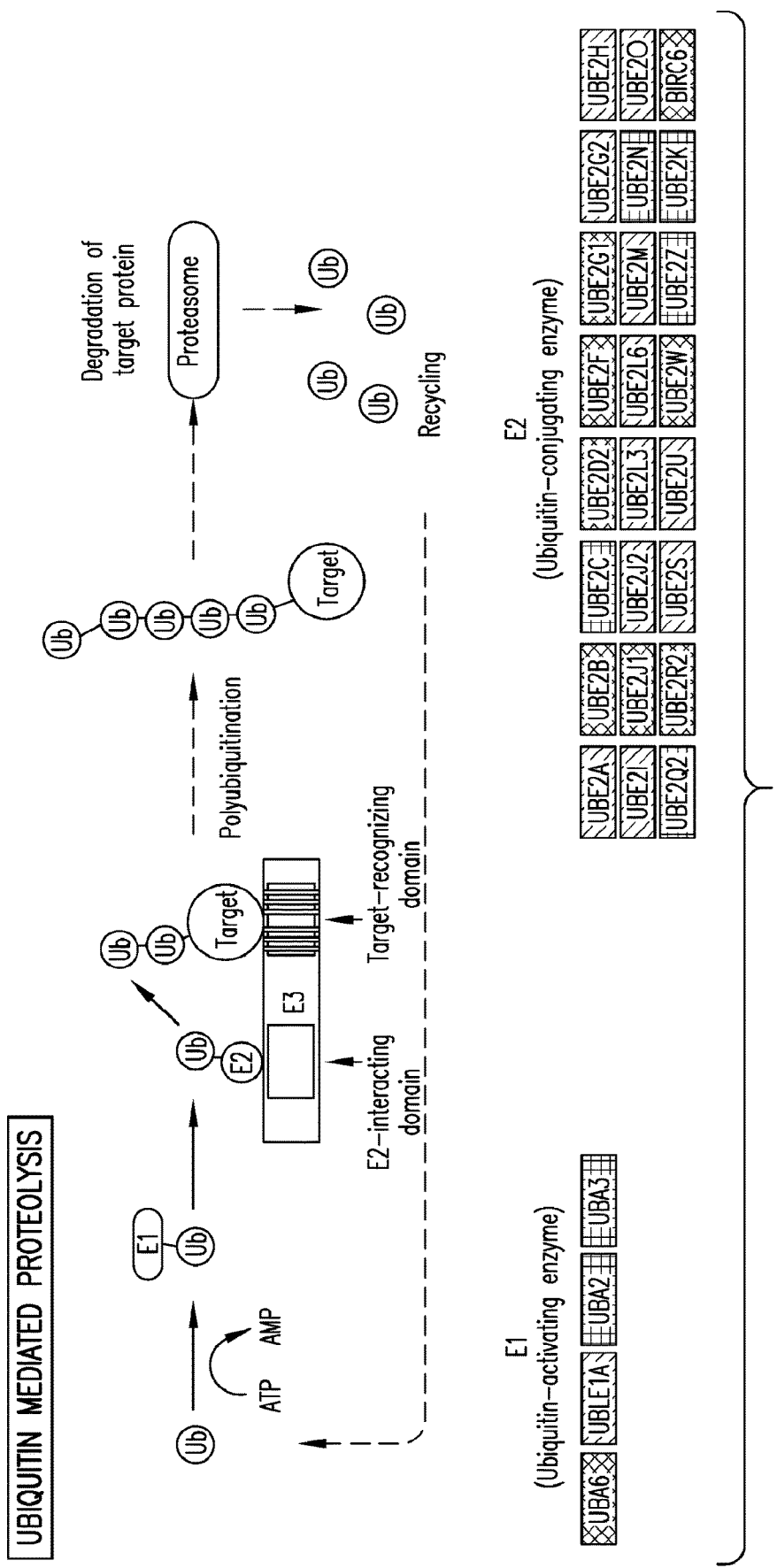

| | miR-769-5P | miR-4792 | miR-629-5p | let-7a-5p | miR-320c-1 | miR-140-3p | miR-133a-5 | let-7b-5p | miR-192-5P | miR-30e | miR-4508 | miR-1307-3P | miR-200b-3p | miR-145-5p | miR-629 | PCS Risk Score | Parent SCAT-3 | Child SCAT-3 | 4wk Attention | 4wk Memory | 4wk Confusion | 4wk Learning | 4wk Headache | 4wk Dizziness | 4wk Fatigue | 4wk Nausea |
|---|---|---|---|---|---|---|---|---|---|---|---|---|---|---|---|---|---|---|---|---|---|---|---|---|---|---|
| miR-769-5P | 1.00 | -0.07 | -0.13 | -0.41 | -0.35 | 0.49 | -0.01 | -0.37 | 0.28 | 0.49 | -0.27 | 0.04 | -0.47 | 0.71 | -0.17 | -0.16 | 0.07 | -0.13 | -0.29 | -0.30 | -0.09 | -0.01 | -0.30 | -0.27 | -0.39 | -0.09 |
| miR-4792 | -0.07 | 1.00 | -0.41 | -0.22 | -0.12 | 0.43 | 0.17 | -0.28 | 0.09 | 0.10 | 0.46 | 0.34 | -0.11 | 0.06 | -0.23 | -0.08 | -0.28 | -0.20 | -0.17 | -0.30 | -0.28 | -0.23 | -0.20 | -0.15 | -0.25 | -0.35 |
| miR-629-5p | -0.13 | -0.41 | 1.00 | 0.46 | 0.09 | -0.32 | 0.01 | 0.50 | -0.09 | -0.38 | -0.04 | -0.13 | 0.27 | -0.15 | 0.91 | 0.07 | 0.20 | 0.32 | 0.29 | 0.21 | -0.02 | 0.18 | 0.42 | -0.01 | 0.38 | 0.28 |
| let-7a-5p | -0.41 | -0.22 | 0.46 | 1.00 | 0.27 | -0.48 | -0.18 | 0.85 | -0.15 | -0.63 | 0.23 | 0.02 | 0.54 | -0.30 | 0.52 | -0.02 | 0.04 | 0.33 | 0.24 | 0.40 | -0.05 | -0.05 | 0.32 | 0.16 | 0.33 | -0.10 |
| miR-320c-1 | -0.35 | -0.12 | 0.09 | 0.27 | 1.00 | -0.21 | -0.13 | 0.01 | -0.06 | -0.24 | 0.01 | -0.17 | 0.02 | -0.16 | 0.09 | -0.30 | -0.07 | -0.11 | 0.35 | 0.55 | 0.08 | -0.09 | 0.03 | -0.01 | 0.32 | -0.09 |
| miR-140-3p | 0.49 | 0.43 | -0.32 | -0.48 | -0.21 | 1.00 | -0.04 | -0.18 | 0.02 | 0.60 | -0.04 | 0.12 | -0.64 | 0.62 | -0.19 | 0.03 | -0.03 | -0.22 | -0.29 | -0.35 | -0.18 | -0.15 | -0.29 | -0.20 | -0.33 | -0.07 |
| miR-133a-5 | -0.01 | 0.17 | 0.01 | -0.18 | -0.13 | -0.04 | 1.00 | -0.11 | -0.12 | 0.17 | -0.16 | -0.07 | 0.07 | 0.07 | 0.05 | 0.23 | -0.02 | 0.14 | 0.05 | 0.08 | 0.14 | -0.06 | 0.08 | 0.01 | 0.14 | 0.06 |
| let-7b-5p | -0.37 | -0.28 | 0.50 | 0.85 | 0.01 | -0.35 | -0.11 | 1.00 | -0.25 | -0.55 | 0.20 | -0.03 | 0.51 | -0.34 | 0.54 | 0.10 | 0.03 | 0.35 | 0.18 | 0.30 | 0.09 | 0.07 | 0.27 | 0.23 | 0.45 | 0.06 |
| miR-192-5P | 0.28 | 0.09 | -0.09 | -0.15 | -0.06 | 0.02 | -0.12 | -0.25 | 1.00 | 0.17 | -0.02 | -0.27 | -0.65 | 0.13 | -0.15 | 0.08 | 0.24 | 0.24 | 0.05 | -0.13 | -0.09 | -0.09 | -0.13 | -0.16 | -0.34 | -0.02 |
| miR-30e | 0.49 | 0.10 | -0.38 | -0.63 | -0.24 | 0.60 | 0.17 | -0.55 | 0.17 | 1.00 | -0.39 | -0.09 | -0.65 | 0.48 | -0.37 | 0.03 | 0.22 | -0.03 | -0.25 | -0.34 | -0.06 | -0.03 | -0.31 | -0.21 | -0.37 | 0.01 |
| miR-4508 | -0.27 | 0.46 | -0.04 | 0.23 | 0.01 | -0.04 | -0.16 | 0.20 | -0.02 | -0.39 | 1.00 | 0.63 | 0.18 | -0.18 | 0.09 | 0.07 | -0.08 | 0.15 | 0.05 | -0.22 | -0.24 | -0.12 | -0.15 | 0.00 | -0.21 | -0.25 |
| miR-1307-3P | 0.04 | 0.34 | -0.13 | 0.02 | -0.17 | 0.12 | -0.07 | -0.03 | -0.27 | -0.09 | 0.63 | 1.00 | 0.07 | 0.16 | -0.09 | -0.03 | -0.28 | 0.01 | -0.29 | -0.33 | -0.18 | -0.06 | -0.20 | 0.07 | -0.37 | -0.16 |
| miR-200b-3p | -0.47 | -0.11 | 0.27 | 0.54 | 0.02 | -0.64 | -0.07 | 0.51 | -0.65 | -0.65 | 0.18 | 0.07 | 1.00 | -0.52 | 0.35 | -0.18 | -0.02 | 0.05 | -0.09 | -0.26 | -0.23 | -0.09 | 0.39 | 0.30 | 0.39 | -0.01 |
| miR-145-5p | 0.71 | 0.06 | -0.15 | -0.30 | -0.16 | 0.62 | 0.07 | -0.34 | 0.13 | 0.48 | -0.18 | 0.16 | -0.52 | 1.00 | -0.18 | 0.01 | 0.02 | -0.09 | -0.22 | -0.23 | -0.08 | -0.22 | -0.23 | -0.21 | -0.32 | 0.03 |
| miR-629 | -0.17 | -0.23 | 0.91 | 0.52 | 0.09 | -0.19 | 0.05 | 0.54 | -0.15 | -0.37 | 0.09 | -0.09 | 0.35 | -0.18 | 1.00 | 0.08 | 0.19 | 0.32 | 0.35 | 0.27 | 0.01 | 0.08 | 0.47 | 0.14 | 0.39 | 0.18 |
| PCS Risk Score | -0.16 | -0.08 | 0.07 | -0.02 | -0.30 | 0.03 | 0.23 | 0.10 | 0.08 | 0.03 | 0.07 | -0.03 | -0.18 | 0.01 | 0.08 | 1.00 | 0.38 | 0.53 | 0.24 | 0.21 | 0.21 | 0.29 | 0.20 | 0.30 | 0.15 | 0.21 |
| Parent SCAT-3 | 0.07 | -0.28 | 0.20 | 0.04 | -0.07 | -0.03 | -0.02 | 0.03 | 0.24 | 0.22 | -0.08 | -0.28 | -0.02 | 0.02 | 0.19 | 0.38 | 1.00 | 0.69 | 0.05 | 0.00 | -0.01 | -0.25 | -0.01 | -0.08 | -0.08 | -0.05 |
| Child SCAT-3 | -0.13 | -0.20 | 0.32 | 0.33 | -0.11 | -0.22 | 0.14 | 0.35 | 0.24 | -0.03 | 0.15 | 0.01 | 0.05 | -0.09 | 0.32 | 0.53 | 0.69 | 1.00 | 0.12 | 0.15 | -0.08 | 0.16 | 0.13 | 0.13 | 0.13 | 0.01 |
| 4wk Attention | -0.29 | -0.17 | 0.29 | 0.24 | 0.35 | -0.29 | 0.10 | 0.18 | -0.13 | -0.25 | -0.22 | -0.29 | 0.24 | -0.26 | 0.35 | 0.24 | 0.05 | 0.12 | 1.00 | 0.83 | 0.63 | 0.45 | 0.69 | 0.65 | 0.80 | 0.07 |
| 4wk Memory | -0.30 | -0.30 | 0.21 | 0.40 | 0.55 | -0.35 | 0.08 | 0.30 | -0.13 | -0.34 | -0.24 | -0.33 | 0.24 | -0.23 | 0.27 | 0.21 | 0.00 | 0.15 | 0.83 | 1.00 | 0.64 | 0.27 | 0.41 | 0.54 | 0.73 | 0.10 |
| 4wk Confusion | -0.09 | -0.28 | -0.02 | -0.05 | 0.08 | -0.18 | 0.14 | 0.09 | -0.09 | -0.06 | -0.27 | -0.18 | 0.15 | -0.08 | 0.01 | 0.21 | -0.25 | -0.08 | 0.63 | 0.64 | 1.00 | 0.42 | 0.44 | 0.70 | 0.69 | 0.54 |
| 4wk Learning | -0.01 | -0.23 | 0.18 | -0.05 | -0.09 | -0.15 | -0.06 | 0.07 | -0.09 | -0.03 | -0.12 | -0.06 | -0.09 | -0.22 | 0.08 | 0.29 | -0.01 | 0.16 | 0.45 | 0.27 | 0.42 | 1.00 | 0.27 | 0.39 | 0.43 | 0.21 |
| 4wk Headache | -0.30 | -0.20 | 0.42 | 0.32 | 0.03 | -0.29 | 0.08 | 0.27 | -0.13 | -0.31 | -0.15 | -0.20 | 0.39 | -0.23 | 0.47 | 0.20 | 0.11 | 0.13 | 0.69 | 0.41 | 0.44 | 0.27 | 1.00 | 0.49 | 0.60 | 0.38 |
| 4wk Dizziness | -0.27 | -0.15 | -0.01 | 0.16 | -0.01 | -0.20 | 0.01 | 0.23 | -0.16 | -0.21 | 0.00 | 0.07 | 0.30 | -0.21 | 0.14 | 0.30 | -0.08 | 0.13 | 0.65 | 0.54 | 0.70 | 0.39 | 0.49 | 1.00 | 0.56 | 0.23 |
| 4wk Fatigue | -0.39 | -0.25 | 0.38 | 0.33 | 0.32 | -0.33 | 0.14 | 0.45 | -0.34 | -0.37 | -0.21 | -0.37 | 0.39 | -0.32 | 0.39 | 0.15 | -0.08 | 0.13 | 0.80 | 0.73 | 0.69 | 0.43 | 0.60 | 0.56 | 1.00 | 0.30 |
| 4wk Nausea | -0.09 | -0.35 | 0.28 | -0.10 | -0.09 | -0.07 | 0.06 | 0.06 | -0.02 | 0.01 | -0.25 | -0.16 | -0.01 | 0.03 | 0.18 | 0.21 | -0.05 | 0.01 | 0.07 | 0.10 | 0.54 | 0.21 | 0.38 | 0.23 | 0.30 | 1.00 |

Fig. 21

Logistic Regression Model with Selected Compounds:

logit(P) = log(P/(1−P)) = 0.604 + 1.841 hsa-let-7f-5p/hsa-miR-769-5p + 0.877 hsa-miR-421-5p + 0.751 hsa-miR-200b/hsa-miR-149-5p
, where P is Pr(y=1|x). The best threshold (or Cutoff) for the predicted P is 0.67.
Original Label: ACS/PCS ---> Labels in Logistic Regression: 0/1
Note) The class/response value is recommended as (Case:1 and Control:0)

Logistic Regression Model-Summary of Each Feature:

| | Estimate | Std. Error | z value | Pr(>|z|) | Odds |
|---|---|---|---|---|---|
| (Intercept) | 0.604 | 0.406 | 1.488 | 0.137 | - |
| hsa-let-7f-5p/hsa-miR-769-5p | 1.481 | 0.566 | 2.615 | 0.009 | 4.4 |
| hsa-miR-421-pre/hsa-miR-215-5p | 0.877 | 0.452 | 1.94 | 0.052 | 2.4 |
| hsa-miR-200b/hsa-miR-149-5p | 0.751 | 0.481 | 1.563 | 0.118 | 2.12 |

Performance of Logistic Regression Model:

| | AUC | Sensitivity | Sensitivity |
|---|---|---|---|
| Training/Discovery | 0.898 (0.871~0.926) | 0.752 (0.700~0.803) | 0.929 (0.894~0.965) |
| 10-fold Cross Validation | 0.870 (0.770~0.970) | 0.767 (0.767~0.918) | 0.955 (0.868~1.000) |

ROC plot with 10-fold Cross-Validation:
-Show with 95% confidence band (Caution: it will take longer time) ☐ Show

*Fig. 29A*

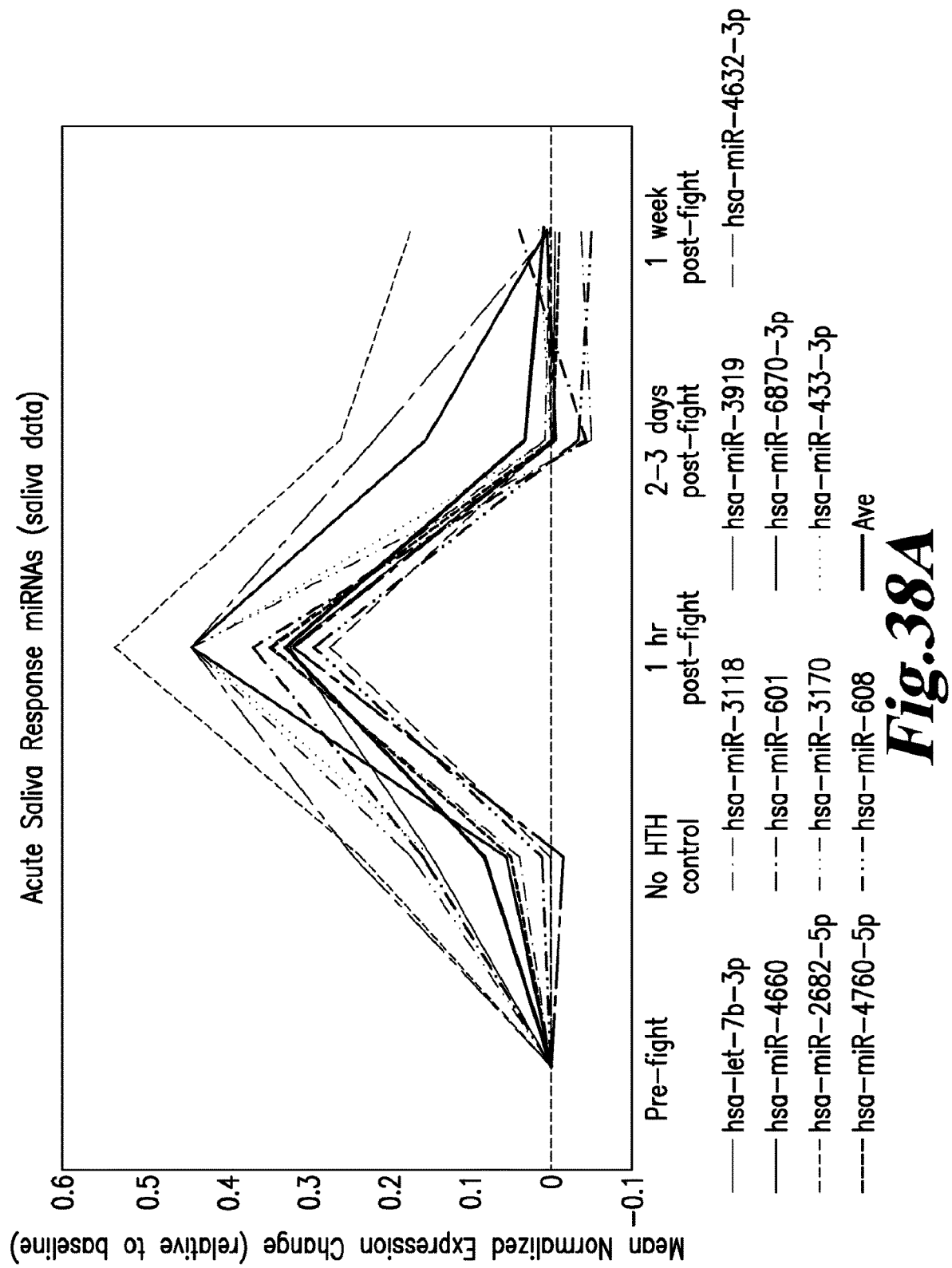

ANALYSIS AND PREDICTION OF TRAUMATIC BRAIN INJURY AND CONCUSSION SYMPTOMS

CROSS-REFERENCE TO RELATED APPLICATIONS

This application claims priority Provisional Patent Application Nos. 62/475,698, filed Mar. 23, 2017; 62/480,079, filed Mar. 31, 2017; 62/502,107, filed May 5, 2017; and 62/623,145, filed Jan. 29, 2018, the contents of which are hereby incorporated herein by reference in their entirety.

BACKGROUND

Field of the Disclosure

The present invention relates to the field of diagnosing and identifying adults and pediatric subjects that have sustained traumatic brain injuries (TBIs) and those subjects who are likely to develop a post-concussion syndrome (PCS) resulting from the TBI. The invention involves methods for correcting or normalizing values of salivary micro RNA (miRNA) levels to compensate for temporal variations, such as circadian fluctuations, in salivary miRNA levels, as well as detecting abnormal temporal variations in salivary mi-RNA levels that correlate with a disease, injury or other disorder or with health status.

Description of the Related Art

Three million concussions occur in the United States each year and approximately two-thirds take place in children and adolescents which is an increase of nearly 250% since 2007 (McCarthy et al., 2015). Over 80% of pediatric concussions result from mild traumatic brain injuries (mTBIs) (Kirkwood, et al., 2006). A mTBI is defined as a traumatic disruption of brain function that manifests as altered mental status, loss of consciousness (<20 minutes), or amnesia (<24 hours), with an initial Glasgow Coma Scale score of ≥13 and lack of focal neurological deficits (J. Head Trauma Rehabil., 1993). For most children concussion symptoms will resolve within two weeks, but some children will experience cognitive, somatic, emotional, and behavioral symptoms that extend past this period (Babcock et al., 2013; Barlow et al., 2011; Scorza et al., 2012). Those individuals with symptoms lasting longer than 28 days can be classified as having post-concussion syndrome (PCS) which has an incidence in children ranging from 6% to 59% (Ayr et al., 2009; Burton et al., 1997; Yeates et al., 1999; Barlow et al., 2010).

While most pediatricians feel capable of diagnosing a concussion, there are currently no established clinical tools that can reliably identify the subset of children that will develop PCS (Zemek et al., 2013; Zonfrillo et al., 2012). A lack of knowledge about factors that predispose some children with concussions to PCS makes developing anticipatory guidelines difficult for pediatricians. The absence of objective measures in assessing children with concussions can delay specialist referral and execution of an individualized treatment plan (Bazarian et al., 2001).

Previous pediatric studies have found correlations between PCS risk and factors such as female sex, older age, the initial presence of headache, and admission to the hospital (Babcock et al., 2013; Zemek et al., 2013; Scopaz et al., 2013). The 2012 Consensus Statement on Concussion in Sport recommended that age-appropriate symptom checklists be administered to children, parents, teachers, and caregivers for accurate clinical assessment of concussions. Clinical risk scores utilizing checklist features have demonstrated modest ability to predict PCS risk in patients presenting within 48 hours of head injury (Zemek et al., 2016). However, the feasibility of administering and scoring multiple age-specific questionnaires within the time constraints of a typical clinical encounter has prevented physicians from adopting a common concussion evaluation tool (Zonfrillo et al., 2012). Instead, many investigators have begun to explore alternative diagnostic approaches to concussions.

Research into the use of protein biomarkers as a means of diagnosing, monitoring, and predicting the course of concussions has increased markedly over the past decade (Papa et al., 2013). One of the most extensively examined biomarkers has been $S100\beta$, a low molecular weight protein expressed in astrocytes and found at low levels in cerebrospinal fluid (CSF) and serum (Papa et al., 2015; Berger et al., 2002). Levels of $S100\beta$ correlate with head computed tomography (CT) findings after mTBI in adults, but there are conflicting reports regarding its accuracy in pediatric head trauma (Jeter et al., 2013; Unden et al., 2009).

Though reference ranges for $S100\beta$ exist, they are based largely on adult data and must account for variations across age and sex during child development (Gazzolo et al., 2003). $S100\beta$ is also produced outside the central nervous system (CNS) and is influenced by disease states including bone fractures and intra-abdominal injury (Kovesdi et al., 2010). These factors give it poor specificity as an mTBI diagnostic test (Bazarian et al., 2006). In addition, $S100\beta$ is influenced by exercise, limiting its utility in sports-concussions, a mechanism common in adolescents (Otto et al., 2000). Regardless of age, most of the protein biomarkers currently being studied have a low sensitivity for detecting mTBI in individuals who do not have a detectible intracranial lesion (Bhomia et al., 2016). There have also been no protein biomarkers that have reliably been able to predict PCS after a mTBI (Ma et al., 2008; Begaz et al., 2006).

Micro ribonucleic acids (miRNAs) are small, endogenous, non-coding molecules that influence protein translation throughout the human body (Nam et al., 2014). They are transported through the extracellular space by protective exosomes and micro-vesicles, or bound to proteins, which allows them to be easily detected in serum, CSF, or saliva (Bhomia et al., 2016; Valadi et al., 2007). Levels of tissue-specific mRNAs released by damaged cells might act as biomarkers of a human disease. Due to their abundance, stability at fluctuating pH levels, resistance to enzymatic degradation, and essential role in transcriptional regulation, miRNAs may be good biomarker candidates (Gilad et al., 2008).

Seven previous studies have examined the utility of miRNAs biomarkers in human TBIs. Pasinetti and colleagues found one miRNA (miR-671-5p) to be decreased in the peripheral blood mononuclear cells of nine military veterans with comorbid post-traumatic stress disorder (PTSD) and mTBI compared to nine control veterans with PTSD only Pasinetti et al., 2012). Redell and colleagues found that of the 108 miRNAs identified in the plasma of age-, gender-, and race-matched controls, 52 were "altered" in 10 subjects after a severe TBI (sTBI). The study further examined the utility of miRNAs for identifying both sTBI (GCS<6) and mTBI (GCS>12) within the first 24 hours after an injury. They found one miRNA increased (miR-765) and two miRNAs decreased (miR-16 and miR-92a) in eight subjects with sTBI; as well as two miRNAs (miR-92a and miR-16) increased in 11 subjects with mTBI compared to healthy volunteers (Redell et al., 2010).

Bhomia and colleagues identified a group of 10 miRNAs (miR-151-5p, miR-195, miR-20a, miR-30d, miR-328, miR-362-3p, miR-486, miR-505, miR-92a, and mmu-miR-451) that were present in the serum of eight subjects suffering from mild to moderate TBIs (GCS≥9) and in eight subjects suffering from sTBI (GCS≤8). To validate the presence of miRNAs found in serum, the study examined the CSF of 8 subjects with a severe TBI and found an increase in four out the 10 miRNAs (miR-328, miR-362-3p, miR-451, and miR-486) (Bhomia et al., 2016). A study by Di Pietro and colleagues examined serum miRNA expression in five individuals with mTBI, five individuals with sTBI, and five healthy controls. The authors found two miRNAs (miR-425-5p and miR-502) were downregulated in the mTBI group and two miRNAs (miR-21 and miR-335) were upregulated in the sTBI group (Di Pietro et al., 2017).

Yang and colleagues identified three miRNAs (mir-93, mir-191, and mir-499) that were upregulated in the serum of 25 subjects with mild TBI (GCS≥13), 26 subjects with moderate TBI (GCS 9-12), and 25 subjects with severe TBI (GCS≤8) when compared with healthy controls. They also recognized that these miRNA levels were increased to a higher level in the severe TBI group when compared with the mild and moderate TBI groups (Yang et al., 2016). Mitra and colleagues found that two miRNAs (mir-142-3p and mir-423-3p) were elevated in the serum of twelve subjects having a combination of TBI and amnesia when compared with twelve subjects with TBI only (Mitra et al., 2017).

Traumatic brain injury (TBI) is an important public health problem, affecting at least 1.7 million individuals annually in the U.S. alone and is predicted to "surpass many diseases as the major cause of death and disability by the year 2020" according to the WHO. The disorder is classified on a spectrum ranging from mild to severe, with mild TBI (mTBI) accounting for at least 85% of total TBI cases. Notably, the incidence of mTBI is commonly regarded as under-reported, particularly in the context of sports competitions, where athletes often want to avoid being forced to stop participation and drop out of sporting competitions until completion of a formal medical evaluation and a return to play protocol. As a result, mTBI has been referred to as a "silent epidemic".

A typical head impact in mTBI induces rapid percussive (coup/contracoup) and/or torsional (rotational) damage to the brain, leading to parenchymal bruising and subarachnoid hemorrhage with direct brain cell loss, as well as stretching of axons, and diffuse axonal injury that may persist for years. Furthermore, repetitive mTBI is associated with serious long-term sequelae including post-concussive syndrome and chronic traumatic encephalopathy (CTE), the latter often leading to cognitive impairment, neuropsychiatric symptoms, dementia, and pugilistic parkinsonism. Moreover, mTBI often goes undiagnosed due to under-reporting, delayed onset of symptoms and the limited sensitivity of conventional assessment techniques in detecting mild brain injury, thereby hampering diagnostic, prognostic, and therapeutic approaches.

Because these symptoms develop across time and the initial injuries often escape detection by conventional neuroimaging techniques, mTBI presents a diagnostic challenge, which has slowed efforts to examine the time course of its pathophysiology. Consequently, diagnostic, prognostic, and therapeutic approaches for mTBI are lacking. Compounding this issue, the failure to ascertain that mTBI has occurred in the first place can easily lead to repetitive mTBI and increase the risk of CTE. Thus, it is critically important to establish accurate and reliable diagnostic markers to aid in the early detection and diagnosis of mTBI, inform its prognosis, and ultimately provide a means to monitor response to treatment.

MicroRNAs (miRNA) are small non-coding RNAs (~22 nucleotides) that suppress target mRNA translation and stability for a large fraction of the transcriptome, and have emerged as useful biomarkers of several disorders including cancer and diabetes. The influence of miRNAs on gene expression occurs both within the cells that synthesize them as well as within remote cells through extracellular trafficking. Once released from donor cells, miRNAs can travel through various extracellular fluids and exert regulatory effects on gene expression in recipient cells. Hence, miRNAs are important master regulators of cellular function within and between a wide range of cells and tissues. Recent data indicating that circulating miRNAs are elevated in plasma following injury, and that miRNA expression profiles differ between healthy and disease states, has generated considerable interest in their potential to serve as peripheral biomarkers of cell and tissue damage or cancer. In addition, dysregulation of specific miRNAs networks has been associated with several neurodegenerative disorders including Alzheimer's and Parkinson's disease, as well as alcoholism. While brain tissue is not readily available from living subjects with neurodegenerative disease, the fact that brain-specific miRNAs are released into peripheral biofluids suggests that miRNA profiles can serve as a proxy, or indirect readout of pathological processes occurring in the CNS. Thus, identifying specific biomarkers for mTBI could facilitate early detection at the presymptomatic stage and will provide insight into novel targets to minimize or even prevent post-mTBI sequelae. Support for the feasibility of using peripheral miRNA biomarkers to predict outcome measures following mTBI was recently provided in two studies on pediatric populations. The first study demonstrated considerable overlap in the miRNA present in both cerebrospinal fluid (CSF) and saliva (63%), and also indicated parallel changes for a number of these miRNAs in children with severe and mild TBI. A follow up study from the same group showed that salivary miRNA patterns in children who were brought to a concussion clinic within a few days after mTBI could predict whether those children would develop acute concussive syndrome (ACS) or prolonged concussive syndrome (PCS) with high accuracy. Notably, one of the elements missing from the aforementioned studies is any type of molecular or functional baseline assessment in the individuals that subsequently experienced a mTBI episode.

This has now been specifically addressed by the inventors who directly compare the pattern of changes in saliva and serum miRNAs, and changes in numerous neurocognitive functional measures in adult athletes after they likely experienced an mTBI event during an amateur mixed martial arts (MMA) competition. Furthermore, the inventors quantified the strength of association between the changes in miRNAs and functional measures, and assessed their potential diagnostic utility.

The inventors have also evaluated the utility of microRNAs (miRNAs) to serve as sensitive and specific peripheral biomarkers of mTBI. As mentioned above, miRNAs are small non-coding RNAs that suppress protein expression that have emerged as useful biomarker candidates in cancer, diabetes, neurodevelopmental, and neurodegenerative disorders. Although miRNAs are made in all tissues and organs of the body, many of them show tissue-specificity. Moreover, miRNAs can act within the cells that synthesize them or be released into the extracellular space (EC) and travel in biofluids to affect other cells. Numerous studies have shown that miRNA expression profiles differ between healthy and diseased states and that the release of miRNAs into the EC appears elevated following tissue damage. As shown herein the inventors establish relationships between peripheral measures of miRNA, such as their salivary levels, objective assessment of likely mTBI severity, and sensitive indices of balance and cognitive function. Though many studies have identified miRNA targets that are dysregulated in adult TBI, none have examined their utility in predicting PCS in children.

The inventors investigated the biomarker potential of salivary miRNAs in 60 children with mTBI and identified six miRNAs dysregulated in both the CSF of children with sTBI and the saliva of children with mTBI. The inventors have also assessed the clinical accuracy of salivary miRNAs in predicting occurrence and severity of PCS relative to the Sport Concussion Assessment Tool (SCAT-3). The inventors sought to find whether miRNAs physiologically related to brain injury and repair would be altered in children with PCS, relative to controls with typical concussion duration, and whether the predictive value of salivary miRNAs would exceed that of current clinical tools, such as the SCAT-3. As shown herein, they found that salivary miRNA profiles can predict duration of concussion symptoms. For example, they found that salivary miRNA profiles of children and adolescents with mTBI: 1) reflect CSF profiles in children and adolescents with TBI; 2) accurately identify the presence of mTBI; and 3) differ from adult miRNA biomarkers of mTBI. Disrupted miRNAs are functionally related to brain injury and repair.

The systems and methods described herein solve many of the problems with existing methodologies of detecting, diagnosing and monitoring TBIs including those resulting from sporting injuries.

SUMMARY OF THE INVENTION

Methods of detecting, diagnosing and prognosing traumatic brain injuries, including concussions and mild traumatic brain injuries by measuring the level, such as its abundance or molar concentration, in biological fluids such as saliva. These methods are applicable to both pediatric and adult subjects and may be applied to monitor treatment and recovery from a TBI. Read data on miRNA levels, such as that obtained by RNA sequencing procedures, may be further normalized, for example, by comparison to levels of one or more invariant RNAs. In some embodiments levels of miRNAs are further normalized based on ciracadian fluctuations in miRNA levels in a biological fluid like saliva. Assay kits containing probes and/or primers that detect and quantify levels of the miRNAs disclosed herein to be associated with TBIs may be used to detect levels of TBI-associated miRNAs in saliva and other biological fluids. These and other objects of the present invention will become more apparent in conjunction with the following detailed description of the preferred embodiments, either alone or in combinations thereof.

BRIEF DESCRIPTION OF THE DRAWINGS

A more complete appreciation of an object of the present disclosure and many of the advantages thereof will be readily obtained as the same becomes better understood by reference to the following detailed description when considered in connection with the accompanying drawings which are described below.

FIG. 21 shows a correlation matrix that identifies individual miRNAs whose concentrations at the time of initial presentation (within 2 weeks of injury) correlate with specific symptoms 4 weeks later.

FIGS. 38A-B show: 12 miRNAs were identified with acute temporal effects (all increases) at the 1 hr Post-fight time point (blue/grayscale shaded area) in saliva samples (A-upper) that exceeded those at the non-specific exercise- or event-related timepoint (green/grayscale shaded area). Note that most of the miRNAs returned to near baseline by 2-3 days Post-fight. The pattern for the same miRNAs was distinctly different in serum (B-lower) (several were unchanged and several had delayed decreases).

DETAILED DESCRIPTION OF THE EMBODIMENTS

Figure 1:
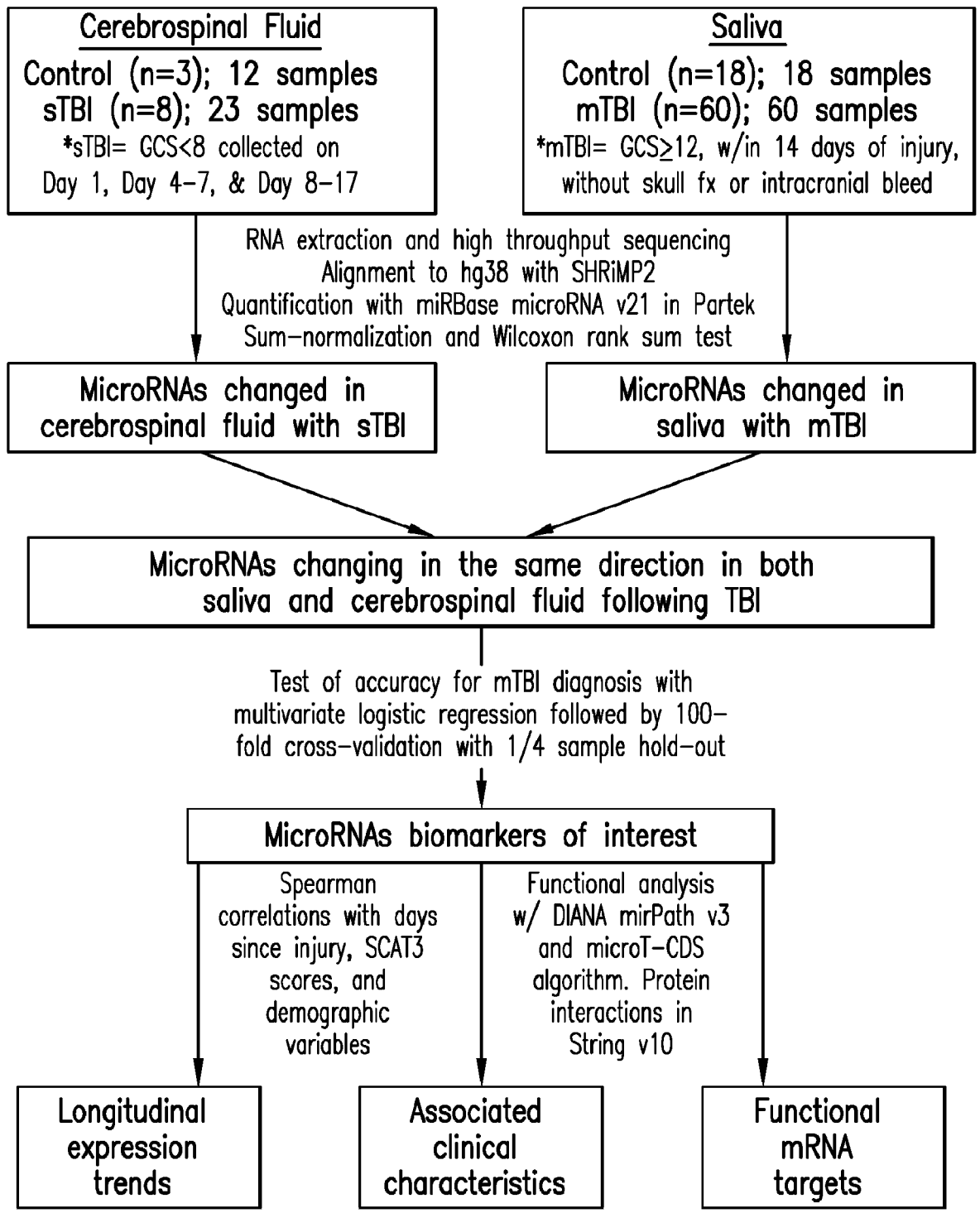
FIG. 1 shows a methodologic pipeline for identifying accurate and physiologically relevant miRNA markers of concussion. Abbreviations: fracture (fx); mild traumatic brain injury (mTBI); severe traumatic brain injury (sTBI).
Figure 2A:
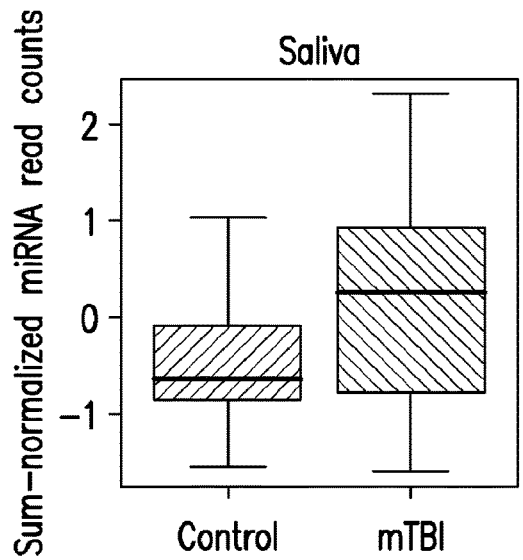
FIGS. 2A-L show whisker box plots depicting mean concentrations in CSF and saliva for the six miRNAs of interest across concussion and control groups. Nominally significant changes were detected for miR-29c-3p (CSF $p=0.032$; Saliva $p=0.008$), miR-26b-5p (CSF $p=0.003$; Saliva $p=0.016$), miR-30e-5p (CSF $p=0.045$; Saliva $p=0.009$), miR-182-5p (CSF $p=0.009$; Saliva $p=0.013$), miR-320c (CSF $p=0.037$; Saliva $p=0.016$), and miR-221-3p (CSF $p=0.014$; Saliva $p=0.005$) with Wilcoxon rank sum testing. False detection rate correction was $\leq 0.15$ for all six miRNAs. Abbreviations: cerebrospinal fluid (CSF); mild traumatic brain injury (mTBI); severe traumatic brain injury (sTBI).
Figure 2B:
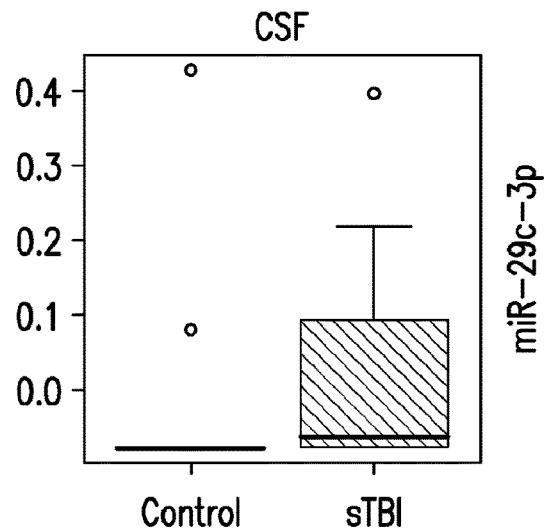
Figure 2C:
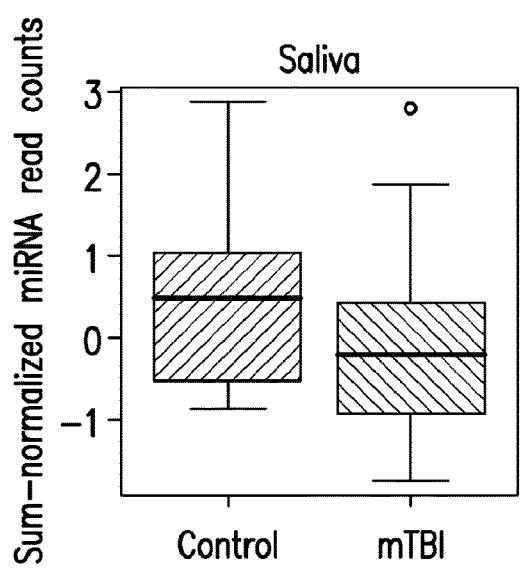
Figure 2D:
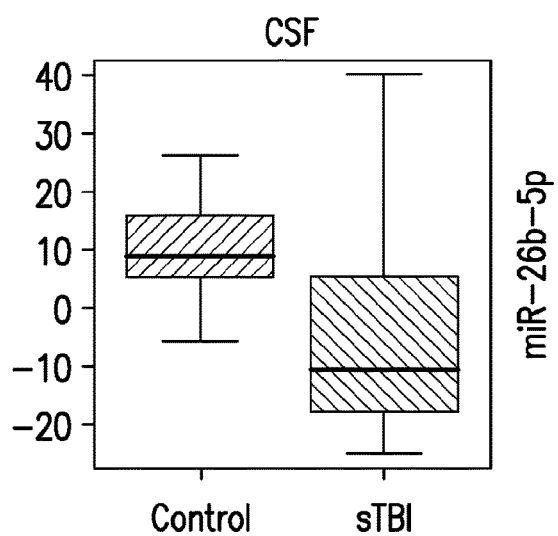
Figure 2E:
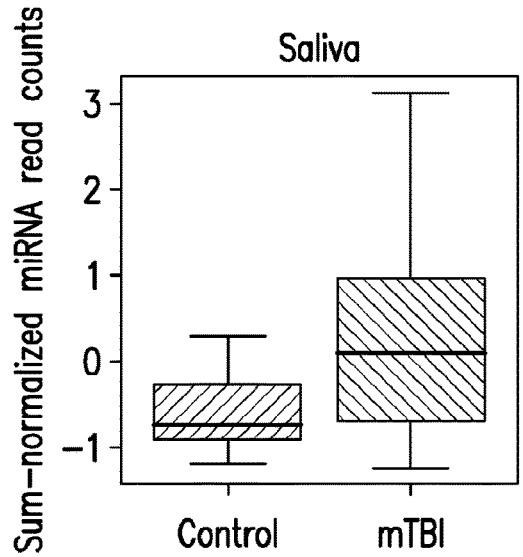
Figure 2F:
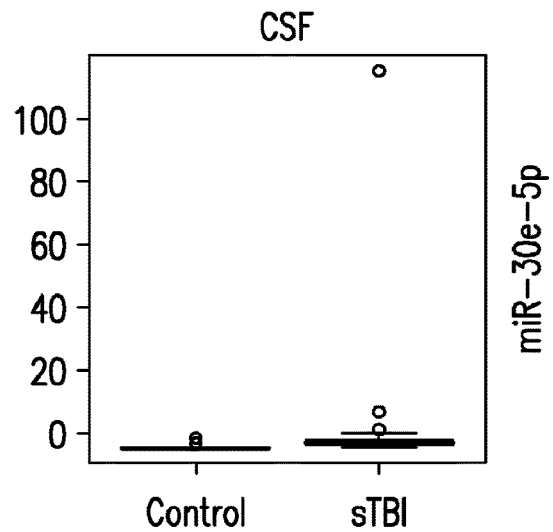
Figure 2G:
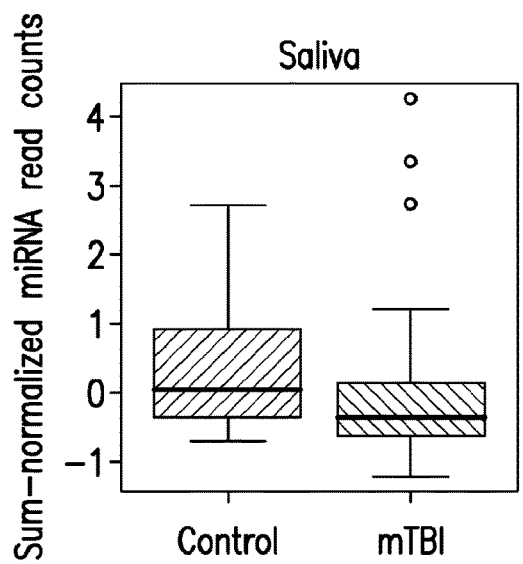
Figure 2H:
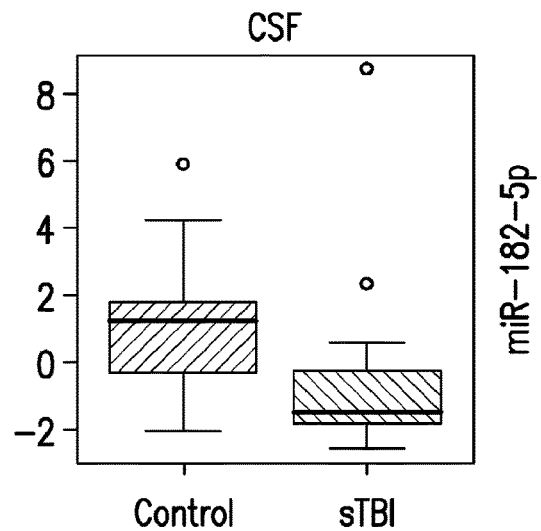
Figure 2I:
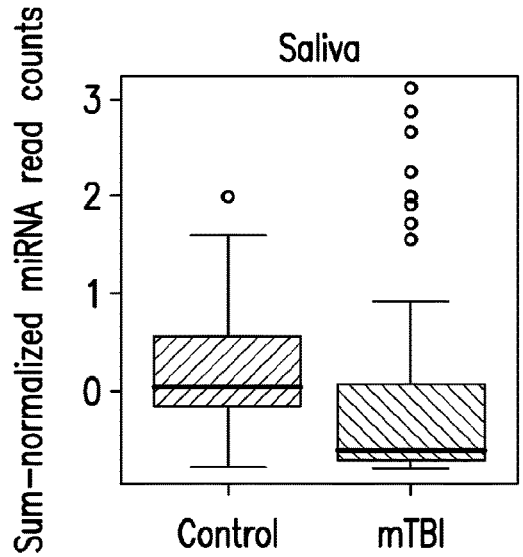
Figure 2J:
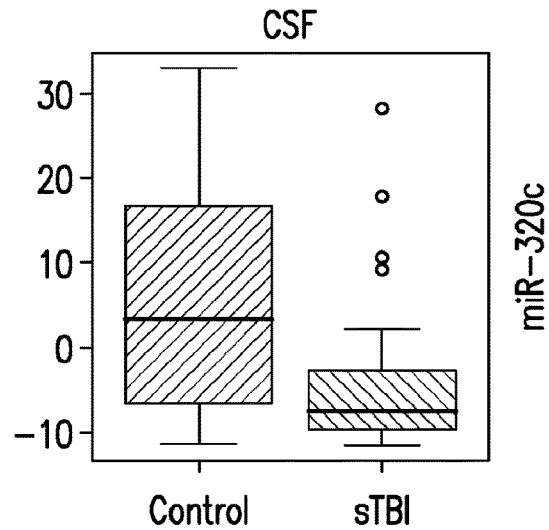
Figure 2K:
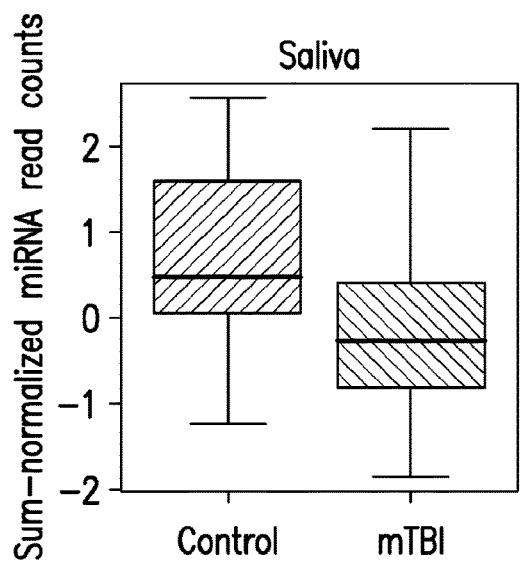
Figure 2L:
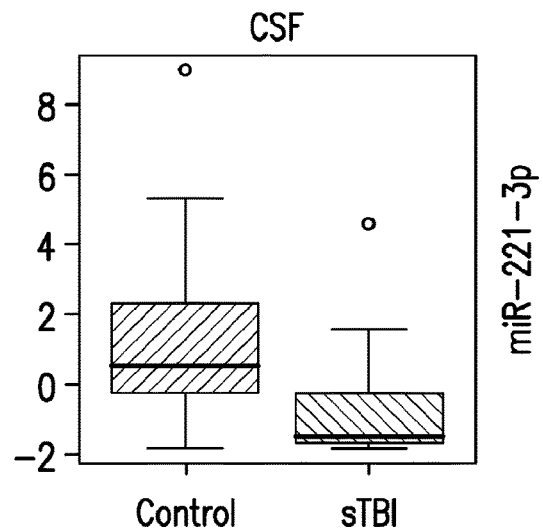

All methods and materials similar or equivalent to those described herein can be used in the practice of the present invention, with suitable methods and materials being described herein. The materials, methods, and examples described herein are illustrative only and are not intended to be limiting, unless otherwise specified.

Saliva is a slightly alkaline secretion of water, mucin, protein, salts, and often a starch-splitting enzyme (as ptyalin) that is secreted into the mouth by salivary glands, lubricates ingested food, and often begins the breakdown of starches. Saliva is released by the submandibular gland, parotid gland, and/or sublingual glands and saliva release may be stimulated by the sympathetic and/or parasympathetic nervous system activity. Saliva released primarily by sympathetic or parasympathetic induction may be used to isolate microRNAs.

Saliva may be collected by expectoration, swabbing the mouth, passive drool, or by other methods known in the art. In some embodiments it may be withdrawn from a salivary gland. In some embodiments, a saliva sample may be further purified, for example, by centrifugation or filtration. For example, it may be filtered through a 0.22 micron or 0.45 micron membrane, and all membrane sizes in between, and the separated components used to recover microRNAs. In other embodiments, proteins or enzymes that degrade microRNA may be removed, inactivated or neutralized in a saliva sample.

Some representative, but not limiting saliva collection and miRNA purification procedures include purifying salivary RNA in accordance with, for example, the Oragene RNA purification protocol using TRI Reagent LS, a TriZol purification method, or similar method. The Oragene purification protocol generally includes multiple parts. In the first part, a sample is shaken vigorously for 8 seconds or longer and the sample is incubated in the original vial at 50° C. for one hour in a water bath or for two hours in an air incubator. In the second part, a 250-500 µL aliquot of saliva is transferred to a microcentrifuge tube, the microcentrifuge tube is incubated at 90° C. for 15 minutes and cooled to room temperature, the microcentrifuge tube is incubated on ice for 10 minutes, the saliva sample is centrifuged at maximum speed (>13,000×g) for 3 minutes, the clear supernatant is transferred into a fresh microcentrifuge tube and the precipitate is discarded, two volumes of cold 95% EtOH is added to the clear supernatant and mixed, the supernatant mixture is incubated at −20° C. for 30 minutes, the microcentrifuge tube is centrifuged at maximum speed, the precipitate is collected while the supernatant is discarded, the precipitate is dissolved in 350 µL of buffer RLT, and 350 µL of 70% EtOH is added to the dissolved pellet mixture and mixed by vortexing. The first two parts may be followed by the Qiagen RNeasy cleanup procedure.

The purification process may further include a second purification step of, for example, purifying the saliva sample using a RNeasy mini spin column by Qiagen. The purification of a biological sample may include any suitable number of steps in any suitable order. Purification processes may also differ based on the type of a biological sample collected from the subject. The yield and quality of the purified biological sample may be assessed via a device such as an Agilent Bioanalyzer, for example, to determine if the yield and quality of RNA is above a predetermined threshold.

microRNA or miRNA is a small non-coding RNA molecule containing about 22 nucleotides, which is found in plants, animals and some viruses, that functions in RNA silencing and post-transcriptional regulation of gene expression (see Ambros et al., 2004; Bartel et al., 2004). MicroRNAs affect expression of the majority of human genes, including CLOCK, BMAL1, and other circadian genes. Notably, miRNAs are released by cells that make them and circulate throughout the body in all extracellular fluids where they interact with other tissues and cells. Recent evidence has shown that human miRNAs even interact with the population of bacterial cells that inhabit the lower gastrointestinal tract, termed the gut microbiome. Moreover, circadian changes in the gut microbiome have recently been established. Small non-coding RNAs (miRNAs) suppress protein expression and that have emerged as useful biomarkers in cancer, diabetes, neurodevelopmental, and neurodegenerative disorders. Although miRNAs are made in all tissues and organs of the body, many of them show tissue-specificity. Moreover, miRNAs can act within the cells that synthesize them or be released into the extracellular space (EC) and travel in biofluids to affect other cells. Numerous studies have shown that miRNA expression profiles differ between healthy and diseased states, and that the release of miRNAs into the EC appears elevated following tissue damage. Epigenetic data includes data about miRNAs. Among the objectives of the inventors were to establish the relationship between peripheral measures of miRNA, objective assessment of likely mTBI severity, and sensitive indices of balance and cognitive function.

A miRNA standard nomenclature system uses the prefix "miR" followed by a dash and a number, the latter often indicating order of naming. For example, miR-120 was named and likely discovered prior to miR-241. A capitalized "miR-" refers to the mature form of the miRNA, while the uncapitalized "mir-" refers to the pre-miRNA and the pri-miRNA, and "MIR" refers to the gene that encodes them. The prefix "hsa-" denotes a human miRNA.

The sequences of miRNAs are known and may be obtained by reference to MirBase, Hyper Text Transfer Protocol (HTTP)://WorldWideWeb.mirbase.org/blog/2018/03/mirbase-22-release/(last accessed Mar. 19, 2018, incorporated by reference) and/or to Hyper Text Transfer Protocol (HTTP)://WorldWideWeb.mirbase.org/index.shtml (last accessed Mar. 19, 2018; incorporated by reference).

miRNA Elements.

Extracellular transport of miRNA via exosomes and other microvesicles and lipophilic carriers is an established epigenetic mechanism for cells to alter gene expression in nearby and distant cells. The microvesicles and carriers are extruded into the extracellular space, where they can dock and enter cells, and block the translation of mRNA into proteins (Hu et al., 2012). In addition, the microvesicles and carriers are present in various bodily fluids, such as blood and saliva (Gallo et al., 2012), enabling us to measure epigenetic material that may have originated from the central nervous system (CNS) simply by collecting saliva. In fact, the inventors believe that many of the detected miRNAs in saliva are secreted into the oral cavity via sensory nerve afferent terminals and motor nerve efferent terminals that innervate the tongue and salivary glands and thereby provide a relatively direct window to assay miRNAs which might be dysregulated in the CNS of individuals. Thus, extracellular miRNA quantification in saliva provides an attractive and minimally-invasive technique for brain-related biomarker identification in children with a disease or disorder or injury. Moreover, this method minimizes many of the limitations associated with analysis of post-mortem brain tissue or peripheral leukocytes (relevance of expression changes, painful blood draws) employed previously.

miRNA isolation from biological samples such as saliva and their analysis may be performed by methods known in the art, including the methods described by Yoshizawa, et al., Salivary MicroRNAs and Oral Cancer Detection, Methods Mol. Biol., 2013; 936: 313-324 or by using commercially available kits, such as mirVana™ miRNA Isolation Kit).

During sleep-wake cycles there are numerous molecular, cellular, and physiological changes that occur. Many of these changes are driven by what are referred to as circadian regulatory genes, such as CLOCK and BMAL1. These, in turn, cause numerous changes in the expression of physiologically relevant genes, proteins, and hormones. Apart from light-dark cycles, the factors that influence expression of circadian genes are not fully understood. Taken together, the inventors' data suggest a previously unknown relationship between saliva miRNA and microbe content as well as temporal influences (i.e., temporal variations) on miRNAs (and/or microbes) themselves. The systems and methods described herein to normalize epigenetic data (sequencing data or other data) that experience temporal variations may be used in any suitable application where temporal variations may affect the data.

One aspect of the invention is a kit suitable for determining whether a subject has a disease, disorder, or condition including 2 or more miRNA probes of a probe set. Each miRNA probe may include a ribonucleotide sequence corresponding to a specific miRNA described herein. In an implementation, the kit further may include a solid support attached to the 2 or more miRNA probes. In an implementation, the kit may further include at least one of the following: (a) one randomly generated miRNA sequence adapted to be used as a negative control; (b) at least one oligonucleotide sequence derived from a housekeeping gene, used as a standardized control for total RNA degradation; or (c) at least one randomly-generated sequence used as a positive control. Alternatively, a probe set may include miRNA probes having ribonucleotide sequences corresponding to DNA sequences from particular microbiomes described herein.

These and other objects of the present invention, which will become more apparent in conjunction with the following detailed description of the preferred embodiments, either alone or in combinations thereof, have been satisfied by the method, systems, kits, arrays and provided herein by the inventors.

One objective of the inventors was to compare changes in salivary miRNA and cerebrospinal fluid (CSF) miRNA following childhood TBI and to investigate the utility of circulating concentrations of miRNA as accurate and physiologically relevant markers of pediatric concussion.

Another objective of the inventors was to establish the relationship between peripheral measures of miRNA, objective assessment of likely mTBI severity, and sensitive indices of balance and cognitive function.

Another objective of the inventors was to determine the relationship between peripheral measures of miRNA in the blood and saliva with objective measures of balance and cognitive function in adult subjects exposed to recent mild head trauma; to examine if any of the identified miRNAs are involved in specific biological pathways relevant to brain function and injury response; and to quantify the strength of the relationship between the miRNAs and functional measures and determine their potential diagnostic utility.

One objective of the inventors was to provide a method of comparing the epigenetic data for a subject with a suspected traumatic brain injury (TBI) to one or more healthy control-subjects or a compendium of healthy control subjects, wherein each healthy control-subject is known not to have sustained a TBI or symptoms of a TBI, comprising:

determining a count of one or more microRNAs (miRNAs) in a biological sample taken from a subject, normalizing the subject's epigenetic data to account for inter-sample count variations, wherein count normalization uses one or more invariant miRNAs, determining the time of day that the biological sample was taken, applying a time-of-day normalization to the count normalized miRNAs by using the time-of-day to further normalize subject's miRNA expression levels relative to time-of-day, and comparing the count and time-of-day normalized expression levels of the one or more miRNAs against counts and time-of-day normalized expression levels of one or more control miRNAs from one or more healthy control-subjects or a compendium of healthy control-subjects, wherein an increase or decrease in the expression levels of the one or more of the subject's miRNAs as compared to the same one or more miRNAs from one or more healthy control-subjects or a compendium of healthy control-subjects is indicative that the subject may have sustained a TBI.

Another objective of the inventors was to provide a method of comparing epigenetic data for a subject having a suspected traumatic brain injury (TBI) to one or more healthy control-subjects or a compendium of healthy control subjects, wherein each healthy control-subject is known not to have sustained a TBI or symptoms of a TBI, comprising:

determining a count of one or more microRNAs (miR-NAs) in a biological sample taken from a subject, normalizing the subject's epigenetic data to account for inter-sample count variations, wherein count normalization uses one or more invariant miRNAs, determining the time of day that the biological sample was taken, applying a time-of-day normalization to the count normalized miRNAs by using the time-of-day to further normalize the subject's miRNA expression levels relative to time-of-day, and comparing the count and time-of-day normalized expression levels of the one or more of the subject's miRNAs against counts and time-of-day normalized expression levels of the same one or more miRNAs from one or more healthy control-subjects or a compendium of healthy control-subjects, wherein an increase or decrease in the expression levels of the one or more of the subject's miRNAs against the same one or more miRNAs from one or more healthy control-subjects or a compendium of healthy control-subjects is indicative of the symptoms the subject may be experiencing or will likely experience.

Another objective was to provide a method of comparing epigenetic data for a subject with a suspected traumatic brain injury (TBI) to one or more healthy control-subjects or a compendium of healthy control subjects, wherein each healthy control-subject is known not to have sustained a TBI or symptoms of a TBI, comprising:

determining a count of one or more microRNAs (miR-NAs) in a biological sample taken from a subject, normalizing subject's epigenetic data to account for inter-sample count variations, wherein count normalization uses one or more invariant miRNAs, determining the time of day that the biological sample was taken, and applying a time-of-day normalization to the count normalized miRNAs by using the time-of-day to further normalize the subject's miRNA expression levels relative to time-of-day, comparing the count and time-of-day normalized expression levels of the one or more of the subject's miRNAs against counts and time-of-day normalized expression levels of the same one or more miRNAs from one or more healthy control-subjects or a compendium of healthy control-subjects, wherein a positive or negative difference in the expression levels of the one or more of the subject's miRNAs as compared to the same one or more miRNAs from one or more healthy control-subjects or a compendium of healthy control-subjects is indicative of severity of the TBI and indicative of the potential duration of symptoms the subject experiencing or likely to experience.

In one embodiment, the miRNAs are selected from a group consisting of hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs.

Another objective of the inventors was to provide method of monitoring the progression of an injury, disorder or disease state in a subject, comprising:

analyzing at least two biological samples from the same subject taken at different time points to determine a count and time-of-day normalized expression levels of one or more miRNAs in each of the at least two biological samples, and comparing the determined levels of the one or more miRNAs over time to determine if the subject's count and time-of-day normalized expression levels of the one or more specific miRNAs is changing over time;

wherein an increase or decrease in the count and time-of-day normalized expression levels of the one or more miRNAs over time is indicative of a progression of TBI in the subject, and/or a positive or negative difference in the expression levels of the count and time-of-day normalized expression levels of the one or more miRNAs over time is indicative of the progression of TBI in the subject.

In one embodiment, the miRNAs subject to time-of-day normalization are selected from the group consisting of hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs.

In another embodiment, the miRNAs subject to time-of-day normalization are selected from the group consisting of hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsamiR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs.

Another objective of the inventors was to provide a method of detecting a miRNA sequence or a plurality of miRNA sequences in a biological sample, comprising:

obtaining a biological sample from a subject;

creating a double-stranded, complementary DNA sequence (cDNA) for each of one or more miRNA sequences selected from the group consisting of hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs found in the biological sample; and detecting the cDNA with Northern Blot, real-time PCR, or Next Generation Sequencing, and the presence, absence or relative quantity of cDNA, wherein the presence, absence or relative quantity of cDNA is indicative of the presence, absence or relative quantity of the complementary miRNA sequences.

In one embodiment, the biological sample is a first biological sample taken at a first time point and the cDNA is a first cDNA, and the method further comprises:

obtaining a second biological sample from said subject at a second time point;

creating a second cDNA for each of one or more miRNA sequences selected from the group consisting of: hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs found in the second biological sample; and detecting the second cDNA with Northern Blot, real-time PCR, or Next Generation Sequencing, and the presence, absence or relative quantity of second cDNA, wherein the presence, absence or relative quantity of second cDNA in said biological sample from said second time point is indicative of the presence, absence or relative quantity of the complementary miRNA sequences at that second time point; and optionally tracking the progression of the TBI by comparing results from the first time point to results from the second time point.

An objective of the inventors was also to provide a kit for determining whether a subject has a traumatic brain injury, comprising:

a probe set comprising 2 or more miRNA probes having ribonucleotide sequences corresponding to ribonucleotide sequences of miRNAs selected from the group consisting of: hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the miRNAs found in the second biological sample.

In one embodiment, the kit further comprises a solid support attached to said probe set. In another embodiment, the kit further comprises:

at least one of (a) one randomly-generated ribonucleotide sequence used as a negative control; (b) at least one oligonucleotide sequence derived from a housekeeping gene, used as a standardized control for total RNA degradation; or (c) at least one randomly-generated ribonucleotide sequence used as a positive control.

Another objective of the inventors was to provide a method for assessing a post-concussion syndrome (PCS) in a subject that has had mild traumatic brain injury (mTBI), comprising:

measuring an array of micro RNA (miRNA) expression from a saliva sample from the subject and comparing an expression profile of the miRNA array to a control array of miRNA from a healthy subject and/or from a subject having an acute concussion symptom (ACS) such that an increase or decrease of the expression level of miRNA in the subject's sample is indicative that the subject is likely to develop PCS, wherein the array of miRNA comprises at least 10, preferable at least 15, more preferably at least 20 miRNA, the miRNAs in the array are selected from the group consisting of miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p.

Another objective was to provide a method of detecting an array of micro RNAs (miRNA) in a saliva sample of a subject, the method comprising:

obtaining a saliva sample from the subject, detecting the presence or absence of an array of miRNAs in the sample, the array comprising at least 10, 11, 12, 13, 14, 15, 16, 17, 18, 19, 20 or more miRNAs, preferably at least 15 miRNAs, more preferably at least 20 miRNAs, wherein the miRNAs are selected from the group consisting miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p.

Another objective was to provide a kit for assessing a post-concussion syndrome (PCS) in a subject diagnosed with a mild traumatic brain injury (mTBI) that had a concussion, comprising:

an array of nucleic acid probes that correspond to sequences of miRNA selected from the group consisting miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p, or that have at least 90% homology to the sequences and specifically bind to the miRNA, wherein the array comprises at least 10, preferably at least 15 and more preferably at least 20 nucleic acid probes.

Another objective of the inventors was to provide a method of treating a subject having post-concussion syndrome, comprising providing to the subject at least one of migraine medication, tension headache medication, an antidepressant, cognitive therapy, psychotherapy, anxiety medication, and depression medication, wherein the subject was identified as having post-concussive syndrome by the methods of the present invention.

In one embodiment, a subject has at least of one symptom selected from the group consisting of headache, dizziness, fatigue, irritability, anxiety, insomnia, loss of concentration, loss of memory, noise sensitivity, and light sensitivity.

Another objective of the inventors was to provide a method for monitoring brain injury status or prognosis in a subject, comprising:

detecting one or more micro-RNAs associated with brain injury in saliva of the subject and evaluating or prognosing brain injury status when said microRNA is present in an amount significantly below or above that of a control subject without a brain injury, and optionally treating the subjects having brain injury.

In one embodiment, prognosing comprises detecting an abnormal level of one or more microRNAs associated with balance and/or cognition.

In another embodiment, the subject is a neonate or the subject is at least 0, 1, 2, 3, 4, 5, 6, 7, 8, 9, 10, 11, or 12 months, or 1, 2, 3, 4, 5, 6, 7, 8, 9, 10, 11, 12, 13, 14, 15, 16, 17, 18, 19, 20, 21, 22, 23, 24 or 25 years old.

Another objective was to provide a method for detecting pediatric TBI comprising detecting a level of let-7f microRNA above that of a value from a child not having pediatric TBI.

One objective of the inventors was to provide a method for detecting, diagnosing, prognosing or monitoring traumatic brain injury ("TBI"), comprising:

detecting in saliva or serum of a subject one or more micro-RNAs associated with TBI, detecting, diagnosing, prognosing or monitoring TBI when said microRNA is present in an amount significantly below or above that detected in a control subject; and optionally, when an abnormal lower or higher level is detected, further evaluating the patient for other symptoms of TBI or treating the subject for TBI.

In one embodiment, the TBI is mild TBI. In another embodiment, the detecting detects at least 2, 3, 4, 5, 6, 7, 8, 9, 10, 20 or 50 miRNAs. In yet another embodiment, detecting comprises detecting one or more miRNAs in saliva. In a different embodiment, detecting comprises detecting one or more miRNAs in serum. In another embodiment, detecting comprises detecting an abnormal level of one or more miRNAs associated with one or more measurements of balance of cognition or symptoms measurements described by the ClearEdge™ assessment system (Hyper Text Transfer Protocol Secure (HTTPS)://WorldWideWeb.clearedgetest.com/, last accessed Jan. 22, 2018) or other functional measurement of balance and/or cognition.

In one embodiment, at least one miRNA targets at least one of pathway associated with proteoglycan synthesis, mucin-type 0-glycan biosynthesis, glycosaminoglycan biosynthesis or keratin sulfate biosynthesis, FoxO signaling, endocytosis, arrhythmogenic right ventricular cardiomyopathy, ErbB signaling, GABAergic synapses, regulation of stem cell pluripotency, morphine addiction, viral carcinogenesis, cAMP signaling, prolactin signaling, glioma, regulation of actin cytoskeleton, biotin metabolism, and adherens junction (zonula adherens).

In another a detecting detects at least one miRNA that is enriched in an ubiquitin-mediated proteolysis pathway, an axon guidance pathway, or a TGF-beta signally pathway.

In another embodiment, the method detects a subject with TBI or mTBI with an accuracy of at least 75, 76, 77, 78, 79, 80, 81, 82, 83, 84, 85, 86, 87, 88, 89, 90, 91, 92, 93, 94, or 95%.

In a different embodiment, the method comprises monitoring the levels of one or more miRNAs as an index of exacerbation or amelioration of TBI or mTBI.

In another embodiment, the method comprises treating a subject for TBI or mTBI and monitoring the levels of one or more miRNAs as an index of exacerbation or amelioration of TBI or mTBI before, during or after treatment.

Another objective of the inventors was to provide a composition comprising probes and/or primers that identify at least one miRNA associated with TBI or mTBI in saliva or serum. In one embodiment, the probes and/or primers identify at least 2, 3, 4, 5, 6, 7, 8, 9, 10, 15, 20, 50 or more miRNAs. In another embodiment, the composition comprises probes and/or primers that detect at least one miRNA that is enriched in an ubiquitin-mediated proteolysis pathway, an axon guidance pathway, or a TGF-beta signally pathway in a subject having TBI or mTBI. In another embodiment, the composition is a microarray, biochip or chip.

Another objective of the inventors was to provide a system for detecting miRNA in saliva comprising a microarray comprising probes or primers that collectively recognize multiple miRNA associated with TBI or mTBI, and optionally signal transmission, information processing, and data display or output elements.

In one embodiment, the system further comprises at least one elements for receiving, and optionally purifying or isolating miRNA.

Another objective of the inventors was to provide a composition comprising one or more miRNAs that is/are deficient (lower than a healthy control) in a subject at risk of, or a subject having, TBI or mTBI in a form suitable for administration to an organelle, cellular compartment, tissue or site affected by TBI or mTBI; or a composition comprising one or more agents that lower or inactivate one or more miRNAs elevated, compared to a healthy control, in a subject at risk of, or a subject having, TBI or mTBI, in a form suitable for administration to organelle, cellular compartment, tissue or site affected by TBI or mTBI.

In one embodiment, the composition is in a form of a natural or synthetic liposome, microvesicle, protein complex, lipoprotein complex, exosome or multivesicular body; or probiotic or prebiotic product.

One objective of the inventors was to provide a method for treating a subject at risk of TBI, or having TBI, comprising administering the composition disclosed herein 44 to a subject in need thereof.

In many or most embodiments of the invention the subject is a human.

A biological sample could be at least one of saliva, cerebral spinal fluid, blood, serum, plasma, urine, feces, mucosal excretions, tears, and tissue. Advantageously, the invention is practiced using a saliva sample.

In some embodiments of the invention expression levels of miRNAs can be determined by RNA sequencing, a real-time PCR, next generation sequencing or by other appropriate methods.

In the recent study, the inventors have examined the relationship of microRNA (miRNA) levels to diurnal variations. The inventors have hypothesized that a portion of the miRNAs that target circadian genes would show strong circadian rhythms themselves. Because miRNAs can circulate throughout the body in all extracellular fluids, we measured them in human saliva. An additional reason to use saliva samples was to enable analysis of the relationship of miRNAs to the levels and diversity of microbes present in the human mouth, termed the microbiome. Previous research in the lower GI tract has shown a strong relationship between host miRNAs and the resident bacteria. Moreover, circadian changes in the gut microbiome have been established. Consequently, one objective of the inventors was to obtain evidence for correlated changes in a subset of circadian oscillating miRNAs and microbes. U.S. Provisional Application 62/475,705, filed Mar. 23, 2017, and PCT/US18/23336, filed Mar. 20, 2108, are hereby incorpored herein in their entirety.

Eleven human subject volunteers participated in the initial study and provided saliva samples at various times of day on repeated days. Identification and quantification of saliva miRNA and microbial content was performed using next generation sequencing (NGS), real time PCR, or otherwise followed by a statistical analysis. The inventors have first used a two-way analysis of variance (ANOVA) in two independent sample sets to identify miRNAs and microbes that varied significantly according to the time of collection but not the day of collection (which could have been strongly affected by daily variation in routines). A subset of these miRNAs and microbes were then used in a third sample set to predict the time of collection using a multivariate regression. The results indicated that human saliva contained approximately 400 miRNAs and 2000 microbes that were reliably quantified. Of these, strong and predictable changes with time of collection were apparent for 19 distinct miRNAs and many microbes. A model was developed from the miRNA data in the first two sample sets that was able to predict time of collection in the third sample set within a 15% margin of error. The microbial data also showed a strong correlation with time of collection in the first two sample sets, but was not as accurate at predicting collection time in the third sample set. Also highly significant correlations between several of the miRNAs and microbes were observed. Interestingly, a bioinformatic analysis of the best time predictor miRNAs indicated that most target at least one or more circadian genes, in addition to genes involved in brain and immune function. Taken together, our data suggest a previously unknown relationship between saliva miRNA and microbe content as well as temporal influences (i.e., temporal variations) on miRNAs (and/or microbes) themselves. The systems and methods described herein to normalize epigenetic data (sequencing data or other data) that experience temporal variations may be used in any suitable application where temporal variations may affect the data. In an example, the systems and methods describes herein may be used in applications to detect the onset of medical conditions and/or changes in medical conditions—more specifically, to detect onset and/or changes in neurological disorders such as autism, sleep disorders and traumatic brain injury (TBI).

Accordingly, an objective of the inventors was to provide a method of normalizing epigenetic sequence data to account for temporal variations in microRNA (miRNA) expression, comprising:

determining read-counts of one or more miRNAs in a biological sample taken from a subject, normalizing epigenetic data of the subject to account for inter-sample read-count variations, wherein the read-count normalization uses one or more invariant miRNAs, determining time of day that the biological sample was taken, and applying an algorithm to the read-count normalized miRNAs, wherein the algorithm uses the time-of-day to normalize the subject's miRNA expression levels relative to time-of-day.

Another objective of the inventors was to provide a method a method of monitoring progression of a disorder, disease state or injury in a subject, comprising:

analyzing at least two biological samples from the subject taken at different time points to determine a read-count and time-of-day normalized expression levels of one or more specific miRNAs in each of the at least two biological samples, and comparing the determined levels of the one or more specific miRNAs over time to determine if the subject's read-count and time-of-day normalized expression levels of the one or more specific miRNAs is changing over time, wherein an increase or decrease in the read-count and time-of-day normalized expression levels of the one or more specific miRNAs over time is indicative that the subject's disorder or disease state or injury is improving or deteriorating.

In one embodiment, miRNAs subject to time-of-day normalization are selected from the group consisting of Group A circaMiRs and/or those miRNA which share the seed sequences of the Group A circaMiRs.

In another embodiment, miRNAs subject to time-of-day normalization are selected from the group consisting of Group A circaMiRs and Group B circaMiRs and/or those miRNA which share the seed sequences of the Group A circaMiRs and Group B circaMiRs.

In one embodiment, the subject is a subject having a post-concussion syndrome (PCS). In another embodiment, the subject is a subject having TBI or mTBI.

Another objective of the inventors was to provide a method of detecting a miRNA or a plurality of miRNAs in a first biological sample, comprising:

obtaining a biological sample from a subject;

creating a double-stranded, complementary DNA sequence (cDNA) for each of one or more miRNA selected from Group A circaMiRs and Group B circaMiRs; and detecting a presence, absence or relative quantity of cDNAs, wherein the presence, absence or relative quantity of cDNA is indicative of the presence, absence or relative quantity of the complementary miRNA.

Another objective was to provide a method of detecting a miRNA or a plurality of miRNAs in a second biological sample, comprising:

obtaining a biological sample from said subject at a second time point;

creating a double-stranded, complementary DNA sequence (cDNA) for each of one or more miRNA selected from Group A circaMiRs and Group B circaMiRs; and detecting the presence, absence or relative quantity of cDNAs, wherein the presence, absence or relative quantity of cDNA in said biological sample from said second time point is indicative of the presence, absence or relative quantity of the complementary miRNAs at the second time point; and optionally tracking the progression of a disorder, disease or injury by comparing results from the first time point to results from the second time point.

The subject could be a subject having TBI, mTBI or a post-concussion syndrome (PCS).

Another objective of the inventors was to provide a method for detecting an alteration in a temporal rhythm comprising:

detecting at least one abnormal or altered pattern of miRNA levels in saliva or serum compared to a control value from one or more normal subjects, and selecting a subject having at least one abnormal or altered pattern of amounts of miRNA; and, optionally, selecting a subject having TBI, mTBI, or PCS-related symptoms associated with an altered temporary rhythm, and optionally, administering a treatment that reduces or resynchronizes the at least one abnormal or altered pattern of amounts of the miRNA.

The abnormal or altered pattern in an amount of one or more miRNAs is detected in one embodiment.

In various embodiments of the invention, a biological sample could be saliva, cerebral spinal fluid, blood, serum, plasma, urine, feces, mucosal excretions, tears or tissue.

Nonlimiting embodiments of this technology include the following:

1. A method for detecting or diagnosing a concussion, mild traumatic brain injury ("mTBI") or other traumatic brain injury ("TBI") comprising:

(a) determining a concentration level(s) of one or more micro RNAs ("miRNAs") in a saliva sample taken from a human subject, and (b) comparing the determined concentration level(s) of the one or more miRNAs against normal level(s) of the same one or more miRNAs, wherein the normal (or control) level is that found in a subject, an average from two, three, four, five, six, seven, eight, nine, tenor or more subjects, not having a concussion, mild traumatic brain injury; or concentration level(s) determined in the subject prior to an event that could produce a concussion, mTBI or TBI, and (c) selecting a subject having an abnormal level of said one or more miRNAs as having, or as being at higher risk for having, a concussion, mild traumatic brain injury ("mTBI") or other traumatic brain injury ("TBI");

wherein the one or more miRNAs is selected from the group consisting hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs; and/or are selected from the group consisting of at least one of miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p; and those miRNA which share the seed sequences as the above listed miRNAs. Events that may precede a TBI include sports-related falls and injuries such as those resulting from high-speed collisions in football, flag football, soccer, rugby ice hockey, lacrosse, basketball, and other contact sports, tennis, golf, baseball, cricket, field and track, gymnastics, boxing, judo, karate, tae kwan do and other martial arts, equine sports, rodeo sports, diving including high diving and skin diving, skydiving, climbing, cycling, cheerleading, vehicular sports, and other sports; as well as vehicular accidents, and work-related impacts, falls and injuries. Other events such as impacts such as gunshots, blasts or explosions, exposure to ultrasonic or sonic energy, shaking (such as violent shaking of an infant) or physical battery, such as with fists, feet, or heavy, dense or blunt object, may precede a TBI.

2. The method of embodiment 1, wherein said miRNA expression levels are normalized to an expression level, or average expression level, of 1, 2, 3, 4, 5, 6, 7, 8, 9, 10 or more housekeeping genes whose RNA expression level is substantially invariant; and/or wherein said miRNA levels are normalized to compensate for diurnal or circadian fluctuations in the expression of the one or more miRNA levels, normalized to compensate for fluctuations in the expression of the one or more miRNA levels due to food intake, or exercise that raises the heart rate; or adjusted to compensate for differences in age, sex or genetic background. Housekeeping genes include those useful for calibration of RNA sequencing data such as those described by Eisenberg, et al., Trends in Genetics 29(10: 569-574, Cell Press (2013; incorporated herein by reference)

3. The method of embodiment 1 or 2, wherein (a) determining a concentration of one or more miRNAs is done by RNA sequencing ("RNA-seq"), qPCR, a miRNA array, or multiplex miRNA profiling. Such methods are known in the art and are also described at Hyper Text Transfer Protocol (HTTP)://WorldWideWeb.abcam.com/kits/review-of-mirna-assay-methods-qper-arrays-and-sequencing (last accessed Mar. 19, 2018, incorporated by reference).

4. The method of embodiment 1, 2 or 3, wherein the saliva sample is taken from a human subject suspected of having a mTBI and wherein the miRNAs are selected from the group consisting of at least one of miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p; and those miRNA which share the seed sequences as the above listed miRNAs.

5. The method of embodiment 1, 2, 3 or 4, wherein the saliva sample is taken from a human subject suspected of having a concussion and wherein the miRNAs are selected from the group consisting of at least one of miR-29c-3p, miR-26b-5p, miR-30e-5p, miR-182-5p, miR-320c, and miR-221-3p; and those miRNA which share the seed sequences as the above listed miRNAs.

6. The method of embodiment of any one of embodiments 1-5, wherein the saliva sample is taken from the human subject at a particular time of day and the concentration level(s) of miRNAs in said sample are compared to normal miRNA values in saliva taken at the same time of day under otherwise identical conditions.

7. The method of any one of embodiments 1-5, wherein the saliva sample is taken from the human subject at a different time of day than the time of day at which the normal level(s) of miRNAs were determined, further comprising adjusting or normalizing the value of the miRNA level(s) determined in the saliva sample to compensate for diurnal or circadian fluctuations in miRNA level(s).

8. The method of any one of embodiments 1-5, wherein the saliva sample is taken from the human subject at a different time of day than the time of day at which the normal level(s) of miRNAs were determined, further comprising adjusting or normalizing the value of the miRNA level(s) determined in the saliva sample to compensate for diurnal or circadian fluctuations in miRNA level(s) using a regression model or other statistical analysis; or to compensate for age, sex, or genetic background.

9. The method of any one of embodiments 1-8, wherein the saliva sample is taken within 1 hour of waking, before brushing or rinsing the mouth, before eating or drinking, and/or before exercise that elevates heart rate.

10. The method of any one of embodiments 1-9, wherein said selecting comprises selecting a subject having abnormal levels of four or more of said miRNAs, and, optionally calculating a Pearson correlation coefficient of said abnormal miRNA levels with at least one symptom of a concussion, mTBI or TBI.

11. The method of any one of embodiments 1-9, wherein said selecting comprises selecting a subject having abnormal levels of ten or more of said miRNAs, and, optionally calculating a Pearson correlation coefficient of said abnormal miRNA levels with at least one symptom of a concussion, mTBI or TBI.

12. The method of any one of embodiments 1-11, further comprising determining an expression level of RNA(s) from one or more salivary microbes selected from the group consisting of *Falconid herpesvirus*, *Prevotella melaninogenica* ATCC 25845, *Haemophilus parainfluenzae* T3T1, *Veillonella parvula* DSM 2008, *Macrococcus caseolyticus* JSCC5402, *Fusobaterium nucleatum* subsp. *nucleatum* 25586, *Haemophilus*, *Fusobacterium nucleatum* subsp. *vincentii*, Mason-Pfizer monkey virus, *Camplyobacer hominis* ATCC, and *Prevotella*; or a microbe having RNA that is at least 90, 95, 96, 97, 98, 99, 99.5 or 100% similar or identical thereto; and comparing the expression level(s) of the microbial RNAs against normal level(s) of the same one or more microbial RNAs, wherein the normal (or control) expression level is that found in a subject, an average from two of more subjects, not having a TBI; or concentration level(s) determined in the subject prior to appearance of one or more symptoms of a TBI; and further selecting a subject having an abnormal expression level of said one or more microbial RNAs as having or as being at higher risk for having said TBI.

BLASTN may be used to identify a polynucleotide sequence having at least 70%, 75%, 80%, 85%, 87.5%, 90%, 92.5%, 95%, 97.5%, 98%, 99% sequence identity to a reference polynucleotide or a known genomic sequence. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered/masked. Default settings are described by and incorporated by reference to http://blast.ncbi.nlm.nih.gov/Blast.cgi?PROGRAM=blastn& BLAST_PROGRAMS=megaBla st&PAGE_TYPE=Blast-Search&SHOW_DEFAULTS=on&LINK_LOC=blasthome (last accessed Mar. 19, 2018) (incorporated herein by reference).

13. The method of any one of embodiments 1-12, wherein determining salivary miRNA levels is done by RNA sequencing (RNA-seq).

14. The method of embodiment 13, wherein the sequencing data raw read counts are quantile-normalized, mean-centered, and divided by the standard deviation of each variable; data are normalized to account for inter-sample count variations; and/or wherein data are normalized to expression of one or more invariant miRNAs to describe relative and/or absolute expression levels; and optionally further statistically analyzing the normalized data.

15. The method of any one of embodiments 1-14, further comprising treating a subject having at least one abnormal level of miRNA and/or abnormal microbial expression level with a regimen that reduces the at least one abnormal salivary level of one or more miRNAs.

16. The method of embodiment 15, further comprising obtaining saliva samples on at least two different points in time from the subject and determining efficacy of a treatment regimen when said second or subsequent saliva sample has miRNA level(s).

17. The method of any one of embodiments 1-15, further comprising treating a subject selected as having or as being at higher risk for having a concussion, mild traumatic brain injury ("mTBI") with a regimen that reduces at least one abnormal salivary level of one or more miRNAs, wherein said regimen comprises administering one or more of surgical therapy, drug therapy, a miRNA or miRNA antagonist therapy, diet or nutritional therapy, physical therapy, phototherapy, psychotherapy, behavior therapy, or an alternative medical therapy.

18. An miRNA assay kit for detecting miRNAs comprising one, two or more probes or primers complementary to or otherwise suitable for amplification and/or detection of miRNAs selected from the group consisting hsa-let-7f-5p, hsa-let-7i, hsa-miR-10a-5p, hsa-miR-10b-5p, hsa-miR-23a-3p, hsa-mir-23b, hsa-mir-25, hsa-miR-25-3p, hsa-mir-26a-1, hsa-mir-26a-2, hsa-miR-26a-5p, hsa-mir-26b, hsa-miR-26b-5p, hsa-mir-28, hsa-miR-28-3p, hsa-miR-28-5p, hsa-miR-29c-3p, hsa-mir-30b, hsa-miR-30e-3p, hsa-miR-30e-5p, hsa-mir-92a-1, hsa-mir-92a-2, hsa-mir-103a-1, hsa-mir-103a-2, hsa-miR-125b-1-3p, hsa-miR-125b-2-3p, hsa-miR-141-3p, hsa-miR-148b-3p, hsa-mir-151a, hsa-miR-151a-3p, hsa-miR-151a-5p, hsa-miR-155-5p, hsa-mir-181a-2, hsa-miR-181a-5p, hsa-miR-182-5p, hsa-miR-193a-3p, hsa-miR-203a-3p, hsa-miR-205-5p, hsa-mir-218-2, hsa-miR-221-3p, hsa-miR-320c, hsa-miR-338-3p, hsa-miR-338-5p, hsa-miR-342-5p, hsa-miR-374a-5p, hsa-miR-378d, hsa-miR-378f, hsa-miR-378g, hsa-miR-378i, hsa-miR-454-3p, hsa-miR-501-3p, hsa-miR-532-5p, hsa-miR-577, hsa-miR-625-3p, hsa-miR-744-5p, hsa-miR-944, hsa-miR-1273g-5p, hsa-miR-1285-3p, hsa-miR-1303, hsa-miR-1307-3p, hsa-miR-3074-5p, hsa-mir-3160-1, hsa-mir-3613, hsa-miR-3613-5p, hsa-miR-3916, hsa-mir-4532, hsa-mir-5091, hsa-miR-6770-5p and those miRNA which share the seed sequences as the above listed miRNAs; and/or wherein said assay kit detects at least one of miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p; and those miRNA which share the seed sequences as the above listed miRNAs;

reagents for amplification and/or detection of said miRNAs, and optionally a reaction substrate, platform, apparatus, array, packaging materials and/or instructions for use.

19. The assay kit of embodiment 18 for diagnosis or detection of a mTBI, wherein said assay kit detects at least one of miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p; and those miRNA which share the seed sequences as the above listed miRNAs.

20. The assay kit of embodiment 18 for diagnosis or detection of a concussion, wherein said assay kit detects levels of miR-29c-3p, miR-26b-5p, miR-30e-5p, miR-182-5p, miR-320c, and miR-221-3p; and those miRNA which share the seed sequences as the above listed miRNAs.

21. A method for identifying a miRNA, a concentration of which in human saliva, fluctuates according to a diurnal or circadian rhythm, comprising:
(a) collecting saliva samples from one or more subjects at 2, 3, 4, 5, 6, 7, 8, 9, 10, 11, 12 or more times or intervals during a 24 hour period,
(b) sequencing miRNA in said samples,
(c) identifying differently expressed miRNAs by counting sequencing reads per miRNA, normalizing sequence read data, and comparing normalized sequence read counts among saliva samples taken at different times,
(d) normalizing sequence read data to RNA expression of a housekeeping gene or miRNA (which exhibits invariant expression over a 24 hour period), or to an averaged RNA expression from two or more housekeeping genes,
(e) performing a multivariate regression analysis or other statistical analysis on the normalized RNA expression data from different time points or intervals,
(f) optionally, calculating a Pearson correlation coefficient for data obtained describing concentration levels of one or more miRNAs found in saliva,
(g) selecting one or more miRNAs as having an expression level that fluctuates according to a diurnal or circadian rhythm; and (h) optionally, determining target genes for miRNAs using DIANA miRpath or other software.

Having generally described this invention, a further understanding can be obtained by reference to certain specific examples which are provided herein for purposes of illustration only, and are not intended to be limiting unless otherwise specified.

Example 1

Pediatric Concussion

To assess the utility of circulating concentrations of miRNA as accurate and physiologically relevant markers of pediatric concussion, the inventors have compared changes in salivary miRNA and cerebrospinal fluid (CSF) miRNA following childhood TBI. Abbreviations: Area under the curve (AUC); Central nervous system (CNS); cerebrospinal fluid (CSF); extra-ventricular drain (EVD); Glasgow coma score (GCS); micro-ribonucleic acid (miRNA); mild traumatic brain injury (mTBI); receiver operating characteristic (ROC); severe traumatic brain injury (sTBI).

Study Design.

A case-cohort design was used to compare longitudinal miRNA concentrations in CSF of seven children with severe TBI with three controls without TBI. The miRNAs "altered" in CSF were interrogated in saliva of 60 children with mild TBI and compared with 18 age- and gender-matched controls. The miRNAs with parallel changes (Wilcoxon rank sum test) in CSF and saliva were interrogated for predictive accuracy of TBI status using a multivariate regression technique. Correlations between miRNAs of interest and clinical features were investigated with Spearman rank correlation. Functional analysis with DIANA mirPath software identified related mRNA targets/pathways.

Results.

As shown herein salivary miRNA is an easily measured, physiologically relevant, and accurate biomarker for identifying pediatric TBI. There were 214 miRNAs detected in CSF and 135 (63%) were also present in saliva. Six miRNAs had parallel changes in both CSF and saliva (miR-182-5p, miR-221-3p, mir-26b-5p, miR-320c, miR-29c-3p, miR-30e-5p). These six miRNAs demonstrated an area under the curve of 0.852 for identifying mild TBI status in pediatric subjects. Three of the miRNAs (miR-182-5p, miR-29c-3p, miR-320c) exhibited longitudinal trends in CSF and/or saliva following TBI and all three targeted mRNAs related to neuronal development. Concentrations of miR-320c were directly correlated with both child (R=0.36, FDR=0.02) and parent (R=0.37, FDR=0.003) reports of attention difficulty on the Sports Concussion Assessment Tool-3.

sTBI Recruitment and Sample Collection.

CSF samples previously collected for a study of $F_2$-isoprostane levels in children and adolescents with sTBI (Varma et al., 2003) were utilized for a longitudinal characterization of CSF miRNA. Briefly, ventricular CSF samples collected from 8 children with sTBI were selected at random for the current study. To remove sample selection bias, researchers were blind to participant characteristics prior to sample selection. The selected cohort included children ages 4-17 years with a Glasgow coma score (GCS) <8 with a clinically-indicated extra-ventricular drain (EVD) for increased intracranial pressure following sTBI. Mechanisms of injury included fall and motor vehicle collision. CSF was passively extracted from each subject's EVD in a sterile fashion at three times following injury: day 1, day 4-7, and day 8-17. Age, sex, mechanism of injury, and times of collection were recorded for each subject (Table 1). Control CSF included 12 samples from three subjects (ages 1-8 years) undergoing clinically indicated spinal tap for epilepsy, or as part of a rule-out-sepsis protocol.

TABLE 1

Subject characteristics for sTBI and CSF controls

| Subject | Age (years) | Gender | Mechanism of injury | Day and time of collection 1 | Day and time of collection 2 | Day and time of collection 3 |
|---|---|---|---|---|---|---|
| sTBI-1 | 4 | F | bike vs car | Day 1, 0800 (6 hrs after EVD, 12 hrs after injury) | Day 5, 0900 | Day 10, 1000 |
| sTBI-2 | 16 | M | MVA | Day 1, 1500 (1 hr after EVD, 21 hrs after injury) | Day 5, 0900 | Day 10, 1000 |
| sTBI-3 | 9 | M | MVA | Day 1, 0800 (6 hr after EVD, 9 hrs after injury) | Day 5, 1000 | Day 10, 1100 |
| sTBI-4 | 14 | F | ped vs car | Day 1, 2300 | Day 5, 2000 | Day 8, 0930 |
| sTBI-5 | 17 | F | MVA vs tree | Day 1, 2000 (2 hrs after EVD, 17 hrs after injury) | Day 4, 1500 | Day 9, 1100 |
| sTBI-6 | 17 | M | MVA vs tree | Day 1, 1400 | Day 5, 1045 | Day 9, 0920 |
| sTBI-7 | 8 | F | hit by fallen tree branch | Day 1, 0945 | Day 5, 0915 | Day 10, 1600 |
| sTBI-8 | 14 | F | ped vs car | Day 1, 1000 | Day 7, 0900 | Day 17, 0920 |
| CTRL-1 | 8 | F | status epilepticus - known sz disorder | hospital day 1 | | |
| CTRL-2 | 4 | M | status epilepticus - new onset | hospital day 0 | | |
| CTRL-3 | 0 | M | hypoxia, strep pneumococcal meningitis, HIE | hospital day 17 | | | mTBI Recruitment and Sample Collection

Salivary miRNA profiles obtained as part of the current study were investigated in subjects (age 5-21 years) with or without a clinical diagnosis of mTBI. The mTBI cohort included 61 children and adolescents presenting to a Medical Center for evaluation of mTBI within 14 days of initial injury. The 14 day cut-off was chosen based upon previous investigations that suggested most clinical symptoms and biomarker profiles return to baseline within two weeks of concussion (Yokobori et al., 2013). Exclusion criteria for the mTBI group included GCS<12, clinical diagnosis of severe TBI, penetrating head injury, skull fracture, intracranial bleed, or symptoms attributable to underlying psychologic disorder (e.g. depression or anxiety). The control cohort included 19 children and adolescents presenting to a Pediatrics Clinic for a regularly scheduled well child visit. Exclusion criteria for this group included a history of previous concussion, ongoing rheumatologic condition, or recent orthopedic injury. Subjects with periodontal disease, upper respiratory infection, seizure disorder, intellectual disability, history of migraine headaches, or drug/alcohol use disorder were excluded from both groups. Saliva samples were collected from each participant at the time of enrollment in a non-fasting state following an oral tap-water rinse through expectoration into an Oragene RE-100 saliva collection kit (DNA Genotek; Ottawa, Canada). Samples were shaken by hand 5-10 times and stored at room temperature for up to ten days prior to transfer into a 4° C. refrigerator. Medical and demographic information was collected from both mTBI and control participants, including: age, sex, race/ethnicity, height, weight, dietary restrictions, medical history, selective serotonin reuptake inhibitor use, allergies, medications, and oropharyngeal status (Table 2A-B). The mTBI cohort also reported history of previous concussions, details of current concussion (days since injury, mechanism, associated emesis, weakness, amnesia, fractures, or loss of consciousness), and time of last analgesic use (non-steroidal anti-inflammatory or acetaminophen). Finally, mTBI subjects and their parent/guardian completed an inventory of concussive symptoms using the child sport concussion assessment tool (SCAT-3).

tions as previously reported (Xia et al., 2016). Final RNA concentrations were quantified with a Nanodrop Spectrophotmeter and extracted RNA was stored at −80° C. prior to sequencing. RNA yield and quality were assessed with the Agilent 2100 Bioanalyzer before library construction. Sequencing of salivary RNA occurred using a NEXTflex® Small RNA-Seq Kit v3 (Bioo Scientific; Austin, Tex.), an Illumina HiSeq® 2500 Instrument, and a targeted depth of three million reads per sample. CSF RNA samples were sequenced at the SUNY Molecular Analysis Core at Upstate Medical University using an Illumina TruSeq Small RNA Sample Prep protocol (Illumina; San Diego, Calif.), an Illumina MiSeq instrument, and a targeted depth of three million reads per sample. Reads were aligned to the hg38 build of the human genome in Partek Flow (Partek; St. Louis, Mo.) using the SHRiMP2 aligner. Total miRNA counts within each sample were quantified with miRBase mature-microRNA v21. Saliva samples with less than $5 \times 10^3$ total counts were excluded from the final analysis, resulting in 60 mTBI and 18 control saliva samples. Only miRNAs with raw read counts greater than 10 in at least 25% of samples were evaluated in the differential expression analysis for CSF and saliva respectively. The miRNAs present in 25% of sTBI CSF samples and absent from all control CSF samples were also investigated as "up-regulated" miRNAs. Prior to statistical analysis read counts were sum-normalized, mean-centered, and divided by the standard deviation of each variable. The term "reads" or "read-counts" should be understood to apply to any method for adjusting miRNA or microbiome expression data to account for variations between samples, such as using the expression levels of certain control miRNAs or metabolites that are always present at a predictable level in saliva to normalize the levels of all miRNAs in the samples so they can be compared more accurately.

TABLE 2A

Subject characteristics for mTBI and saliva control groups

| | Age (Years) | Sex (% F) | Ethnic White (%) | Height (percentile) | Weight (percentile) | Diet Restriction (%) | SSRI Use (%) | Food/Med Allergies (%) | Dental carries (%) | Zofran Use (%) | NSAID Use (%) |
|---|---|---|---|---|---|---|---|---|---|---|---|
| TBI (n = 60) | 14 ± 3 | 49 | 88 | 59 ± 28 | 67 ± 27 | 6.6 | 16 | 20 | 3.2 | 3.3 | 31 |
| CTRL (n = 18) | 14 ± 3 | 35 | 85 | 38 ± 21 | 64 ± 21 | 0.05 | 0.15 | 0.25 | 0.05 | 0 | 0.05 |
| P-value | 0.481 | 0.272 | 0.703 | 0.002 | 0.610 | 0.794 | 0.884 | 0.637 | 0.757 | 0.159 | 0.001 |

Percentage (%) of participants with medical or demographic characteristic are reported for each variable, with the exception of age (years), height/weight (percentiles), collection time (military hours), and child/parent SCAT3 score (total raw score).
Abbreviations: mild traumatic brain injury (mTBI); selective serotonin re-uptake inhibitor (SSRI); Med (medicine); non-steroidal anti-inflammatory (NSAID); loss of consciousness (LOC); sport concussion assessment tool-3 (SCAT-3).

TABLE 2B

Subject characteristics for mTBI and saliva control groups

| | Acetaminophen Use (%) | Collection Time | Days Since Injury | Sport (%) | LOC (%) | Memory Loss (%) | Emesis (%) | Weakness (%) | Broken Bone (%) | Previous Concussion (%) | Child SCAT-3 Score | Parental SCAT3 score |
|---|---|---|---|---|---|---|---|---|---|---|---|---|
| TBI (n = 60) | 13 | 1300 ± 0330 | 6.5 | 38 | 25 | 44 | 21 | 31 | 8.2 | 43 | 23.7 | 21.8 |
| CTRL (n = 18) | 0 | 1330 ± 0300 | | | | | | | | | | |
| P-value | 0.004 | 0.429 | | | | | | | | | | |

RNA Processing and Quantification

RNA was extracted from saliva and CSF samples using a Norgen Circulating and Exosomal RNA Purification Kit (Norgen Biotek, Ontario, Canada) per manufacturer instruc- In an alternative embodiment, fluorescence methods may be used to determine miRNA and/or microbiome levels. In an example, ligands may be anchored in groups on a substrate. The target miRNA and microbiome sequences may be tagged with a fluorescent tag (or non-fluorescent dye) either before or after it binds to the ligand. In this application, relative intensity at each ligand group may be a measure of quantity of miRNA and/or microbiome present. This method may be implemented on a chip-type assay. One skilled in the art will recognize that other suitable chip-type-assays may be used to determine miRNA and/or microbiome levels. In yet another embodiment, isothermal amplification may be used to detect miRNA levels.

Figures 5A, 5B:
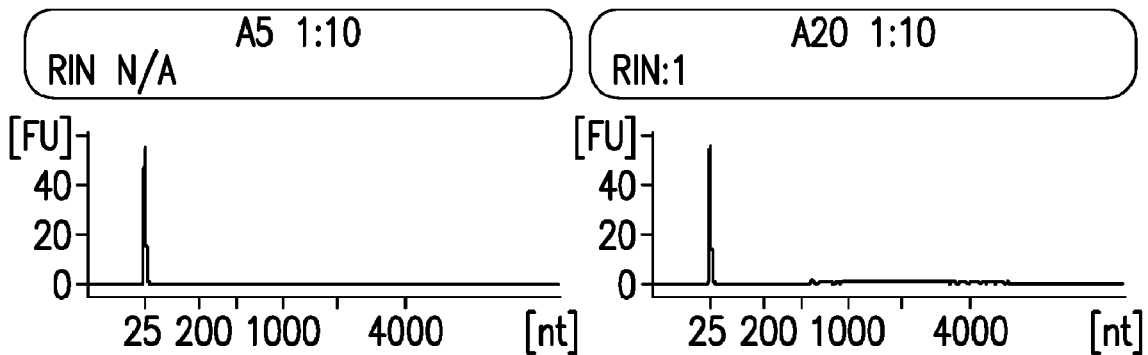
FIGS. 5A-F show quality analysis of cerebrospinal fluid RNA. Examination of extracted RNA using an Agilent Bioanalyzer RNA Nanochip demonstrated relatively low RNA yields in cerebrospinal fluid samples, but consistent peaks at 18-25 nucleotides (consistent with successful miRNA extraction).
Figures 5C, 5D:
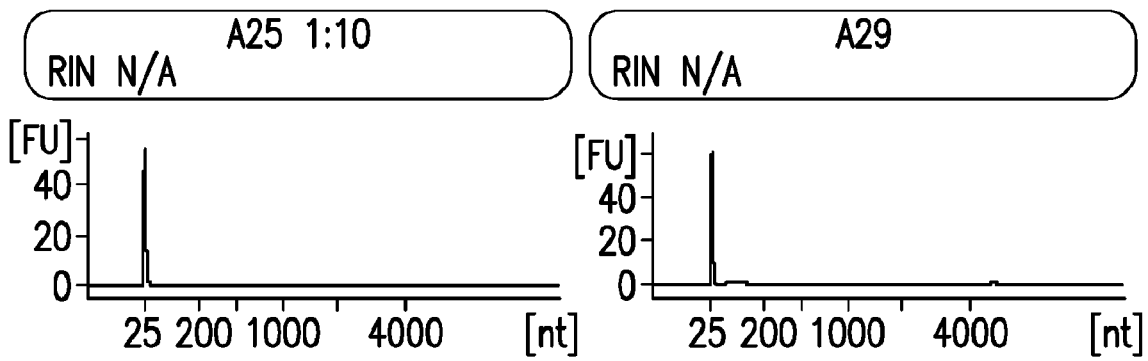
Figures 5E, 5F:
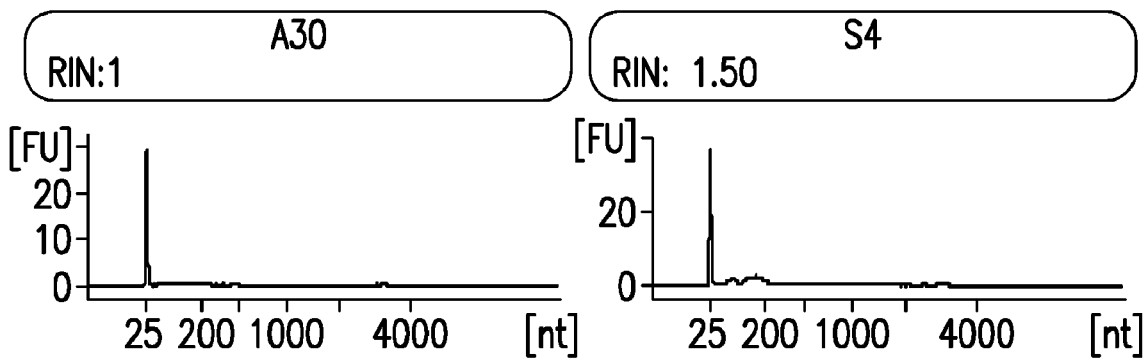

FIG. 5 shows quality analysis of cerebrospinal fluid RNA. Examination of extracted RNA using an Agilent Bioanalyzer RNA Nanochip demonstrated relatively low RNA yields in cerebrospinal fluid samples, but consistent peaks at 18-25 nucleotides (consistent with successful miRNA extraction).

Statistical Analysis.

The miRNAs with the greatest physiologic relevance as concussion biomarkers were identified using a three-step procedure: 1) The miRNAs present only in sTBI CSF samples, or miRNAs with "altered" concentrations in sTBI CSF (measured as reads per million; RPM) were identified with a non-parametric Wilcoxon rank sum test with Benjamini Hochberg false detection rate (FDR) correction; 2) Concentrations (RPM) of these miRNA targets were investigated in mTBI saliva samples (compared to control saliva) using a Wilcoxon rank sum test; 3) The miRNAs "altered" in both CSF and saliva TBI samples were examined for parallel up- or down-regulation relative to controls (FIG. 1). The miRNAs of interest were inspected for longitudinal trends in both CSF and saliva concussion samples using a Spearman's rank correlation metric (correlating miRNA concentrations with days since injury). The diagnostic accuracy of these biomarker prospects was assessed with a multivariate logistic regression analysis and results were visualized with a receiver operating characteristic (ROC) curve. To avoid "over-modeling" of the dataset and ensure that the miRNA biomarkers accurately differentiated control and mTBI subjects a secondary approach was employed involving a 100-fold Monte-Carlo Cross Validation (MCCV) technique alongside a ¼ sample hold-out procedure in Metaboanalyst software (Xia et al., 2016). Relationships between medical/demographic characteristics and salivary miRNAs of interest were examined with Spearman's rank correlations. Analysis of medical and demographic data across mTBI and control groups was accomplished with a two-tailed student's t-test.

Functional Analysis.

The miRNA biomarkers of mTBI underwent functional annotation analysis in DIANA mirPath v3 online software (Hypertext Transfer Protocol (HTTP)://snf-515788.vm.okeanos.grnet.gr/) using the microT-CDS algorithm to identify species-specific mRNA targets (Vlachos et al., 2015) DIANA® mirPath identified gene ontology (GO) categories with significant (FDR<0.05) target enrichment using a Fisher's Exact Test. A list of high confidence mRNA targets (microT-CDS score≥0.99) was interrogated for protein-protein interaction networks using moderate stringency settings (interaction score>0.40) in String v10 software (Hypertext Transfer Protocol (HTTP)://string-db.org) (Szklarczyk et al., 2015).

Accounting for Temporal Variations in miRNA Biomarkers.

In an embodiment, because epigenetic data (e.g., epigenetic sequencing data) may include temporal variations (e.g. the data may vary in a sinusoidal or circadian cycle), the epigenetic data may be normalized based on a time of day before analysis is performed to determine if a subject has experienced a traumatic brain injury, detect the severity or prognosis of the injury, or detect if a change in disease state due to traumatic brain injury has occurred. In an example, miRNA quantities/levels may be normalized based on the time of day to account for naturally occurring changes in miRNA quantities/levels in a human/subject. The time-of-day normalized miRNA quantities may be compared to a control/healthy reference subject or a compendium of control/healthy subjects to determine if the human/subject has traumatic brain injury or a change in their disease state. Further discussion of systems and methods for normalizing epigenetic data can be found in U.S. provisional patent application No. 62/475,705, filed Mar. 23, 2017, incorporated herein by reference in its entirety.

Medical and Demographic Characteristics.

There was no significant difference in participant age (p=0.48), sex (p=0.27), or race/ethnicity (% white; p=0.70) between the mTBI and control groups (Table 2). There was no difference in the percentage of participants with food/medicine allergies (p=0.63), dietary restrictions (p=0.79), or anti-depressant medications (p=0.88). The mTBI group was significantly taller (p=0.002) and had utilized non-steroidal anti-inflammatory medications (p=0.001), and acetaminophen (p=0.003) with a higher frequency in the six hours prior to saliva collection. The mean time of collection for mTBI and control groups was 13:00 and 13:30 respectively (p=0.43). Salivary collection for mTBI participants occurred, on average, 6.5 days post-concussion. The most common mechanisms of injury for this group included sport-related injury (59%), motor vehicle accident (18%), and fall (16%). Post-concussive symptoms within the mTBI group included loss of consciousness (25%), emesis (21%), weakness (31%), and memory loss (44%). The mean SCAT3 score for mTBI participants was 23.7 on child report and 21.8 on parental report, consisting of an average of 11 symptoms per participant. Symptoms lasted beyond four weeks in 66% of mTBI participants and 43% reported a previous history of concussion.

CSF miRNA in Severe TBI (sTBI).

There was more robust miRNA expression in CSF following sTBI (mean aligned miRNA reads per sample=565,805) than in control CSF (22,885 aligned reads per sample). Of the 2813 mature human miRNAs interrogated, 214 (7.6%) were present in CSF samples (Table 3). One-hundred and fourteen those miRNAs had nominal differences in expression (p<0.05) and 86 had significant changes (FDR<0.05) between sTBI and control groups. Seventy-two were down-regulated and 42 were up-regulated in sTBI.

TABLE 3

| miRNAs with differences in CSF sTBI samples | | | | | |
|---|---|---|---|---|---|
| CSF miRNA | p.value | −LOG10(p) | FDR | Fold Change | log2(FC) |
| hsa-miR-10a-5p | 6.52E−07 | 6.1858 | 9.54E−05 | 5.1928 | 2.3765 |
| hsa-miR-10b-5p | 8.92E−07 | 6.0498 | 9.54E−05 | 6.4554 | 2.6905 |
| hsa-miR-1285-3p | 3.37E−05 | 4.4722 | 0.002405 | 5.16E−40 | −130.51 |
| hsa-miR-203a-3p | 5.75E−05 | 4.2404 | 0.0024381 | 3.3894 | 1.761 |

TABLE 3-continued miRNAs with differences in CSF sTBI samples

| CSF miRNA | p.value | −LOG10(p) | FDR | Fold Change | log2(FC) |
|---|---|---|---|---|---|
| hsa-miR-338-3p | 5.99E−05 | 4.2227 | 0.0024381 | 0.071836 | −3.7991 |
| hsa-miR-181a-5p | 7.00E−05 | 4.1549 | 0.0024381 | 0.10308 | −3.2782 |
| hsa-miR-6770-5p | 0.00010494 | 3.9791 | 0.0024381 | 0.058771 | −4.0888 |
| hsa-miR-141-3p | 0.00012283 | 3.9107 | 0.0024381 | 1.9856 | 0.98957 |
| hsa-miR-205-5p | 0.00012354 | 3.9082 | 0.0024381 | 2.9357 | 1.5537 |
| hsa-miR-3916 | 0.00013324 | 3.8754 | 0.0024381 | 21.274 | 4.4111 |
| hsa-miR-1273g-5p | 0.00014811 | 3.8294 | 0.0024381 | 2.53E−40 | −131.54 |
| hsa-miR-342-5p | 0.00014811 | 3.8294 | 0.0024381 | 5.52E−40 | −130.41 |
| hsa-miR-577 | 0.00014811 | 3.8294 | 0.0024381 | 3.38E−40 | −131.12 |
| hsa-msR-1303 | 0.0002384 | 3.6227 | 0.0036442 | 0.045508 | −4.4577 |
| hsa-miR-125b-1-3p | 0.0002862 | 3.5433 | 0.0037022 | 0.15485 | −2.6911 |
| hsa-miR-1285-5p | 0.0002941 | 3.5315 | 0.0037022 | 7.82E−40 | −129.91 |
| hsa-miR-181c-3p | 0.0002941 | 3.5315 | 0.0037022 | 1.02E−39 | −129.52 |
| hsa-miR-338-5p | 0.00056473 | 3.2482 | 0.0063606 | 1.06E−39 | −129.48 |
| hsa-miR-589-5p | 0.00056473 | 3.2482 | 0.0063606 | 1.36E−39 | −129.11 |
| hsa-miR-223- 3p | 0.00061854 | 3.2086 | 0.0066184 | 2.1116 | 1.0784 |
| hsa-miR-3613-5p | 0.00081222 | 3.0903 | 0.0077525 | 0.76991 | −0.37723 |
| hsa-miR-130a-3p | 0.00089823 | 3.0466 | 0.0077525 | 3.4136 | 1.7713 |
| hsa-miR-665 | 0.00096479 | 3.0156 | 0.0077525 | 0.09145 | −3.4509 |
| hsa-miR-375 | 0.001041 | 2.9826 | 0.0077525 | 1.615 | 6.6915 |
| hsa-miR-1277-5p | 0.0010506 | 2.9786 | 0.0077525 | 1.12E−39 | −129.39 |
| hsa-miR-128-3p | 0.0010506 | 2.9786 | 0.0077525 | 5.29E−40 | −1.3047 |
| hsa-miR-144-3p | 0.0010506 | 2.9786 | 0.0077525 | 6.37E−40 | −130.21 |
| hsa-miR-4448 | 0.0010506 | 2.9786 | 0.0077525 | 2.74E−40 | −131.42 |
| hsa-miR-584-5p | 0.0010506 | 2.9786 | 0.0077525 | 4.95E−40 | −130.57 |
| hsa-miR-200a-3p | 0.0016591 | 2.7801 | 0.011835 | 2.87 | 1.521 |
| hsa-miR-3960 | 0.0017997 | 2.7448 | 0.012071 | 0.27673 | −1.8535 |
| hsa-miR-574-5p | 0.0018067 | 2.7431 | 0.012071 | 0.1541 | −2.6981 |
| hsa-miR-7-5p | 0.0018919 | 2.7231 | 0.012071 | 0.21905 | −2.1907 |
| hsa-miR-767-5p | 0.0019179 | 2.7172 | 0.012071 | 0.11213 | −3.1568 |
| hsa-miR-7-5p | 0.0024064 | 2.6186 | 0.014713 | 0.23879 | −2.0662 |
| hsa-miR-451a | 0.0026281 | 2.5804 | 0.015623 | 0.12852 | −2.96 |
| hsa-miR-219a-2-3p | 0.0027851 | 2.5552 | 0.016108 | 0.14594 | −2.7765 |
| hsa-miR-1911-5p | 0.0029571 | 2.5291 | 0.016576 | 2.5802 | 1.3675 |
| hsa-miR-26b-5p | 0.0031193 | 2.5059 | 0.016576 | 1.7747 | 0.8276 |
| hsa-miR-873-3p | 0.0033028 | 2.4811 | 0.016576 | 0.084475 | −3.5653 |
| hsa-miR-124-3p | 0.0033306 | 2.4775 | 0.016576 | 8.85E−40 | −129.73 |
| hsa-miR-126-5p | 0.0033306 | 2.4775 | 0.016576 | 2.13E−39 | −128.46 |
| hsa-miR-410-3p | 0.0033306 | 2.4775 | 0.016576 | 3.03E−40 | −131.28 |
| hsa-miR-5096 | 0.0036312 | 2.44 | 0.017661 | 0.21784 | −2.1987 |
| hsa-miR-122-5p | 0.004738 | 2.3244 | 0.022532 | 0.039899 | −4.6475 |
| hsa-miR-4429 | 0.0051341 | 2.2895 | 0.023368 | 3.4447 | 1.7844 |
| hsa-miR-486-5p | 0.0051341 | 2.2895 | 0.023368 | 0.12653 | −2.9824 |
| hsa-miR-744-5p | 0.0053295 | 2.2733 | 0.023368 | 0.25385 | −1.978 |
| hsa-miR-106b-3p | 0.0055402 | 2.2565 | 0.023368 | 0.070712 | −3.8219 |
| hsa-miR-129-5p | 0.005697 | 2.2444 | 0.023368 | 1.17E−39 | −129.33 |
| hsa-miR-1304-3p | 0.005697 | 2.2444 | 0.023368 | 2.71E−39 | −128.12 |
| hsa-miR-3065-5p | 0.005697 | 2.2444 | 0.023368 | 5.98E−40 | −130.3 |
| hsa-miR-27a-3p | 0.0057873 | 2.2375 | 0.023368 | 1.1757 | 0.23352 |
| hsa-miR-6783-3p | 0.0059868 | 2.2228 | 0.023725 | 0.41087 | −1.2833 |
| hsa-miR-6748-3p | 0.0062726 | 2.2025 | 0.024406 | 3.4629 | 1.792 |
| hsa-miR-16-5p | 0.0067105 | 2.1732 | 0.025216 | 0.25394 | −1.9774 |
| hsa-miR-432-5p | 0.0067163 | 2.1729 | 0.025216 | 0.35408 | −1.4978 |
| hsa-miR-8071 | 0.0074571 | 2.1274 | 0.027514 | 0.63077 | −0.66481 |
| hsa-miR-1180-3p | 0.0080769 | 2.0928 | 0.029239 | 0.23054 | −2.1169 |
| hsa-miR-486-3p | 0.0081979 | 2.0863 | 0.029239 | 0.32621 | −1.6161 |
| hsa-miR-182-5p | 0.009174 | 2.0374 | 0.032184 | 1.8179 | 0.86224 |
| hsa-miR-409-3p | 0.0095109 | 2.0218 | 0.032307 | 1.54E−39 | −128.93 |
| hsa-miR-541-3p | 0.0095109 | 2.0218 | 0.032307 | 1.76E−39 | 128.74 |
| hsa-miR-6733-3p | 0.011372 | 1.9441 | 0.038026 | 0.10234 | −3.2886 |
| hsa-miR-4705 | 0.011904 | 1.9243 | 0.03919 | 0.2803 | −1.8349 |
| hsa-miR-532-5p | 0.012275 | 1.911 | 0.039766 | 1.0083 | 0.011975 |
| hsa-miR-412-5p | 0.01271 | 1.8959 | 0.039766 | 0.19602 | −2.3509 |
| hsa-miR-340-5p | 0.012822 | 1.8921 | 0.039766 | 0.30263 | −1.7272 |
| hsa-miR-93-5p | 0.012822 | 1.8921 | 0.039766 | 0.40851 | −1.2916 |
| hsa-miR-146b-5p | 0.014143 | 1.8495 | 0.042159 | 0.50565 | −0.98379 |
| hsa-miR-221-3p | 0.014148 | 1.8493 | 0.042159 | 3.1576 | 1.6588 |
| hsa-miR-1972 | 0.014184 | 1.8482 | 0.042159 | 0.20765 | −2.2678 |
| hsa-miR-144-5p | 0.015527 | 1.8089 | 0.043363 | 6.16E−39 | −126.93 |
| hsa-miR-219b-5p | 0.015527 | 1.8089 | 0.043363 | 5.86E−40 | −130.33 |
| hsa-miR-7706 | 0.015527 | 1.8089 | 0.043363 | 2.71E−39 | −128.12 |
| hsa-miR-96-5p | 0.015527 | 1.8089 | 0.043363 | 6.73E−39 | −126.8 |
| hsa-miR-6873-3p | 0.015602 | 1.8068 | 0.043363 | 0.83876 | −0.25367 |
| hsa-miR-361-5p | 0.016707 | 1.7771 | 0.045838 | 0.46959 | −1.0905 |
| hsa-miR-335-5p | 0.01723 | 1.7637 | 0.045913 | 0.35961 | −1.4755 |
| hsa-let-7f-5p | 0.017387 | 1.7598 | 0.045913 | 0.21264 | −2.2335 |

TABLE 3-continued miRNAs with differences in CSF sTBI samples

| CSF miRNA | p.value | −LOG10(p) | FDR | Fold Change | log2(FC) |
|---|---|---|---|---|---|
| hsa-miR-1307-3p | 0.017593 | 1.7547 | 0.045913 | 0.40168 | −1.3159 |
| hsa-miR-19b-3p | 0.017593 | 1.7547 | 0.045913 | 0.47771 | −1.0658 |
| hsa-miR-3184-3p | 0.018242 | 1.7389 | 0.047033 | 0.060624 | −4.044 |
| hsa-miR-29a-3p | 0.019036 | 1.7204 | 0.048496 | 0.52802 | −0.92134 |
| hsa-miR-345-5p | 0.019552 | 1.7088 | 0.048652 | 0.52497 | −0.9297 |
| hsa-miR-4677-3p | 0.019552 | 1.7088 | 0.048652 | 14.254 | 3.8333 |
| hsa-miR-132-3p | 0.024815 | 1.6053 | 0.060399 | 0.2951 | −1.7607 |
| hsa-miR-146b-3p | 0.024837 | 1.6049 | 0.060399 | 3.68E−39 | −127.68 |
| hsa-miR-421 | 0.02548 | 1.5938 | 0.060455 | 0.84395 | −0.24477 |
| hsa-miR-1298-5p | 0.025788 | 1.5886 | 0.060455 | 2.0441 | 1.0315 |
| hsa-miR-127-3p | 0.02599 | 1.5852 | 0.060455 | 0.072852 | −3.7789 |
| hsa-miR-363-3p | 0.02599 | 1.5852 | 0.060455 | 0.55816 | −0.84126 |
| hsa-miR-484 | 0.027511 | 1.5605 | 0.063304 | 0.54991 | −0.86274 |
| hsa-miR-152-3p | 0.02835 | 1.5475 | 0.064541 | 1.5836 | 0.66321 |
| hsa-miR-2110 | 0.030455 | 1.5163 | 0.06789 | 3.0082 | 1.5889 |
| hsa-miR-92b-5p | 0.030455 | 1.5163 | 0.06789 | 1.1704 | 0.22701 |
| hsa-miR-1273g-3p | 0.031121 | 1.507 | 0.068658 | 1.649 | 0.72155 |
| hsa-miR-29c-3p | 0.0316 | 1.5003 | 0.069004 | 0.61571 | −0.69969 |
| hsa-miR-181b-5p | 0.034112 | 1.4671 | 0.073738 | 0.32726 | −1.6115 |
| hsa-miR-21-5p | 0.037338 | 1.4278 | 0.078337 | 1.2524 | 0.32475 |
| hsa-miR-320c | 0.037338 | 1.4278 | 0.078337 | 2.1813 | 1.1252 |
| hsa-miR-98-5p | 0.037338 | 1.4278 | 0.078337 | 1.6364 | 0.71048 |
| hsa-miR-151a-5p | 0.039837 | 1.3997 | 0.082768 | 0.32282 | −1.6312 |
| hsa-miR-21-3p | 0.041764 | 1.3792 | 0.085865 | 1.8331 | 0.87431 |
| hsa-miR-203b-5p | 0.04213 | 1.3754 | 0.085865 | 0.44137 | −1.18 |
| hsa-miR-30e-5p | 0.044543 | 1.3512 | 0.089086 | 0.076321 | −3.7118 |
| hsa-miR-99a-5p | 0.044543 | 1.3512 | 0.089086 | 1.2338 | 0.30311 |
| hsa-miR-629-5p | 0.045461 | 1.3329 | 0.090281 | 0.76768 | −0.38142 |
| hsa-miR-6832-3p | 0.046461 | 1.3329 | 0.090281 | 0.57042 | −0.80991 |
| hsa-miR-3135b | 0.046967 | 1.3282 | 0.090281 | 0.58391 | −0.77618 |
| hsa-miR-106a-5p | 0.04725 | 1.3256 | 0.090281 | 0.41554 | −1.2669 |
| hsa-miR-17-5p | 0.04725 | 1.3256 | 0.090281 | 0.37989 | −1.3964 |
| hsa-miR-425-5p | 0.048501 | 1.3143 | 0.091851 | 0.55024 | −0.86186 |
| hsa-miR-3615 | 0.049701 | 1.3036 | 0.093299 | 1.1258 | 0.17092 |
| hsa-miR-195-5p | 0.051622 | 1.2872 | 0.094873 | 0.49573 | −1.0124 |
| hsa-miR-3925-5p | 0.051784 | 1.2858 | 0.094873 | 101.23 | 6.6615 |
| hsa-miR-502-3p | 0.05187 | 1.2851 | 0.094873 | 0.33042 | −1.5976 |
| hsa-miR-25-3p | 0.053426 | 1.2723 | 0.09689 | 0.28863 | −1.7927 |
| hsa-miR-424-3p | 0.060327 | 1.2195 | 0.10849 | 2.46E−38 | −124.94 |
| hsa-miR-552-3p | 0.06328 | 1.1987 | 0.11285 | 0.61224 | −0.70783 |
| hsa-miR-143-3p | 0.067595 | 1.1701 | 0.11955 | 1.5343 | 0.61761 |
| hsa-miR-1294 | 0.069522 | 1.1579 | 0.12096 | 1.7148 | 0.77803 |
| hsa-miR-9-3p | 0.069522 | 1.1579 | 0.12096 | 1.4491 | 0.53521 |
| hsa-let-7i-5p | 0.073184 | 1.1356 | 0.1243 | 0.73384 | −0.44646 |
| hsa-miR-151a-3p | 0.073184 | 1.1356 | 0.1243 | 0.62088 | −0.68761 |
| hsa-miR-30a-5p | 0.073184 | 1.1356 | 0.1243 | 1.8628 | 0.8975 |
| hsa-miR-769-5p | 0.076738 | 1.115 | 0.12931 | 0.19676 | −2.3455 |
| hsa-miR-155-5p | 0.08646 | 1.0632 | 0.14455 | 1.1656 | 0.2211 |
| hsa-miR-30a-3p | 0.089162 | 1.0498 | 0.14791 | 2.1602 | 1.1111 |
| hsa-miR-136-3p | 0.092106 | 1.0357 | 0.15056 | 1.62E−39 | −128.86 |
| hsa-miR-145a-5p | 0.092163 | 1.0354 | 0.15056 | 0.56217 | −0.83092 |
| hsa-miR-5724-5p | 0.093768 | 1.0279 | 0.15202 | 1.5162 | 0.60049 |
| hsa-miR-139-3p | 0.095367 | 1.0206 | 0.15345 | 0.25335 | −1.9808 |
| hsa-miR-204-5p | 0.099277 | 1.0032 | 0.15737 | 1.3541 | 0.43739 |
| hsa-miR-27b-3p | 0.099277 | 1.0032 | 0.15737 | 1.0944 | 0.13018 |
| hsa-miR-548e-3p | 0.10219 | 0.99059 | 0.1608 | 2.3851 | 1.254 |
| hsa-miR-361-3p | 0.112 | 0.95078 | 0.17495 | 0.69555 | −0.52376 |
| hsa-miR-30d-5p | 0.11477 | 0.94018 | 0.17669 | 1.5262 | 0.60993 |
| hsa-miR-378i | 0.11477 | 0.94018 | 0.17669 | 1.8604 | 0.89564 |
| hsa-miR-4750-3p | 0.12114 | 0.91672 | 0.18517 | 8.7284 | 3.1257 |
| hsa-miR-92b-3p | 0.12317 | 0.90949 | 0.18694 | 1.4228 | 0.50872 |
| hsa-miR-148b-3p | 0.13203 | 0.87931 | 0.19898 | 1.416 | 0.50184 |
| hsa-miR-222-3p | 0.13485 | 0.87016 | 0.2018 | 0.49059 | −1.0274 |
| hsa-miR-100-5p | 0.13913 | 0.85659 | 0.20676 | 0.37898 | −1.3998 |
| hsa-miR-941 | 0.14578 | 0.83629 | 0.21515 | 0.589 | −0.76365 |
| hsa-miR-34a-5p | 0.14779 | 0.83036 | 0.21515 | 1.1356 | 0.1835 |
| hsa-miR-598-3p | 0.14779 | 0.83036 | 0.21515 | 2.7866 | 1.4785 |
| hsa-miR-16-2-3p | 0.14963 | 0.82498 | 0.21636 | 0.20413 | −2.2924 |
| hsa-miR-130b-3p | 0.16663 | 0.77825 | 0.23932 | 0.90571 | −0.14288 |
| hsa-miR-30e-3p | 0.16981 | 0.77004 | 0.24226 | 0.63668 | −0.65136 |
| hsa-miR-423-3p | 0.17412 | 0.75914 | 0.24677 | 0.76313 | −0.38999 |
| hsa-let-7d-3p | 0.17942 | 0.74614 | 0.2526 | 1.717 | 0.7799 |
| hsa-let-7c-5p | 0.19549 | 0.70888 | 0.27343 | 0.95246 | −0.070269 |
| hsa-miR-342-3p | 0.2068 | 0.68444 | 0.28552 | 2.0395 | 1.0282 |
| hsa-miR-592 | 0.2068 | 0.68444 | 0.28552 | 2.3034 | 1.2037 |
| hsa-miR-374c-5p | 0.21736 | 0.66283 | 0.29817 | 0.64825 | −0.62538 |

TABLE 3-continued miRNAs with differences in CSF sTBI samples

| CSF miRNA | p.value | −LOG10(p) | FDR | Fold Change | log2(FC) |
|---|---|---|---|---|---|
| hsa-miR-191-5p | 0.24832 | 0.60499 | 0.33847 | 1.2604 | 0.33338 |
| hsa-miR-9-5p | 0.26615 | 0.57487 | 0.35049 | 0.97599 | −0.035065 |
| hsa-miR-3160-3p | 0.27661 | 0.55813 | 0.3696 | 26.269 | 4.7153 |
| hsa-miR-3160-5p | 0.27661 | 0.55813 | 0.3696 | 34.443 | 5.1061 |
| hsa-miR-183-5p | 0.27806 | 0.55585 | 0.3696 | 0.42158 | −1.2461 |
| hsa-miR-15a-5p | 0.29263 | 0.53368 | 0.38571 | 0.7619 | −0.39233 |
| hsa-miR-378a-3p | 0.29378 | 0.53197 | 0.38571 | 2.583 | 1.369 |
| hsa-miR-619-5p | 0.29962 | 0.52343 | 0.39097 | 0.33723 | −1.5682 |
| hsa-miR-199a-3p | 0.30365 | 0.51762 | 0.39146 | 2.5984 | 1.3776 |
| hsa-miR-199b-3p | 0.30365 | 0.51762 | 0.39146 | 2.5984 | 1.3776 |
| hsa-let-7a-5p | 0.31007 | 0.50854 | 0.39663 | 0.94331 | −0.0842 |
| hsa-miR-1298-3p | 0.31508 | 0.50158 | 0.39663 | 1.7221 | 0.78416 |
| hsa-miR-1911-3p | 0.31508 | 0.50158 | 0.39663 | 2.452 | 1.294 |
| hsa-miR-660-5p | 0.31508 | 0.50158 | 0.39663 | 1.116 | 0.15832 |
| hsa-miR-34b-5p | 0.32182 | 0.49238 | 0.40275 | 1.8649 | 0.89911 |
| hsa-miR-1307-5p | 0.32935 | 0.48234 | 0.40977 | 1.6395 | 0.71321 |
| hsa-miR-1253-5p | 0.33909 | 0.46968 | 0.41946 | 1.4998 | 0.58477 |
| hsa-miR-423-5p | 0.36233 | 0.44089 | 0.44529 | 1.0791 | 0.10989 |
| hsa-miR-19a-3p | 0.36414 | 0.43873 | 0.44529 | 3.7835 | 1.9197 |
| hsa-miR-142-5p | 0.37147 | 0.43008 | 0.45142 | 0.70165 | −0.51118 |
| hsa-miR-4668-5p | 0.37512 | 0.42583 | 0.45142 | 1.5667 | 0.64772 |
| hsa-miR-101-3p | 0.37548 | 0.42541 | 0.45142 | 0.64269 | −0.6378 |
| hsa-miR-874-3p | 0.39541 | 0.40295 | 0.47273 | 1.1981 | 0.26075 |
| hsa-miR-15b-5p | 0.40185 | 0.39594 | 0.47775 | 0.8306 | −0.26777 |
| hsa-miR-889-3p | 0.4185 | 0.37831 | 0.49389 | 2.9929 | 1.5816 |
| hsa-miR-263-5p | 0.41961 | 0.37715 | 0.49389 | 1.0137 | 0.01961 |
| hsa-miR-181c-5p | 0.42887 | 0.36767 | 0.50152 | 0.74443 | −0.4258 |
| hsa-miR-184 | 0.47808 | 0.3205 | 0.55602 | 0.52259 | −0.93624 |
| hsa-miR-148a-3p | 0.5257 | 0.27927 | 0.60483 | 1.4806 | 0.56617 |
| hsa-miR-320b | 0.5257 | 0.27927 | 0.60483 | 0.73946 | −0.43546 |
| hsa-miR-28-3p | 0.54279 | 0.26536 | 0.61815 | 1.3154 | 0.3955 |
| hsa-miR-125b-2-3p | 0.54305 | 0.26516 | 0.61815 | 0.80618 | −0.31083 |
| hsa-miR-210-3p | 0.57036 | 0.24385 | 0.6458 | 1.7708 | 0.32442 |
| hsa-miR-103a-3p | 0.57593 | 0.23963 | 0.64751 | 1.3094 | 0.3889 |
| hsa-miR-24-3p | 0.57792 | 0.23813 | 0.64751 | 1.4857 | 0.57111 |
| hsa-miR-28-5p | 0.60296 | 0.21971 | 0.67204 | 12.408 | 3.6332 |
| hsa-miR-186-5p | 0.64362 | 0.19137 | 0.71365 | 1.1288 | 0.17482 |
| hsa-miR-320a | 0.66842 | 0.17495 | 0.73733 | 1.4823 | 0.56788 |
| hsa-miR-30b-5p | 0.70057 | 0.15455 | 0.76884 | 2.6816 | 1.4231 |
| hsa-miR-99b-5p | 0.71908 | 0.14322 | 0.78512 | 0.86384 | −0.21117 |
| hsa-let-7b-5p | 0.74094 | 0.13022 | 0.80488 | 1.0507 | 0.0714 |
| hsa-miR-148a-5p | 0.76577 | 0.1159 | 0.82397 | 2.375 | 1.2479 |
| hsa-miR-125b-5p | 0.76753 | 0.1149 | 0.32397 | 1.2332 | 0.30244 |
| hsa-miR-223-5p | 0.77007 | 0.11347 | 0.82397 | 2.6816 | 1.4231 |
| hsa-miR-140-3p | 0.79357 | 0.10041 | 0.8449 | 1.1963 | 0.25856 |
| hsa-miR-142-3p | 0.82185 | 0.08547 | 0.87015 | 10.383 | 3.3622 |
| hsa-miR-150-5p | 0.82912 | 0.081381 | 0.87405 | 5.0698 | 2.3419 |
| hsa-miR-185-5p | 0.8371 | 0.07722 | 0.37814 | 3.5403 | 1.8239 |
| hsa-miR-598-5p | 0.84533 | 0.072976 | 0.88135 | 1.2484 | 0.32005 |
| hsa-miR-23a-3p | 0.84841 | 0.071396 | 0.88135 | 1.2896 | 0.36696 |
| hsa-miR-34c-5p | 0.86196 | 0.064515 | 0.89111 | 0.74612 | −0.42252 |
| hsa-miR-23b-3p | 0.87572 | 0.057635 | 0.90098 | 1.5883 | 0.66747 |
| hsa-miR-103b | 0.88917 | 0.051014 | 0.91044 | 1.7581 | 0.81403 |
| hsa-miR-192-5p | 0.95826 | 0.018516 | 0.97189 | 1.4564 | 0.54241 |
| hsa-miR-215-5p | 0.95826 | 0.018516 | 0.97189 | 1.4564 | 0.54241 |
| hsa-miR-22-3p | 0.98634 | 0.005972 | 0.99097 | 0.85387 | −0.22791 |
| hsa-miR-92a-3p | 0.98634 | 0.005972 | 0.99097 | 0.97948 | −0.029909 |
| hsa-miR-107 | 1 | 0 | 1 | 1.982 | 0.98698 |

Salivary miRNA in Miled TBI (mTBI).

There were 214 salivary miRNAs with robust expression across both control and mTBI samples (Table 4). Forty of the miRNAs measured in saliva had nominal differences in normalized read counts and 10 had significant differences between control and mTBI groups. Nine of the miRNAs were down-regulated in mTBI saliva and 31 were up-regulated.

TABLE 4 miRNA differences in saliva mTBI samples

| miRNA | p.value | −log(p)10 | FDR | Fold Change | log2(FC) |
|---|---|---|---|---|---|
| hsa-miR-378d | 4.57E−06 | 5.3402 | 0.00095645 | 8.8605 | 3.1474 |
| hsa-miR-28-3p | 8.94E−06 | 5.0487 | 0.00095645 | 1.9592 | 0.97027 |
| hsa-miR-373f | 4.40E−05 | 4.3569 | 0.0031362 | 6.2996 | 2.6553 |

TABLE 4-continued miRNA differences in saliva mTBI samples

| miRNA | p.value | −log(p)10 | FDR | Fold Change | log2(FC) |
|---|---|---|---|---|---|
| hsa-miR-378g | 0.00013739 | 3.862 | 0.0073504 | 3.3091 | 1.7264 |
| hsa-miR-125b-2-3p | 0.00065008 | 3.187 | 0.026079 | 1.3746 | 0.459 |
| hsa-miR-151a-3p | 0.0008425 | 3.0744 | 0.026079 | 1.7361 | 0.79582 |
| hsa-miR-501-3p | 0.00091666 | 3.0378 | 0.026079 | 2.0061 | 1.0044 |
| hsa-miR-532-5p | 0.00097493 | 3.011 | 0.026079 | 1.4852 | 0.57063 |
| hsa-miR-155-5p | 0.0013366 | 2.874 | 0.031781 | 1.7931 | 0.84247 |
| hsa-miR-625-3p | 0.0022803 | 2.642 | 0.048798 | 0.18862 | −2.4064 |
| hsa-miR-193a-3p | 0.0028541 | 2.5445 | 0.055525 | 2.4165 | 1.2729 |
| hsa-miR-28-5p | 0.0043657 | 2.3599 | 0.068885 | 0.3154 | −1.6647 |
| hsa-miR-221-3p | 0.0045065 | 2.3462 | 0.068885 | 1.5194 | 0.60347 |
| hsa-miR-23a-3p | 0.0045065 | 2.3462 | 0.068885 | 1.458 | 0.54402 |
| hsa-miR-30e-3p | 0.0056197 | 2.2503 | 0.080174 | 1.8858 | 0.91514 |
| hsa-miR-29c-3p | 0.0077574 | 2.1103 | 0.10376 | 0.60523 | −0.72445 |
| hsa-miR-30e-5p | 0.0086174 | 2.0646 | 0.10848 | 0.49312 | −1.02 |
| hsa-miR-25-3p | 0.0092371 | 2.0345 | 0.10982 | 1.5734 | 0.65386 |
| hsa-miR-99b-5p | 0.0098962 | 2.0045 | 0.11006 | 1.423 | 0.50898 |
| hsa-miR-151a-5p | 0.011729 | 1.9307 | 0.11006 | 1.5683 | 0.54924 |
| hsa-let-7f-5p | 0.011731 | 1.9307 | 0.11006 | 1.8273 | 0.86974 |
| hsa-miR-25a-5p | 0.011731 | 1.9307 | 0.11006 | 1.4193 | 0.50517 |
| hsa-miR-944 | 0.011829 | 1.9271 | 0.11006 | 1.7534 | 0.81015 |
| hsa-miR-182-5p | 0.012971 | 1.887 | 0.11566 | 1.4654 | 0.55125 |
| hsa-miR-452-5p | 0.014191 | 1.848 | 0.12147 | 1.6664 | 0.73675 |
| hsa-miR-744-5p | 0.015297 | 1.8154 | 0.12478 | 1.348 | 0.43082 |
| hsa-miR-320c | 0.015804 | 1.8012 | 0.12478 | 1.3607 | 0.44439 |
| hsa-miR-26b-5p | 0.016326 | 1.7871 | 0.12478 | 1.3672 | 0.45124 |
| hsa-miR-135a-5p | 0.01823 | 1.7392 | 0.13052 | 0.56158 | −0.83243 |
| hsa-miR-6S87-5p | 0.018298 | 1.7376 | 0.13052 | 0.26242 | −1.93 |
| hsa-miR-200b-3p | 0.023142 | 1.6356 | 0.15476 | 1.2917 | 0.36925 |
| hsa-miR-3074-5p | 0.023142 | 1.6356 | 0.15476 | 0.56907 | −0.81333 |
| hsa-miR-183-5p | 0.023869 | 1.6222 | 0.15479 | 1.3794 | 0.46404 |
| hsa-miR-200c-3p | 0.025384 | 1.5954 | 0.15977 | 1.2787 | 0.35472 |
| hsa-miR-200a-5p | 0.027693 | 1.5576 | 0.16933 | 1.4504 | 0.53645 |
| hsa-miR-378i | 0.029539 | 1.5296 | 0.1756 | 0.37549 | −1.4131 |
| hsa-miR-146a-5p | 0.033273 | 1.4779 | 0.19244 | 1.4282 | 0.51423 |
| hsa-miR-4321 | 0.035902 | 1.4449 | 0.20011 | 0.56286 | −0.82915 |
| hsa-miR-374a-5p | 0.037189 | 1.4302 | 0.20011 | 2.1905 | 1.1312 |
| hsa-miR-30b-5p | 0.037403 | 1.4271 | 0.20011 | 1.3205 | 0.40107 |
| hsa-miR-4763-5p | 0.051071 | 1.2918 | 0.25924 | 0.88504 | −0.17619 |
| hsa-miR-338-5p | 0.054687 | 1.2621 | 0.25924 | 1.6238 | 0.6994 |
| hsa-miR-424-5p | 0.054709 | 1.2619 | 0.25924 | 0.59201 | −0.7563 |
| hsa-miR-345-5p | 0.056159 | 1.2506 | 0.25924 | 0.68253 | −0.55104 |
| h5a-miR-378a-3p | 0.056983 | 1.2443 | 0.25924 | 0.59551 | −0.7478 |
| hsa-miR-450a-5p | 0.056988 | 1.2442 | 0.25924 | 0.54842 | −0.86665 |
| hsa-miR-140-3p | 0.058546 | 1.2325 | 0.25924 | 1.686 | 0.75358 |
| hsa-miR-92a-3p | 0.058546 | 1.2325 | 0.25924 | 1.1085 | 0.14866 |
| hsa-miR-29a-3p | 0.061781 | 1.2091 | 0.25924 | 0.7667 | −0.38326 |
| hsa-miR-320a | 0.061781 | 1.2091 | 0.25924 | 0.63852 | −0.6472 |
| hsa-miR-4429 | 0.061781 | 1.2091 | 0.25924 | 1.1552 | 0.20811 |
| hsa-miR-142-5p | 0.065155 | 1.1861 | 0.26475 | 0.46607 | −1.1014 |
| hsa-miR-145-5p | 0.066013 | 1.1804 | 0.26475 | 0.56252 | −0.83003 |
| hsa-miR-126-3p | 0.069606 | 1.1574 | 0.26475 | 0.48677 | −1.0387 |
| hsa-miR-590-3p | 0.069711 | 1.1567 | 0.26475 | 0.56773 | −0.81672 |
| hsa-miR-1307-3p | 0.070511 | 1.1517 | 0.26475 | 1.3408 | 0.42308 |
| hsa-miR-361-5p | 0.070518 | 1.1517 | 0.26475 | 1.1546 | 0.20735 |
| hsa-miR-423-5p | 0.072382 | 1.1404 | 0.26705 | 0.60558 | −0.72382 |
| hsa-miR-95-3p | 0.075188 | 1.1238 | 0.27272 | 1.3063 | 0.38551 |
| hsa-miR-598-5p | 0.079549 | 1.0994 | 0.28151 | 0.47782 | −1.0655 |
| hsa-miR-27b-3p | 0.080244 | 1.0956 | 0.28151 | 0.67154 | −0.57445 |
| hsa-miR-331-3p | 0.086346 | 1.0638 | 0.28951 | 0.55873 | −0.83979 |
| hsa-miR-199a-3p | 0.086583 | 1.0626 | 0.28951 | 0.65918 | −0.60125 |
| hsa-miR-199b-3p | 0.086583 | 1.0626 | 0.28951 | 0.65918 | −0.60125 |
| hsa-miR-27a-5p | 0.090103 | 1.0453 | 0.29245 | 0.56118 | −0.83346 |
| hsa-miR-31-5p | 0.093209 | 1.0305 | 0.29245 | 1.3093 | 0.38878 |
| hsa-miR-542-3p | 0.093742 | 1.0281 | 0.29245 | 0.50608 | −0.98256 |
| hsa-miR-339-3p | 0.095411 | 1.0204 | 0.29245 | 0.72753 | −0.45892 |
| hsa-miR-1273g-3p | 0.09566 | 1.0193 | 0.29245 | 1.0148 | 0.021154 |
| hsa-miR-3515 | 0.095663 | 1.0193 | 0.29245 | 0.56536 | −0.82276 |
| hsa-miR-130b-3p | 0.10012 | 0.99946 | 0.29865 | 1.4087 | 0.4944 |
| hsa-miR-146b-5p | 0.10048 | 0.99793 | 0.29865 | 1.5831 | 0.6628 |
| hsa-miR-21-3p | 0.10468 | 0.98012 | 0.304 | 0.68355 | −0.54888 |
| hsa-miR-628-3p | 0.10512 | 0.9783 | 0.304 | 1.2363 | 0.30604 |
| hsa-miR-195-5p | 0.10806 | 0.96632 | 0.30834 | 0.71889 | −0.47616 |
| hsa-miR-3135b | 0.11609 | 0.93519 | 0.3269 | 0.75474 | −0.40594 |
| hsa-miR-450b-5p | 0.12556 | 0.90116 | 0.3365 | 0.62054 | −0.6884 |
| hsa-miR-7-5p | 0.12596 | 0.89975 | 0.3365 | 0.59185 | 0.75671 |
| hsa-miR-200b-5p | 0.12752 | 0.89442 | 0.3365 | 1.0336 | 0.047655 |

TABLE 4-continued miRNA differences in saliva mTBI samples

| miRNA | p.value | −log(p)10 | FDR | Fold Change | log2(FC) |
|---|---|---|---|---|---|
| hsa-miR-342-3p | 0.12752 | 0.89441 | 0.3365 | 1.0699 | 0.097413 |
| hsa-miR-140-5p | 0.12852 | 0.89101 | 0.3365 | 0.62492 | −0.67825 |
| hsa-miR-21-5p | 0.13051 | 0.88435 | 0.3365 | 0.71908 | −0.47577 |
| hsa-miR-375 | 0.13051 | 0.88435 | 0.3365 | 0.83611 | −0.25823 |
| hsa-miR-502-3p | 0.13565 | 0.86438 | 0.34814 | 0.75584 | −0.40385 |
| hsa-miR-24-1-5p | 0.14187 | 0.84812 | 0.35717 | 0.66448 | −0.5897 |
| hsa-miR-34a-5p | 0.14619 | 0.83507 | 0.36379 | 1.457 | 0.54295 |
| hsa-miR-16-5p | 0.15642 | 0.8057 | 0.38476 | 0.81909 | −0.2879 |
| hsa-miR-148b-3p | 0.16709 | 0.77706 | 0.40632 | 1.2568 | 0.32978 |
| hsa-miR-680-5p | 0.17389 | 0.75972 | 0.41468 | 1.3228 | 0.40362 |
| hsa-miR-505-3p | 0.1744 | 0.75846 | 0.41468 | 0.72927 | −0.45547 |
| hsa-miR-4485-3p | 0.17829 | 0.74888 | 0.41927 | 0.59326 | −0.75326 |
| hsa-miR-6724-5p | 0.18606 | 0.73035 | 0.43263 | 0.69208 | −0.53098 |
| hsa-miR-374c-5p | 0.18804 | 0.72576 | 0.43263 | 0.71281 | −0.4884 |
| hsa-miR-191-5p | 0.19004 | 0.72116 | 0.43263 | 1.1654 | 0.22081 |
| hsa-miR-184 | 0.19279 | 0.71491 | 0.43263 | 0.4988 | −1.0035 |
| hsa-miR-3950 | 0.19408 | 0.71203 | 0.43263 | 0.7882 | −0.34336 |
| hsa-miR-193b-3p | 0.21517 | 0.66722 | 0.46524 | 1.4181 | 0.50399 |
| hsa-miR-200a-3p | 0.21523 | 0.6671 | 0.46524 | 1.3751 | 0.45956 |
| hsa-miR-222-3p | 0.21523 | 0.6671 | 0.46524 | 1.1593 | 0.21329 |
| hsa-miR-574-5p | 0.21882 | 0.65992 | 0.46595 | 1.0172 | 0.02462 |
| hsa-miR-16-2-3p | 0.22853 | 0.64106 | 0.46595 | 0.79451 | −0.33186 |
| hsa-miR-185-5p | 0.22866 | 0.64081 | 0.46595 | 1.2907 | 0.36819 |
| hsa-miR-107 | 0.22869 | 0.64075 | 0.46595 | 1.147 | 0.19781 |
| hsa-miR-564a-3p | 0.23306 | 0.63253 | 0.45595 | 1.312 | 0.39172 |
| hsa-let-7a-5p | 0.23331 | 0.63207 | 0.46595 | 0.98153 | −0.026894 |
| hsa-miR-365a-3p | 0.23331 | 0.63207 | 0.46595 | 1.1524 | 0.20461 |
| hsa-miR-365b-3p | 0.23331 | 0.63207 | 0.46595 | 1.1524 | 0.20461 |
| hsa-miR-142-3p | 0.23515 | 0.62865 | 0.46595 | 0.63023 | −0.66604 |
| hsa-miR-30a-5p | 0.23799 | 0.62344 | 0.46725 | 0.96231 | −0.055433 |
| hsa-miR-374a-3p | 0.2463 | 0.50853 | 0.47728 | 0.65261 | −0.61571 |
| hsa-miR-152-3p | 0.24756 | 0.60632 | 0.47728 | 1.1801 | 0.23887 |
| hsa-miR-185-5p | 0.25986 | 0.58526 | 0.49485 | 0.75524 | −0.40498 |
| hsa-miR-3607-5p | 0.2613 | 0.58286 | 0.49485 | 0.62817 | −0.67077 |
| hsa-miR-353-3p | 0.28284 | 0.54845 | 0.51024 | 0.83201 | −0.26532 |
| hsa-miR-224-5p | 0.28314 | 0.548 | 0.51024 | 1.0877 | 0.12132 |
| hsa-miR-181c-5p | 0.285 | 0.54516 | 0.51024 | 0.71258 | −0.48888 |
| hsa-miR-194-5p | 0.28556 | 0.54431 | 0.51024 | 0.7951 | −0.33079 |
| hsa-miR-192-5p | 0.28839 | 0.54002 | 0.51024 | 0.83394 | −0.26198 |
| hsa-miR-215-5p | 0.28839 | 0.54002 | 0.51024 | 0.83394 | −0.26198 |
| hsa-let-7i-5p | 0.2885 | 0.53986 | 0.51024 | 1.1003 | 0.1379 |
| hsa-miR-484 | 0.2885 | 0.53986 | 0.51024 | 0.99493 | −0.0073389 |
| hsa-miR-150-5p | 0.2912 | 0.53581 | 0.51079 | 0.83939 | −0.25258 |
| hsa-miR-425-3p | 0.29375 | 0.53202 | 0.51107 | 1.3248 | 0.40582 |
| hsa-miR-3916 | 0.31042 | 0.50805 | 0.53572 | 0.49144 | −1.0249 |
| hsa-miR-210-3p | 0.3454 | 0.46167 | 0.59133 | 1.2717 | 0.34677 |
| hsa-miR-1249-3p | 0.34878 | 0.45745 | 0.59237 | 1.0074 | 0.010696 |
| hsa-let-7g-5p | 0.35804 | 0.44607 | 0.59627 | 1.2395 | 0.30975 |
| hsa-let-7c-5p | 0.36427 | 0.43857 | 0.59627 | 0.81617 | −0.29305 |
| hsa-miR-101-3p | 0.36427 | 0.43857 | 0.59627 | 0.8037 | −0.31527 |
| hsa-miR-19b-1-5p | 0.36794 | 0.43422 | 0.59627 | 0.28796 | −1.7961 |
| hsa-miR-132-3p | 0.37022 | 0.43155 | 0.59627 | 1.4905 | 0.57578 |
| hsa-miR-143-3p | 0.37058 | 0.43112 | 0.59627 | 0.67618 | −0.56452 |
| hsa-miR-425-5p | 0.37058 | 0.43112 | 0.59627 | 0.86188 | −0.21445 |
| hsa-miR-629-5p | 0.38336 | 0.4164 | 0.60462 | 1.1671 | 0.22288 |
| hsa-miR-320b | 0.38339 | 0.41635 | 0.60462 | 0.87555 | −0.19175 |
| hsa-miR-106b-3p | 0.38988 | 0.40907 | 0.60462 | 1.2592 | 0.33247 |
| hsa-miR-197-3p | 0.38989 | 0.40905 | 0.60462 | 1.041 | 0.058034 |
| hsa-miR-652-3p | 0.38989 | 0.40905 | 0.60462 | 0.9131 | −0.13115 |
| hsa-miR-6763-3p | 0.39645 | 0.40181 | 0.61037 | 0.60982 | −0.71356 |
| hsa-miR-15b-5p | 0.4031 | 0.39458 | 0.61617 | 0.89861 | −0.15423 |
| hsa-miR-4673 | 0.41326 | 0.38378 | 0.62653 | 0.80263 | −0.3172 |
| hsa-miR-769-5p | 0.41573 | 0.38119 | 0.62653 | 1.2429 | 0.31372 |
| hsa-miR-22-3p | 0.44431 | 0.35231 | 0.66491 | 0.7898 | −0.34044 |
| hsa-miR-103a-3p | 0.4514 | 0.34543 | 0.66621 | 1.1025 | 0.14077 |
| hsa-miR-181a-5p | 0.4514 | 0.34543 | 0.66621 | 0.99707 | −0.0042348 |
| hsa-miR-19b-5p | 0.49882 | 0.30206 | 0.72705 | 0.96596 | −0.049971 |
| hsa-miR-223-3p | 0.50282 | 0.29859 | 0.72705 | 0.81467 | −0.29572 |
| hsa-miR-23b-3p | 0.50282 | 0.29859 | 0.72705 | 0.94807 | −0.076936 |
| hsa-miR-5793-5p | 0.51801 | 0.28567 | 0.74092 | 0.4442 | −1.1707 |
| hsa-miR-218-5p | 0.51933 | 0.28455 | 0.74092 | 1.3009 | 0.37953 |
| hsa-miR-198 | 0.54413 | 0.2643 | 0.77115 | 1.2358 | 0.30542 |
| hsa-miR-6748-3p | 0.56427 | 0.24851 | 0.79049 | 0.33713 | −1.5686 |
| hsa-miR-15a-5p | 0.56517 | 0.24782 | 0.79049 | 0.89288 | −0.16346 |
| hsa-miR-7-5p | 0.5691 | 0.24481 | 0.79082 | 0.78433 | −0.35047 |
| hsa-miR-130a-3p | 0.57723 | 0.23865 | 0.79237 | 0.481 | −1.0559 |

TABLE 4-continued miRNA differences in saliva mTBI samples

| miRNA | p.value | −log(p)10 | FDR | Fold Change | log2(FC) |
|---|---|---|---|---|---|
| hsa-miR-149-5p | 0.58131 | 0.23559 | 0.79237 | 1.0857 | 0.11861 |
| hsa-miR-205-5p | 0.58131 | 0.23559 | 0.79237 | 1.0062 | 0.0089534 |
| hsa-miR-32-5p | 0.59406 | 0.22617 | 0.80328 | 0.83343 | −0.26287 |
| hsa-miR-454-3p | 0.59683 | 0.22415 | 0.80328 | 1.3783 | 0.4529 |
| hsa-miR-148a-5p | 0.61298 | 0.21255 | 0.81986 | 1.163 | 0.21785 |
| hsa-miR-335-5p | 0.6226 | 0.20579 | 0.82012 | 1.3022 | 0.3809 |
| hsa-miR-574-3p | 0.6226 | 0.20579 | 0.82012 | 0.85953 | −0.21837 |
| hsa-miR-145-3p | 0.62467 | 0.20435 | 0.82012 | 0.73315 | −0.44782 |
| hsa-miR-221-5p | 0.63053 | 0.20029 | 0.82277 | 0.89485 | −0.16028 |
| hsa-miR-451a | 0.64772 | 0.18861 | 0.82695 | 0.24494 | −2.0295 |
| hsa-miR-22-5p | 0.65627 | 0.18292 | 0.82695 | 0.81729 | −0.29108 |
| hsa-miR-133a-5p | 0.65647 | 0.18278 | 0.82695 | 1.0477 | 0.067267 |
| hsa-miR-203a-3p | 0.65651 | 0.18276 | 0.82695 | 1.0819 | 0.11355 |
| hsa-miR-429 | 0.65651 | 0.18276 | 0.82695 | 0.99933 | −0.00097272 |
| hsa-miR-582-3p | 0.65719 | 0.18231 | 0.82695 | 1.0526 | 0.07396 |
| hsa-miR-340-5p | 0.66079 | 0.17994 | 0.82695 | 0.88644 | −0.1739 |
| hsa-miR-93-5p | 0.66511 | 0.17711 | 0.82752 | 1.0759 | 0.10559 |
| hsa-miR-103b | 0.68243 | 0.16594 | 0.83212 | 1.0617 | 0.086357 |
| hsa-miR-223-5p | 0.68243 | 0.16594 | 0.83212 | 3.4465 | 1.7851 |
| hsa-miR-30c-5p | 0.69115 | 0.16043 | 0.83212 | 0.85102 | −0.23273 |
| hsa-miR-424-3p | 0.6997 | 0.15509 | 0.83212 | 0.9188 | −0.12217 |
| hsa-miR-128-3p | 0.6999 | 0.15496 | 0.83212 | 6.94772 | −0.077464 |
| hGa-miR-141-3p | 0.69992 | 0.15495 | 0.83212 | 1.0462 | 0.065201 |
| hsa-miR-3p | 0.69992 | 0.15495 | 0.83212 | 1.1536 | 0.20618 |
| hsa-miR-30d-5p | 0.69992 | 0.15495 | 0.83212 | 1.2035 | 0.26722 |
| hsa-miR-199b-5p | 0.70833 | 0.14976 | 0.83333 | 0.88477 | −0.17662 |
| hsa-miR-99a-5p | 0.70872 | 0.14952 | 0.83333 | 1.0025 | 0.0036018 |
| hsa-miR-125b-5p | 0.73537 | 0.1335 | 0.85526 | 0.9124 | −0.13227 |
| hsa-miR-181b-5p | 0.73537 | 0.1335 | 0.85526 | 1.0712 | 0.099223 |
| hsa-miR-941 | 0.73984 | 0.13086 | 0.85581 | 1.2653 | 0.33952 |
| hsa-miR-3613-5p | 0.75313 | 0.12313 | 0.86208 | 1.0321 | 0.04565 |
| hsa-miR-7b-5p | 0.75331 | 0.12303 | 0.86208 | 0.37466 | −1.4163 |
| hsa-miR-193a-5p | 0.76233 | 0.11785 | 0.86428 | 0.77858 | −0.35109 |
| hsa-miR-6786-3p | 0.77099 | 0.11295 | 0.86428 | 1.2248 | 0.29253 |
| hsa-let-7d-3p | 0.77139 | 0.11273 | 0.86428 | 0.84858 | −0.23687 |
| hsa-miR-361-3p | 0.77139 | 0.11273 | 0.86428 | 0.89235 | −0.16432 |
| hsa-miR-92b-3p | 0.78048 | 0.10764 | 0.86991 | 0.80929 | −0.30528 |
| hsa-miR-324-3p | 0.81711 | 0.087718 | 0.90602 | 0.99979 | −0.00030913 |
| hsa-miR-1301-3p | 0.82594 | 0.08305 | 0.91109 | 1.1926 | 0.25417 |
| hsa-miR-24-3p | 0.83559 | 0.078008 | 0.917 | 1.0383 | 0.05426 |
| hsa-miR-106a-5p | 0.85415 | 0.068464 | 0.92786 | 1.0912 | 0.12586 |
| hsa-miR-125a-5p | 0.85415 | 0.068464 | 0.92786 | 0.80007 | −0.3218 |
| hsa-miR-4698 | 0.8728 | 0.059087 | 0.94333 | 8.8691 | 3.1488 |
| hsa-miR-485-3p | 0.88677 | 0.052188 | 0.95135 | 0.51201 | −0.96577 |
| hsa-miR-421 | 0.90083 | 0.045359 | 0.95135 | 0.97984 | −0.029381 |
| hsa-miR-340-3p | 0.90087 | 0.04534 | 0.95135 | 0.95073 | −0.072899 |
| hsa-miR-98-5p | 0.9009 | 0.045323 | 0.95135 | 0.68113 | −0.554 |
| hsa-miR-1-3p | 0.91962 | 0.036391 | 0.95135 | 1.0641 | 0.089672 |
| hsa-miR-328-3p | 0.91969 | 0.036356 | 0.95135 | 0.85276 | −0.22979 |
| hsa-miR-17-5p | 0.9197 | 0.036352 | 0.95135 | 1.0863 | 0.11941 |
| hsa-miR-27a-3p | 0.9197 | 0.036352 | 0.95135 | 0.97203 | −0.040923 |
| hsa-miR-4642 | 0.92861 | 0.032167 | 0.95135 | 0.53027 | −0.9152 |
| hsa-miR-8089 | 0.92907 | 0.031951 | 0.95135 | 0.54733 | −0.86953 |
| hsa-miR-1299 | 0.92912 | 0.031926 | 0.95135 | 0.82987 | −0.25904 |
| hsa-miR-582-5p | 0.94761 | 0.023368 | 0.96135 | 1.0035 | 0.005083 |
| hsa-miR-29b-3p | 0.94787 | 0.02325 | 0.96135 | 1.2327 | 0.30184 |
| hsa-miR-330-3p | 0.95738 | 0.018916 | 0.96641 | 0.70784 | −0.4985 |
| hsa-miR-19a-3p | 0.96687 | 0.014634 | 0.9714 | 0.99885 | −0.0016562 |
| hsa-miR-423-3p | 0.97635 | 0.010396 | 0.97635 | 0.93521 | −0.096632 |

Combined Analysis of CSF and Salivary miRNAs.

Of the 214 miRNAs detected in CSF, 135 (63%) were also present in saliva. Of the 114 miRNAs with nominal changes in the CSF of sTBI subjects, 64 (56%) were present in saliva and 10 (8.7%) demonstrated nominal differences in the mTBI group. Six of these ten miRNAs have been reported in previous concussion studies (Redell et al., 2010; Bhoma et al., 2016); Mitra et al., 2017). None of the miRNAs have overlapping seed sequences. Of the 10 overlapping miRNAs, six were altered in the same direction in both saliva and CSF TBI samples (Table 5). Four were down-regulated (miR-182-5p, miR-221-3p, mir-26b-5p, miR-320c) and two (miR-29c-3p, miR-30e-5p) were up-regulated (FIGS. 2A-2L).

TABLE 5 miRNAs altered in both CSF and saliva following traumatic brain injury

| MicroRNA | Seed Sequence | CSF | Saliva | Previous Study |
|---|---|---|---|---|
| hsa-let-7f-5p | GAGGUAG | ↑ | ↓ | Mitra et al., 2017 |
| hsa-miR-151a-5p | CGAGGAG | ↑ | ↓ | |
| hsa-miR-182-5p | UUGGCAA | ↓ | ↓ | Mitra et al., 2017 |
| hsa-miR-221-3p | GCUACAU | ↓ | ↓ | Redell et al., 2010 |
| hsa-miR-26b-5p | UCAAGUA | ↓ | ↓ | Redell et al., 2010 |
| hsa-miR-29c-3p | AGCACCA | ↑ | ↑ | Bhomia et al., 2016 |
| hsa-miR-30e-5p | GUAAACA | ↑ | ↑ | |
| hsa-miR-320c | AAAGCUG | ↓ | ↓ | Redell et al., 2010 |
| hsa-miR-532-5p | AUGCCUU | ↑ | ↓ | |
| hsa-miR-744-5p | GCGGGGC | ↑ | ↓ | |

Arrows indicate direction of change in TBI samples.

Predictive Accuracy of miRNA Biomarker Panel.

Figure 3A:
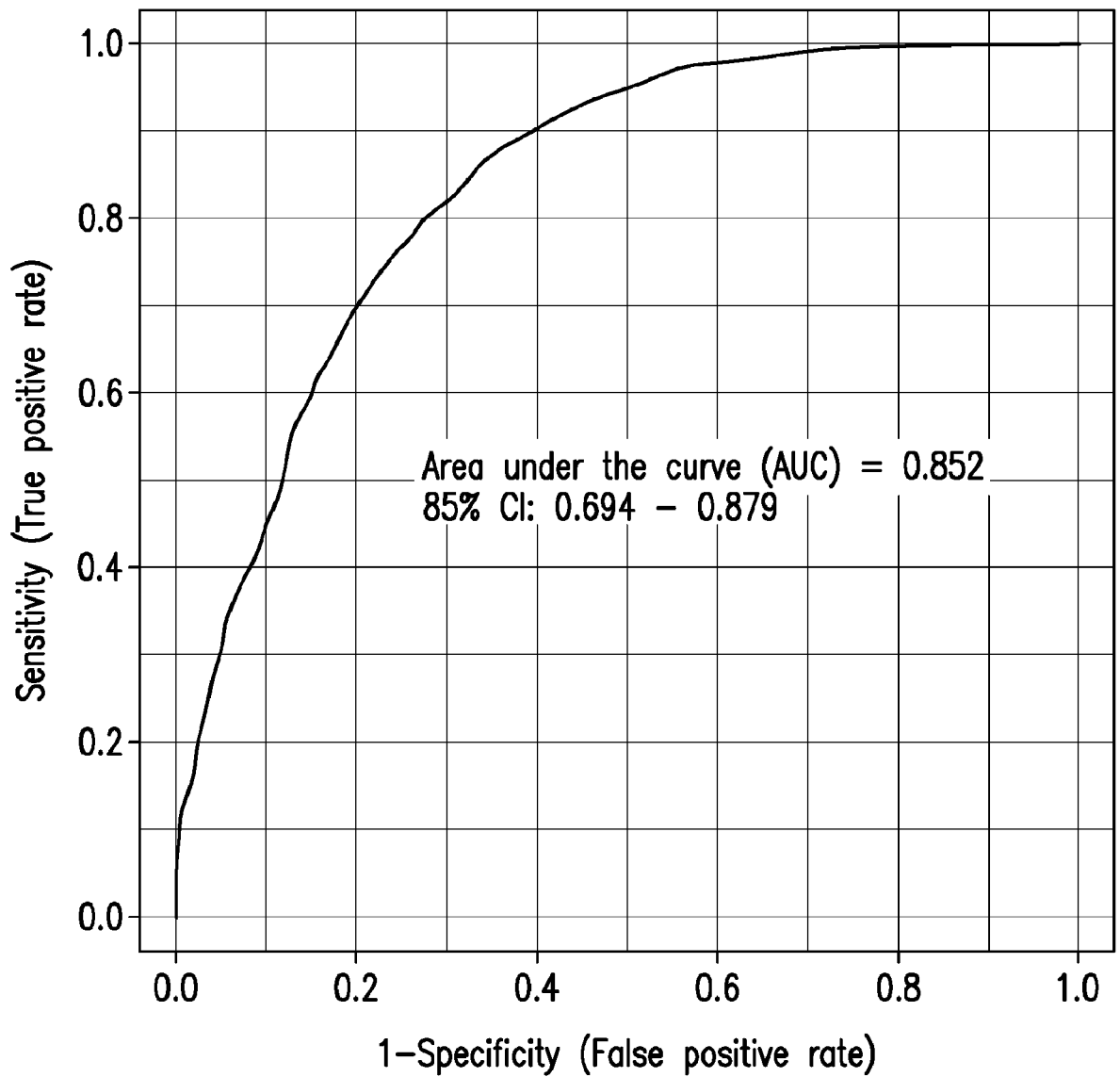
FIGS. 3A, B, C show six miRNAs of interest accurately identify mTBI status in a multivariate regression analysis. A receiver operator characteristics curve utilizing salivary concentrations of six miRNAs (miR-29c-3p, miR-26b-5p, miR-30e-5p, miR-182-5p, miR-320c, and miR-221-3p) demonstrated an area under the curve (AUC) of 0.852 on random forest testing of mTBI status (A). The established algorithm misclassified 2 control subjects and 15 mTBI subjects (B). 100-fold cross-validation of this tool holding out ¼ of control and mTBI subjects at random exhibited similar accuracy (C).
Figure 3B:
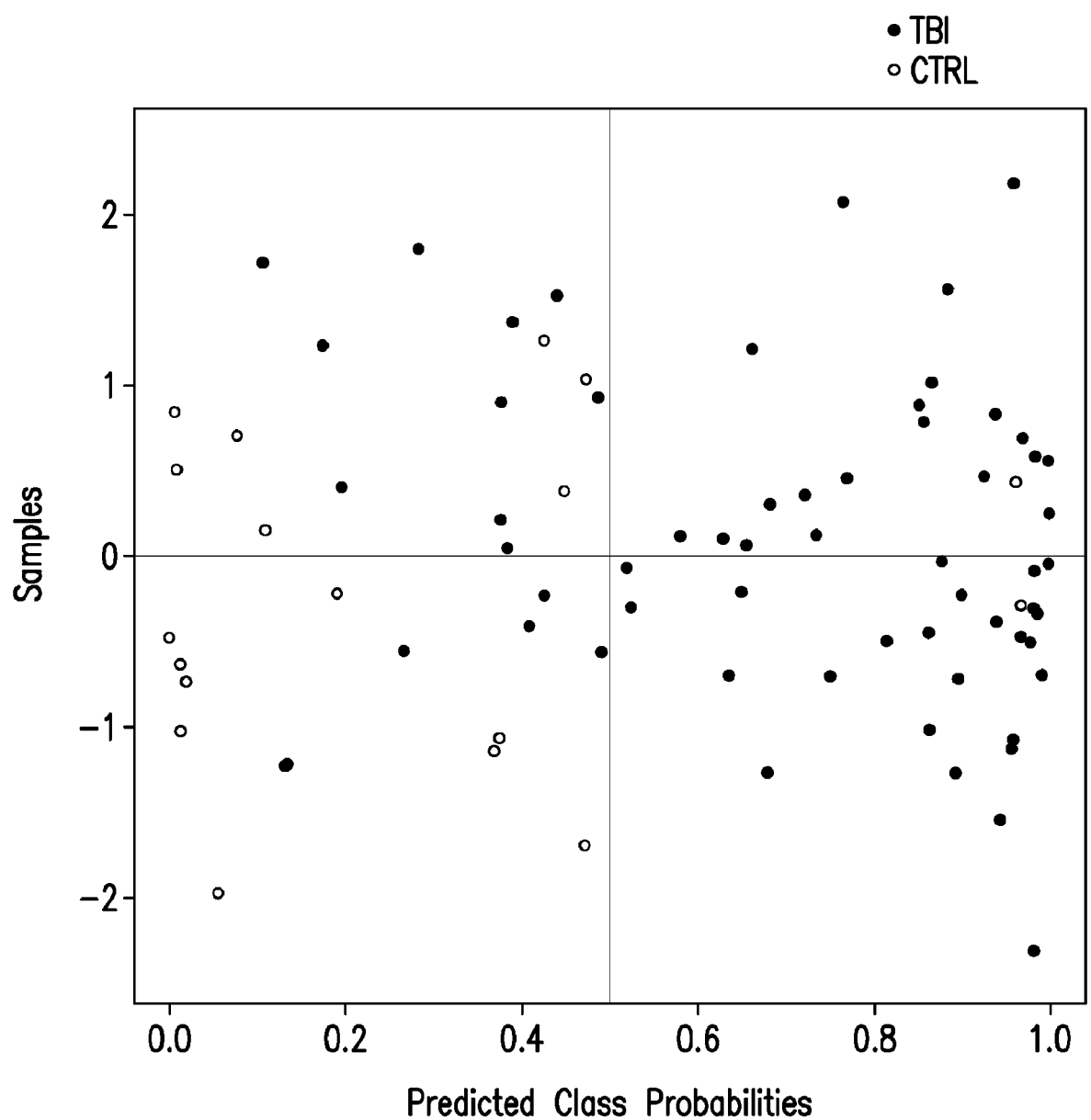
Figure 3C:
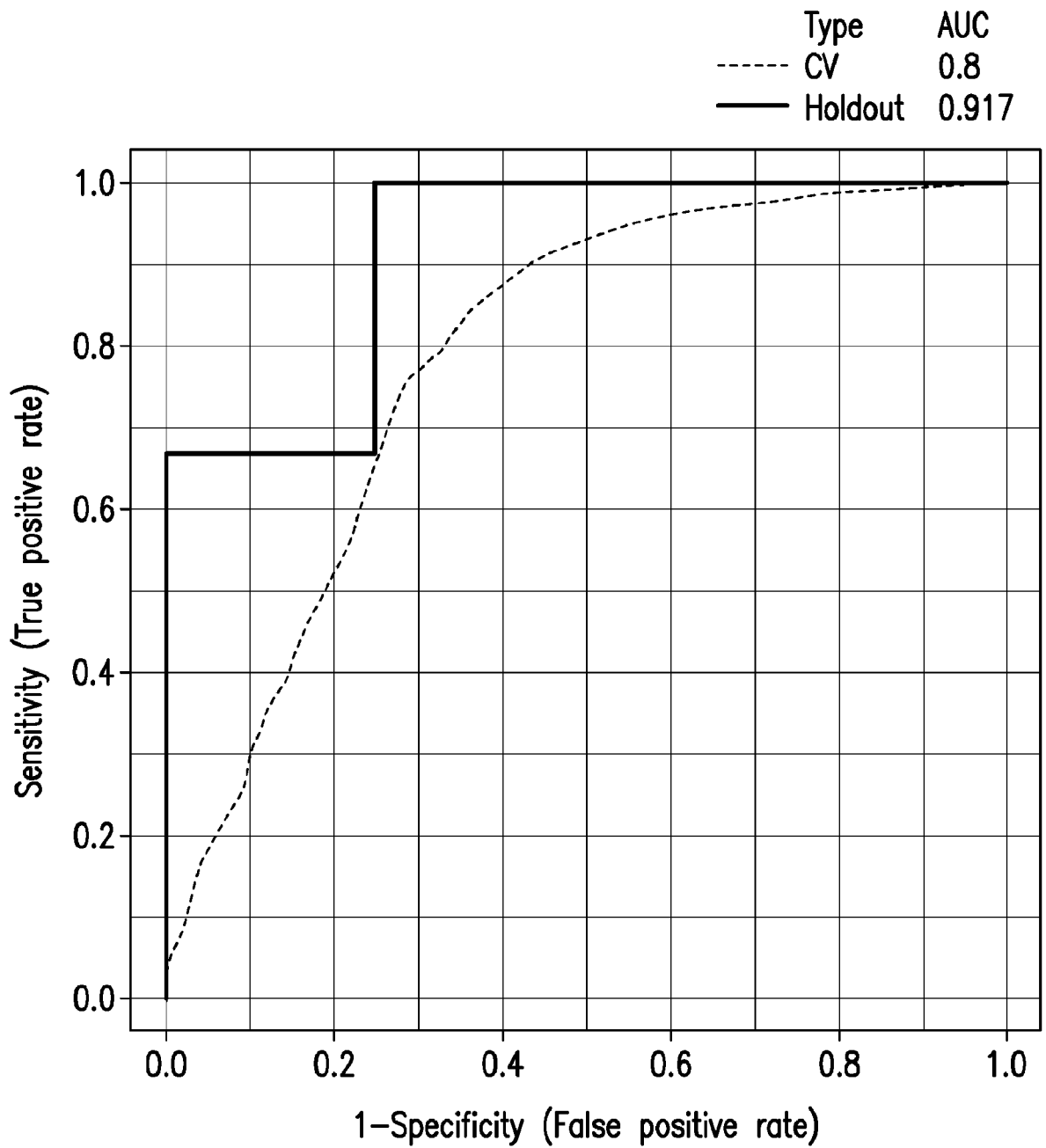

When used in a random forest multivariate regression analysis differentiating mTBI and control saliva samples the six miRNAs had a combined area under the curve (AUC) of 0.852 (FIG. 3A). The algorithm misclassified 2/18 control subjects and 15/60 mTBI subjects (FIG. 3B), yielding a sensitivity of 75% and a specificity of 89% with 78% accuracy. A 100-fold cross validation procedure holding out 25% of samples at random validated this model with an AUC of 0.800 in the cross-validation set and an AUC of 0.917 in the hold-out set (FIG. 3C).

Longitudinal Changes in Concussion-Related miRNAs.

The six miRNAs with parallel changes in CSF and saliva samples were interrogated for longitudinal trends following concussion. Spearman rank correlation between miRNA concentration and time since injury (in days) was determined for both CSF and saliva samples (Table 6).

TABLE 6

Spearman Correlations between miRNA concentration and days since injury in saliva and CSF

| MicroRNA | correlation | t-stat | Saliva p-value | FDR | correlation | t-stat | CSF p-value | FDR |
|---|---|---|---|---|---|---|---|---|
| hsa-miR-30e-5p | −0.55454 | 23598 | 7.73E−05 | 0.00084986 | 0.24704 | 1524 | 0.25463 | 0.38553 |
| hsa-miR-29c-3p | −0.51964 | 23068 | 0.00025409 | 0.0016304 | −0.17512 | 2378.4 | 0.42418 | 0.55609 |
| hsa-miR-320c | 0.45662 | 8248.5 | 0.0016166 | 0.0058091 | 0.7164 | 574 | 0.00018118 | 0.0038954 |
| hsa-miR-221-3p | −0.28325 | 19480 | 0.059372 | 0.10095 | 0.13452 | 1751.7 | 0.54057 | 0.66832 |
| hsa-miR-182-5p | −0.051928 | 15958 | 0.73479 | 0.79369 | −0.075099 | 2176 | 0.73298 | 0.82011 |
| hsa-miR-26b-5p | −0.40024 | 21256 | 0.0064454 | 0.016234 | 0.70652 | 594 | 0.00024294 | 0.0040971 |

Of the six miRNAs, three showed parallel correlations in CSF and saliva. Relative concentrations (RPM) of miR-29c-3p and miR-182-5p trended down over time in both CSF and saliva. Relative concentrations of miR-320c trended up over time in both bio-fluids. This trend was significant (FDR<0.05) for miR-320c in both CSF and saliva, and for miR-29c-3p in saliva.

Functional Analysis.

The 6 miRNAs with predictive utility for mTBI status had 700 predicted high-confidence mRNA targets, 354 of which had been experimentally validated (Table 7).

TABLE 7

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR30e-5p | ACVR1 | ENSG00000115170 | 1 | No |
| miR-182-5p | AEBP2 | ENSG00000139154 | 1 | No |
| miR-182-5p | AKAP8 | ENSG00000105127 | 1 | No |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | ATP8A1 | ENSG00000124406 | 1 | No |
| miR-182-5p | C11orf71 | ENSG00000180425 | 1 | No |
| miR-30e-5p | C9orf72 | ENSG00000147894 | 1 | No |
| miR-182-5p | CBFA2T3 | ENSG00000129993 | 1 | No |
| miR-30e-5p | CDH20 | ENSG00000101542 | 1 | No |
| miR-26b-5p | CEP350 | ENSG00000135837 | 1 | No |
| miR-26b-5p | CIPC | ENSG00000198894 | 1 | No |
| miR-30e-5p | COL25A1 | ENSG00000188517 | 1 | No |
| miR-29c-3p | COL2A1 | ENSG00000139219 | 1 | No |
| miR-182-5p | DOK4 | ENSG00000125170 | 1 | No |
| miR-30e-5p | ELMOD2 | ENSG00000179387 | 1 | No |
| miR-30e-5p | EVX2 | ENSG00000174279 | 1 | No |
| miR-182-5p | FAM171A1 | ENSG00000148458 | 1 | No |
| miR-30e-5p | FAM49A | ENSG00000197872 | 1 | No |
| miR-29c-3p | GRIP1 | ENSG00000155974 | 1 | No |
| miR-29c-3p | HIF3A | ENSG00000124440 | 1 | No |
| miR-26b-5p | HLA-F | ENSG00000204642 | 1 | No |
| miR-29c-3p | IGF1 | ENSG00000017427 | 1 | No |
| miR-30e-5p | IP6K3 | ENSG00000161896 | 1 | No |
| miR-30e-5p | KIAA1549 | ENSG00000122778 | 1 | No |
| miR-30e-5p | LGI1 | ENSG00000108231 | 1 | No |
| miR-30e-5p | LHX1 | ENSG00000132130 | 1 | No |
| miR-30e-5p | LHX8 | ENSG00000162624 | 1 | No |
| miR-29c-3p | UN7A | ENSG00000111052 | 1 | No |
| miR-29c-3p | MEX3B | ENSG00000183496 | 1 | No |
| miR-30e-5p | MMP16 | ENSG00000156103 | 1 | No |
| miR-182-5p | NRN1 | ENSG00000124785 | 1 | No |
| miR-30e-5p | NT5E | ENSG00000135318 | 1 | No |
| miR-182-5p | PAIP2 | ENSG00000120727 | 1 | No |
| miR-26b-5p | PALM3 | ENSG00000187867 | 1 | No |
| miR-30e-5p | PCDH10 | ENSG00000138650 | 1 | No |
| miR-29c-3p | PCDHA1 | ENSG00000204970 | 1 | No |
| miR-29c-3p | PCDHA10 | ENSG00000250120 | 1 | No |
| miR-29c-3p | PCDHA11 | ENSG00000249158 | 1 | No |
| miR-29c-3p | PCDHA12 | ENSG00000251664 | 1 | No |
| miR-29c-3p | PCDHA13 | ENSG00000239389 | 1 | No |
| miR-29c-3p | PCDHA2 | ENSG00000204969 | 1 | No |
| miR-29c-3p | PCDHA3 | ENSG00000255408 | 1 | No |
| miR-29c-3p | PCDHA4 | ENSG00000204967 | 1 | No |
| miR-29c-3p | PCDHA5 | ENSG00000204965 | 1 | No |
| miR-29c-3p | PCDHA6 | ENSG00000081842 | 1 | No |
| miR-29c-3p | PCDHA7 | ENSG00000204963 | 1 | No |
| miR-29c-3p | PCDHA8 | ENSG00000204962 | 1 | No |
| miR-29c-3p | PCDHAC1 | ENSG00000248383 | 1 | No |
| miR-29c-3p | PCDHAC2 | ENSG00000243232 | 1 | No |
| miR-182-5p | PRTG | ENSG00000166450 | 1 | No |
| miR-182-5p | RAPGEF5 | ENSG00000136237 | 1 | No |
| miR-26b-5p | RBM24 | ENSG00000112183 | 1 | No |
| miR-30e-5p | RFX6 | ENSG00000185002 | 1 | No |
| miR-182-5p | RHOBTB1 | ENSG00000072422 | 1 | No |
| miR-29c-3p | ROBO1 | ENSG00000169855 | 1 | No |
| miR-30e-5p | SCN1A | ENSG00000144285 | 1 | No |
| miR-30e-5p | SCN2A | ENSG00000136531 | 1 | No |
| miR-30e-5p | SCN3A | ENSG00000153253 | 1 | No |
| miR-26b-5p | SENP5 | ENSG00000119231 | 1 | No |
| miR-29c-3p | SLC16A14 | ENSG00000163053 | 1 | No |
| miR-29c-3p | SMIM17 | ENSG00000268182 | 1 | No |
| miR-26b-5p | SNN | ENSG00000184602 | 1 | No |
| miR-26b-5p | ST6GAL2 | ENSG00000144057 | 1 | No |
| msR-30e-5p | STIM2 | ENSG00000109689 | 1 | No |
| miR-26b-5p | STK39 | ENSG00000198648 | 1 | No |
| miR-30e-5p | STOX2 | ENSG00000173320 | 1 | No |
| miR-25b-5p | STRADB | ENSG00000082146 | 1 | No |
| miR-26b-5p | THRAP3 | ENSG00000054118 | 1 | No |
| miR-29c-3p | TLL1 | ENSG00000038295 | 1 | No |
| miR-29c-3p | TMEM183A | ENSG00000163444 | 1 | No |
| miR-29b-5p | TRIB2 | ENSG00000071575 | 1 | No |
| miR-30e-5p | VAT1L | ENSG00000171724 | 1 | No |
| miR-28b-5p | ZBTB37 | ENSG00000185278 | 1 | No |
| miR-182-5p | ZNF2808 | ENSG00000198477 | 1 | No |
| miR-26b-5p | ZNF462 | ENSG00000148143 | 1 | No |
| miR-30e-5p | ZNF644 | ENSG00000122482 | 1 | No |
| miR-26b-5p | ACBD5 | ENSG00000107897 | 1 | Yes |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-132-5p | ARF4 | ENSG00000168374 | 1 | Yes |
| miR-26b-5p | ATAD2B | ENSG00000119778 | 1 | Yes |
| miR-29c-3p | ATAD2B | ENSG00000119778 | 1 | Yes |
| miR-182-5p | BCL11A | ENSG00000119866 | 1 | Yes |
| miR-182-5p | BCL2L12 | ENSG00000126453 | 1 | Yes |
| miR-30e-5p | BECN1 | ENSG00000126581 | 1 | Yes |
| miR-30e-5p | BRWD1 | ENSG00000185658 | 1 | Yes |
| miR-30e-5p | BRWD3 | ENSG00000165288 | 1 | Yes |
| miR-26b-5p | CASZ1 | ENSG00000130940 | 1 | Yes |
| miR-30e-5p | CCDC117 | ENSG00000159873 | 1 | Yes |
| miR-26b-5p | CDK8 | ENSG00000132964 | 1 | Yes |
| miR-30e-5p | CELSR3 | ENSG00000008300 | 1 | Yes |
| miR-26b-5p | CHFR | ENSG00000072609 | 1 | Yes |
| miR-29c-3p | COL3A1 | ENSG00000168542 | 1 | Yes |
| miR-29c-3p | COL4A1 | ENSG00000187498 | 1 | Yes |
| miR-29c-3p | COL4A5 | ENSG00000188153 | 1 | Yes |
| miR-29c-3p | COL5A3 | ENSG00000080573 | 1 | Yes |
| miR-29c-3p | COL6A3 | ENSG00000163359 | 1 | Yes |
| miR-29c-3p | COL7A1 | ENSG00000114270 | 1 | Yes |
| miR-30e-5p | CPNE8 | ENSG00000139117 | 1 | Yes |
| miR-182-5p | CTTN | ENSG00000085733 | 1 | Yes |
| miR-30e-5p | DCUN1D3 | ENSG00000188215 | 1 | Yes |
| miR-29c-3p | DDX3X | ENSG00000215301 | 1 | Yes |
| miR-30e-5p | DESI2 | ENSG00000121644 | 1 | Yes |
| miR-30e-5p | DGKH | ENSG00000102780 | 1 | Yes |
| miR-26b-5p | E2F7 | ENSG00000165891 | 1 | Yes |
| miR-30e-5p | EED | ENSG00000074266 | 1 | Yes |
| miR-29c-3p | ELN | ENSG00000049540 | 1 | Yes |
| miR-26b-5p | EPC1 | ENSG00000120616 | 1 | Yes |
| miR-182-5p | EVI5 | ENSG00000067208 | 1 | Yes |
| miR-26b-5p | FAM98A | ENSG00000119812 | 1 | Yes |
| miR-29c-3p | FEM1B | ENSG00000169018 | 1 | Yes |
| miR-29c-3p | FOXJ2 | ENSG00000065970 | 1 | Yes |
| miR-182-5p | FOXN3 | ENSG00000053254 | 1 | Yes |
| miR-182-5p | FOXO3 | ENSG00000118689 | 1 | Yes |
| miR-26b-5p | FRMD4B | ENSG00000114541 | 1 | Yes |
| miR-182-5p | FRS2 | ENSG00000166225 | 1 | Yes |
| miR-30e-5p | GALNT7 | ENSG00000109586 | 1 | Yes |
| miR-30e-5p | GLCCI1 | ENSG00000106415 | 1 | Yes |
| miR-26b-5p | GSK3B | ENSG00000082701 | 1 | Yes |
| miR-29c-3p | HBP1 | ENSG00000105856 | 1 | Yes |
| miR-26b-5p | HGF | ENSG00000019991 | 1 | Yes |
| miR-26b-5p | HMGA1 | ENSG00000137309 | 1 | Yes |
| miR-29c-3p | IFI30 | ENSG00000216490 | 1 | Yes |
| miR-29c-3p | IREB2 | ENSG00000136381 | 1 | Yes |
| miR-26b-5p | KIAA2013 | ENSG00000116685 | 1 | Yes |
| miR-29c-3p | KIAA2022 | ENSG00000050030 | 1 | Yes |
| miR-29c-3p | KIF26B | ENSG00000162849 | 1 | Yes |
| miR-30e-5p | KLHL20 | ENSG00000076321 | 1 | Yes |
| miR-26b-5p | KLHL42 | ENSG00000087448 | 1 | Yes |
| miR-182-5p | KTN1 | ENSG00000126777 | 1 | Yes |
| miR-26b-5p | LARP1 | ENSG00000155506 | 1 | Yes |
| miR-30e-5p | MAML1 | ENSG00000161021 | 1 | Yes |
| miR-29c-3p | MBTD1 | ENSG00000011258 | 1 | Yes |
| miR-30e-5p | MEX3B | ENSG00000183496 | 1 | Yes |
| miR-26b-5p | MFHAS1 | ENSG00000147324 | 1 | Yes |
| miR-182-5p | MITF | ENSG00000187098 | 1 | Yes |
| miR-29c-3p | MMP16 | ENSG00000156103 | 1 | Yes |
| miR-30e-5p | MTDH | ENSG00000147649 | 1 | Yes |
| miR-26b-5p | NABP1 | ENSG00000173559 | 1 | Yes |
| miR-29c-3p | NFIA | ENSG00000162599 | 1 | Yes |
| miR-29c-3p | NSD1 | ENSG00000165671 | 1 | Yes |
| miR-26b-5p | OTUD4 | ENSG00000164164 | 1 | Yes |
| miR-29c-3p | PAN2 | ENSG00000135473 | 1 | Yes |
| miR-182-5p | PCMT1 | ENS600000120265 | 1 | Yes |
| miR-30e-5p | PDE7A | ENSG00000205268 | 1 | Yes |
| miR-30e-5p | PFN2 | ENSG00000070087 | 1 | Yes |
| miR-30e-5p | PIP4K2A | ENSG00000150867 | 1 | Yes |
| miR-30e-5p | PPARGC1B | ENSG00000155846 | 1 | Yes |
| miR-26b-5p | PRKCD | ENSG00000163932 | 1 | Yes |
| miR-29c-3p | PXDN | ENSG00000130508 | 1 | Yes |
| miR-29c-3p | PXYLP1 | ENSG00000155893 | 1 | Yes |
| miR-30e-5p | R3HDM1 | ENSG00000048991 | 1 | Yes |
| miR-30e-5p | RAB1S | ENSG00000139998 | 1 | Yes |
| miR-30e-5p | RASA1 | ENSG00000145715 | 1 | Yes |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-182-5p | RGS17 | ENSG00000091844 | 1 | Yes |
| miR-29c-3p | RNF19A | ENSG00000034677 | 1 | Yes |
| miR-30e-5p | RNF220 | ENSG00000187147 | 1 | Yes |
| miR-30e-5p | SEMA3A | ENSG00000075213 | 1 | Yes |
| miR-29c-3p | SESTD1 | ENSG00000187231 | 1 | Yes |
| miR-30e-5p | SETD7 | ENSG00000145391 | 1 | Yes |
| miR-26b-5p | SLC7A11 | ENSG00000151012 | 1 | Yes |
| miR-26b-5p | SMAD1 | ENSG00000170365 | 1 | Yes |
| miR-30e-5p | SNAI1 | ENSG00000124216 | 1 | Yes |
| miR-30e-5p | SOCS1 | ENSG00000185338 | 1 | Yes |
| miR-26b-5p | SRP19 | ENSG00000153037 | 1 | Yes |
| miR-26b-5p | STYX | ENSG00000198252 | 1 | Yes |
| miR-30e-5p | TBC1D10B | ENSG00000159221 | 1 | Yes |
| miR-26b-5p | TET2 | ENSG00000168769 | 1 | Yes |
| miR-26b-5p | TET3 | ENSG00000187605 | 1 | Yes |
| miR-29c-3p | TET3 | ENSG00000187605 | 1 | Yes |
| miR-30e-5p | TNRC6A | ENSG00000090905 | 1 | Yes |
| miR-26b-5p | TNRC6B | ENSG00000100354 | 1 | Yes |
| miR-30e-5p | UBN2 | ENSG00000157741 | 1 | Yes |
| miR-29c-3p | YBX3 | ENSG00000060138 | 1 | Yes |
| miR-182-5p | ZCCHC14 | ENSG00000140948 | 1 | Yes |
| miR-26b-5p | ZDHHC6 | ENSG00000023041 | 1 | Yes |
| miR-30e-5p | AC005035.1 | ENSG00000233404 | 0.999 | No |
| miR-29c-3p | ADAMTS12 | ENSG00000151388 | 0.999 | No |
| miR-29c-3p | ADAMTS9 | ENSG00000163638 | 0.999 | No |
| miR-29c-3p | ASXL3 | ENSG00000141431 | 0.999 | No |
| miR-26b-5p | ATP11C | ENSG00000101974 | 0.999 | No |
| miR-29c-3p | C10orf67 | ENSG00000179133 | 0.999 | No |
| miR-182-5p | C19orf26 | ENSG00000099625 | 0.999 | No |
| miR-30e-5p | CHST2 | ENSG00000175040 | 0.999 | No |
| miR-29c-3p | COL4A4 | ENSG00000081052 | 0.999 | No |
| miR-29c-3p | COL8A1 | ENSG00000144810 | 0.999 | No |
| miR-182-5p | CREB3L1 | ENSG00000157613 | 0.999 | No |
| miR-26b-5p | DCDC2 | ENSG00000146038 | 0.999 | No |
| miR-26b-5p | EZH2 | ENSG00000106462 | 0.999 | No |
| miR-2Gb-5p | FGD1 | ENSG00000102302 | 0.999 | No |
| miR-182-5p | GLB1L | ENSG00000163521 | 0.999 | No |
| miR-30e-5p | GLDC | ENSG00000178445 | 0.999 | No |
| miR-29c-3p | GPATCH2 | ENSG00000092978 | 0.999 | No |
| miR-30e-5p | JAKMIP2 | ENSG00000176049 | 0.999 | No |
| miR-30e-5p | JPH4 | ENSG00000092051 | 0.999 | No |
| miR-26b-5p | KCNJ2 | ENSG00000123700 | 0.999 | No |
| miR-182-5p | LHX1 | ENSG00000132130 | 0.999 | No |
| miR-30e-5p | LHX9 | ENSG00000143355 | 0.999 | No |
| miR-30e-5p | MBOAT1 | ENSG00000172197 | 0.999 | No |
| miR-30e-5p | NAALADL2 | ENSG00000177694 | 0.999 | No |
| miR-2Sb-5p | NAB1 | ENSG00000138386 | 0.999 | No |
| miR-29c-3p | NPAS3 | ENSG00000151322 | 0.999 | No |
| miR-30e-5p | NR4A2 | ENSG00000153234 | 0.999 | No |
| miR-30e-5p | NUS1 | ENSG00000153989 | 0.999 | No |
| miR-182-5p | PRRG3 | ENSG00000130032 | 0.999 | No |
| miR-182-5p | RNF152 | ENSG00000176641 | 0.999 | No |
| miR-30e-5p | RRAD | ENSG00000166592 | 0.999 | No |
| miR-30e-5p | RUNX2 | ENSG00000124813 | 0.999 | No |
| miR-30e-5p | SCARA5 | ENSG00000168079 | 0.999 | No |
| miR-182-5p | SHC4 | ENSG00000185634 | 0.999 | No |
| miR-182-5p | SLC1A2 | ENSG00000110436 | 0.999 | No |
| miR-26b-Sp | SLC25A16 | ENSG00000122912 | 0.999 | No |
| miR-30e-5p | ST8SIA4 | ENSG00000113532 | 0.999 | No |
| miR-25b-5p | SULF1 | ENSG00000137573 | 0.999 | No |
| miR-182-5p | TECTB | ENSG00000119913 | 0.999 | No |
| miR-30e-5p | TENM3 | ENSG00000218336 | 0.999 | No |
| miR-30e-5p | TMEM170B | ENSG00000205269 | 0.999 | No |
| miR-182-5p | TMEM50B | ENSG00000142188 | 0.999 | No |
| miR-182-5p | TRABD2B | ENSG00000269113 | 0.999 | No |
| miR-30e-5p | TILL7 | ENSG00000137941 | 0.999 | No |
| miR-30e-5p | UBE2J1 | ENSG00000198833 | 0.999 | No |
| miR-2Gb-5p | ULK2 | ENSG00000083290 | 0.999 | No |
| miR-26b-5p | WBSCR16 | ENSG00000174374 | 0.999 | No |
| miR-30e-5p | XPR1 | ENSG00000143324 | 0.999 | No |
| miR-182-5p | ZFC3H1 | ENSG00000133858 | 0.999 | No |
| miR-30e-5p | ADAM19 | ENSG00000135074 | 0.999 | Yes |
| miR-26b-5p | BAZ2B | ENSG00000123636 | 0.999 | Yes |
| miR-30e-5p | BAZ2B | ENSG00000123636 | 0.999 | Yes |
| miR-30e-5p | BNIP3L | ENSG00000104765 | 0.999 | Yes |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | CCNE2 | ENSG00000175305 | 0.999 | Yes |
| miR-29c-3p | CCNJ | ENSG00000107443 | 0.999 | Yes |
| miR-30e-5p | CDC37L1 | ENSG00000106993 | 0.999 | Yes |
| miR-26b-5p | CHAC1 | ENSG00000128965 | 0.999 | Yes |
| miR-29c-3p | COL15A1 | ENSG00000204291 | 0.999 | Yes |
| miR-30e-5p | CPSF6 | ENSG00000111605 | 0.999 | Yes |
| miR-30e-5p | ERLIN1 | ENSG00000107566 | 0.999 | Yes |
| miR-30e-5p | EXTL2 | ENSG00000162694 | 0.999 | Yes |
| miR-30e-5p | FAM160B1 | ENSG00000151553 | 0.999 | Yes |
| miR-26b-5p | FBXO11 | ENSG00000138081 | 0.999 | Yes |
| miR-30e-5p | FOXD1 | ENSG00000251493 | 0.999 | Yes |
| miR-182-5p | FOXF2 | ENSG00000137273 | 0.999 | Yes |
| miR-30e-5p | FZD3 | ENSG00000104290 | 0.999 | Yes |
| miR-30e-5p | LIMCH1 | ENSG00000064042 | 0.999 | Yes |
| miR-30e-5p | LIN28B | ENSG00000187772 | 0.999 | Yes |
| miR-182-5p | LPHN2 | ENSG00000117114 | 0.999 | Yes |
| miR-182-5p | LPP | ENSG00000145012 | 0.999 | Yes |
| miR-29c-3p | LYSMD1 | ENSG00000163155 | 0.999 | Yes |
| miR-26b-5p | MAB21L1 | ENSG00000180660 | 0.999 | Yes |
| miR-182-5p | MFAP3 | ENSG00000037749 | 0.999 | Yes |
| miR-26b-5p | MTDH | ENSG00000147649 | 0.999 | Yes |
| miR-182-5p | MTSS1 | ENSG00000170873 | 0.999 | Yes |
| miR-30e-5p | MYBL2 | ENSG00000101057 | 0.999 | Yes |
| miR-26b-5p | NAP1L5 | ENSG00000177432 | 0.999 | Yes |
| miR-29c-3p | NAV3 | ENSG00000067798 | 0.999 | Yes |
| miR-30e-5p | PHTF2 | ENSG00000006576 | 0.999 | Yes |
| miR-30e-5p | PLAGL2 | ENSG00000126003 | 0.999 | Yes |
| miR-29c-3p | PMP22 | ENSG00000109099 | 0.993 | Yes |
| miR-30e-5p | PRDM1 | ENSG00000057657 | 0.999 | Yes |
| miR-26b-5p | PTEN | ENSG00000171862 | 0.999 | Yes |
| miR-30e-5p | RAB38 | ENSG00000123892 | 0.999 | Yes |
| miR-30e-5p | RARG | ENSG00000172819 | 0.999 | Yes |
| miR-30e-5p | RBM26 | ENSG00000139746 | 0.999 | Yes |
| miR-320c | RC3H2 | ENSG00000056586 | 0.999 | Yes |
| miR-30e-5p | RHEBL1 | ENSG00000167550 | 0.999 | Yes |
| miR-29c-3p | RLF | ENSG00000117000 | 0.999 | Yes |
| miR-29c-3p | RNF39 | ENSG00000204618 | 0.999 | Yes |
| miR-26b-5p | RNF6 | ENSG00000127870 | 0.999 | Yes |
| miR-182-5p | SNX30 | ENSG00000148158 | 0.999 | Yes |
| miR-30e-5p | SPEN | ENSG00000065526 | 0.999 | Yes |
| miR-30e-5p | STK39 | ENSG00000198648 | 0.999 | Yes |
| miR-30e-5p | SYNGR3 | ENSG00000127561 | 0.999 | Yes |
| miR-30e-5p | TLE1 | ENSG00000196781 | 0.999 | Yes |
| miR-26b-5p | TLK1 | ENSG00000198586 | 0.999 | Yes |
| miR-30e-5p | TMEM181 | ENSG00000145433 | 0.999 | Yes |
| miR-26b-5p | TOB1 | ENSG00000141232 | 0.999 | Yes |
| miR-182-5p | TP53INP1 | ENSG00000164938 | 0.999 | Yes |
| miR-26b-5p | UBR3 | ENSG00000144357 | 0.999 | Yes |
| miR-182-5p | USP6NL | ENSG00000148429 | 0.999 | Yes |
| miR-182-5p | VAMP3 | ENSG00000049245 | 0.999 | Yes |
| miR-182-5p | WIPI2 | ENSG00000157954 | 0.999 | Yes |
| miR-26b-5p | ZBTB18 | ENSG00000179456 | 0.999 | Yes |
| miR-26b-5p | ZIC5 | ENSG00000139800 | 0.999 | Yes |
| miR-30e-5p | ZNRF1 | ENSG00000186187 | 0.999 | Yes |
| miR-26b-5p | ACVR1C | ENSG00000123612 | 0.998 | No |
| miR-26b-5p | ADAM23 | ENSG00000114948 | 0.998 | No |
| miR-30e-5p | ADRA1D | ENSG00000171873 | 0.998 | No |
| miR-182-5p | ARID2 | ENSG00000189079 | 0.998 | No |
| miR-26b-5p | ATP1A2 | ENSG00000018625 | 0.998 | No |
| miR-182-5p | BNC2 | ENSG00000173068 | 0.998 | No |
| miR-221-3p | CCDC144NL | ENSG00000205212 | 0.998 | No |
| miR-29c-3p | CEP76 | ENSG00000101624 | 0.998 | No |
| miR-26b-5p | CLASP2 | ENSG00000163539 | 0.998 | No |
| miR-221-3p | CLVS2 | ENSG00000146352 | 0.998 | No |
| miR-182-5p | DENR | ENSG00000139726 | 0.998 | No |
| miR-29e-3p | DGKH | ENS600000102780 | 0.998 | No |
| miR-30e-5p | EPB41 | ENSG00000159023 | 0.998 | No |
| miR-26b-5p | FA2H | ENSG00000103089 | 0.998 | No |
| miR-29c-3p | FAM23B | ENSG00000184040 | 0.998 | No |
| miR-30e-5p | FAM83F | ENSG00000133477 | 0.998 | No |
| miR-182-5p | FGF9 | ENSG00000102678 | 0.998 | No |
| miR-182-5p | FTH1 | ENSG00000157996 | 0.998 | No |
| miR-30e-5p | GMNC | ENSG00000205835 | 0.998 | No |
| miR-30e-5p | KXD1 | ENSG00000105700 | 0.998 | No |
| miR-182-5p | L1CAM | ENSG00000198910 | 0.998 | No |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | LPPR4 | ENSG00000117600 | 0.998 | No |
| miR-30e-5p | MAT2A | ENSG00000168906 | 0.998 | No |
| miR-26b-5p | MRAS | ENSG00000158186 | 0.998 | No |
| miR-30e-5p | MSANTD3-TMEFF1 | ENSG00000251349 | 0.998 | No |
| miR-26b-5p | MTM1 | ENSG00000171100 | 0.998 | No |
| miR-26b-5p | NHS | ENSG00000188158 | 0.998 | No |
| miR-30e-5p | OMG | ENSG00000126861 | 0.998 | No |
| miR-182-5p | PAX5 | ENSG00000196092 | 0.998 | No |
| miR-182-5p | PCDH8 | ENSG00000136099 | 0.998 | No |
| miR-30e-5p | PDSS1 | ENSG00000148459 | 0.998 | No |
| miR-182-5p | PPP4R2 | ENSG00000163605 | 0.998 | No |
| miR-182-5p | RAB10 | ENSG00000084733 | 0.998 | No |
| miR-30e-5p | ROR1 | ENSG00000185483 | 0.998 | No |
| miR-30e-5p | SH3PXD2A | ENSG00000107957 | 0.998 | No |
| miR-26b-5p | SRCAP | ENSG00000080603 | 0.998 | No |
| miR-26b-5p | THAP2 | ENSG00000173451 | 0.998 | No |
| miR-30e-5p | TMEFF1 | ENSG00000241697 | 0.998 | No |
| miR-26b-5p | UBE4B | ENSG00000130939 | 0.998 | No |
| miR-320c | ZNF430 | ENSG00000118620 | 0.998 | No |
| miR-25b-5p | ACSL3 | ENSG00000123983 | 0.998 | Yes |
| miR-26b-5p | ADAM19 | ENSG00000135074 | 0.998 | Yes |
| miR-29c-3p | ADAMTS2 | ENSG00000087116 | 0.998 | Yes |
| miR-29t-3p | BACH2 | ENSG00000112182 | 0.998 | Yes |
| miR-30e-5p | CAMK2N1 | ENSG00000162545 | 0.998 | Yes |
| miR-26b-5p | CCDC6 | ENSG00000108091 | 0.998 | Yes |
| miR-26b-5p | CHORDC1 | ENSG00000110172 | 0.998 | Yes |
| miR-26b-5p | CPSF2 | ENSG00000165934 | 0.998 | Yes |
| miR-29c-3p | DPYSL5 | ENSG00000157851 | 0.998 | Yes |
| miR-30e-5p | ELOVL5 | ENSG00000012660 | 0.998 | Yes |
| miR-182-5p | EPAS1 | ENSG00000116016 | 0.998 | Yes |
| miR-182-5p | FLOT1 | ENSG00000137312 | 0.998 | Yes |
| miR-30e-5p | GFPT2 | ENSG00000131459 | 0.998 | Yes |
| miR-30e-5p | HNRNPUL2 | ENSG00000214753 | 0.998 | Yes |
| miR-182-5p | HOXA9 | ENSG00000078399 | 0.998 | Yes |
| miR-30e-5p | LMBR1L | ENSG00000139636 | 0.998 | Yes |
| miR-30e-5p | MAST4 | ENSG00000069020 | 0.998 | Yes |
| miR-30e-5p | MIER3 | ENSG00000155545 | 0.998 | Yes |
| miR-182-5p | MTURN | ENSG00000180354 | 0.998 | Yes |
| miR-26b-5p | PLCB1 | ENSG00000182621 | 0.998 | Yes |
| miR-26b-5p | PLOD2 | ENSG00000152952 | 0.998 | Yes |
| miR-30e-5p | PPP1R18 | ENSG00000146112 | 0.998 | Yes |
| miR-30e-5p | PRLR | ENSG00000113494 | 0.998 | Yes |
| miR-30e-5p | PROSER1 | ENSG00000120685 | 0.998 | Yes |
| miR-25b-5p | REEP3 | ENSG00000165476 | 0.998 | Yes |
| miR-30e-5p | RORA | ENSG00000069667 | 0.998 | Yes |
| miR-30e-5p | SOCS3 | ENSG00000184557 | 0.998 | Yes |
| miR-29c-3p | STMN2 | ENSG00000104435 | 0.998 | Yes |
| msR-29e-3p | SUV420H2 | ENSG00000133247 | 0.998 | Yes |
| miR-30e-5p | TMCC1 | ENSG00000172765 | 0.998 | Yes |
| miR-30e-5p | TNRC6B | ENSG00000100354 | 0.998 | Yes |
| miR-182-5p | USP13 | EN5G00000058056 | 0.998 | Yes |
| miR-30e-5p | USP48 | ENSG00000090686 | 0.998 | Yes |
| miR-182-5p | VLDLR | ENSG00000147852 | 0.998 | Yes |
| miR-30e-5p | ANKHD1 | ENSG00000131503 | 0.997 | No |
| miR-182-5p | ARHGEF35 | ENSG00000213214 | 0.997 | No |
| miR-30e-5p | ASXL3 | ENSG00000141431 | 0.997 | No |
| miR-30e-5p | ATP2B1 | ENSG00000070961 | 0.997 | No |
| miR-30e-5p | B3GNT5 | ENSG00000176597 | 0.997 | No |
| miR-30e-5p | BAHD1 | ENSG00000140320 | 0.997 | No |
| miR-320c | C12orf36 | ENSG00000180861 | 0.997 | No |
| miR-182-5p | CELF6 | ENSG00000140488 | 0.997 | No |
| miR-25b-5p | CEP76 | ENSG00000101624 | 0.997 | No |
| miR-30e-5p | CHL1 | ENSG00000134121 | 0.997 | No |
| miR-26b-5p | CILP | ENSG00000138615 | 0.997 | No |
| miR-30e-5p | CLIP4 | ENSG00000115295 | 0.997 | No |
| miR-30e-5p | COL13A1 | ENSG00000197467 | 0.997 | No |
| miR-320c | CREB5 | ENSG00000146592 | 0.997 | No |
| miR-30e-5p | DCBLD1 | ENSG00000164465 | 0.997 | No |
| miR-30e-5p | DLL4 | ENSG00000128917 | 0.997 | No |
| miR-182-5p | EBF3 | ENSG00000108001 | 0.997 | No |
| miR-30e-5p | FAM214A | ENSG00000047346 | 0.997 | No |
| miR-29c-3p | GSTA4 | ENSG00000170899 | 0.997 | No |
| miR-182-5p | HBEGF | ENSG00000113070 | 0.997 | No |
| miR-182-5p | INTS6 | ENSG00000102786 | 0.997 | No |
| miR-28b-5p | ITGA5 | ENSG00000161638 | 0.997 | No |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | LOX | ENSG00000113083 | 0.997 | No |
| miR-26b-5p | LOXL2 | ENSG00000134013 | 0.997 | No |
| miR-30e-5p | LRFN2 | ENSG00000156564 | 0.997 | No |
| miR-182-5p | MAK | ENSG00000111837 | 0.997 | No |
| miR-30e-5p | MAP4K4 | ENSG00000071054 | 0.997 | No |
| miR-30e-5p | MMD | ENSG00000108960 | 0.997 | No |
| miR-25b-5p | NUDT11 | ENSG00000196368 | 0.997 | No |
| miR-182-5p | OGFRL1 | ENSG00000119900 | 0.997 | No |
| miR-30e-5p | PAPD4 | ENSG00000164329 | 0.997 | No |
| miR-182-5p | PBX2 | ENSG00000204304 | 0.997 | No |
| miR-30e-5p | PEX5L | ENSG00000114757 | 0.997 | No |
| miR-30e-5p | RAB22A | ENSG00000124209 | 0.997 | No |
| miR-30e-5p | TMEM194B | ENSG00000189362 | 0.997 | No |
| miR-29c-3p | TMEM236 | ENSG00000148483 | 0.997 | No |
| miR-30e-5p | UNC5C | ENSG00000182168 | 0.997 | No |
| miR-26b-5p | USP15 | ENSG00000135655 | 0.997 | No |
| miR-182-5p | ACTR2 | ENSG00000138071 | 0.997 | Yes |
| miR-30e-5p | AMOTL2 | ENSG00000114019 | 0.997 | Yes |
| miR-30e-5p | ANKRA2 | ENSG00000164331 | 0.997 | Yes |
| miR-29c-3p | ANKRD13B | ENSG00000198720 | 0.997 | Yes |
| miR-26b-5p | ANKS1A | ENSG00000064999 | 0.997 | Yes |
| miR-30e-5p | ARID4A | ENSG00000032219 | 0.997 | Yes |
| miR-182-5p | CAMSAP2 | ENSG00000118200 | 0.997 | Yes |
| miR-30e-5p | CBFB | ENSG00000067955 | 0.997 | Yes |
| miR-29c-3p | CCSAP | ENSG00000154429 | 0.997 | Yes |
| miR-25b-5p | COL19A1 | ENSG00000082293 | 0.997 | Yes |
| miR-26b-5p | EPHA2 | ENSG00000142627 | 0.997 | Yes |
| miR-29c-3p | FAM167A | ENSG00000154319 | 0.997 | Yes |
| miR-30e-5p | FNDC3A | ENSG00000102531 | 0.997 | Yes |
| miR-30e-5p | FST | ENSG00000134363 | 0.997 | Yes |
| miR-30e-5p | GALNT2 | ENSG00000143641 | 0.997 | Yes |
| miR-30e-5p | GIGYF1 | ENSG00000146830 | 0.997 | Yes |
| miR-30e-5p | INO80D | ENSG00000114933 | 0.997 | Yes |
| miR-29c-3p | ISG2OL2 | ENSG00000143319 | 0.997 | Yes |
| miR-30e-5p | JOSD1 | ENSG00000100221 | 0.997 | Yes |
| miR-30e-5p | KLHL28 | ENSG00000179454 | 0.997 | Yes |
| miR-30e-5p | KMT2C | ENSG00000055609 | 0.997 | Yes |
| miR-30e-5p | LCLAT1 | ENSG00000172954 | 0.997 | Yes |
| miR-30e-5p | LRCH2 | ENSG00000130224 | 0.997 | Yes |
| miR-30e-5p | MLK4 | ENSG00000143674 | 0.997 | Yes |
| miR-182-5p | MOB1B | ENSG00000173542 | 0.997 | Yes |
| miR-30e-5p | NUDT5 | ENSG00000165609 | 0.997 | Yes |
| miR-25b-5p | PDCD10 | ENSG00000114209 | 0.997 | Yes |
| miR-26b-5p | PITPNC1 | ENSG00000154217 | 0.997 | Yes |
| miR-26b-5p | POLR3G | ENSG00000113356 | 0.997 | Yes |
| miR-30e-5p | PTGFRN | ENSG00000134247 | 0.997 | Yes |
| miR-30e-5p | RAB32 | ENSG00000118508 | 0.997 | Yes |
| miR-182-5p | RARG | ENSG00000172819 | 0.997 | Yes |
| miR-3Ge-5p | RASA2 | ENSG00000155903 | 0.997 | Yes |
| miR-30e-5p | RHOB | ENSG00000143878 | 0.997 | Yes |
| miR-26b-5p | RSPRY1 | ENSG00000159579 | 0.997 | Yes |
| miR-30e-5p | S100PBP | ENSG00000116497 | 0.997 | Yes |
| miR-29c-3p | SH3PXD2A | ENSG00000107957 | 0.997 | Yes |
| miR-30e-5p | WDR82 | ENSG00000164091 | 0.997 | Yes |
| miR-26b-5p | ZSWIM6 | ENSG00000130449 | 0.997 | Yes |
| miR-30e-5p | ACTC1 | ENSG00000159251 | 0.996 | No |
| miR-26b-5p | ATF2 | ENSG00000115966 | 0.996 | No |
| miR-26b-5p | CCNJL | ENSG00000135083 | 0.996 | No |
| miR-221-3p | DGKH | ENSG00000102780 | 0.996 | No |
| miR-30e-5p | EAF1 | ENSG00000144597 | 0.996 | No |
| miR-29c-3p | EML6 | ENSG00000214595 | 0.996 | No |
| miR-29c-3p | GPR37 | ENSG00000170775 | 0.996 | No |
| miR-29c-3p | HAS3 | ENSG00000103044 | 0.996 | No |
| miR-29c-3p | HMCN1 | ENSG00000143341 | 0.996 | No |
| miR-30e-5p | HSPA4L | ENSG00000164070 | 0.996 | No |
| miR-30e-5p | HTR1F | ENSG00000179097 | 0.996 | No |
| miR-30e-5p | KCNJ6 | ENSG00000157542 | 0.996 | No |
| miR-182-5p | KIAA0907 | ENSG00000132680 | 0.996 | No |
| miR-320c | LPPR1 | ENSG00000148123 | 0.996 | No |
| miR-29c-3p | PiK3R2 | ENSG00000268173 | 0.996 | No |
| miR-26b-5p | PTPRD | ENSG00000153707 | 0.996 | No |
| miR-182-5p | RNF222 | ENSG00000189051 | 0.996 | No |
| miR-26b-5p | RP5-1021I20.4 | ENSG00000258653 | 0.996 | No |
| miR-26b-5p | RPGR | ENSG00000156313 | 0.996 | No |
| miR-29c-3p | SETDB2 | ENSG00000136169 | 0.996 | No |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | SLC38A7 | ENSG00000103042 | 0.996 | No |
| miR-182-5p | SYNCRIP | ENSG00000135316 | 0.996 | No |
| miR-30e-5p | TASP1 | ENSG00000089123 | 0.996 | No |
| miR-29c-3p | TFEB | ENSG00000112561 | 0.996 | No |
| miR-30e-5p | WDR44 | ENSG00000131725 | 0.996 | No |
| miR-320c | ZBTB37 | ENSG00000185278 | 0.996 | No |
| miR-26b-5p | ARPP19 | ENSG00000128989 | 0.996 | Yes |
| miR-30e-5p | CCNT2 | ENSG00000082258 | 0.996 | Yes |
| miR-30e-5p | CEP350 | ENSG00000135837 | 0.996 | Yes |
| miR-182-5p | CLOCK | ENSG00000134852 | 0.996 | Yes |
| miR-26b-5p | DCBLD1 | ENSG00000164465 | 0.996 | Yes |
| miR-26b-5p | FBXL19 | ENSG00000099364 | 0.996 | Yes |
| miR-26b-5p | FLVCR1 | ENSG00000162769 | 0.996 | Yes |
| miR-26b-5p | FRAT2 | ENSG00000181274 | 0.996 | Yes |
| miR-30e-5p | GALNT1 | ENSG00000141429 | 0.996 | Yes |
| miR-29c-3p | KIDINS220 | ENSG00000134313 | 0.996 | Yes |
| miR-30e-5p | LCOR | ENSG00000196233 | 0.996 | Yes |
| miR-30e-5p | LRRC8D | ENSG00000171492 | 0.996 | Yes |
| miR-30e-5p | MAN1A2 | ENSG00000198162 | 0.996 | Yes |
| miR-29c-3p | MEST | ENSG00000106484 | 0.996 | Yes |
| miR-182-5p | NCALD | ENSG00000104490 | 0.996 | Yes |
| miR-182-5p | PALLD | ENSG00000129116 | 0.996 | Yes |
| miR-30e-5p | PAWR | ENSG00000177425 | 0.996 | Yes |
| miR-30e-5p | PIGA | ENSG00000165195 | 0.996 | Yes |
| miR-182-5p | PTCHD1 | ENSG00000165186 | 0.996 | Yes |
| miR-26b-5p | SRGAP1 | ENSG00000196935 | 0.996 | Yes |
| miR-30e-5p | TAOK1 | ENSG00000160551 | 0.996 | Yes |
| miR-30e-5p | TMEM87A | ENSG00000103978 | 0.996 | Yes |
| miR-26b-5p | UBN2 | ENSG00000157741 | 0.996 | Yes |
| miR-26b-5p | VANGL2 | ENSG00000162738 | 0.996 | Yes |
| miR-182-5p | VGLL3 | ENSG00000206538 | 0.996 | Yes |
| miR-182-5p | YWHAG | ENSG00000170027 | 0.996 | Yes |
| mtR-26b-5p | ZNF410 | ENSG00000119725 | 0.996 | Yes |
| miR-30e-5p | ZNF521 | ENSG00000198795 | 0.996 | Yes |
| miR-182-5p | ADAMTS18 | ENSG00000140873 | 0.995 | No |
| miR-320c | ADAMTS6 | ENSG00000049192 | 0.995 | No |
| miR-182-5p | CACNB4 | ENSG00000182389 | 0.995 | No |
| miR-182-5p | DSCAM | ENSG00000171587 | 0.995 | No |
| miR-30e-5p | EFNA3 | ENSG00000143590 | 0.995 | No |
| miR-182-5p | ELAVL4 | ENSG00000162374 | 0.995 | No |
| miR-320c | ENAH | ENSG00000154380 | 0.995 | No |
| miR-29c-3p | ENHO | ENSG00000168913 | 0.995 | No |
| miR-182-5p | FXR1 | ENSG00000114416 | 0.995 | No |
| miR-182-5p | KPNA3 | ENSG00000102753 | 0.995 | No |
| miR-26b-5p | LIN28B | ENSG00000187772 | 0.995 | No |
| miR-30e-5p | PCDH17 | ENSG00000118946 | 0.995 | No |
| miR-182-5p | RAB6B | ENSG00000154917 | 0.995 | No |
| miR-26b-5p | RHOQ | ENSG00000119729 | 0.995 | No |
| miR-221-3p | SUGT1 | ENSG00000165416 | 0.995 | No |
| miR-182-5p | TMEM115 | ENSG00000126062 | 0.995 | No |
| miR-30e-5p | TMOD2 | ENSG00000128872 | 0.995 | No |
| miR-182-5p | TNFAIP8 | ENSG00000145779 | 0.995 | No |
| miR-320c | XPO1 | ENSG00000082898 | 0.995 | No |
| miR-26b-5p | ZNF598 | ENSG00000167962 | 0.995 | No |
| miR-26b-5p | ADAM17 | ENSG00000151694 | 0.995 | Yes |
| miR-26b-5p | ADM | ENSG00000148926 | 0.995 | Yes |
| miR-26b-5p | BAG4 | ENSG00000156735 | 0.995 | Yes |
| miR-26b-5p | CCDC28A | ENSG00000024862 | 0.995 | Yes |
| miR-182-5p | CD2AP | ENSG00000198087 | 0.995 | Yes |
| miR-182-5p | CHAMP1 | ENSG00000198824 | 0.995 | Yes |
| miR-30e-5p | DPY19L1 | ENSG00000173852 | 0.995 | Yes |
| miR-26b-5p | G3BP2 | ENSG00000138757 | 0.995 | Yes |
| miR-25b-5p | HOXA5 | ENSG00000106004 | 0.995 | Yes |
| miR-30e-5p | LIN7C | ENSG00000148943 | 0.995 | Yes |
| miR-182-5p | MBNL2 | ENSG00000139793 | 0.995 | Yes |
| miR-30e-5p | MFSD6 | ENSG00000151690 | 0.995 | Yes |
| miR-26b-5p | MSMO1 | ENSG00000052802 | 0.995 | Yes |
| miR-26b-5p | OSBPL11 | ENSG00000144909 | 0.995 | Yes |
| miR-30e-5p | PICALM | ENSG00000073921 | 0.995 | Yes |
| miR-182-5p | QKI | ENSG00000112531 | 0.995 | Yes |
| miR-182-5p | S100PBP | ENSG00000116497 | 0.995 | Yes |
| miR-30e-5p | SEC23A | ENSG00000100934 | 0.995 | Yes |
| miR-29c-3p | TET2 | ENSG00000168769 | 0.995 | Yes |
| miR-26b-5p | C4orf22 | ENSG00000197826 | 0.994 | No |
| miR-182-5p | CADM2 | ENSG00000175161 | 0.994 | No |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-26b-5p | CTTNBP2NL | ENSG00000143079 | 0.994 | No |
| miR-182-5p | ELMO1 | ENSG00000155849 | 0.994 | No |
| miR-182-5p | EOMES | ENSG00000163508 | 0.994 | No |
| miR-26b-5p | ERC2 | ENSG00000187672 | 0.994 | No |
| miR-30e-5p | FAM110B | ENSG00000169122 | 0.994 | No |
| miR-182-5p | FAM78A | ENSG00000126882 | 0.994 | No |
| miR-30e-5p | GCNT2 | ENSG00000111846 | 0.994 | No |
| miR-182-5p | HAS2 | ENSG00000170961 | 0.994 | No |
| miR-26b-5p | LSM12 | ENSG00000161654 | 0.994 | No |
| miR-182-5p | MAST4 | ENSG00000069020 | 0.994 | No |
| miR-182-5p | NUP107 | ENSG00000111581 | 0.994 | No |
| miR-30e-5p | PLA2G2C | ENSG00000187980 | 0.994 | No |
| miR-26b-5p | PRKCQ | ENSG00000065675 | 0.994 | No |
| miR-30e-5p | REV1 | ENSG00000135945 | 0.994 | No |
| miR-221-3p | RIMS3 | ENSG00000117016 | 0.994 | No |
| miR-182-5p | RNF208 | ENSG00000212864 | 0.994 | No |
| miR-30e-5p | SGCB | ENSG00000163069 | 0.994 | No |
| miR-26b-5p | SSX2IP | ENSG00000117155 | 0.994 | No |
| miR-182-5p | TNFSF11 | ENSG00000120659 | 0.994 | No |
| miR-182-5p | TSPAN9 | ENSG00000011105 | 0.994 | No |
| miR-30e-5p | YPEL2 | ENSG00000175155 | 0.994 | No |
| miR-26b-5p | ZNF430 | ENSG00000118620 | 0.994 | No |
| miR-29c-3p | ARID1B | ENSG00000049618 | 0.994 | Yes |
| msR-320c | BVES | ENSG00000112276 | 0.994 | Yes |
| miR-26b-5p | CD200 | ENSG00000091972 | 0.994 | Yes |
| miR-26b-5p | FAM136A | ENSG00000035141 | 0.994 | Yes |
| miR-182-5p | FAM188A | ENSG00000148481 | 0.994 | Yes |
| miR-30e-5p | GALNT3 | ENSG00000115339 | 0.994 | Yes |
| miR-320c | GSPT1 | ENSG00000103342 | 0.994 | Yes |
| miR-320c | HELZ | ENSG00000198265 | 0.994 | Yes |
| miR-29c-3p | KDM6B | ENSG00000132510 | 0.994 | Yes |
| miR-29c-3p | LAMA2 | ENSG00000196569 | 0.994 | Yes |
| miR-26b-5p | LRRC2 | ENSG00000163827 | 0.994 | Yes |
| miR-26b-5p | MIER3 | ENSG00000155545 | 0.994 | Yes |
| miR-29c-3p | NOVA1 | ENSG00000139910 | 0.994 | Yes |
| miR-30e-5p | PPWD1 | ENSG00000113593 | 0.994 | Yes |
| miR-26b-5p | RPS6KA6 | ENSG00000072133 | 0.994 | Yes |
| miR-30e-5p | SEC24A | ENSG00000113615 | 0.994 | Yes |
| miR-182-5p | SH3BGRL | ENSG00000131171 | 0.994 | Yes |
| miR-30e-5p | SNX16 | ENSG00000104497 | 0.994 | Yes |
| miR-29c-3p | TMEM178B | ENSG00000261115 | 0.994 | Yes |
| miR-29c-3p | TNFAiP3 | ENSG00000118503 | 0.994 | Yes |
| miR-30e-5p | TWF1 | ENSG00000151239 | 0.994 | Yes |
| miR-30e-5p | VKORC1L1 | ENSG00000196715 | 0.994 | Yes |
| miR-320c | ZNF117 | ENSG00000152926 | 0.994 | Yes |
| miR-26b-5p | ANKS1B | ENSG00000185046 | 0.993 | No |
| miR-320c | BX255923.1 | ENSG00000196400 | 0.993 | No |
| miR-29c-3p | CAMK4 | ENSG00000152495 | 0.993 | No |
| miR-182-5p | CELF2 | ENSG00000048740 | 0.993 | No |
| miR-182-5p | DAB1 | ENSG00000173406 | 0.993 | No |
| miR-182-5p | DCUN1D3 | ENSG00000188215 | 0.993 | No |
| miR-320c | FAM89A | ENSG00000182118 | 0.993 | No |
| msR-182-5p | FMR1 | ENSG00000102081 | 0.993 | No |
| miR-26b-5p | GPR52 | ENSG00000203737 | 0.993 | No |
| miR-30e-5p | HNRNPA3 | ENSG00000170144 | 0.993 | No |
| miR-221-3p | IRX5 | ENSG00000176842 | 0.993 | No |
| miR-26b-5p | KBTBD8 | ENSG00000163376 | 0.993 | No |
| miR-182-5p | QPN1MW | ENSG00000147380 | 0.993 | No |
| msR-30e-5p | RAP1B | ENSG00000127314 | 0.993 | No |
| miR-25b-5p | RBM46 | ENSG00000151962 | 0.993 | No |
| miR-29c-3p | RHOBTB1 | ENSG00000072422 | 0.993 | No |
| miR-30e-5p | RTKN2 | ENSG00000182010 | 0.993 | No |
| miR-182-5p | SAE1 | ENSG00000142230 | 0.993 | No |
| miR-182-5p | SC5D | ENSG00000109929 | 0.993 | No |
| miR-182-5p | SNAP23 | ENSG00000092531 | 0.993 | No |
| miR-30e-5p | SOCS6 | ENSG00000170677 | 0.993 | No |
| miR-26b-5p | SYT10 | ENSG00000110975 | 0.993 | No |
| miR-30e-5p | TTBK1 | ENSG00000146216 | 0.993 | No |
| miR-26b-5p | TTC13 | ENSG00000143643 | 0.993 | No |
| miR-29c-3p | BRWD3 | ENSG00000165288 | 0.993 | Yes |
| miR-26b-5p | CAMSAP1 | ENSG00000130559 | 0.993 | Yes |
| miR-26b-5p | DNAJC21 | ENSG00000168724 | 0.993 | Yes |
| miR-30e-5p | FAP | ENSG00000078098 | 0.993 | Yes |
| miR-26b-5p | GAN | ENSG00000261609 | 0.993 | Yes |
| msR-182-Sp | GMFB | ENSG00000197045 | 0.993 | Yes |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | GNPDA1 | ENSG00000113552 | 0.993 | Yes |
| miR-25b-5p | GPALPP1 | ENSG00000133114 | 0.993 | Yes |
| miR-182-5p | HOOK3 | ENSG00000168172 | 0.993 | Yes |
| miR-182-5p | INO80C | ENSG00000153391 | 0.993 | Yes |
| miR-182-5p | LIMS1 | ENSG00000159756 | 0.993 | Yes |
| miR-182-5p | MECOM | ENSG0000085276 | 0.993 | Yes |
| miR-29c-3p | MYBL2 | ENSG00000101057 | 0.993 | Yes |
| miR-30e-5p | MYO5A | ENSG00000197535 | 0.993 | Yes |
| miR-30e-5p | NFATC3 | ENSG00000072736 | 0.993 | Yes |
| miR-30e-5p | NFIB | ENSG00000147862 | 0.993 | Yes |
| miR-182-5p | NT5DC5 | ENSG00000111696 | 0.993 | Yes |
| miR-182-5p | OTUD6B | ENSG00000155100 | 0.993 | Yes |
| miR-182-5p | PCNX | ENSG00000100731 | 0.993 | Yes |
| msR-29c-3p | PDIK1L | ENSG30000175087 | 0.993 | Yes |
| miR-182-5p | RDX | ENSG90000137710 | 0.993 | Yes |
| miR-30e-5p | RFX7 | ENSG00000181827 | 0.993 | Yes |
| miR-182-5p | TMEM245 | ENSG00000106771 | 0.993 | Yes |
| miR-26b-5p | TNRC6C | ENSG00000078687 | 0.993 | Yes |
| miR-30e-5p | UBN1 | ENSG00000118900 | 0.993 | Yes |
| miR-30e-5p | YOD1 | ENSG00000180667 | 0.993 | Yes |
| miR-182-5p | ZFP36L1 | ENSG00000185650 | 0.993 | Yes |
| miR-182-5p | ZNF200 | ENSG00000010539 | 0.993 | Yes |
| miR-30e-5p | ANO4 | ENSG00000151572 | 0.992 | No |
| miR-26b-5p | ART3 | ENSG00000156219 | 0.992 | No |
| miR-26b-5p | BOD1 | ENSG00000145919 | 0.992 | No |
| miR-182-5p | BRMS1L | ENSG00000100916 | 0.992 | No |
| miR-320c | C1orf95 | ENSG00000203685 | 0.992 | No |
| miR-30e-5p | CHST1 | ENSG00000175264 | 0.992 | No |
| miR-221-3p | DMRT3 | ENSG00000064218 | 0.992 | No |
| miR-29c-3p | FER | ENSG00000151422 | 0.992 | No |
| miR-30e-5p | GATM | ENSG00000171766 | 0.992 | No |
| miR-182-5p | KIAA1324L | ENSG00000164659 | 0.992 | No |
| miR-30e-5p | KLHL2 | ENSG00000109466 | 0.992 | No |
| miR-30e-5p | LMLN | ENSG00000185621 | 0.992 | No |
| miR-30e-5p | OXR1 | ENSG00000164830 | 0.992 | No |
| miR-26b-5p | PAPD4 | ENSG00000164329 | 0.992 | No |
| miR-26b-5p | POM121C | ENSG00000272391 | 0.992 | No |
| miR-26b-5p | SAMD8 | ENSG00000156671 | 0.992 | No |
| miR-182-5p | SH3RF2 | ENSG00000156463 | 0.992 | No |
| miR-182-5p | SLC35B4 | ENSG00000205060 | 0.992 | No |
| miR-30e-5p | TENM1 | ENSG00000009694 | 0.992 | No |
| miR-29c-3p | TRIB2 | ENSG00000071575 | 0.992 | No |
| miR-30e-5p | VPS26B | ENSG00000151502 | 0.992 | No |
| miR-30e-5p | YTHDC1 | ENSG00000083896 | 0.992 | No |
| miR-182-5p | AGO3 | ENSG00000126070 | 0.992 | Yes |
| miR-30e-5p | ELL2 | ENSG00000118985 | 0.992 | Yes |
| miR-182-5p | GPATCH8 | ENSG00000186566 | 0.992 | Yes |
| miR-182-5p | SLAIN2 | ENSG00000109171 | 0.992 | Yes |
| miR-30e-5p | SRSF7 | ENSG00000115875 | 0.992 | Yes |
| miR-26b-5p | TBC1D15 | ENSG00000121749 | 0.992 | Yes |
| miR-30e-5p | UBE3C | ENSG00000009335 | 0.992 | Yes |
| miR-26b-5p | ALDH5A1 | ENSG00000112294 | 0.991 | No |
| miR-26b-5p | ARPP21 | ENSG00000172995 | 0.991 | No |
| miR-182-5p | C17orf66 | ENSG00000172653 | 0.991 | No |
| miR-182-5p | CLCN5 | ENSG00000171365 | 0.991 | No |
| miR-30e-5p | CNKSR2 | ENSG00000149970 | 0.991 | No |
| miR-320c | EBF2 | ENSG00000221818 | 0.991 | No |
| miR-265b-5p | HPGD | ENSG00000164120 | 0.991 | No |
| miR-30e-5p | IL1RAPL2 | ENSG00000189108 | 0.991 | No |
| miR-30e-5p | LIN28A | ENSG00000131914 | 0.991 | No |
| miR-182-5p | LMTK2 | ENSG00000164715 | 0.991 | No |
| miR-320c | MMP16 | ENSG00000156103 | 0.991 | No |
| miR-320c | PLXNC1 | ENSG00000136040 | 0.991 | No |
| miR-26b-5p | PWWP2A | ENSG00000170234 | 0.991 | No |
| miR-182-5p | REV1 | ENSG00000135945 | 0.991 | No |
| msR-182-5p | TRIM52 | ENSG00000183718 | 0.991 | No |
| miR-182-5p | ZBTB37 | ENSG00000185278 | 0.991 | No |
| miR-30e-5p | ZMYND8 | ENSG00000101040 | 0.991 | No |
| miR-30e-5p | ADRA2A | ENSG00000150594 | 0.991 | Yes |
| miR-26b-5p | BFAR | ENSG00000103429 | 0.991 | Yes |
| miR-29c-3p | C7orf60 | ENSG00000164603 | 0.991 | Yes |
| miR-30e-5p | CCDC97 | ENSG00000142039 | 0.991 | Yes |
| miR-29c-3p | CLMN | ENSG00000165959 | 0.991 | Yes |
| miR-26b-5p | CTH | ENSG00000116761 | 0.991 | Yes |
| miR-30e-5p | FOSL2 | ENSG00000075426 | 0.991 | Yes |

TABLE 7-continued

Gene targets for the six miRNAs of interest in concussion
(mRNAs targeted by >1 miRNA are highlighted)

| MicroRNA | mRNA target | Ensembl ID | MicroT-CDS score | Experimentally Validated |
|---|---|---|---|---|
| miR-30e-5p | KLF10 | ENSG00000155090 | 0.991 | Yes |
| miR-30e-5p | MZT1 | ENSG00000204899 | 0.991 | Yes |
| miR-182-5p | PPP3R1 | ENSG00000221823 | 0.991 | Yes |
| miR-26b-5p | RCBTB1 | ENSG00000136144 | 0.991 | Yes |
| miR-29c-3p | SPARC | ENSG00000113140 | 0.991 | Yes |
| miR-26b-5p | TNRC6A | ENSG00000090905 | 0.991 | Yes |
| miR-30e-5p | XPO1 | ENSG00000082896 | 0.991 | Yes |
| miR-320c | ABI2 | ENSG00000138443 | 0.99 | No |
| miR-182-5p | ARHGEF7 | ENSG00000102606 | 0.99 | No |
| miR-320c | CDK13 | ENSG00000065883 | 0.99 | No |
| miR-30e-5p | HDAC5 | ENSG00000108840 | 0.99 | No |
| miR-29c-3p | MXD1 | ENSG00000059728 | 0.99 | No |
| miR-182-5p | OAS3 | ENSG00000111331 | 0.99 | No |
| miR-26b-5p | PAN3 | ENSG00000152520 | 0.99 | No |
| miR-30e-5p | SLC30A4 | ENSG00000104154 | 0.99 | No |
| miR-30e-5p | STX2 | ENSG00000111450 | 0.99 | No |
| miR-320c | TGOLN2 | ENSG00000152291 | 0.99 | No |
| miR-182-5p | MED1 | ENSG00000125686 | 0.99 | Yes |
| miR-30e-5p | NOL4L | ENSG00000197183 | 0.99 | Yes |
| miR-30e-5p | PHF16 | ENSG00000102221 | 0.99 | Yes |
| miR-30e-5p | RAB23 | ENSG00000112210 | 0.99 | Yes |
| miR-30e-5p | RUNX1 | ENSG00000159216 | 0.99 | Yes |
| miR-26b-5p | TTPAL | ENSG00000124120 | 0.99 | Yes |
| miR-30e-5p | SCNBA | ENSG00000196876 | 0.371 | No |

The data in the tables above will permit one skilled in the art to select particular miRNAs or subsets of miRNAs suitable for the methods disclosed herein.

Figure 30:
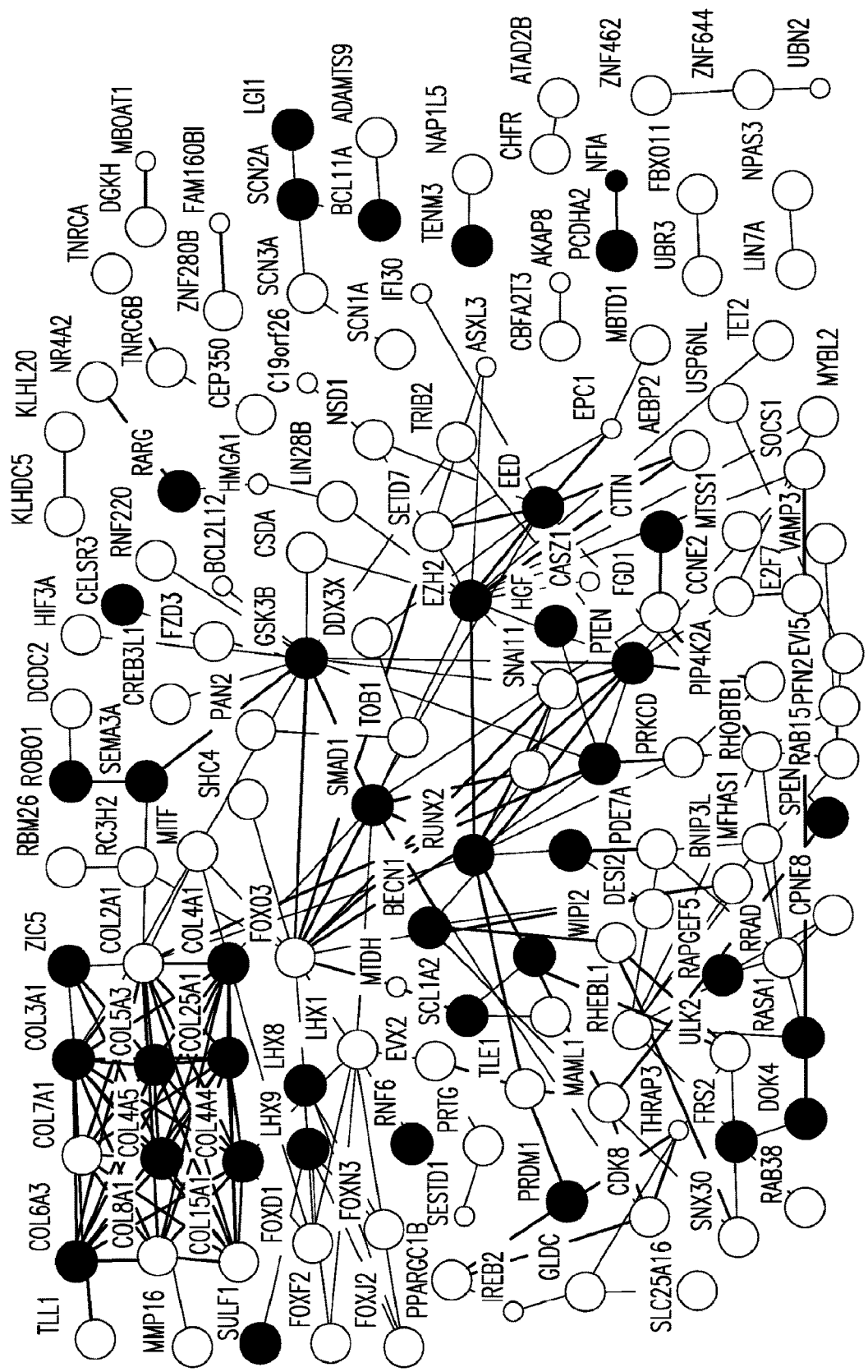
FIG. 30 shows a protein interaction network for high-confidence mRNA targets. This network includes 280 mRNAs targeted by the six miRNAs of interest interrogated in String v10 software. Of the 280 mRNAs, 247 have protein products with functional interactions, which represents a clustering coefficient of 0.775 and exceeds the number of interactions expected by chance alone (p<0.0001). The mRNAs in red represent those functionally related to nervous system development (61 genes; p=8.56E-09). Large nodes have known three-dimensional structures, while small node structures are unknown. Edge width defines the meaningfulness of the interaction, with thick edges representing experimentally determined co-expression or homology.

There were 34 mRNAs targeted by more than one miRNA. The 700 mRNA targets had significant associations with 30 GO categories (Table 8). Notably, there was significant enrichment for mRNA targets associated with nervous system development (p=2.67E-07), a pathway including 37 genes targeted by four miRNAs (miR-182-5p, miR-29c-3p, miR-30e-5p, and miR-320c). Protein-protein interaction networks were defined for the 280 of the highest confidence mRNA targets (microT-CDS score≥0.999) in String v10. This analysis identified a significant protein-protein interaction network (p<0.0001) containing 269 nodes and 247 edges with a clustering coefficient of 0.775 (FIG. 30). Analysis of this network identified 67 biologic processes with significant enrichment (Table 8B) including nervous system development (61 genes; p=8.56E-09), neuron development (29 genes; p=8.45E-05), and axon development (21 genes; p=4.89E-04).

TABLE 8

Gene Ontology (GO) categories with targeted enrichment by the six miRNAs of interest

| GO Category | p-valus | #genes | #miRNAs |
|---|---|---|---|
| ion binding | 9.70E-19 | 256 | 6 |
| organelle | 1.14E-18 | 364 | 6 |
| cellular protein modification process | 4.42E-11 | 113 | 5 |
| extracellular matrix disassembly | 4.22E-10 | 18 | 5 |
| collagen catabolic process | 2.36E-09 | 16 | 4 |
| nervous system development | 2.68E-07 | 37 | 4 |
| cellular nitrogen compound metabolic process | 2.68E-07 | 171 | 6 |
| extracellular matrix organization | 3.81E-07 | 31 | 5 |
| cellular_component | 4.20E-07 | 592 | 6 |
| molecular_function | 2.04E-06 | 583 | 6 |
| Fc-epsilon receptor signaling pathway | 2.13E-06 | 15 | 4 |
| neurotrophin TRK receptor signaling pathway | 1.95E-05 | 18 | 4 |
| catabolic process | 7.89E-05 | 81 | 5 |
| biosynthetic process | 0.000339672 | 140 | 6 |
| epidermal growth factor receptor signaling pathway | 0.000477945 | 16 | 4 |
| axon guidance | 0.000769255 | 29 | 5 |
| protein binding transcription factor activity | 0.001718716 | 26 | 4 |
| btolagical_process | 0.001751363 | 562 | 6 |
| post-translational protein modification | 0.001907822 | 12 | 3 |
| phosphatidylinositol-medlated signaling | 0.002290475 | 12 | 4 |
| nucleic acid binding transcription factor activity | 0.002349644 | 44 | 6 |
| protein complex | 0.003538065 | 138 | 6 |
| cell adhesion | 0.004557418 | 51 | 5 |
| hemophilic cell adhesion via plasma membrane adhesion molecules | 0.007172356 | 22 | 3 |
| extracellular matrix structural constituent | 0.015279057 | 10 | 2 |
| fibroblast growth factor receptor signaling pathway | 0.015279057 | 13 | 4 |
| endoplasmic reticulum lumen | 0.020376758 | 13 | 3 |
| protein O-linked glycosylation via serine | 0.026008691 | 3 | 1 |

TABLE 8-continued

Gene Ontology (GO) categories with targeted enrichment by the six miRNAs of interest

| GO Category | p-valus | #genes | #miRNAs |
| --- | --- | --- | --- |
| JAK-STAT cascade involved in growth hormone signaling pathway | 0.042937767 | 4 | 2 |
| cytoskeletal protein binding | 0.048083642 | 33 | 5 |

TABLE 9

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
| --- | --- | --- | --- | --- |
| GO.0007156 | homophilic cell adhesion via plasma membrane adhesion molecules | 19 | 4.37E−10 | CDH20, CELSR3, PCDH10, PCDHA1, PCDHA10, PCDHA11, PCDHA12, PCDHA13, PCDHA2, PCDHA3, PCDHA4, PCDHA5, PCDHA6, PCDHA7, PCDHA8, PCDHAC1, PCDHAC2, ROBO1, TENM3 |
| GO.0007275 | multicellular organismal development | 97 | 6.92E−09 | ACVR1, ADAM19, ADAMTS9, ATP11C, BCL11A, BECN1, CASZ1, CBFA2T3, CELSR3, CHAC1, CHST2, COL15A1, COL25A1, COL2A1, COL4A1, COL4A4, COL4A5, COL5A3, COL6A3, COL7A1, CREB3L1, CSDA, CTTN, DOK4, E2F7, EED, EPC1, EVI5, EVX2, EZH2, FEM1B, FGD1, FOXD1, FOXO3, FRS2, GRIP1, GSK3B, HIF3A, IGF1, KIAA2022, KIF26B, LGI1, LHX8, LIN7A, MAB21L1, MAML1, MBTD1, MITF, MMP16, NAB1, NFIA, NRN1, NT5E, NUS1, PCDHA1, PCDHA10, PCDHA11, PCDHA2, PCDHA3, PCDHA4, PCDHA5, PCDHA6, PCDHA7, PCDHA8, PCDHAC1, PCDHAC2, PIP4K2A, PLAGL2, PPARGC1B, PRDM1, PRTG, PTEN, RAPGEF5, RARG, RASA1, RC3H2, RFX6, RNF6, ROBO1, SCN2A, SEMA3A, SLC1A2, SLC7A11, SNAI1, SOCS1, SPEN, ST6GAL2, ST8SIA4, STOX2, SULF1, SYNGR3, TENM3, TET3, TLE1, TLL1, TTLL7, ZIC5 |
| GO.0044767 | single-organism developmental process | 104 | 6.99E−09 | ACVR1, ADAM19, ADAMTS9, ATP11C, BCL11A, BECN1, CASZ1, CBFA2T3, CELSR3, CHAC1, CHST2, COL15A1, COL25A1, COL2A1, COL4A1, COL4A4, COL4A5, COL5A3, COL6A3, COL7A1, CREB3L1, CSDA, CTTN, DOK4, E2F7, EED, EPC1, EVI5, EVX2, EZH2, FEM1B, FGD1, FOXD1, FOXJ2, FRS2, GRIP1, GSK3B, HIF3A, HMGA1, IGF1, KIAA2022, KIF26B, LGI1, LHX8, LIN7A, MAB21L1, MAML1, MBTD1, MMP16, NAB1, NFIA, NRN1, NT5E, NUS1, PCDHA1, PCDHA10, PCDHA11, PCDHA2, PCDHA3, PCDHA4, PCDHA5, PCDHA6, PCDHA7, PCDHA8, PCDHAC1, PCDHAC2, PIP4K2A, PLAGL2, PPARGC1B, PRDM1, PRKCD, PRTG, PTEN, RAB38, RAPGEF5, RARG, RASA1, RBM24, RC3H2, RFX6, RNF6, ROBO1, SCN2A, SEMA3A, SHC4, SLC1A2, SLC7A11, SNAI1, SOCS1, SPEN, ST6GAL2, ST8SIA4, STOX2, STRADB, SULF1, SYNGR3, TENM3, TET3, TLE1, TLL1, TTLL7, UBE2J1, VAMP3, ZIC5 |
| GO.0048731 | system development | 88 | 6.99E−09 | ACVR1, ADAM19, ATP11C, BCL11A, BECN1, CBFA2T3, CELSR3, CHAC1, COL15A1, COL25A1, COL2A1, COL4A1, COL4A4, COL4A5, COL5A3, COL6A3, COL8A1, CSDA, CTTN, DOK4, E2F7, EED, EPC1, EZH2, FEM1B, FGD1, FOXD1, FOXO3, FRS2, GRIP1, GSK3B, HIF3A, IGF1, KIAA2022, KIF26B, LGI1, LHX8, LIN7A, MAB21L1, MAML1, MBTD1, MITF, MMP16, NAB1, NFIA, NRN1, NT5E, NUS1, PCDHA1, PCDHA10, PCDHA11, PCDHA2, PCDHA3, PCDHA4, PCDHA5, PCDHA6, PCDHA7, PCDHA8, PCDHAC1, PCDHAC2, PIP4K2A, PPARGC1B, PRDM1, PTEN, RAPGEF5, RARG, RASA1, RC3H2, RFX6, RNF6, ROBO1, SCN2A, SEMA3A, SLC1A2, SLC7A11, SMAD1, SNAI1, SOCS1, SPEN, ST8SIA4, STOX2, SULF1, SYNGR3, TENM3, TLE1, TLL1, TTLL7, ZIC5 |
| GO.0007399 | nervous system development | 61 | 8.56E−09 | BCL11A, BECN1, CELSR3, CHAC1, COL25A1, COL3A1, COL4A1, COL4A4, COL4A5, COL5A3, COL6A3, CTTN, DOK4, EED, EZH2, FRS2, GRIP1, GSK3B, HGF, IGF1, KIAA2022, LGI1, LHX8, LHX9, NAB1, NFIA, NRN1, NT5E, PCDHA1, PCDHA10, PCDHA11, PCDHA2, PCDHA3, PCDHA4, PCDHA5, PCDHA6, PCDHA7, PCDHA8, PCDHAC1, PCDHAC2, PRDM1, PTEN, RAPGEF5, RARG, RASA1, RNF6, ROBO1, RUNX2, SCN2A, SEMA3A, SLC1A2, SLC7A11, SMAD1, SPEN, ST8SIA4, SULF1, SYNGR3, TENM3, TTLL7, ZIC5, ZNF238 |
| GO.0032502 | developmental process | 104 | 8.56E−09 | ACVR1, ADAM19, ADAMTS9, ATP11C, BCL11A, BECN1, CASZ1, CBFA2T3, CELSR3, CHAC1, CHST2, COL15A1, COL25A1, COL2A1, COL4A1, COL4A4, COL4A5, COL5A3, COL6A3, COL7A1, CREB3L1, CSDA, CTTN, DOK4, E2F7, EED, EPC1, EVI5, EVX2, EZH2, FEM1B, FGD1, FOXD1, FOXJ2, FRS2, GRIP1, GSK3B, HIF3A, HMGA1, IGF1, KIAA2022, KIF26B, LGI1, LHX8, LIN7A, MAML1, MBTD1, MMP16, NFIA, NPAS3, NRN1, NT5E, NUS1, PCDHA1, PCDHA10, PCDHA11, PCDHA2, PCDHA3, PCDHA4, PCDHA5, PCDHA6, PCDHA7, PCDHA8, PCDHAC1, PCDHAC2, PIP4K2A, PLAGL2, PPARGC1B, PRDM1, PRKCD, PRTG, PTEN, RAB38, RAPGEF5, RARG, RASA1, RBM24, RC3H2, RFX6, RNF6, ROBO1, SCN2A, SEMA3A, SHC4, SLC1A2, SLC7A11, SNAI1, SOCS1, SPEN, ST6GAL2, ST8SIA4, STOX2, STRADB, SULF1, SYNGR3, TENM3, TET3, TLE1, TLL1, TTLL7, UBE2J1, VAMP3, ZIC5 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0010628 | positive regulation of gene expression | 53 | 9.73E-08 | ACVR1, ARF4, ATAD2B, BCL11A, BCL2L12, CDK8, CREB3L1, CSDA, DDX3X, E2F7, EPC1, ERLIN1, FOXD1, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, PLAGL2, PPARGC1B, PRDM1, PTEN, RARG, RFX6, RHEBL1, RLF, RNF6, RUNX2, SETD7, SMAD1, SNAI1, SPEN, TET2, TET3, THRAP3, TLE1, TNRC6B, TOB1, TP53INP1, ZNF462 |
| GO.0030574 | collagen catabolic process | 12 | 1.73E-07 | COL15A1, COL25A1, COL2A1, COL3A1, COL4A1, COL4A4, COL4A5, COL5A3, COL6A3, COL7A1, COL8A1, MMP16 |
| GO.0051254 | positive regulation of RNA metabolic process | 48 | 3.43E-07 | ACVR1, ARF4, ATAD2B, BCL11A, BCL2L12, CDK8, CREB3L1, DDX3X, E2F7, EPC1, ERLIN1, FOXF2, FOXJ2, FOXO3, GRIP1, GSK3B, HGF, HIF3A, HMGA1, IGF1, LHX1, MITF, MTDH, MYBL2, NFIA, NPAS3, NR4A2, NSD1, PLAGL2, PPARGC1B, PTEN, RARG, RFX6, RHEBL1, RLF, RNF6, RUNX2, SETD7, SMAD1, SNAI1, SPEN, TET2, TET3, THRAP3, TNRC6B, TOB1, TP53INP1, ZNF462 |
| GO.0045893 | positive regulation of transcription, DNA-templated | 46 | 6.08E-07 | ACVR1, ARF4, ATAD2B, BCL11A, BCL2L12, CDK8, CREB3L1, DDX3X, E2F7, EPC1, ERLIN1, FOXF2, FOXJ2, FOXO3, GRIP1, GSK3B, HGF, HIF3A, HMGA1, IGF1, LHX1, MITF, MTDH, MYBL2, NFIA, NPAS3, NR4A2, NSD1, PLAGL2, PPARGC1B, PTEN, RARG, RFX6, RHEBL1, RLF, RNF6, RUNX2, SETD7, SMAD1, SNAI1, SPEN, TET2, TET3, THRAP3, TP53INP1, ZNF462 |
| GO.0048856 | anatomical structure development | 90 | 7.54E-07 | ACVR1, ADAM19, ATP11C, BCL11A, BECN1, CBFA2T3, CELSR3, CHAC1, COL15A1, COL25A1, COL2A1, COL4A1, COL4A4, COL4A5, COL5A3, COL6A3, COL7A1, CSDA, CTTN, DOK4, E2F7, EED, EPC1, EVX2, EZH2, FEM1B, FGD1, FOXD1, FOXJ2, FRS2, GRIP1, GSK3B, HIF3A, IGF1, KIAA2022, KIF26B, LGI1, LHX8, LIN7A, MAML1, MBTD1, MMP16, NAB1, NFIA, NRN1, NT5E, NUS1, PCDHA1, PCDHA10, PCDHA11, PCDHA2, PCDHA3, PCDHA5, PCDHA6, PCDHA7, PCDHA8, PCDHAC1, PCDHAC2, PIP4K2A, PPARGC1B, PRDM1, PTEN, RAPGEF5, RARG, RASA1, RC3H2, RFX6, RNF6, ROBO1, SCN2A, SEMA3A, SLC1A2, SLC7A11, SNAI1, SOCS1, SPEN, ST8SIA4, STOX2, STRADB, SULF1, SYNGR3, TENM3, TET3, TLE1, TLL1, TTLL7, UBE2J1, VAMP3, ZIC5 |
| GO.0051173 | positive regulation of nitrogen compound metabolic process | 51 | 1.51E-06 | ACVR1, ARF4, ATAD2B, BCL11A, BCL2L12, CDK8, CREB3L1, CSDA, DDX3X, E2F7, EPC1, ERLIN1, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, PLAGL2, PPARGC1B, PRKCD, PTEN, RARG, RFX6, RHEBL1, RLF, RNF6, RUNX2, SETD7, SMAD1, SNAI1, SPEN, TET2, TET3, THRAP3, TNRC6B, TOB1, TP53INP1, ZNF462 |
| GO.0022617 | extracellular matrix disassembly | 13 | 1.94E-06 | COL15A1, COL25A1, COL2A1, COL3A1, COL4A1, COL4A4, COL4A5, COL5A3, COL6A3, COL7A1, COL8A1, MMP16, TLL1 |
| GO.0010557 | positive regulation of macromolecule biosynthetic process | 48 | 2.46E-06 | ACVR1, ARF4, ATAD2B, BCL11A, BCL2L12, CDK8, CREB3L1, CSDA, DDX3X, E2F7, EPC1, ERLIN1, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, PLAGL2, PPARGC1B, PTEN, RARG, RFX6, RHEBL1, RLF, RNF6, RUNX2, SETD7, SMAD1, SNAI1, SPEN, TET2, TET3, THRAP3, TP53INP1, ZNF462 |
| GO.0009891 | positive regulation of biosynthetic process | 50 | 5.06E-06 | ACVR1, ARF4, ATAD2B, BCL11A, BCL2L12, CDK8, CREB3L1, CSDA, DDX3X, E2F7, EPC1, ERLIN1, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, NT5E, PLAGL2, PPARGC1B, PRKCD, PTEN, RARG, RFX6, RHEBL1, RLF, RNF6, RUNX2, SETD7, SMAD1, SNAI1, SPEN, TET2, TET3, THRAP3, TP53INP1, ZNF462 |
| GO.0031328 | positive regulation of cellular biosynthetic process | 49 | 6.91E-06 | ACVR1, ARF4, ATAD2B, BCL11A, BCL2L12, CDK8, CREB3L1, CSDA, DDX3X, E2F7, EPC1, ERLIN1, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, PLAGL2, PPARGC1B, PRKCD, PTEN, RARG, RFX6, RHEBL1, RLF, RNF6, RUNX2, SETD7, SMAD1, SNAI1, SPEN, TET2, TET3, THRAP3, TP53INP1, ZNF462 |
| GO.0044707 | single-multicellular organism process | 103 | 3.15E-05 | ACVR1, ADAM19, ADAMTS9, ATP11C, ATP8A1, BCL11A, BECN1, CASZ1, CBFA2T3, CELSR3, CHAC1, CHST2, COL15A1, COL2A1, COL4A1, COL4A4, COL4A5, COL5A3, COL6A3, COL7A1, CREB3L1, CSDA, CTTN, DGKH, DOK4, E2F7, EED, EPC1, EVI5, EVX2, EZH2, FBXO11, FEM1B, FGD1, FOXD1, FOXO3, FRS2, GRIP1, GSK3B, HIF3A, IGF1, JPH4, KCNJ2, KIAA2022, KIF26B, LGI1, LHX8, LIN7A, MAB21L1, MAML1, MBTD1, MITF, MMP16, NAB1, NFIA, NPAS3, NRN1, NT5E, NUS1, PAIP2, PCDHA1, PCDHA10, PCDHA11, PCDHA2, PCDHA3, PCDHA4, PCDHA5, PCDHA6, PCDHA7, PCDHA8, PCDHAC1, PCDHAC2, PIP4K2A, PPARGC1B, PRDM1, PRTG, PTEN, RAPGEF5, RARG, RASA1, RC3H2, RFX6, RNF6, ROBO1, SCN2A, SCN3A, SEMA3A, SLC1A2, SNAI1, SOCS1, SPEN, ST6GAL2, ST8SIA4, STK39, STOX2, SULF1, SYNGR3, TENM3, TET3, TLE1, TLL1, TTLL7, ZIC5 |
| GO.0006357 | regulation of transcription from RNA polymerase II promoter | 46 | 4.92E-05 | ACVR1, AEBP2, ARF4, ATAD2B, BCL11A, BCL2L12, BRWD1, BRWD3, CBFA2T3, CDK8, CREB3L1, DDX3X, EED, EPC1, ERLIN1, FOXD1, FOXF2, FOXJ2, FOXO3, GSK3B, HGF, HIF3A, IGF1, MITF, MTDH, MYBL2, NFIA, NPAS3, NSD1, PLAGL2, PPARGC1B, PRDM1, RARG, RFX6, RLF, RUNX2, SMAD1, SNAI1, SPEN, TET2, TET3, THRAP3, TLE1, UBN2, ZNF238, ZNF462 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0010604 | positive regulation of macromolecule metabolic process | 62 | 5.13E−05 | ACVR1, ARF4, ATAD2B, BCL11A, BCL2L12, CDK8, CHFR, CREB3L1, CSDA, DDX3X, E2F7, EED, EPC1, ERLIN1, EZH2, FOXD1, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, PFN2, PLAGL2, PRDM1, PRKCD, PTEN, RARG, RFX6, RHEBL1, RLF, RNF6, ROBO1, RUNX2, SETD7, SMAD1, SNAI1, SPEN, STK39, STRADB, TET2, TET3, THRAP3, TLE1, TNRC6B, TOB1, TP53INP1, TRIB2, VAMP3, ZNF462 |
| GO.0032501 | multicellular organismal process | 105 | 5.67E−05 | ACVR1, ADAM19, ADAMTS9, ATP11C, ATP8A1, BCL11A, BECN1, CASZ1, CBFA2T3, CELSR3, CHAC1, CHST2, COL15A1, COL2A1, COL4A1, COL4A4, COL4A5, COL5A3, COL6A3, COL7A1, CREB3L1, CSDA, CTTN, DGKH, DOK4, E2F7, EED, EPC1, EVI5, EVX2, EZH2, FBXO11, FEM1B, FGD1, FOXD1, FOXO3, FRS2, GRIP1, GSK3B, HIF3A, IGF1, JPH4, KCNJ2, KIAA2022, KIF26B, LGI1, LHX8, LIN7A, MAB21L1, MAML1, MBTD1, MITF, MMP16, NAB1, NFIA, NPAS3, NRN1, NT5E, NUS1, PAIP2, PCDHA1, PCDHA10, PCDHA11, PCDHA2, PCDHA3, PCDHA4, PCDHA5, PCDHA6, PCDHA7, PCDHA8, PCDHAC1, PCDHAC2, PIP4K2A, PPARGC1B, PRDM1, PRTG, PTEN, RAPGEF5, RARG, RASA1, RC3H2, RFX6, RNF6, ROBO1, SCN2A, SCN3A, SEMA3A, SLC1A2, SNAI1, SOCS1, SPEN, ST6GAL2, ST8SIA4, STK39, STOX2, STYX, SULF1, SYNGR3, TENM3, TET3, TLE1, TLL1, TTLL7, UBE2J1, ZIC5 |
| GO.0048518 | positive regulation of biological process | 96 | 5.78E−05 | ACVR1, ADAMTS9, ARF4, ATAD2B, ATP11C, ATP8A1, BCL11A, BCL2L12, BECN1, BNIP3L, CDK8, CHFR, COL3A1, COL8A1, CREB3L1, CSDA, CTTN, DCDC2, DCUN1D3, DDX3X, E2F7, EED, ELMOD2, EPC1, ERLIN1, EVI5, FGD1, FOXD1, FOXF2, FOXJ2, FOXO3, FZD3, GRIP1, GSK3B, HBP1, HGF, HIF3A, HMGA1, IGF1, KCNJ2, KIF26B, LARP1, LGI1, LHX1, MAB21L1, MITF, MMP16, MTDH, MTSS1, MYBL2, NFIA, NPAS3, NR4A2, NSD1, NT5E, PAN2, PFN2, PRDM1, PRKCD, PTEN, RAB15, RAPGEF5, RARG, RASA1, RC3H2, RFX6, RGS17, RHEBL1, RLF, RNF220, RNF6, ROBO1, RUNX2, SEMA3A, SETD7, SHC4, SLC1A2, SMAD1, SNAI1, SPEN, STIM2, STRADB, SULF1, SYNGR3, TBC1D10B, TENM3, TET2, TET3, THRAP3, TLE1, TNRC6B, TOB1, TRIB2, USP6NL, VAMP3, ZNF462 |
| GO.0098609 | cell-cell adhesion | 24 | 7.29E−05 | BCL11A, CDH20, CELSR3, NT5E, PCDH10, PCDHA1, PCDHA10, PCDHA11, PCDHA12, PCDHA13, PCDHA2, PCDHA3, PCDHA4, PCDHA5, PCDHA6, PCDHA7, PCDHA8, PCDHAC1, PCDHAC2, RC3H2, ROBO1, RUNX2, SLC7A11, TENM3 |
| GO.0048666 | neuron development | 29 | 8.45E−05 | ARF4, BECN1, CELSR3, COL25A1, COL2A1, COL3A1, COL4A1, COL4A4, COL4A5, COL5A3, COL6A3, CTTN, DCDC2, FZD3, GRIP1, GSK3B, LGI1, LHX1, LHX8, LHX9, NR4A2, PRDM1, PTEN, RASA1, ROBO1, SEMA3A, ST8SIA4, ULK2, ZNF238 |
| GO.0045944 | positive regulation of transcription from RNA polymerase II promoter | 33 | 8.82E−05 | ACVR1, ARF4, ATAD2B, BCL11A, BCL2L12, CDK8, CREB3L1, DDX3X, E2F7, EPC1, ERLIN1, FOXF2, FOXJ2, FOXO3, GSK3B, HGF, HIF3A, IGF1, MITF, MYBL2, NFIA, NR4A2, PLAGL2, PPARGC1B, RARG, RFX6, RLF, RUNX2, SMAD1, TET2, TET3, THRAP3, ZNF462 |
| GO.0048468 | cell development | 44 | 9.95E−05 | ACVR1, ARF4, BECN1, CELSR3, COL25A1, COL2A1, COL3A1, COL4A1, COL4A4, COL4A5, COL5A3, COL6A3, CTTN, DCDC2, FEM1B, FOXF2, FOXO3, FRS2, FZD3, GRIP1, GSK3B, HGF, IGF1, LGI1, LHX1, LHX8, LHX9, MAML1, NR4A2, PIP4K2A, PRDM1, PTEN, RARG, RASA1, ROBO1, RUNX2, SEMA3A, SNAI1, ST8SIA4, SULF1, UBE2J1, ULK2, VAMP3, ZNF238 |
| GO.0043170 | macromolecule metabolic process | 124 | 0.00017 | ACVR1, ADAM19, ADAMTS12, AEBP2, ARF4, ASXL3, BAZ2B, BCL11A, BECN1, BNIP3L, BRWD1, CASZ1, CBFA2T3, CCNE2, CDC37L1, CHST2, COL15A1, COL25A1, COL3A1, COL4A1, COL4A4, COL4A5, COL5A3, COL6A3, COL7A1, COL8A1, CPSF6, CREB3L1, CSDA, DDX3X, DESI2, DOK4, E2F7, EED, EPC1, ERLIN1, EXTL2, FBXO11, FEM1B, FOXD1, FOXF2, FOXJ2, FOXN3, FOXO3, GALNT7, GSK3B, HBP1, HGF, HIF3A, HMGA1, IGF1, IP6K3, KIAA2022, KLHDC5, KLHL20, LARP1, LHX1, LHX8, LIN28B, MAML1, MBTD1, MEX3B, MITF, MMP16, MYBL2, NAB1, NABP1, NFIA, NPAS3, NSD1, NT5E, NUS1, OTUD4, PAN2, PCMT1, PHTF2, PLAGL2, PPARGC1B, PRDM1, PRKCD, PTEN, RARG, RBM26, RC3H2, RFX6, RLF, RNF152, RNF19A, ROBO1, SENP5, SETD7, SMAD1, SOCS1, SPEN, SRP19, ST6GAL2, ST8SIA4, STK39, STRADB, STYX, SULF1, TENM3, TET3, THRAP3, TLE1, TLK1, TLL1, TNRC6A, TNRC6B, TP53INP1, TRABD2B, TTLL7, UBE2J1, UBR3, ULK2, WIPI2, ZBTB37, ZDHHC6, ZFC3H1, ZNF238, ZNF280B, ZNF462, ZNF644, ZNRF1 |
| GO.0000904 | cell morphogenesis involved in differentiation | 25 | 0.00025 | COL25A1, COL2A1, COL3A1, COL4A1, COL4A4, COL4A5, COL5A3, COL6A3, DCDC2, FOXF2, FZD3, GSK3B, HGF, LGI1, LHX1, LHX9, NR4A2, PTEN, RASA1, ROBO1, SEMA3A, SNAI1, ST8SIA4, ULK2, VAMP3 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0009653 | anatomical structure morphogenesis | 51 | 0.00025 | ACVR1, CELSR3, COL15A1, COL25A1, COL2A1, COL4A1, COL4A4, COL4A5, COL5A3, COL6A3, COL7A1, CTTN, DCDC2, E2F7, EVX2, FEM1B, FGD1, FOXD1, FOXJ2, FOXO3, FRS2, FZD3, HGF, HIF3A, IGF1, KIF26B, LGI1, LHX8, MAB21L1, MMP16, MTSS1, NAB1, NR4A2, NUS1, PMP22, PPARGC1B, PRDM1, PTEN, RARG, RASA1, ROBO1, RUNX2, SEMA3A, SMAD1, ST8SIA4, STRADB, TENM3, TET2, TLE1, ULK2, VAMP3 |
| GO.0030198 | Extracellular matrix organization | 18 | 0.00025 | COL15A1, COL25A1, COL2A1, COL3A1, COL4A1, COL4A4, COL4A5, COL5A3, COL6A3, COL7A1, COL8A1, CREB3L1, FOXF2, MFAP3, MMP16, PXDN, SULF1, TLL1 |
| GO.0031175 | neuron projection development | 25 | 0.00025 | ARF4, CELSR3, COL25A1, COL2A1, COL3A1, COL4A1, COL4A4, COL4A5, COL5A3, COL6A3, CTTN, DCDC2, FZD3, GRIP1, GSK3B, LGI1, LHX1, LHX9, NR4A2, PTEN, RASA1, ROBO1, SEMA3A, ST8SIA4, ULK2 |
| GO.0009893 | Positive regulation of metabolic process | 72 | 0.00031 | ACVR1, ARF4, ATAD2B, BCL11A, BCL2L12, CDK8, CHFR, CREB3L1, CSDA, DDX3X, E2F7, EED, ELMOD2, EPC1, ERLIN1, EVI5, EZH2, FGD1, FOXD1, FOXF2, FOXJ2, FOXO3, GRIP1, GSK3B, HGF, HIF3A, HMGA1, IGF1, LARP1, LHX1, MITF, MMP16, MTDH, MYBL2, NFIA, NPAS3, NR4A2, NSD1, NT5E, PFN2, PLAGL2, PRDM1, PRKCD, PTEN, RAPGEF5, RARG, RASA1, RFX6, RGS17, RHEBL1, RLF, RNF6, ROBO1, RUNX2, SETD7, SMAD1, SNAI1, SPEN, STK39, STRADB, TBC1D10B, TET2, TET3, THRAP3, TLE1, TNRC6B, TOB1, TP53INP1, TRIB2, USP6NL, VAMP3, ZNF462 |
| GO.0048522 | positive regulation of cellular process | 84 | 0.00034 | ACVR1, ADAMTS9, ARF4, ATAD2B, ATP11C, ATP8A1, BCL11A, BCL2L12, BECN1, BNIP3L, CDK8, CHFR, COL3A1, COL8A1, CREB3L1, CSDA, CTTN, DCDC2, DCUN1D3, DDX3X, E2F7, EED, EPC1, ERLIN1, FGD1, FOXD1, FOXF2, FOXJ2, FOXO3, FZD3, GRIP1, GSK3B, HGF, HIF3A, HMGA1, IGF1, KCNJ2, KIF26B, LARP1, LGI1, LHX1, MAB21L1, MITF, MTDH, MTSS1, MYBL2, NFIA, NPAS3, NR4A2, NSD1, PAN2, PFN2, PRDM1, PRKCD, PTEN, RAB15, RARG, RC3H2, RFX6, RHEBL1, RLF, RNF220, RNF6, ROBO1, RUNX2, SEMA3A, SETD7, SHC4, SMAD1, SNAI1, SPEN, STIM2, STK39, STRADB, SULF1, TENM3, TET2, TET3, THRAP3, TNRC6B, TOB1, TRIB2, VAMP3, ZNF462 |
| GO.0048812 | neuron projection morphogenesis | 22 | 0.00039 | COL25A1, COL2A1, COL3A1, COL4A1, COL4A4, COL4A5, COL5A3, COL6A3, CTTN, DCDC2, FZD3, GSK3B, LGI1, LHX1, LHX9, NR4A2, PTEN, RASA1, ROBO1, SEMA3A, ST8SIA4, ULK2 |
| GO.0061564 | axon development | 21 | 0.00049 | CELSR3, COL25A1, COL2A1, COL3A1, COL4A1, COL4A4, COL4A5, COL5A3, COL6A3, FZD3, GSK3B, LGI1, LHX1, LHX9, NR4A2, PTEN, RASA1, ROBO1, SEMA3A, ST8SIA4, ULK2 |
| GO.0048667 | cell morphogenesis involved in neuron differentiation | 21 | 0.00094 | COL25A1, COL2A1, COL3A1, COL4A1, COL4A4, COL4A5, COL5A3, COL6A3, DCDC2, FZD3, GSK3B, LGI1, LHX1, LHX9, NR4A2, PTEN, RASA1, ROBO1, SEMA3A, ST8SIA4, ULK2 |
| GO.0007409 | axonogenesis | 20 | 0.00096 | COL25A1, COL2A1, COL3A1, COL4A1, COL4A4, COL4A5, COL5A3, COL6A3, FZD3, GSK3B, LGI1, LHX1, LHX9, NR4A2, PTEN, RASA1, ROBO1, SEMA3A, ST8SIA4, ULK2 |
| GO.0009887 | organ morphogenesis | 28 | 0.00096 | ACVR1, COL2A1, COL3A1, COL8A1, FEM1B, FGD1, FOXD1, FOXF2, FRS2, FZD3, GSK3B, IGF1, KIF26B, LHX8, LHX9, MMP16, NAB1, PPARGC1B, PRDM1, PTEN, RARG, ROBO1, RUNX2, SEMA3A, SNAI1, TENM3, TET2, TLE1 |
| GO.2001233 | regulation of apoptotic signaling pathway | 17 | 0.00219 | ACVR1, BCL2L12, COL2A1, CREB3L1, CSDA, CTTN, DDX3X, FEM1B, GSK3B, HGF, IGF1, PLAGL2, PRKCD, PTEN, SNAI1, STRADB, TP53INP1 |
| GO.0048523 | Negative regulation of cellular process | 75 | 0.00237 | ACVR1, ADAMTS12, AEBP2, ARF4, ATAD2B, BCL11A, BNIP3L, CDK8, CHAC1, CHFR, COL2A1, COL3A1, COL6A3, COL7A1, CREB3L1, CSDA, CTTN, DCUN1D3, DDX3X, EPC1, ERLIN1, FOXD1, FOXF2, FOXN3, FOXO3, FZD3, GPATCH2, GSK3B, HBP1, HGF, HIF3A, HMGA1, IFI30, IGF1, IREB2, KLHL20, LHX1, LHX9, MITF, MTDH, MTSS1, NAB1, NABP1, NFIA, NR4A2, NSD1, PAIP2, PALM3, PFN2, PPARGC1B, PRKCD, PTEN, PXDN, RARG, RASA1, RBM26, RGS17, RNF6, ROBO1, RRAD, SEMA3A, SMAD1, SNAI1, SOCS1, SPEN, SULF1, TLE1, TNRC6A, TP53INP1, TRABD2B, TRIB2, UBE2J1, ULK2, VAMP3, ZNF238 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0031325 | positive regulation of cellular metabolic process | 59 | 0.00255 | ACVR1, ARF4, ATAD2B, BCL11A, BCL2L12, CDK8, CHFR, CREB3L1, CSDA, DDX3X, E2F7, EED, EPC1, ERLIN1, EZH2, FOXF2, FOXJ2, FOXO3, GRIP1, GSK3B, HGF, HIF3A, HMGA1, IGF1, LARP1, LHX1, MITF, MTDH, MYBL2, NFIA, NPAS3, NR4A2, NSD1, PFN2, PLAGL2, PRKCD, PTEN, RARG, RFX6, RHEBL1, RLF, RNF6, ROBO1, RUNX2, SETD7, SMAD1, SNAI1, SPEN, STK39, STRADB, TET2, TET3, THRAP3, TNRC6B, TOB1, TP53INP1, TRIB2, VAMP3, ZNF462 |
| GO.0030154 | cell differentiation | 63 | 0.00273 | ACVR1, ARF4, ATP11C, BCL11A, BECN1, CBFA2T3, CELSR3, CHAC1, COL15A1, COL25A1, COL3A1, COL4A4, COL4A5, COL5A3, COL6A3, COL7A1, COL8A1, CREB3L1, CTTN, E2F7, EPC1, EZH2, FEM1B, FOXD1, FOXF2, FOXJ2, FRS2, GRIP1, IGF1, LGI1, LHX1, LHX8, LHX9, MAML1, MTSS1, NAB1, NUS1, PIP4K2A, PRDM1, PTEN, RAB38, RARG, RASA1, RBM24, RC3H2, RFX6, RNF6, ROBO1, SEMA3A, SHC4, SLC7A11, SMAD1, SOCS1, SPEN, ST8SIA4, SULF1, TENM3, TLL1, TTLL7, UBE2J1, VAMP3, ZIC5, ZNF238 |
| GO.0010556 | regulation of macromolecule biosynthetic process | 72 | 0.00291 | ACVR1, AEBP2, ARF4, ASXL3, ATAD2B, BAZ2B, BCL11A, BCL2L12, BRWD1, BRWD3, CASZ1, CDK8, CREB3L1, CSDA, DDX3X, EPC1, ERLIN1, EVX2, FOXD1, FOXJ2, FOXO3, GRIP1, HBP1, HGF, HIF3A, HMGA1, IGF1, IREB2, LARP1, LHX1, LHX8, LHX9, LIN28B, MBTD1, MITF, MTDH, MYBL2, NAB1, NFIA, NPAS3, NSD1, PAIP2, PHTF2, PLAGL2, PRDM1, PRKCD, PTEN, RARG, RFX6, RHEBL1, RLF, RNF6, RUNX2, SETD7, SMAD1, SNAI1, SPEN, TET2, TET3, THRAP3, TLE1, TNRC6A, TNRC6B, TP53INP1, TRIB2, UBE2J1, UBN2, ZBTB37, ZNF280B, ZNF462, ZNF644 |
| GO.0048869 | cellular developmental process | 65 | 0.00301 | ACVR1, ARF4, ATP11C, BCL11A, BECN1, CBFA2T3, CELSR3, CHAC1, COL15A1, COL25A1, COL3A1, COL4A4, COL4A5, COL5A3, COL6A3, COL7A1, COL8A1, CREB3L1, CTTN, E2F7, EPC1, EZH2, FEM1B, FOXD1, FOXF2, FOXJ2, FRS2, GRIP1, IGF1, LGI1, LHX1, LHX8, LHX9, MAML1, MTSS1, NAB1, NUS1, PIP4K2A, PMP22, PRDM1, PTEN, RAB38, RARG, RASA1, RBM24, RC3H2, RFX6, RNF6, ROBO1, SEMA3A, SHC4, SLC7A11, SMAD1, SOCS1, SPEN, ST8SIA4, STRADB, SULF1, TENM3, TLL1, TTLL7, UBE2J1, VAMP3, ZIC5, ZNF238 |
| GO.0000902 | Cell morphogenesis | 28 | 0.00317 | CELSR3, COL25A1, COL2A1, COL3A1, COL4A1, COL4A4, COL4A5, COL5A3, COL6A3, CTTN, DCDC2, FOXF2, FZD3, GSK3B, HGF, LGI1, LHX1, LHX9, NR4A2, PTEN, RASA1, ROBO1, SEMA3A, SNAI1, ST8SIA4, STRADB, ULK2, VAMP3 |
| GO.0009968 | negative regulation of signal transduction | 30 | 0.00329 | ACVR1, ADAMTS12, BCL2L12, CHAC1, COL2A1, CREB3L1, CSDA, CTTN, DDX3X, EZH2, FOXO3, GSK3B, HGF, IGF1, PALM3, PRDM1, PRKCD, PTEN, PXDN, RASA1, RGS17, ROBO1, RUNX2, SNAI1, SOCS1, STRADB, SULF1, TLE1, TOB1, TRABD2B |
| GO.0010468 | regulation of gene expression | 74 | 0.00472 | ACVR1, ARF4, ASXL3, ATAD2B, BAZ2B, BCL11A, BCL2L12, BRWD1, BRWD3, CASZ1, CDK8, CHAC1, COL2A1, CREB3L1, CSDA, DDX3X, EPC1, ERLIN1, EVX2, FOXD1, FOXJ2, FOXO3, GRIP1, GSK3B, HBP1, HGF, HIF3A, HMGA1, IGF1, IREB2, LARP1, LHX1, LHX8, LHX9, MBTD1, MITF, MTDH, MYBL2, NAB1, NFIA, NPAS3, NSD1, PAIP2, PHTF2, PLAGL2, PTEN, RARG, RBM24, RC3H2, RFX6, RHEBL1, RLF, RNF6, RUNX2, SCARA5, SETD7, SHC4, SMAD1, SNAI1, SPEN, TET2, TET3, THRAP3, TLE1, TNRC6A, TNRC6B, TOB1, TP53INP1, UBN2, ZBTB37, ZNF238, ZNF280B, ZNF462, ZNF644 |
| GO.0048519 | negative regulation of biological process | 78 | 0.00472 | ACVR1, ADAMTS12, ARF4, ATAD2B, BCL11A, BNIP3L, CDK8, CHAC1, CHFR, COL2A1, COL3A1, COL6A3, COL7A1, CREB3L1, CSDA, CTTN, DCUN1D3, DDX3X, EPC1, ERLIN1, FOXD1, FOXF2, FOXN3, FOXO3, FZD3, GPATCH2, GSK3B, HBP1, HGF, HIF3A, HMGA1, IFI30, IGF1, IREB2, KLHL20, LHX1, LHX9, LIN28B, MITF, MTDH, MTSS1, NAB1, NABP1, NFIA, NR4A2, NSD1, NT5E, PAIP2, PALM3, PFN2, PPARGC1B, PRKCD, PTEN, PXDN, RARG, RASA1, RBM26, RGS17, RNF6, ROBO1, RRAD, SEMA3A, SETD7, SMAD1, SNAI1, SOCS1, SPEN, SULF1, TLE1, TNRC6A, TNRC6B, TP53INP1, TRABD2B, TRIB2, UBE2J1, ULK2, VAMP3, ZNF238 |
| GO.0032989 | cellular component morphogenesis | 29 | 0.00498 | CELSR3, COL25A1, COL2A1, COL3A1, COL4A1, COL4A4, COL4A5, COL5A3, COL6A3, CTTN, DCDC2, FOXF2, FZD3, GSK3B, HGF, LGI1, LHX1, LHX9, NR4A2, PMP22, PTEN, RASA1, ROBO1, SEMA3A, SNAI1, ST8SIA4, STRADB, ULK2, VAMP3 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.2000112 | regulation of cellular macromolecule biosynthetic process | 70 | 0.00498 | ACVR1, AEBP2, ARF4, ASXL3, ATAD2B, BAZ2B, BCL11A, BCL2L12, BRWD1, BRWD3, CASZ1, CDK8, CREB3L1, CSDA, DDX3X, EPC1, ERLIN1, EVX2, FOXD1, FOXJ2, FOXO3, GRIP1, HBP1, HGF, HIF3A, HMGA1, IGF1, IREB2, LARP1, LHX1, LHX8, LHX9, LIN28B, MBTD1, MITF, MTDH, MYBL2, NAB1, NFIA, NPAS3, NSD1, PAIP2, PHTF2, PLAGL2, PRDM1, PTEN, RARG, RFX6, RHEBL1, RLF, RNF6, RUNX2, SETD7, SMAD1, SNAI1, SPEN, TET2, TET3, THRAP3, TLE1, TNRC6A, TNRC6B, TOB1, TP53INP1, UBN2, ZBTB37, ZNF238, ZNF280B, ZNF462, ZNF644 |
| GO.0048585 | negative regulation of response to stimulus | 34 | 0.00499 | ACVR1, ADAMTS12, BCL2L12, CHAC1, COL2A1, COL3A1, CREB3L1, CSDA, CTTN, DDX3X, EZH2, FOXO3, GSK3B, HGF, IGF1, NT5E, PALM3, PRDM1, PRKCD, PTEN, PXDN, RASA1, RGS17, ROBO1, RUNX2, SEMA3A, SNAI1, SOCS1, STRADB, SULF1, TLE1, TOB1, TRABD2B, UBE2J1 |
| GO.0030182 | neuron differentiation | 28 | 0.00538 | ARF4, BECN1, CELSR3, COL25A1, COL2A1, COL3A1, COL4A1, COL4A4, COL4A5, COL5A3, COL6A3, CTTN, DCDC2, GRIP1, GSK3B, LGI1, LHX1, LHX8, LHX9, PRDM1, PTEN, RASA1, ROBO1, RUNX2, SEMA3A, ST8SIA4, ULK2, ZNF238 |
| GO.1903506 | regulation of nucleic acid-templated transcription | 65 | 0.00601 | ACVR1, AEBP2, ARF4, ASXL3, ATAD2B, BAZ2B, BCL11A, BCL2L12, BRWD1, BRWD3, CASZ1, CDK8, CREB3L1, DDX3X, EPC1, ERLIN1, EVX2, FOXD1, FOXJ2, FOXO3, GRIP1, GSK3B, HBP1, HGF, HIF3A, HMGA1, IGF1, LHX1, LHX8, LHX9, LIN28B, MBTD1, MITF, MTDH, MYBL2, NAB1, NFIA, NPAS3, NSD1, PHTF2, PLAGL2, PRDM1, PTEN, RARG, RFX6, RHEBL1, RLF, RNF6, RUNX2, SETD7, SMAD1, SNAI1, SPEN, TET2, TET3, THRAP3, TLE1, TOB1, TP53INP1, UBN2, ZBTB37, ZNF238, ZNF280B, ZNF462, ZNF644 |
| GO.0022008 | neurogenesis | 35 | 0.00742 | ARF4, BCL11A, BECN1, CELSR3, CHAC1, COL25A1, COL2A1, COL3A1, COL4A1, COL4A4, COL4A5, COL5A3, COL6A3, CTTN, EZH2, FRS2, GRIP1, HGF, IGF1, LGI1, LHX1, LHX8, LHX9, NAB1, PRDM1, PTEN, RASA1, RNF6, ROBO1, RUNX2, SEMA3A, SPEN, ST8SIA4, TENM3, ZNF238 |
| GO.0007411 | axon guidance | 16 | 0.00788 | COL2A1, COL3A1, COL4A1, COL4A4, COL4A5, COL5A3, COL6A3, FZD3, GSK3B, LGI1, LHX1, LHX9, RASA1, ROBO1, SEMA3A, ST8SIA4 |
| GO.0051252 | regulation of RNA metabolic process | 66 | 0.00788 | ACVR1, AEBP2, ARF4, ASXL3, ATAD2B, BAZ2B, BCL11A, BCL2L12, BRWD1, BRWD3, CASZ1, CDK8, CREB3L1, DDX3X, EPC1, ERLIN1, EVX2, FOXD1, FOXJ2, FOXO3, GRIP1, GSK3B, HBP1, HGF, HIF3A, HMGA1, IGF1, LHX1, LHX8, LHX9, LIN28B, MBTD1, MITF, MTDH, MYBL2, NAB1, NFIA, NPAS3, NSD1, PHTF2, PLAGL2, PRDM1, PTEN, RARG, RASA1, RFX6, RHEBL1, RLF, RNF6, RUNX2, SETD7, SMAD1, SNAI1, SPEN, TET2, TET3, THRAP3, TLE1, TNRC6B, TP53INP1, UBN2, ZBTB37, ZNF238, ZNF280B, ZNF462, ZNF644 |
| GO.0006479 | protein methylation | 8 | 0.00847 | EED, EZH2, FBXO11, NSD1, PCMT1, SETD7, TET2, TET3 |
| GO.0009889 | regulation of biosynthetic process | 73 | 0.00847 | ACVR1, AEBP2, ARF4, ASXL3, ATAD2B, BAZ2B, BCL11A, BCL2L12, BRWD1, BRWD3, CASZ1, CDK8, CREB3L1, CSDA, DDX3X, EPC1, ERLIN1, EVX2, FOXD1, FOXJ2, FOXO3, GRIP1, HBP1, HGF, HIF3A, HMGA1, IGF1, IREB2, LARP1, LHX1, LHX8, LHX9, LIN28B, MBTD1, MITF, MTDH, MYBL2, NAB1, NFIA, NPAS3, NSD1, NT5E, PAIP2, PHTF2, PLAGL2, PRDM1, PRKCD, PTEN, RARG, RFX6, RHEBL1, RLF, RNF6, RUNX2, SETD7, SMAD1, SNAI1, SPEN, TET2, TET3, THRAP3, TLE1, TNRC6A, TNRC6B, TP53INP1, TRIB2, UBE2J1, UBN2, ZBTB37, ZNF238, ZNF280B, ZNF462, ZNF644 |
| GO.0048858 | cell projection morphogenesis | 23 | 0.0093 | CELSR3, COL25A1, COL2A1, COL3A1, COL4A1, COL4A4, COL4A5, COL5A3, COL6A3, CTTN, DCDC2, FZD3, GSK3B, LGI1, LHX1, LHX9, NR4A2, PTEN, RASA1, ROBO1, SEMA3A, ST8SIA4, ULK2 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0006355 | regulation of transcription, DNA-templated | 64 | 0.00978 | ACVR1, AEBP2, ARF4, ASXL3, ATAD2B, BAZ2B, BCL11A, BCL2L12, BRWD1, BRWD3, CASZ1, CDK8, CREB3L1, DDX3X, EPC1, ERLIN1, EVX2, FOXD1, FOXJ2, FOXO3, GRIP1, GSK3B, HBP1, HGF, HIF3A, HMGA1, IGF1, LHX1, LHX8, LHX9, LIN28B, MBTD1, MITF, MTDH, MYBL2, NAB1, NFIA, NPAS3, NSD1, PHTF2, PLAGL2, PRDM1, PTEN, RARG, RFX6, RHEBL1, RLF, RNF6, RUNX2, SETD7, SMAD1, SNAI1, SPEN, TET2, TET3, THRAP3, TLE1, TP53INP1, UBN2, ZBTB37, ZNF238, ZNF280B, ZNF462, ZNF644 |
| GO.0031326 | regulation of cellular biosynthetic process | 72 | 0.0103 | ACVR1, AEBP2, ARF4, ASXL3, ATAD2B, BAZ2B, BCL11A, BCL2L12, BRWD1, BRWD3, CASZ1, CDK8, CREB3L1, CSDA, DDX3X, EPC1, ERLIN1, EVX2, FOXD1, FOXJ2, FOXO3, GRIP1, HBP1, HGF, HIF3A, HMGA1, IGF1, IREB2, LARP1, LHX1, LHX8, LHX9, LIN28B, MBTD1, MITF, MTDH, MYBL2, NAB1, NFIA, NPAS3, NSD1, PAIP2, PHTF2, PLAGL2, PRDM1, PRKCD, PTEN, RARG, RFX6, RHEBL1, RLF, RNF6, RUNX2, SETD7, SMAD1, SNAI1, SPEN, TET2, TET3, THRAP3, TLE1, TNRC6A, TNRC6B, TP53INP1, TRIB2, UBE2J1, UBN2, ZBTB37, ZNF238, ZNF280B, ZNF462, ZNF644 |
| GO.2001234 | negative regulation of apoptotic signaling pathway | 11 | 0.0103 | ACVR1, BCL2L12, COL2A1, CREB3L1, CSDA, CTTN, DDX3X, HGF, IGF1, SNAI1, STRADB |
| GO.0030030 | cell projection organization | 27 | 0.0133 | ARF4, CELSR3, COL25A1, COL2A1, COL3A1, COL4A1, COL4A4, COL4A5, COL5A3, COL6A3, DCDC2, FGD1, FZD3, GRIP1, GSK3B, LGI1, LHX1, LHX9, MTSS1, NR4A2, PMP22, PTEN, RASA1, ROBO1, SEMA3A, ST8SIA4, ULK2 |
| GO.0016043 | cellular component organization | 82 | 0.0151 | ACBD5, AEBP2, AKAP8, ARF4, ATP11C, ATP8A1, BCL11A, BECN1, BNIP3L, BRWD1, BRWD3, CELSR3, CEP350, CHFR, COL15A1, COL2A1, COL3A1, COL4A1, COL4A4, COL5A3, COL6A3, COL7A1, COL8A1, CPSF6, CREB3L1, DCDC2, DDX3X, DGKH, EED, EPC1, EZH2, FGD1, FZD3, GRIP1, HGF, HMGA1, KCNJ2, KLHDC5, KLHL20, LGI1, LHX1, LHX9, LIMCH1, LIN7A, MBTD1, MFAP3, MITF, MMP16, MTDH, MYBL2, NAP1L5, NFIA, NR4A2, NSD1, PLAGL2, PRKCD, PTEN, PXDN, RAB15, RARG, RASA1, RLF, RNF19A, RNF6, ROBO1, SCARA5, SEMA3A, SETD7, SMAD1, SNAI1, SNX30, SRP19, ST8SIA4, SULF1, TET2, TET3, TLK1, TLL1, TP53INP1, USP6NL, WIPI2, ZNF462 |
| GO.0031345 | negative regulation of cell projection organization | 8 | 0.0151 | BCL11A, GSK3B, PFN2, PRKCD, PTEN, RNF6, SEMA3A, ULK2 |
| GO.0001655 | urogenital system development | 13 | 0.0161 | COL4A1, COL4A4, FEM1B, FOXD1, FRS2, IGF1, KIF26B, MTSS1, PTEN, RARG, SMAD1, SULF1, TET2 |
| GO.0044260 | cellular macromolecule metabolic process | 107 | 0.0177 | ACVR1, ADAMTS12, ADAMTS9, AEBP2, ARF4, ASXL3, BAZ2B, BCL11A, BECN1, BNIP3L, BRWD1, CASZ1, CBFA2T3, CCNE2, CDC37L1, COL2A1, COL3A1, CPSF6, CREB3L1, CSDA, DDX3X, DOK4, E2F7, EED, EPC1, ERLIN1, EXTL2, FBXO11, FEM1B, FOXD1, FOXF2, FOXJ2, FOXN3, FOXO3, GALNT7, GSK3B, HBP1, HIF3A, HMGA1, IGF1, IP6K3, KIAA2022, KLHDC5, KLHL20, LARP1, LHX1, LHX8, LIN28B, MAML1, MBTD1, MEX3B, MITF, MYBL2, NAB1, NABP1, NFIA, NPAS3, NSD1, NT5E, NUS1, OTUD4, PAN2, PCMT1, PHTF2, PLAGL2, PPARGC1B, PRDM1, PRKCD, PTEN, RARG, RBM26, RC3H2, RFX6, RLF, RNF152, RNF19A, SENP5, SETD7, SMAD1, SOCS1, SPEN, SRP19, ST6GAL2, ST8SIA4, STK39, STRADB, STYX, SULF1, TET3, THRAP3, TLE1, TLK1, TP53INP1, TRABD2B, TTLL7, UBE2J1, UBR3, ULK2, WIPI2, ZBTB37, ZDHHC6, ZFC3H1, ZNF238, ZNF280B, ZNF462, ZNF644, ZNRF1 |
| GO.0043066 | negative regulation of apoptotic process | 24 | 0.018 | ACVR1, ARF4, BECN1, BNIP3L, COL2A1, CREB3L1, CSDA, CTTN, DDX3X, FZD3, GSK3B, HGF, IGF1, KLHL20, MITF, MTDH, NR4A2, PRKCD, PTEN, RARG, RASA1, SNAI1, STRADB, TLE1 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0010608 | post-transcriptional regulation of gene expression | 14 | 0.0193 | CSDA, DDX3X, FOXO3, IREB2, LARP1, LIN28B, PAIP2, RBM24, RC3H2, SMAD1, THRAP3, TNRC6A, TNRC6B, TOB1 |
| GO.0051171 | regulation of nitrogen compound metabolic process | 72 | 0.0195 | ACVR1, AEBP2, ARF4, ASXL3, ATAD2B, BAZ2B, BCL11A, BCL2L12, BRWD1, BRWD3, CASZ1, CDK8, CREB3L1, CSDA, DDX3X, EPC1, ERLIN1, EVX2, FOXD1, FOXJ2, FOXO3, GRIP1, GSK3B, HBP1, HGF, HIF3A, HMGA1, IGF1, IREB2, LARP1, LHX1, LHX8, LHX9, LIN28B, MBTD1, MITF, MTDH, MYBL2, NAB1, NFIA, NPAS3, NSD1, PAIP2, PHTF2, PLAGL2, PRDM1, PRKCD, PTEN, RARG, RASA1, RFX6, RHEBL1, RLF, RNF6, RUNX2, SETD7, SMAD1, SNAI1, SPEN, TET2, TET3, THRAP3, TLE1, TNRC6A, TNRC6B, TP53INP1, UBN2, ZBTB37, ZNF238, ZNF280B, ZNF462, ZNF644 |
| GO.0071470 | cellular response to osmotic stress | 4 | 0.0195 | CSDA, DDX3X, SCN2A, STK39 |
| GO.0034645 | cellular macromolecule biosynthetic process | 68 | 0.0211 | AEBP2, ARF4, ASXL3, BAZ2B, BCL11A, BRWD1, CASZ1, CBFA2T3, CCNE2, CDK8, CREB3L1, CSDA, DDX3X, E2F7, EED, EPC1, EXTL2, EZH2, FOXD1, FOXF2, FOXJ2, FOXN3, FOXO3, GALNT7, HBP1, HIF3A, HMGA1, IGF1, KIAA2022, LARP1, LHX1, LHX8, MAML1, MBTD1, MITF, MYBL2, NAB1, NFIA, NPAS3, NSD1, NUS1, PHTF2, PLAGL2, PPARGC1B, PRDM1, PTEN, RARG, RFX6, RLF, SETD7, SMAD1, SPEN, SRP19, ST6GAL2, ST8SIA4, TET2, TET3, THRAP3, TLE1, TP53INP1, UBE2J1, WIPI2, ZBTB37, ZDHHC6, ZNF238, ZNF280B, ZNF462, ZNF644 |
| GO.0008152 | metabolic process | 140 | 0.0214 | ACBD5, ACVR1, ADAM19, ADAMTS12, AEBP2, ARF4, ASXL3, ATAD2B, ATP11C, ATP8A1, BAZ2B, BCL11A, BECN1, BNIP3L, BRWD1, C9orf72, CASZ1, CBFA2T3, CCNE2, CDC37L1, CHAC1, CHST2, COL15A1, COL25A1, COL3A1, COL4A1, COL4A4, COL4A5, COL5A3, COL6A3, COL7A1, COL8A1, CPSF6, CREB3L1, CSDA, DDX3X, DESI2, DGKH, DOK4, E2F7, EPC1, ERLIN1, FBXO11, FEM1B, FOXD1, FOXF2, FOXJ2, FOXN3, FOXO3, GALNT7, GLB1L, GSK3B, HBP1, HGF, HIF3A, HMGA1, IFI30, IGF1, IREB2, KIAA2022, KIF26B, KLHDC5, KLHL20, LARP1, LHX1, LHX8, LIN28B, MAML1, MBOAT1, MBTD1, MEX3B, MITF, MMP16, MYBL2, NAB1, NABP1, NFIA, NPAS3, NSD1, NT5E, OTUD4, PAN2, PCMT1, PDE7A, PHTF2, PIP4K2A, PPARGC1B, PRDM1, PRKCD, PTEN, PXDN, RAB15, RAB38, RARG, RBM26, RC3H2, RFX6, RLF, RNF152, RNF19A, ROBO1, RRAD, SENP5, SETD7, SLC25A16, SMAD1, SOCS1, SPEN, SRP19, ST6GAL2, ST8SIA4, STK39, STRADB, STYX, SULF1, TENM3, TET3, THRAP3, TLE1, TLK1, TLL1, TNRC6A, TNRC6B, TP53INP1, TRABD2B, TRIB2, TTLL7, UBE2J1, UBR3, ULK2, VAT1L, WIPI2, ZBTB37, ZDHHC6, ZFC3H1, ZNF238, ZNF280B, ZNF462, ZNF644, ZNRF1 |
| GO.0009059 | macromolecule biosynthetic process | 69 | 0.0215 | AEBP2, ARF4, ASXL3, BAZ2B, BCL11A, BRWD1, CASZ1, CBFA2T3, CCNE2, CDK8, CHST2, CREB3L1, CSDA, DDX3X, E2F7, EED, EPC1, EXTL2, EZH2, FOXD1, FOXF2, FOXJ2, FOXN3, FOXO3, GALNT7, HBP1, HIF3A, HMGA1, IGF1, KIAA2022, LARP1, LHX1, LHX8, MAML1, MBTD1, MITF, MYBL2, NAB1, NFIA, NPAS3, NSD1, NUS1, PHTF2, PLAGL2, PPARGC1B, PRDM1, PTEN, RARG, RFX6, RLF, SETD7, SMAD1, SPEN, SRP19, ST6GAL2, ST8SIA4, TET2, TET3, THRAP3, TLE1, TP53INP1, UBE2J1, WIPI2, ZBTB37, ZDHHC6, ZNF238, ZNF280B, ZNF462, ZNF644 |
| GO.0040029 | regulation of gene expression, epigenetic | 11 | 0.0218 | AEBP2, ATAD2B, EPC1, GSK3B, HMGA1, LIN28B, SMAD1, TET2, TET3, TNRC6A, TNRC6B |
| GO.0048699 | generation of neurons | 32 | 0.0229 | ARF4, BCL11A, BECN1, CELSR3, COL25A1, COL2A1, COL3A1, COL4A1, COL4A4, COL4A5, COL5A3, COL6A3, CTTN, EZH2, FRS2, GRIP1, HGF, LGI1, LHX1, LHX8, LHX9, PRDM1, PTEN, RASA1, RNF6, ROBO1, RUNX2, SEMA3A, SPEN, ST8SIA4, TENM3, ZNF238 |

TABLE 9-continued

Biologic pathways over-represented within the protein-interaction network of concussion related miRNA
Table 9. Biologic pathways over-represented within the protein-interaction network of concussion related miRNA

| GO ID | Pathway | Gene count | FDR | Proteins in network |
|---|---|---|---|---|
| GO.0030850 | prostate gland development | 5 | 0.0289 | FEM1B, FRS2, IGF1, PTEN, RARG |
| GO.0060255 | regulation of macromolecule metabolic process | 88 | 0.0307 | ACVR1, ARF4, ASXL3, ATAD2B, BAZ2B, BCL11A, BCL2L12, BRWD1, BRWD3, CASZ1, CDK8, CELSR3, CHAC1, CHFR, COL2A1, COL6A3, COL7A1, CREB3L1, CSDA, DDX3X, EPC1, ERLIN1, EVX2, FEM1B, FOXD1, FOXJ2, FOXO3, GPATCH2, GRIP1, GSK3B, HBP1, HGF, HIF3A, HMGA1, IGF1, IREB2, LARP1, LHX1, LHX8, LHX9, MBTD1, MITF, MTDH, MYBL2, NAB1, NFIA, NPAS3, NSD1, PAIP2, PFN2, PHTF2, PLAGL2, PRKCD, PTEN, RARG, RASA1, RBM24, RBM26, RC3H2, RFX6, RHEBL1, RLF, RNF6, ROBO1, RUNX2, SCARA5, SETD7, SHC4, SMAD1, SNAI1, SPEN, STRADB, STYX, TET2, TET3, THRAP3, TLE1, TNRC6A, TNRC6B, TP53INP1, TRIB2, UBN2, VAMP3, ZBTB37, ZNF238, ZNF280B, ZNF462, ZNF644 |
| GO.0048513 | organ development | 52 | 0.0316 | ACVR1, ADAM19, ARF4, ATP11C, BCL11A, CBFA2T3, COL2A1, COL4A1, COL4A4, COL5A3, COL6A3, COL8A1, CSDA, E2F7, EED, EZH2, FEM1B, FGD1, FOXD1, FOXO3, FRS2, GSK3B, IGF1, KIF26B, LHX8, LHX9, LIN7A, MAB21L1, MAML1, MITF, MMP16, NAB1, NR4A2, NT5E, PIP4K2A, PPARGC1B, PRDM1, PTEN, RARG, RC3H2, RFX6, SEMA3A, SLC1A2, SLC7A11, SMAD1, SNAI1, SOCS1, STOX2, SULF1, SYNGR3, TENM3, TLE1 |
| GO.0048608 | reproductive structure development | 15 | 0.0323 | CSDA, E2F7, FEM1B, FOXF2, FOXO3, FRS2, IGF1, LHX1, LHX8, LHX9, PRDM1, PTEN, RARG, SNAI1, STOX2 |
| GO.0050771 | negative regulation of axonogenesis | 5 | 0.0345 | BCL11A, PTEN, RNF6, SEMA3A, ULK2 |
| GO.0048589 | developmental growth | 13 | 0.0346 | EZH2, FOXO3, IGF1, KIF26B, LHX1, PTEN, RARG, RC3H2, ROBO1, SEMA3A, SLC1A2, SMAD1, ULK2 |
| GO.0060348 | bone development | 9 | 0.0346 | COL2A1, IGF1, MMP16, NAB1, PIP4K2A, RARG, RUNX2, SMAD1, SULF1 |
| GO.0061458 | reproductive system development | 15 | 0.0346 | CSDA, E2F7, FEM1B, FOXF2, FOXO3, FRS2, IGF1, LHX1, LHX8, LHX9, PRDM1, PTEN, RARG, SNAI1, STOX2 |
| GO.0016571 | histone methylation | 6 | 0.0369 | EED, EZH2, NSD1, SETD7, TET2, TET3 |
| GO.0060740 | prostate gland epithelium morphogenesis | 4 | 0.0402 | FEM1B, FRS2, IGF1, RARG |
| GO.0006351 | transcription, DNA-templated | 52 | 0.0427 | AEBP2, ASXL3, BAZ2B, BCL11A, BRWD1, CASZ1, CBFA2T3, CDK8, CREB3L1, CSDA, DDX3X, E2F7, EED, EPC1, EZH2, FOXD1, FOXF2, FOXJ2, FOXN3, FOXO3, HBP1, HIF3A, HMGA1, LHX1, LHX8, MAML1, MBTD1, MITF, MYBL2, NAB1, NFIA, NPAS3, NSD1, PHTF2, PLAGL2, PPARGC1B, PRDM1, PTEN, RARG, RFX6, RLF, SETD7, SMAD1, SPEN, THRAP3, TLE1, TP53INP1, ZBTB37, ZNF238, ZNF280B, ZNF462, ZNF644 |

Relationships Between Medical Characteristics and Salivary miRNAs

Figure 4A:
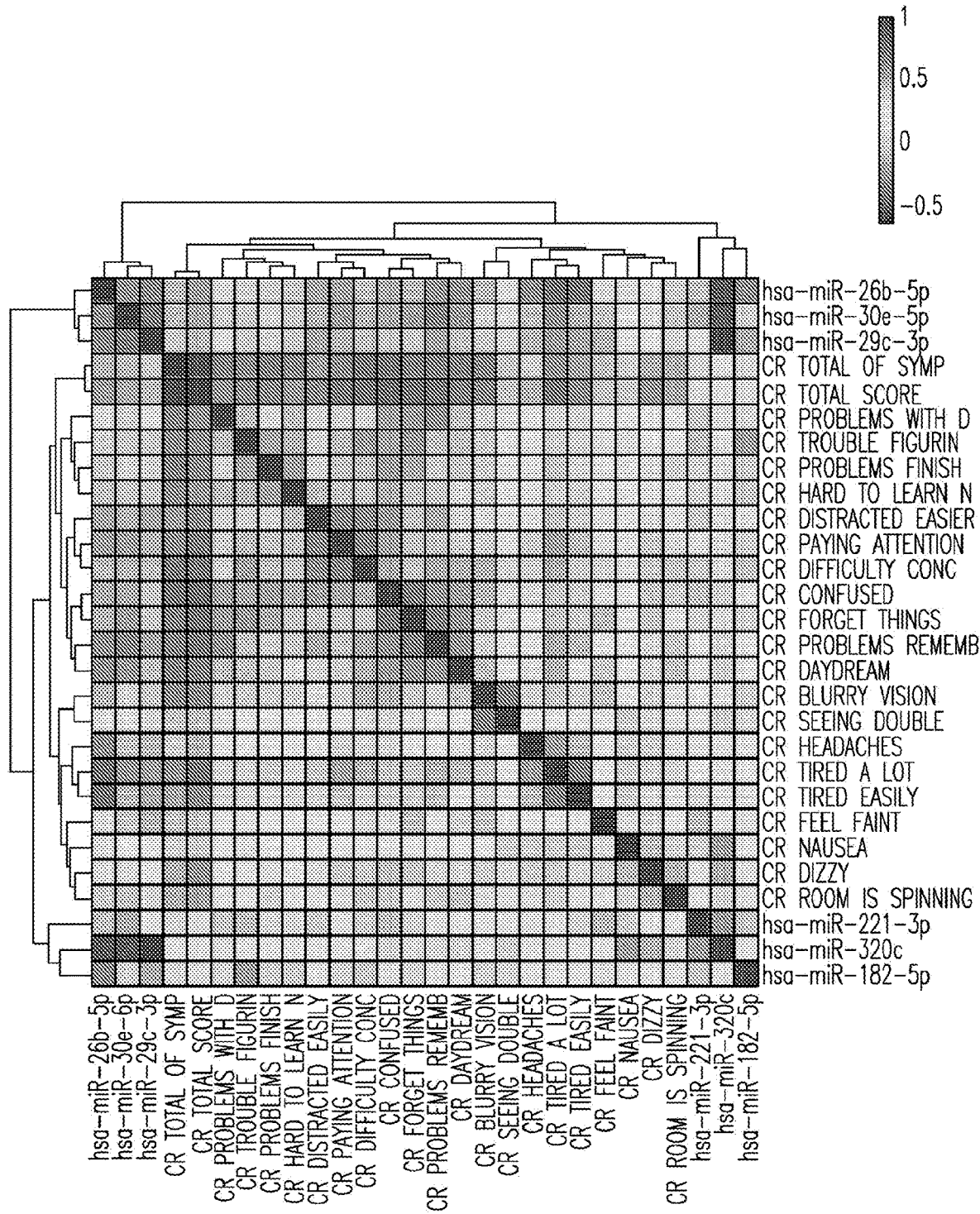
FIGS. 4A, B, C show a hierarchical clustering (HC) analysis. Spearman rank correlation testing was performed for salivary concentrations of the 6 miRNAs of interest and child SCAT-3 scores (A), parent SCAT-3 scores (B), and medical/demographic characteristics (C). Color-scale values indicate Spearman's rank correlation between two features of interest.
Figure 4B:
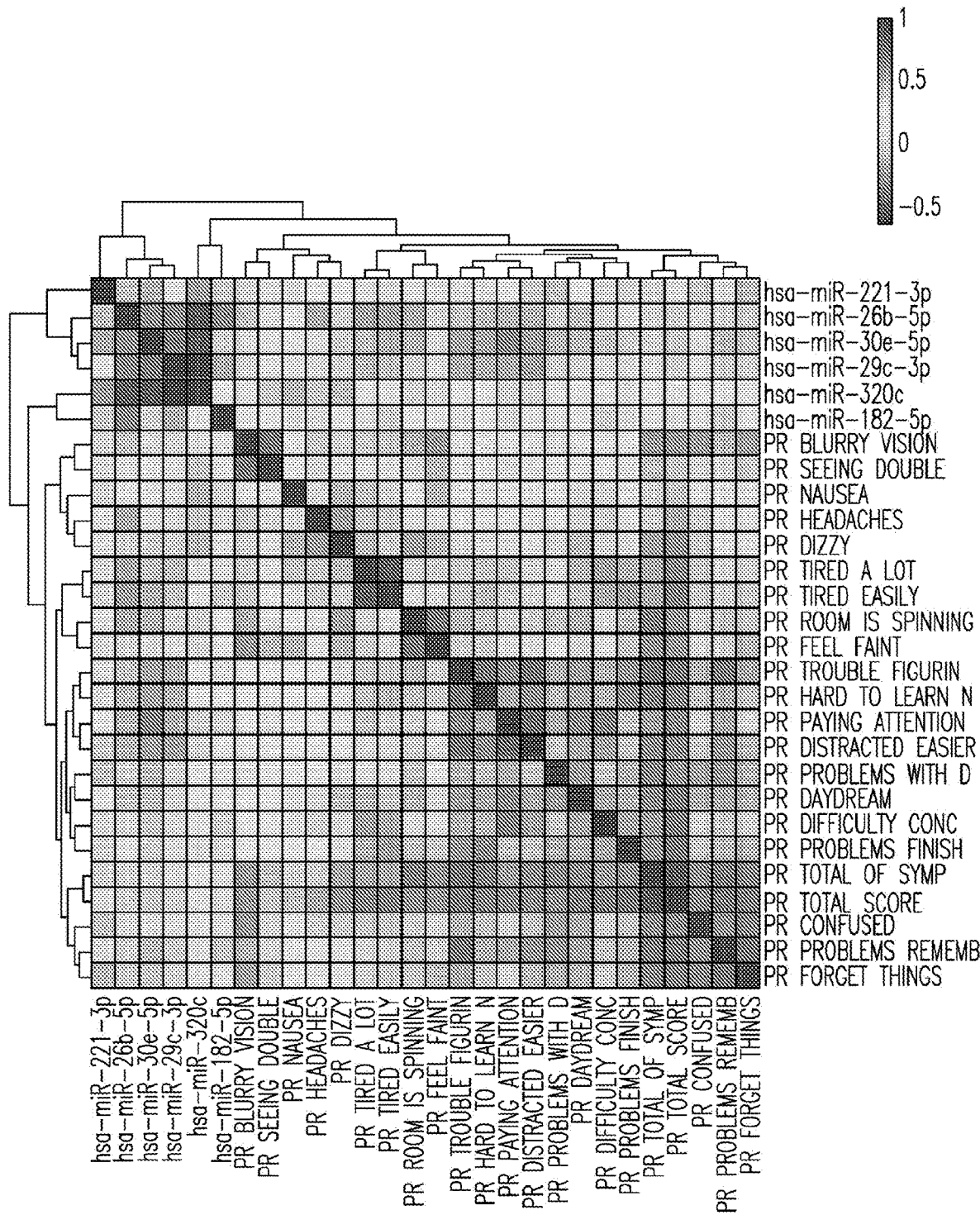
Figure 4C:
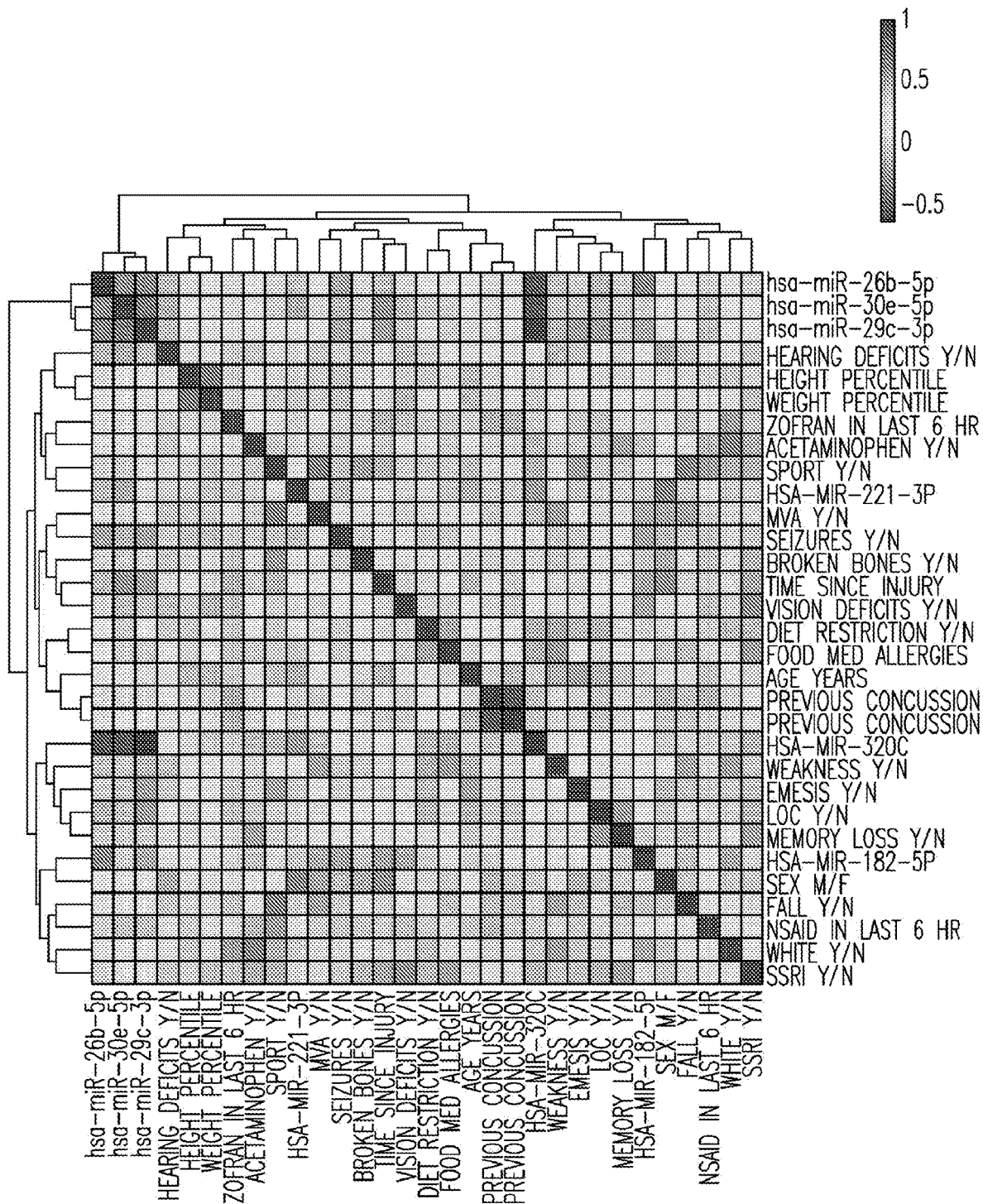

Correlations of the six salivary miRNAs of interest with child SCAT3 scores, parental SCAT3 scores, and medical/demographic factors were explored (FIGS. 4A-C). There were significant correlations between child-reported measures on SCAT-3 and salivary concentrations of miR-26b-5p and miR-320c (Table 10A). Levels of miR-26b-5p were inversely correlated with reports of "I get tired a lot" and "I get tired easily", while levels of miR-320c were directly correlated with reports of "I daydream too much" and "I get confused". There were also significant direct correlations between miR-320c and parent-reported SCAT-3 measures, including "has trouble sustaining attention" and "is easily distracted" (Table 10B). There were nominal correlations between female sex and salivary concentrations of miR-182-5p and miR-221-3p (Table 10C). However, no significant correlations were found between the six miRNAs of interest and other medical/demographic characteristics, including participant age, ethnicity, weight, height, anti-depressant medication use, or dietary restrictions. There was also no correlation between concentrations of the six miRNAs and broken bones or concussion during sport.

TABLE 10A

Spearman corrleations between the six miRNAs of interest, concussion characteristics, and medical/demographic factors
Child SCAT3 Correlations

| MicroRNA | Correlate | Spearman Correlation | t-stat | p-value | FDR |
|---|---|---|---|---|---|
| miR-26b-5p | CR Tired A Lot | −0.45027 | 52195 | 0.0003 | 0.0017 |
| miR-26b-5p | CR Tired Easily | −0.43306 | 51576 | 0.0005 | 0.0026 |
| miR-320c | CR Daydream | 0.36656 | 22797 | 0.0040 | 0.0222 |
| miR-320c | CR Confused | 0.35739 | 23127 | 0.0051 | 0.0236 |
| miR-30e-5p | CR Problems Remembering | −0.35157 | 48643 | 0.0059 | 0.0329 |
| miR-320c | CR Problems Remembering | 0.33114 | 24072 | 0.0098 | 0.0390 |
| miR-26b-5p | CR Headaches | −0.31915 | 47476 | 0.0129 | 0.0482 |
| miR-320c | CR Forget Things | 0.30033 | 25181 | 0.0197 | 0.0690 |
| miR-26b-5p | CR Daydream | −0.29288 | 46531 | 0.0231 | 0.0702 |
| miR-26b-5p | CR Problems Remembering | −0.28912 | 46395 | 0.0251 | 0.0702 |
| miR-320c | CR Feel Faint | 0.27267 | 26177 | 0.0351 | 0.1091 |
| miR-320c | CR Distracted Easily | 0.25695 | 25742 | 0.0475 | 0.1330 |
| miR-30e-5p | CR Tired A Lot | −0.27951 | 46050 | 0.0306 | 0.1426 |
| miR-26b-5p | CR TOTAL SCORE | −0.23948 | 44609 | 0.0653 | 0.1663 |
| miR-320c | CR TOTAL SCORE | 0.22978 | 27720 | 0.0774 | 0.1667 |
| miR-320c | CR usea | −0.23049 | 44285 | 0.0764 | 0.1667 |
| miR-320c | CR Difficulty Concentrating | 0.22349 | 27947 | 0.0861 | 0.1721 |
| miR-26b-5p | CR Paying Attention | −0.22884 | 44226 | 0.0786 | 0.1835 |
| miR-30e-5p | CR Daydream | −0.25793 | 45273 | 0.0466 | 0.1865 |
| miR-30e-5p | CR Paying Attention | −0.24335 | 44748 | 0.0610 | 0.2135 |
| miR-30e-5p | CR Forget Things | −0.23575 | 44475 | 0.0698 | 0.2171 |
| miR-26b-5p | CR Distracted Easily | −0.20572 | 43394 | 0.1148 | 0.2473 |
| miR-320c | CR Tired A lot | 0.19079 | 29124 | 0.1442 | 0.2524 |
| miR-320c | CR Trouble Figuring Things Out | 0.19271 | 29054 | 0.1402 | 0.2524 |
| miR-320c | CR TOTAL of Symps | 0.17562 | 29669 | 0.1795 | 0.2793 |
| miR-26b-5p | CR Confused | −0.18297 | 42575 | 0.1517 | 0.3234 |
| miR-320c | CR Dizzy | −0.15813 | 41681 | 0.2276 | 0.3353 |
| miR-29c-3p | CR Tired A lot | −0.24317 | 44742 | 0.0612 | 0.3426 |
| miR-320c | CR Hard to Learn New Things | 0.1439 | 30811 | 0.2727 | 0.3636 |
| miR-320c | CR Problems Finishing Things | 0.14702 | 30699 | 0.2623 | 0.3636 |
| miR-320c | CR Paying Attention | 0.13895 | 30989 | 0.2897 | 0.3687 |
| miR-30e-5p | CR TOTAL SCORE | −0.19415 | 42978 | 0.1372 | 0.3841 |
| miR-30e-5p | CR Confused | −0.18233 | 42552 | 0.1632 | 0.4032 |
| miR-26b-5p | CR Forget Things | −0.15441 | 41547 | 0.2388 | 0.4179 |
| miR-26b-5p | CR TOTAL of Symps | −0.15449 | 41550 | 0.2386 | 0.4179 |
| miR-29c-3p | CR Distracted Easily | −0.20213 | 43265 | 0.1214 | 0.4262 |
| miR-29c-3p | CR Problems Remembering | −0.21316 | 43662 | 0.1020 | 0.4262 |
| miR-29c-3p | CR Tired Easily | −0.20195 | 43258 | 0.1218 | 0.4262 |
| miR-320c | CR Blurry Vision | 0.11714 | 31774 | 0.3728 | 0.4372 |
| miR-320c | CR Headaches | 0.11666 | 31792 | 0.3747 | 0.4372 |
| miR-26b-5p | CR Blurry Vision | −0.14505 | 41210 | 0.2688 | 0.4428 |
| miR-30e-5p | CR Distracted Easily | −0.15769 | 41665 | 0.2289 | 0.4577 |
| miR-30e-5p | CR Tired Easily | −0.15914 | 41718 | 0.2245 | 0.4577 |
| miR-30e-5p | CR Difficulty Concentrating | −0.14399 | 41172 | 0.2724 | 0.5084 |
| miR-26b-5p | CR Difficulty Concentrating | −0.1261 | 40528 | 0.3370 | 0.5181 |
| miR-30e-5p | CR TOTAL of Symps | −0.13698 | 40920 | 0.2967 | 0.5191 |
| miR-221-3p | CR Dizzy | 0.26346 | 26508 | 0.0420 | 0.5489 |
| miR-29c-3p | CR Feel Faint | −0.15662 | 41627 | 0.2321 | 0.5635 |
| miR-29c-3p | CR Headaches | −0.15354 | 41516 | 0.2415 | 0.5635 |
| miR-29c-3p | CR Paying Attention | −0.15534 | 41581 | 0.2360 | 0.5635 |
| miR-30e-5p | CR Headaches | −0.12303 | 40418 | 0.3490 | 0.5748 |
| miR-320c | CR Tired Easily | 0.08535 | 32918 | 0.5167 | 0.5787 |
| miR-26b-5p | CR Hard to learn New Things | −0.10692 | 39838 | 0.4161 | 0.5826 |
| miR-30e-5p | CR Feel Faint | −0.11241 | 40036 | 0.3925 | 0.5918 |
| miR-30e-5p | CR Room is Spinning | −0.11028 | 39959 | 0.4016 | 0.5918 |
| miR-29c-3p | CR TOTAL SCORE | −0.13655 | 40905 | 0.2982 | 0.6422 |
| miR-182-5p | CR Trouble Figuring Things Out | −0.23631 | 44495 | 0.0691 | 0.6449 |
| miR-30e-5p | CR Hard to Learn New Things | −0.087076 | 39124 | 0.5083 | 0.6469 |
| miR-30e-5p | CR Trouble Figuring Things Out | −0.087549 | 39141 | 0.5060 | 0.6469 |
| miR-30e-5p | CR usea | 0.08738 | 32845 | 0.5068 | 0.6469 |
| miR-320c | CR Problems with directions | 0.0633 | 33712 | 0.6309 | 0.6794 |
| miR-29c-3p | CR Blurry Vision | −0.073241 | 38626 | 0.5781 | 0.6860 |
| miR-29c-3p | CR Confused | −0.087577 | 39142 | 0.5058 | 0.6860 |
| miR-29c-3p | CR Daydream | −0.11162 | 40007 | 0.3958 | 0.6860 |
| miR-29c-3p | CR Difficulty Concentrating | −0.11441 | 40108 | 0.3841 | 0.6860 |
| miR-29c-3p | CR Dizzy | 0.093228 | 32635 | 0.4786 | 0.6860 |
| miR-29c-3p | CR Forget Things | −0.085206 | 39057 | 0.5174 | 0.6860 |
| miR-29c-3p | CR Hard to Learn New Things | −0.095804 | 39438 | 0.4665 | 0.6860 |
| miR-29c-3p | CR TOTAL of Symps | −0.075227 | 38697 | 0.5678 | 0.6860 |
| miR-29c-3p | CR Trouble Figuring Things Out | −0.071356 | 38558 | 0.5880 | 0.6860 |
| miR-29c-3p | CR usea | 0.11814 | 31738 | 0.3686 | 0.6860 |
| miR-221-3p | CR Seeing Double | 0.21551 | 28234 | 0.0982 | 0.6873 |
| miR-29c-3p | CR Problems with directions | 0.066096 | 33611 | 0.6158 | 0.6897 |

TABLE 10A-continued

Spearman corrleations between the six miRNAs of interest,
concussion characteristics, and medical/demographic factors
Child SCAT3 Correlations

| MicroRNA | Correlate | Spearman Correlation | t-stat | p-value | FDR |
|---|---|---|---|---|---|
| miR-221-3p | CR Slurry Vision | 0.17747 | 29603 | 0.1749 | 0.6997 |
| miR-221-3p | CR Tired A Lot | 0.18112 | 29472 | 0.1661 | 0.6997 |
| miR-221-3p | CR Daydream | 0.16405 | 30086 | 0.2104 | 0.7364 |
| miR-26b-5p | CR Room Is Spinning | −0.077734 | 38788 | 0.5550 | 0.7399 |
| miR-26b-5p | CR Problems Finishing Things | −0.068883 | 38469 | 0.6010 | 0.7649 |
| miR-182-5p | CR Distracted Easily | 0.16819 | 29937 | 0.1990 | 0.7958 |
| miR-182-5p | CR Problems Remembering | 0.17784 | 29590 | 0.1740 | 0.7958 |
| miR-221-3p | CR Confused | −0.11499 | 40129 | 0.3816 | 0.8073 |
| miR-221-3p | CR Feel Faint | −0.14095 | 41063 | 0.2827 | 0.8073 |
| miR-221-3p | CR Paying Attention | 0.10119 | 32348 | 0.4417 | 0.8073 |
| miR-221-3p | CR Problems Remembering | 0.099625 | 32405 | 0.4488 | 0.8073 |
| miR-221-3p | CR Problems with directions | −0.090815 | 39258 | 0.4901 | 0.8073 |
| miR-221-3p | CR Room is Spinning | 0.11396 | 31889 | 0.3860 | 0.8073 |
| miR-221-3p | CR Trouble Figuring Things Out | −0.12047 | 40326 | 0.3592 | 0.8073 |
| miR-30e-5p | CR Problems with directions | −0.05509 | 37973 | 0.6759 | 0.8228 |
| miR-30e-5p | CR Seeing Double | 0.046577 | 34314 | 0.7238 | 0.8339 |
| miR-320c | CR Seeing Double | −0.027588 | 36983 | 0.8343 | 0.8652 |
| miR-26b-5p | CR Dizzy | 0.036804 | 34665 | 0.7801 | 0.8742 |
| miR-26b-5p | CR Seeing Double | 0.036724 | 34668 | 0.7806 | 0.8742 |
| miR-26b-5p | CR Trouble Figuring Things Out | −0.043596 | 37559 | 0.7408 | 0.8742 |
| miR-221-3p | CR Difficulty Concentrating | −0.044005 | 37574 | 0.7385 | 0.8990 |
| miR-221-3p | CR Distracted Easily | −0.05349 | 37915 | 0.6848 | 0.8990 |
| miR-221-3p | CR Headaches | 0.064919 | 33654 | 0.6222 | 0.8990 |
| miR-221-3p | CR TOTAL SCORE | 0.06099 | 33795 | 0.6434 | 0.8990 |
| miR-221-3p | CR usea | −0.048148 | 37723 | 0.7149 | 0.8990 |
| miR-26b-5p | CR Problems with directions | 0.027277 | 35008 | 0.8361 | 0.9004 |
| miR-26b-5p | CR usea | 0.020062 | 35268 | 0.8791 | 0.9116 |
| miR-30e-5p | CR Blurry Vision | −0.024992 | 36889 | 0.8497 | 0.9150 |
| miR-29c-3p | CR Problems Finishing Things | −0.023393 | 36832 | 0.8592 | 0.9253 |
| miR-30e-5p | CR Dizzy | 0.011552 | 35574 | 0.9302 | 0.9302 |
| miR-30e-5p | CR Problems Finishing Things | −0.012904 | 36454 | 0.9220 | 0.9302 |
| miR-182-5p | CR Confused | 0.12736 | 31406 | 0.3322 | 0.9308 |
| miR-182-5p | CR Daydream | 0.13884 | 30993 | 0.2901 | 0.9308 |
| miR-182-5p | CR Difficulty Concentrating | −0.075746 | 38716 | 0.5652 | 0.9308 |
| miR-182-5p | CR Dizzy | 0.082373 | 33025 | 0.5315 | 0.9308 |
| miR-182-5p | CR Headaches | 0.086487 | 32877 | 0.5111 | 0.9308 |
| miR-182-5p | CR Room is Spinning | 0.07626 | 33245 | 0.5625 | 0.9308 |
| miR-182-5p | CR Tired A Lot | 0.082694 | 33014 | 0.5299 | 0.9308 |
| miR-182-5p | CR Tired Easily | 0.078457 | 33166 | 0.5513 | 0.9308 |
| miR-182-5p | CR usea | 0.076235 | 33246 | 0.5626 | 0.9308 |
| miR-182-5p | CR Feel Faint | 0.062759 | 33731 | 0.6338 | 0.9555 |
| miR-182-5p | CR Hard to Learn New Things | −0.060083 | 38152 | 0.6484 | 0.9555 |
| miR-182-5p | CR TOTAL SCORE | 0.053787 | 34054 | 0.6832 | 0.9564 |
| miR-221-3p | CR Forget Things | −0.010051 | 36352 | 0.9392 | 0.9573 |
| miR-221-3p | CR Hard to learn New Things | 0.0070545 | 35736 | 0.9573 | 0.9573 |
| miR-221-3p | CR Problems Finishing Things | 0.016558 | 35394 | 0.9001 | 0.9573 |
| miR-221-3p | CR Tired Easily | −0.01005 | 36352 | 0.9393 | 0.9573 |
| miR-221-3p | CR TOTAL of Symps | 0.0076563 | 35714 | 0.9537 | 0.9573 |
| miR-182-5p | CR Blurry Vision | −0.02143 | 36761 | 0.8709 | 0.9621 |
| miR-182-5p | CR Paying Attention | −0.01196 | 36420 | 0.9277 | 0.9621 |
| miR-182-5p | CR Problems Finishing Things | −0.037771 | 37349 | 0.7745 | 0.9621 |
| miR-182-5p | CR Problems with directions | 0.013743 | 35495 | 0.9170 | 0.9621 |
| miR-182-5p | CR Seeing Double | 0.014511 | 35468 | 0.9124 | 0.9621 |
| miR-182-5p | CR TOTAL of Symps | 0.01832 | 35331 | 0.8895 | 0.9621 |
| miR-26b-5p | CR Feel Faint | 0.0046947 | 35821 | 0.9716 | 0.9716 |
| miR-29c-3p | CR Room is Spinning | −0.010131 | 36355 | 0.9388 | 0.9735 |
| miR-29c-3p | CR Seeing Double | 0.0030454 | 35880 | 0.9816 | 0.9816 |
| miR-182-5p | CR Forget Things | −0.0028883 | 36094 | 0.9825 | 0.9825 |
| miR-320c | CR Room is Spinning | −0.00049121 | 36008 | 0.9970 | 0.9970 |

TABLE 10B

Spearman corrleations between the six miRNAs of interest,
concussion characteristics, and medical/demographlc factors
Parent SCAT3 Correlations

| MicroRNA | Correlate | Spearman Correlation | t-stat | p-value | FDR |
|---|---|---|---|---|---|
| miR-320c | PR Paying Attention | 0.37677 | 22430 | 0.0030 | 0.0168 |
| miR-320c | PR Distracted Easily | 0.35464 | 23227 | 0.0054 | 0.0254 |
| miR-30e-5p | PR Paying Attention | −0.3492 | 48558 | 0.0062 | 0.0350 |
| miR-320c | PR Forget Things | 0.24742 | 27085 | 0.0567 | 0.2058 |
| miR-26b-5p | PR Nausea | 0.24664 | 27113 | 0.0575 | 0.2682 |
| miR-182-5p | PR Daydream | 0.25442 | 26833 | 0.0498 | 0.2789 |
| miR-182-5p | PR Feel Faint | 0.26329 | 26514 | 0.0421 | 0.2789 |
| miR-182-5p | PR Seeing Double | 0.25464 | 26825 | 0.0496 | 0.2789 |
| miR-30e-5p | PR Distracted Easily | −0.23569 | 44472 | 0.0699 | 0.2977 |
| miR-30e-5p | PR Seeing Double | 0.23203 | 27639 | 0.0744 | 0.2977 |
| miR-26b-5p | PR Tired Easily | −0.23086 | 44299 | 0.0759 | 0.3038 |
| miR-30e-5p | PR Hard to Learn New Things | −0.20254 | 43279 | 0.1207 | 0.3754 |
| miR-30e-5p | PR Trouble Figuring Things Out | −0.20614 | 43409 | 0.1141 | 0.3754 |
| miR-320c | PR Difficulty Concentrating | 0.16601 | 30015 | 0.2049 | 0.4219 |
| miR-320c | PR Hard to Learn New Things | 0.17913 | 29543 | 0.1709 | 0.4219 |
| miR-320c | PR Problems with directions | 0.15603 | 30375 | 0.2339 | 0.4219 |
| miR-320c | PR Tired A Lot | 0.15954 | 30248 | 0.2234 | 0.4219 |
| miR-320c | PR Tired Easily | 0.17938 | 29534 | 0.1703 | 0.4219 |
| miR-320c | PR Trouble Figuring Things Out | 0.15368 | 30459 | 0.2411 | 0.4219 |
| miR-320c | PR Nausea | −0.15541 | 41583 | 0.2357 | 0.4219 |
| miR-29c-3p | PR Distracted Easily | −0.231 | 44304 | 0.0758 | 0.4243 |
| miR-320c | PR Daydream | 0.13999 | 30952 | 0.2860 | 0.4450 |
| miR-320c | PR Problems Remembering | 0.14085 | 30921 | 0.2831 | 0.4450 |
| miR-26b-5p | PR Headaches | −0.18558 | 42669 | 0.1557 | 0.4709 |
| miR-26b-5p | PR Room is Spinning | −0.18025 | 42477 | 0.1682 | 0.4709 |
| miR-26b-5p | PR Tired A Lot | −0.19507 | 43011 | 0.1353 | 0.4709 |
| miR-320c | PR Dizzy | −0.129 | 40633 | 0.3259 | 0.4803 |
| miR-320c | PR TOTAL SCORE | 0.12357 | 31543 | 0.3469 | 0.4856 |
| miR-30e-5p | PR Room is Spinning | −0.16204 | 41822 | 0.2161 | 0.5043 |
| miR-30e-5p | PR Tired Easily | −0.16766 | 42024 | 0.2004 | 0.5043 |
| miR-25b-5p | PR Distracted Easily | −0.15837 | 41690 | 0.2268 | 0.5293 |
| miR-26b-5p | PR Paying Attention | −0.15854 | 41696 | 0.2263 | 0.5293 |
| miR-320c | PR Contused | 0.10125 | 32346 | 0.4414 | 0.5618 |
| miR-320c | PR Total Number of Symptoms | 0.10531 | 32200 | 0.4232 | 0.5618 |
| miR-30e-5p | PR Problems with directions | −0.14736 | 41293 | 0.2612 | 0.5626 |
| miR-30e-5p | PR Daydream | −0.13621 | 40892 | 0.2994 | 0.5672 |
| miR-30e-5p | PR Problems Remembering | −0.13497 | 40848 | 0.3039 | 0.5672 |
| miR-320c | PR Headaches | −0.093829 | 39367 | 0.4758 | 0.5727 |
| miR-320c | PR Seeing Double | −0.090664 | 39253 | 0.4909 | 0.5727 |
| miR-29c-3p | PR Paying Attention | −0.19271 | 42926 | 0.1402 | 0.6178 |
| miR-29c-3p | PR Trouble Figuring Things Out | −0.17969 | 42457 | 0.1695 | 0.6178 |
| miR-30e-5p | PR Nausea | 0.12189 | 31603 | 0.3535 | 0.6187 |
| miR-30e-5p | PR Tired A Lot | −0.11578 | 40157 | 0.3784 | 0.6232 |
| miR-182-5p | PR Room is Spinning | 0.18985 | 29157 | 0.1463 | 0.6270 |
| miR-26b-5p | PR Daydream | −0.12953 | 40652 | 0.3239 | 0.6479 |
| miR-26b-5p | PR Hard to Learn New Things | −0.1341 | 40816 | 0.3070 | 0.6479 |
| miR-30e-5p | PR Difficulty Concentrating | −0.10398 | 39732 | 0.4292 | 0.6511 |
| miR-30e-5p | PR Forget Things | −0.10117 | 39631 | 0.4418 | 0.6511 |
| miR-320c | PR Blurry Vision | 0.071532 | 33416 | 0.5870 | 0.6575 |
| miR-29c-3p | PR Hard to Learn New Things | −0.16356 | 41877 | 0.2118 | 0.6588 |
| miR-26b-5p | PR Blurry Vision | −0.11054 | 39968 | 0.4005 | 0.6608 |
| miR-26b-5p | PR Trouble Figuring Things Out | −0.11037 | 39962 | 0.4012 | 0.6608 |
| miR-30e-5p | PR TOTAL SCORE | −0.077524 | 38780 | 0.5560 | 0.7784 |
| miR-29c-3p | PR Seeing Double | 0.13953 | 30968 | 0.2877 | 0.8055 |
| miR-320c | PR Problems Finishing Things | 0.038831 | 34592 | 0.7683 | 0.8274 |
| miR-30e-5p | PR Confused | 0.043542 | 34423 | 0.7412 | 0.8339 |
| miR-30e-5p | PR Dizzy | −0.052746 | 37888 | 0.6890 | 0.8339 |
| miR-30e-5p | PR Headaches | 0.059899 | 33834 | 0.6494 | 0.8339 |
| miR-30e-5p | PR Problems Finishing Things | −0.058086 | 38081 | 0.6593 | 0.8339 |
| miR-29c-3p | PR Tired A Lot | −0.12817 | 40603 | 0.3291 | 0.8377 |
| miR-30e-5p | PR Blurry Vision | 0.031613 | 34852 | 0.8105 | 0.8606 |
| miR-30e-5p | PR Total Number of Symptoms | −0.028327 | 37009 | 0.8299 | 0.8606 |
| miR-182-5p | PR Blurry Vision | 0.13725 | 31050 | 0.2957 | 0.8687 |
| miR-182-5p | PR Confused | 0.063622 | 33700 | 0.6291 | 0.8687 |
| miR-182-5p | PR Difficulty Concentrating | −0.056419 | 38021 | 0.6685 | 0.8687 |
| miR-182-5p | PR Distracted Easily | 0.081049 | 33073 | 0.5382 | 0.8687 |
| miR-182-5p | PR Dizzy | 0.13221 | 31232 | 0.3139 | 0.8687 |
| miR-182-5p | PR Forget Things | 0.084109 | 32963 | 0.5229 | 0.8687 |
| miR-182-5p | PR Hard to Learn New Things | 0.11273 | 31933 | 0.3911 | 0.8687 |
| miR-182-5p | PR Problems Remembering | −0.093029 | 39338 | 0.4796 | 0.8687 |
| miR-182-5p | PR Problems with directions | 0.067921 | 33546 | 0.5061 | 0.8687 |
| miR-182-5p | PR Tired A Lot | 0.064735 | 33660 | 0.6231 | 0.8687 |
| miR-182-5p | PR Tired Easily | −0.053125 | 37902 | 0.6869 | 0.8687 |

TABLE 10B-continued

Spearman corrleations between the six miRNAs of interest,
concussion characteristics, and medical/demographic factors
Parent SCAT3 Correlations

| MicroRNA | Correlate | Spearman Correlation | t-stat | p-value | FDR |
| --- | --- | --- | --- | --- | --- |
| miR-182-5p | PR Total Number of Symptoms | 0.073116 | 33359 | 0.5788 | 0.8687 |
| miR-182-5p | PR TOTAL SCORE | 0.04791 | 34266 | 0.7162 | 0.8687 |
| miR-182-5p | PR Trouble Figuring Things Out | 0.050623 | 34168 | 0.7009 | 0.8687 |
| miR-26b-5p | PR Forget Things | −0.067078 | 38404 | 0.6106 | 0.8712 |
| miR-26b-5p | PR Problems Finishing Things | 0.064895 | 33654 | 0.6223 | 0.8712 |
| miR-26b-5p | PR Seeing Double | 0.067641 | 33556 | 0.6076 | 0.8712 |
| miR-320c | PR Room is Spinning | −0.023856 | 36849 | 0.8564 | 0.8882 |
| miR-26b-5p | PR Confused | 0.024343 | 35114 | 0.8535 | 0.8948 |
| miR-26b-5p | PR Dizzy | −0.028395 | 37012 | 0.8295 | 0.8948 |
| miR-26b-5p | PR Feel Faint | −0.02691 | 36958 | 0.8383 | 0.8948 |
| miR-26b-5p | PR Problems Remembering | −0.038647 | 37381 | 0.7694 | 0.8948 |
| miR-26b-5p | PR Problems with directions | −0.052841 | 37892 | 0.6884 | 0.8948 |
| miR-26b-5p | PR Total Number of Symptoms | −0.022784 | 36810 | 0.8628 | 0.8948 |
| miR-26b-5p | PR TOTAL SCORE | −0.040875 | 37461 | 0.7565 | 0.8948 |
| miR-29c-3p | PR Tired Easily | −0.11373 | 40083 | 0.3869 | 0.9028 |
| miR-29c-3p | PR Confused | 0.066562 | 33594 | 0.6133 | 0.9173 |
| miR-29c-3p | PR Daydream | −0.020214 | 36718 | 0.8782 | 0.9173 |
| miR-29c-3p | PR Difficulty Concentrating | 0.029482 | 34929 | 0.8231 | 0.9173 |
| miR-29c-3p | PR Dizzy | −0.042405 | 37516 | 0.7477 | 0.9173 |
| miR-29c-3p | PR Feel Faint | 0.038732 | 34596 | 0.7689 | 0.9173 |
| miR-28c-3p | PR Forget Things | −0.030551 | 37090 | 0.8168 | 0.9173 |
| miR-29c-3p | PR Headaches | 0.019152 | 35301 | 0.8845 | 0.9173 |
| miR-29c-3p | PR Problems Finishing Things | 0.03572 | 34704 | 0.7864 | 0.9173 |
| miR-29c-3p | PR Problems Remembering | −0.063471 | 38274 | 0.6300 | 0.9173 |
| miR-29c-3p | PR Problems with directions | −0.034317 | 37225 | 0.7946 | 0.9173 |
| miR-29c-3p | PR Room is spinning | −0.039903 | 37426 | 0.7621 | 0.9173 |
| miR-29c-3p | PR Total Number of Symptoms | 0.029441 | 34930 | 0.8233 | 0.9173 |
| miR-29c-3p | PR TOTAL SCORE | −0.026972 | 36961 | 0.8379 | 0.9173 |
| miR-29c-3p | PR Nausea | 0.057565 | 33918 | 0.6622 | 0.9173 |
| miR-30e-5p | PR Feel Faint | 0.012991 | 35522 | 0.9215 | 0.9215 |
| miR-26b-5p | PR Difficulty Concentrating | −0.011319 | 36397 | 0.9316 | 0.9316 |
| miR-182-5p | PR Headaches | 0.024159 | 35121 | 0.8546 | 0.9516 |
| miR-182-5p | PR Paying Attention | −0.013639 | 36481 | 0.9176 | 0.9516 |
| miR-182-5p | PR Problems Finishing Things | 0.01494 | 35452 | 0.9098 | 0.9516 |
| miR-221-3p | PR Blurry Vision | −0.01058 | 36371 | 0.9361 | 0.9682 |
| miR-221-3p | PR Confused | −0.1121 | 40025 | 0.3938 | 0.9682 |
| miR-221-3p | PR Daydream | 0.129 | 31347 | 0.3259 | 0.9682 |
| miR-221-3p | PR Difficulty Concentrating | −0.0052646 | 36179 | 0.9682 | 0.9682 |
| miR-221-3p | PR Distracted Easily | −0.080699 | 38894 | 0.5399 | 0.9682 |
| miR-221-3p | PR Dizzy | 0.15364 | 30460 | 0.2412 | 0.9682 |
| miR-221-3p | PR Feel Faint | 0.023816 | 35133 | 0.8567 | 0.9682 |
| miR-221-3p | PR Forget Things | −0.13976 | 41020 | 0.2869 | 0.9682 |
| miR-221-3p | PR Hard to Learn New Things | 0.036258 | 34685 | 0.7833 | 0.9682 |
| miR-221-3p | PR Headaches | 0.15213 | 30515 | 0.2459 | 0.9682 |
| miR-221-3p | PR Paying Attention | 0.10237 | 32306 | 0.4364 | 0.9682 |
| miR-221-3p | PR Problems Finishing Things | −0.029557 | 37054 | 0.8226 | 0.9682 |
| miR-221-3p | PR Problems Remembering | 0.030618 | 34888 | 0.8164 | 0.9682 |
| miR-221-3p | PR Problems with directions | −0.11892 | 40270 | 0.3655 | 0.9682 |
| miR-221-3p | PR Room is Spinning | 0.06336 | 33710 | 0.6306 | 0.9682 |
| miR-221-3p | PR Seeing Double | 0.045745 | 34344 | 0.7285 | 0.9682 |
| miR-221-3p | PR Tired A Lot | 0.050642 | 34167 | 0.7008 | 0.9682 |
| miR-221-3p | PR Tired Easily | 0.0069356 | 35740 | 0.9581 | 0.9682 |
| miR-221-3p | PR Total Number of Symptoms | −0.036015 | 37285 | 0.7847 | 0.9682 |
| miR-221-3p | PR TOTAL SCORE | 0.049551 | 34207 | 0.7069 | 0.9682 |
| miR-221-3b | PR Trouble Figuring Things Out | 0.021333 | 35222 | 0.8715 | 0.9682 |
| miR-221-3p | PR Nausea | −0.0070641 | 36244 | 0.9573 | 0.9682 |
| miR-320c | PR Feel Faint | 0.0047427 | 35819 | 0.9713 | 0.9713 |
| miR-182-5p | PR Nausea | 0.0025551 | 35898 | 0.9845 | 0.9845 |
| miR-29c-3p | PR Blurry Vision | 0.0024949 | 35900 | 0.9849 | 0.9849 |

TABLE 10C

Spearman corrleations between the six miRNAs of interest,
concussion characteristics, and medical/demographic factors
Medical/Demographic Factors

| MicroRNA | Correlate | Spearman Correlation | t-stat | p-value | FDR |
|---|---|---|---|---|---|
| miR-182-5p | Sex (F) | 0.33991 | 23757 | 0.0079 | 0.1221 |
| miR-221-3p | Sex (F) | −0.33798 | 48154 | 0.0083 | 0.1281 |
| miR-320c | Loss of consciousness | 0.24337 | 27231 | 0.0610 | 0.3150 |
| miR-29c-3p | Loss of consciousness | −0.23892 | 44589 | 0.0660 | 0.3542 |
| miR-29c-3p | Weight (%) | 0.23676 | 27469 | 0.0686 | 0.3542 |
| miR-30e-5p | White Ethnicity | 0.23533 | 27520 | 0.0703 | 0.3632 |
| miR-29c-3p | Emesis | −0.22135 | 43956 | 0.0892 | 0.3893 |
| miR-29c-3p | Seizues | −0.20673 | 43430 | 0.1130 | 0.3893 |
| miR-29c-3p | White Ethnicity | 0.19636 | 28923 | 0.1327 | 0.4113 |
| miR-29c-3p | Height (%) | 0.18731 | 29249 | 0.1518 | 0.4279 |
| miR-30e-5p | Weight (%) | 0.2158 | 28223 | 0.0977 | 0.4328 |
| miR-182-5p | Height (%) | 0.24349 | 27227 | 0.0608 | 0.4361 |
| miR-182-5p | MVA | −0.17535 | 42301 | 0.1802 | 0.4361 |
| miR-182-5p | Seizues | −0.21425 | 43701 | 0.1002 | 0.4361 |
| miR-182-5p | Vision Deficits | −0.19115 | 42869 | 0.1435 | 0.4361 |
| miR-182-5p | Weakness | 0.17431 | 29717 | 0.1829 | 0.4361 |
| miR-182-5p | Weight (%) | 0.2039 | 28652 | 0.1181 | 0.4361 |
| miR-182-5p | White Ethnicity | −0.18137 | 42518 | 0.1655 | 0.4361 |
| miR-221-3p | Sport | 0.24564 | 27149 | 0.0585 | 0.4558 |
| miR-29c-3p | MVA | 0.1654 | 30037 | 0.2066 | 0.4927 |
| miR-320c | Diet Restriction | −0.15432 | 41544 | 0.2391 | 0.5294 |
| miR-320c | Food/Med Allergies | −0.16601 | 41965 | 0.2049 | 0.5294 |
| miR-320c | Memory Loss | 0.16896 | 29909 | 0.1969 | 0.5294 |
| miR-320c | Seizues | 0.17666 | 29632 | 0.1769 | 0.5294 |
| miR-320c | SSRI | −0.15494 | 41566 | 0.2372 | 0.5294 |
| miR-320c | Vision Deficits | 0.18687 | 29264 | 0.1528 | 0.5294 |
| miR-320c | Weakness | 0.16381 | 30095 | 0.2111 | 0.5294 |
| miR-30e-5p | Age (years) | 0.16239 | 30146 | 0.2151 | 0.5429 |
| miR-30e-5p | Fall | 0.15236 | 30507 | 0.2452 | 0.5429 |
| miR-30e-5p | Hearing Deficits | −0.16403 | 41894 | 0.2104 | 0.5429 |
| miR-30e-5p | Height (%) | 0.15723 | 30331 | 0.2302 | 0.5429 |
| miR-30e-5p | Sex (F) | 0.17044 | 29856 | 0.1929 | 0.5429 |
| miR-30e-5p | SSRI | 0.15236 | 30507 | 0.2452 | 0.5429 |
| miR-30e-5p | Seizues | −0.14659 | 41266 | 0.2637 | 0.5450 |
| miR-320c | Sport | −0.14579 | 41237 | 0.2664 | 0.5505 |
| miR-320c | Emesis | 0.13955 | 30968 | 0.2876 | 0.5572 |
| miR-25b-5p | Seizues | −0.20673 | 43430 | 0.1130 | 0.5839 |
| miR-29c-3p | Diet Restriction | 0.11189 | 31963 | 0.3947 | 0.5929 |
| miR-23c-3p | Fall | 0.10588 | 32180 | 0.4208 | 0.5929 |
| miR-29c-3p | Hearing Deficits | −0.11606 | 40167 | 0.3772 | 0.5929 |
| miR-29c-3p | NSAID in last 6 hrs | −0.10655 | 39825 | 0.4173 | 0.5929 |
| miR-29c-3p | Sex (F) | 0.12229 | 31589 | 0.3519 | 0.5929 |
| miR-29c-3p | Sport | 0.10984 | 32037 | 0.4035 | 0.5929 |
| miR-29c-3p | SSRI | 0.14203 | 30878 | 0.2790 | 0.5929 |
| miR-29c-3p | Weakness | −0.13861 | 40978 | 0.2909 | 0.5929 |
| miR-29c-3p | Zofran in last 6 hrs | 0.11795 | 31745 | 0.3694 | 0.5929 |
| miR-320c | Acetaminophen | −0.11842 | 40252 | 0.3675 | 0.6015 |
| miR-320c | MVA | −0.11814 | 40242 | 0.3686 | 0.6015 |
| miR-320c | Previous Concussion | −0.11224 | 40030 | 0.3932 | 0.6094 |
| miR-29c-3p | Acetaminophen | 0.097431 | 32483 | 0.4590 | 0.6186 |
| miR-29c-3p | Vision Deficits | −0.090767 | 39257 | 0.4904 | 0.6334 |
| miR-30e-5p | Loss of consciousness | −0.1278 | 40589 | 0.3305 | 0.6381 |
| miR-30e-5p | Vision Deficits | −0.1228 | 40410 | 0.3499 | 0.6381 |
| miR-29c-3p | Previous Concussions | 0.080001 | 33111 | 0.5434 | 0.6673 |
| miR-26b-5p | Acetaminophen | 0.12441 | 31512 | 0.3436 | 0.6699 |
| miR-26b-5p | Age (years) | 0.12058 | 31650 | 0.3588 | 0.6699 |
| miR-26b-5p | Diet Restriction | 0.16204 | 30158 | 0.2161 | 0.6699 |
| miR-26b-5p | Food/Med Allergies | 0.10827 | 32093 | 0.4103 | 0.6699 |
| miR-26b-5p | Hearing Deficits | −0.1375 | 40939 | 0.2948 | 0.6699 |
| miR-26b-5p | Loss of consciousness | −0.16113 | 41789 | 0.2187 | 0.6699 |
| miR-26b-5p | MVA | 0.10819 | 32096 | 0.4106 | 0.6699 |
| miR-26b-5p | Sex (F) | 0.18007 | 29509 | 0.1686 | 0.6699 |
| miR-26b-5p | Weakness | −0.11341 | 40071 | 0.3883 | 0.6699 |
| miR-26b-5p | Weight (%) | 0.12366 | 31539 | 0.3465 | 0.6699 |
| miR-26b-5p | White Ethnicity | 0.1454 | 30757 | 0.2677 | 0.6699 |
| miR-320c | Hearing Deficits | 0.093541 | 32623 | 0.4772 | 0.6724 |
| miR-320c | Previous Concussions | −0.094785 | 39401 | 0.4713 | 0.6724 |
| miR-29c-3p | Memory Loss | −0.069916 | 38506 | 0.5955 | 0.6838 |
| miR-182-5p | NSAID In last 6 hrs | 0.1293 | 31336 | 0.3248 | 0.7192 |
| miR-30e-5p | Emesis | −0.10346 | 39713 | 0.4315 | 0.7270 |
| miR-80e-5p | NSAID in last 6 hrs | −0.10034 | 39601 | 0.4456 | 0.7270 |
| miR-182-5p | Acetaminophen | −0.10942 | 39928 | 0.4053 | 0.7390 |
| miR-182-5p | Emesis | 0.11067 | 32007 | 0.3999 | 0.7390 |

TABLE 10C-continued

Spearman correlations between the six miRNAs of interest,
concussion characteristics, and medical/demographic factors
Medical/Demographic Factors

| MicroRNA | Correlate | Spearman Correlation | t-stat | p-value | FDR |
|---|---|---|---|---|---|
| miR-182-5p | Previous Concussions | 0.11846 | 31727 | 0.3674 | 0.7390 |
| miR-30e-5p | Acetaminophen | 0.091435 | 32699 | 0.4872 | 0.7422 |
| miR-30e-5p | Weakness | −0.088204 | 39164 | 0.5028 | 0.7422 |
| miR-182-5p | Fall | −0.098129 | 39522 | 0.4557 | 0.7587 |
| miR-29c-3p | Food/Med Allergies | −0.052931 | 37895 | 0.6879 | 0.7616 |
| miR-29c-3p | Age (years) | 0.042872 | 34447 | 0.7450 | 0.7698 |
| miR-29c-3p | Broken Bones | 0.047007 | 34298 | 0.7214 | 0.7698 |
| miR-182-5p | Broken Bones | −0.08531 | 39060 | 0.5169 | 0.7731 |
| miR-182-5p | Hearing Deficits | 0.078979 | 33148 | 0.5486 | 0.7731 |
| miR-182-5p | Loss of consciousness | 0.081122 | 33070 | 0.5378 | 0.7731 |
| miR-29c-3p | Previous Concussion | 0.034161 | 34761 | 0.7955 | 0.7955 |
| miR-30e-5p | Previous Concussions | 0.075634 | 33268 | 0.5657 | 0.7972 |
| miR-182-5p | Food/Med Allergies | 0.064961 | 33652 | 0.6219 | 0.8033 |
| miR-182-5p | Memory loss | −0.066032 | 38366 | 0.6162 | 0.8033 |
| miR-320c | White Ethnicity | −0.067452 | 38418 | 0.6086 | 0.8203 |
| miR-26b-5p | Fall | 0.082635 | 33016 | 0.5302 | 0.8218 |
| miR-320c | Weight (%) | −0.62026 | 38222 | 0.6378 | 0.8238 |
| miR-30e-5p | Broken Bones | −0.05049 | 37807 | 0.7016 | 0.8341 |
| miR-30e-5p | Diet Restriction | −0.057872 | 38073 | 0.6605 | 0.8341 |
| miR-30e-5p | Food/Med Allergies | −0.050525 | 37808 | 0.7014 | 0.8341 |
| miR-30e-5p | Memory Loss | −0.062147 | 38227 | 0.6371 | 0.8341 |
| miR-30e-5p | MVA | 0.036064 | 34692 | 0.7844 | 0.8341 |
| miR-30e-5p | Sport | −0.35948 | 37284 | 0.7851 | 0.8341 |
| miR-30e-5p | Zofran in last 6 hrs | 0.032168 | 34832 | 0.8072 | 0.8341 |
| miR-320c | Broken Bones | 0.043525 | 34424 | 0.7412 | 0.8552 |
| miR-320c | Sex (F) | −0.051035 | 37827 | 0.6986 | 0.8552 |
| miR-182-5p | Sport | 0.049927 | 34193 | 0.7048 | 0.8552 |
| miR-320c | Zofran in last 6 hrs | −0.04289 | 37534 | 0.7449 | 0.8552 |
| miR-182-5p | Zofran in last 6 hrs | 0.04289 | 34446 | 0.7449 | 0.8552 |
| miR-320c | Age (years) | −0.030838 | 37100 | 0.8151 | 0.8713 |
| miR-320c | NSAID in last 6 hrs | −0.034136 | 37219 | 0.7957 | 0.8713 |
| miR-182-5p | Age (years) | −0.030139 | 37075 | 0.8192 | 0.8757 |
| miR-182-5p | Diet Restriction | −0.030865 | 37101 | 0.8149 | 0.8757 |
| miR-182-5p | Previous Concussion | −0.024401 | 36868 | 0.8532 | 0.8816 |
| miR-30e-5p | Previous Concussion | 0.014641 | 35463 | 0.9116 | 0.9116 |
| miR-182-5p | SSRI | 0.012912 | 35525 | 0.9220 | 0.9220 |
| miR-26b-5p | Emesis | −0.050525 | 37808 | 0.7014 | 0.9226 |
| miR-26b-5p | Memory Loss | −0.06409 | 38297 | 0.6266 | 0.9226 |
| miR-26b-5p | Previous Concussions | 0.053116 | 34078 | 0.6869 | 0.9226 |
| miR-26b-5p | Zofran in last 6 hrs | 0.048252 | 34253 | 0.7143 | 0.9226 |
| miR-26b-5p | Height (%) | 0.039696 | 34561 | 0.7633 | 0.9349 |
| miR-26b-5p | Previous Concussion | 0.036113 | 34690 | 0.7841 | 0.9349 |
| miR-26b-5p | NSAID In last 6 hrs | −0.025861 | 36921 | 0.8445 | 0.9352 |
| miR-26b-5p | SSRI | −0.025823 | 36919 | 0.8447 | 0.9352 |
| miR-320c | Fall | 0.015494 | 35432 | 0.9065 | 0.9367 |
| miR-26b-5p | Broken Bones | 0.019151 | 35301 | 0.8845 | 0.9455 |
| miR-320c | Height (%) | −0.0076446 | 36265 | 0.9538 | 0.9538 |
| miR-221-3p | Acetaminophen | 0.010493 | 35612 | 0.9366 | 0.9562 |
| miR-221-3p | Age (years) | −0.1604 | 41763 | 0.2208 | 0.9562 |
| miR-221-3p | Broken Bones | 0.092274 | 32669 | 0.4832 | 0.9562 |
| miR-221-3p | Diet Restriction | 0.065588 | 33629 | 0.6186 | 0.9562 |
| miR-221-3p | Emesis | −0.074585 | 38674 | 0.5711 | 0.9562 |
| miR-221-3p | Fall | −0.041318 | 37477 | 0.7539 | 0.9552 |
| miR-221-3p | Food/Med Allergies | −0.079397 | 38847 | 0.5465 | 0.9562 |
| miR-221-3p | Hearing Deficits | −0.072367 | 36250 | 0.9562 | 0.9562 |
| miR-221-3p | Height (%) | −0.46062 | 37648 | 0.7267 | 0.9562 |
| miR-221-3p | Loss of consciousness | 0.016669 | 35390 | 0.8994 | 0.9562 |
| miR-221-3p | Memory Loss | 0.0097105 | 35641 | 0.9413 | 0.9552 |
| miR-221-3p | MVA | 0.033577 | 34782 | 0.7990 | 0.9562 |
| miR-221-3p | NSAID in last 6 hrs | 0.079651 | 33123 | 0.5452 | 0.9562 |
| miR-221-3p | Previous Concussion | −0.032209 | 37149 | 0.8070 | 0.9562 |
| miR-221-3p | Previous Concussions | −0.031501 | 37124 | 0.8112 | 0.9562 |
| miR-221-3p | Seizues | −0.109 | 39913 | 0.4071 | 0.9562 |
| miR-221-3p | SSRI | 0.015494 | 35432 | 0.9065 | 0.9562 |
| miR-221-3p | Vision Deficits | 0.016018 | 35414 | 0.9033 | 0.9562 |
| miR-221-3p | Weakness | 0.1029 | 32286 | 0.4340 | 0.9562 |
| miR-221-3p | Weight (%) | −0.090328 | 39241 | 0.4925 | 0.9562 |
| miR-221-3p | White Ethnicity | −0.043469 | 37554 | 0.7416 | 0.9562 |
| miR-221-3p | Zofran in last 6 hrs | −0.037529 | 37341 | 0.7759 | 0.9562 |
| miR-26b-5p | Sport | −0.0019971 | 36062 | 0.9879 | 0.9879 |
| miR-26b-5p | Vision Deficits | 0.0053393 | 35798 | 0.9677 | 0.9879 |

Over 50% of the miRNAs found in CSF were also found in saliva and nearly 10% undergo parallel changes following concussive head trauma. Salivary concentrations of six of these miRNAs were predictive of concussion status and five have been described in previous studies of adult human serum. Importantly, these six miRNAs had no correlation with bony injury, sports participation, or participant demographic characteristics. They also displayed striking enrichment for mRNA targets related to neuronal development. These factors, coupled with ease of collection and quantification make salivary miRNAs an ideal substrate for concussion assessment.

Potential Mechanisms for Salivary Transfer of Brain-Related miRNAs.

In a medical community dominated by blood-based assays, the idea that salivary sampling provides a window into the brain might be difficult to fathom. Recall, however that the vast majority of medical tests rely on measurements of proteins that are easily degraded in the enzymatic milieu of the mouth. In comparison, the short, single-stranded structure of miRNAs renders them relatively resistant to enzymatic degradation (Gilad et al., 20087). They are also commonly protected by micro-vesicle or protein-bound mechanisms during extracellular transport Valadi et al., 2007). These factors account for the stability and reproducibility of salivary miRNA signatures in healthy subjects over time (Bahn et al., 2015). They also help explain how brain-related miRNA travels to saliva. Exosomal transport of miRNAs may result directly from cranial nerves that innervate the oropharynx (glossopharyngeal, facial, vagus, and trigeminal nerves) (Majem et al., 2015) or indirectly through extraction from the blood by specialized cells in salivary glands (Bahn et al., 2015). This latter mechanism demonstrates, in part, why many of the peptides and lipids found in blood are also present in saliva (Yan et al., 2009), and why the current study finds such high overlap between serum-based miRNA biomarkers of concussion and those detected in saliva. The glymphatic system, which helps regulate CSF turnover via peri-arterial tissue within the myelin sheath of cranial nerves and the olfactory bulb, represents a primary route by which brain-related molecules enter the peripheral circulation (Plog et al., 2015). Given the proximity of these structures to the oropharynx, it seems likely that the glymphatic system also plays a role in the transfer of brain-related miRNA to saliva.

The Role of miRNAs in the Physiologic Response to Traumatic Brain Injury.

The six miRNAs identified in the current investigation are not merely correlated with the presence or absence of concussion. They also have neurobiological implications in the physiologic response to traumatic brain injury. For example, miR-320c is down-regulated in CSF of sTBI subjects and saliva of mTBI subjects. In both bio-fluids concentrations of miR-320c are directly correlated with time since injury (i.e. they return toward baseline over time). MiR-320c is implicated in several pathways critical to nervous system function, including plasticity, mood, and circadian rhythm.

One mRNA target of miR-320c is phospholipid phosphatase related 1 (LPPR1), a member of the plasticity-related gene family that is dynamically expressed during neuronal excitation and regulates neuronal plasticity Savaskan et al., 2004). Plasticity-related genes are implicated in attentional deficits and in the current investigation concentrations of miR-320c were directly correlated with child report of increased daydreaming and parental report of child distraction. Longitudinal return of miR-320 levels toward baseline may mitigate these symptoms. On the other hand, unfettered increases in miR-320c could lead to mood dysregulation commonly reported in post-concussive syndrome. This idea is supported by a study of miRNA expression in the adult forebrain following successful suicide completion that found significant increases in miR-320c (Lopez et al., 2014).

Implications for Concussion Management.

The salivary miRNAs identified in this investigation have potential application in the diagnosis and management of pediatric concussion. This panel provides an objective measure of brain injury that is cheaper than MRI imaging approaches, more easily obtained than serum samples, and less time consuming than administering and scoring subjective concussion surveys. Because miRNA signatures remain elevated nearly two weeks beyond injury and trend towards baseline during that time, they have clinical application at time of initial presentation to an acute clinic or emergency department setting, as well as at follow-up encounters with concussion specialists. Longitudinal trends in miRNA concentrations have potential utility for triaging specialist referrals, initiating personalized medical therapies, and tracking clinical responses to therapy. The panel of miRNAs identified in this investigation misclassified only 17 out of 78 subjects. The misclassified controls included one subject with food allergies and type 1 diabetes mellitus who was taking anti-depressant medication and a non-steroidal anti-inflammatory medicine, as well as one subject with no identifiable medical conditions. The 15 misclassified mTBI subjects were characterized by history of previous concussion (n=5), weakness (n=3), emesis (n=3), myopia (n=3), and anti-inflammatory medication use (n=6). Thus, future investigations will be needed to examine the relationship of these factors to salivary miRNA.

Table 11 of miRNAs is a list of sixty eight (68) miRNAs that may be used in identifying and/or characterizing traumatic brain injury in a patient/subject. miRNAs that share the same seed sequences as any of the miRNAs in Table 1 may be used in identifying and/or characterizing traumatic brain injury in a patient/subject.

TABLE 11

| | TBI miRNA |
|---|---|
| 1 | hsa-let-7f-5p |
| 2 | hsa-let-7i |
| 3 | hsa-miR-10a-5p |
| 4 | hsa-miR-10b-5p |
| 5 | hsa-miR-23a-3p |
| 6 | hsa-mir-23b |
| 7 | hsa-mir-25 |
| 8 | hsa-miR-25-3p |
| 9 | hsa-mir-26a-1 |
| 10 | hsa-mir-26a-2 |
| 11 | hsa-miR-26a-5p |
| 12 | hsa-mir-26b |
| 13 | hsa-miR-26b-5p |
| 14 | hsa-mir-28 |
| 15 | hsa-miR-28-3p |
| 16 | hsa-miR-28-5p |
| 17 | hsa-miR-29c-3p |
| 18 | hsa-mir-30b |
| 19 | hsa-miR-30e-3p |
| 20 | hsa-miR-30e-5p |
| 21 | hsa-mir-92a-1 |
| 22 | hsa-mir-92a-2 |
| 23 | hsa-mir-103a-1 |
| 24 | hsa-mir-103a-2 |
| 25 | hsa-miR-125b-1-3p |
| 26 | hsa-miR-125b-2-3p |
| 27 | hsa-miR-141-3p |

TABLE 11-continued

| | TBI miRNA |
|---|---|
| 28 | hsa-miR-148b-3p |
| 29 | hsa-mir-151a |
| 30 | hsa-miR-151a-3p |
| 31 | hsa-miR-151a-5p |
| 32 | hsa-miR-155-5p |
| 33 | hsa-mir-181a-2 |
| 34 | hsa-miR-181a-5p |
| 35 | hsa-miR-182-5p |
| 36 | hsa-miR-193a-3p |
| 37 | hsa-miR-203a-3p |
| 38 | hsa-miR-205-5p |
| 39 | hsa-mir-218-2 |
| 40 | hsa-miR-221-3p |
| 41 | hsa-miR-320c |
| 42 | hsa-miR-338-3p |
| 43 | hsa-miR-338-5p |
| 44 | hsa-miR-342-5p |
| 45 | hsa-miR-374a-5p |
| 46 | hsa-miR-378d |
| 47 | hsa-miR-378f |
| 48 | hsa-miR-378g |
| 49 | hsa-miR-378i |
| 50 | hsa-miR-454-3p |
| 51 | hsa-miR-501-3p |
| 52 | hsa-miR-532-5p |
| 53 | hsa-miR-577 |
| 54 | hsa-miR-625-3p |
| 55 | hsa-miR-744-5p |
| 56 | hsa-miR-944 |
| 57 | hsa-miR-1273g-5p |
| 58 | hsa-miR-1285-3p |
| 59 | hsa-miR-1303 |
| 60 | hsa-miR-1307-3p |
| 61 | hsa-miR-3074-5p |
| 62 | hsa-mir-3160-1 |
| 63 | hsa-mir-3613 |
| 64 | hsa-miR-3613-5p |
| 65 | hsa-miR-3916 |
| 66 | hsa-mir-4532 |
| 67 | hsa-mir-5091 |
| 68 | hsa-miR-6770-5p |

This investigation identified six salivary miRNAs (miR-182-5p, miR-221-3p, mir-26b-5p, miR-320c, miR-29c-3p, and miR-30e-5p) altered in mTBI that reflect CSF patterns in sTBI and demonstrate diagnostic accuracy for mTBI status. These six miRNAs are functionally related to neuronal development and demonstrate intriguing correlations with concussion symptom reports. Though several have been identified in previous serum studies of adult concussion, here the inventors show that they are easily measured in saliva and exhibit sustained dysregulation for up to two weeks following injury.

Example 2

Comparison of Serum and Saliva miRNAs for Identification and Characterization of mTBI in Adult Mixed Martial Arts Fighters An objective of the inventors in this study was to determine the relationship between peripheral measures of miRNA in the blood and saliva with objective measures of balance and cognitive function in adult subjects exposed to recent mild head trauma; to examine if any of the identified miRNAs are involved in specific biological pathways relevant to brain function and injury response; and to quantify the strength of the relationship between the miRNAs and functional measures and determine their potential diagnostic utility.

Subjects.

All protocols regarding the use of human subjects were reviewed and approved by the Institutional Review Board of SUNY Upstate Medical University. Written consent was obtained from all human subjects prior to study enrollment and sample collection. Subjects received monetary compensation for their participation. A total of 216 samples were collected from 50 MMA fighters (42 unique, 8 repeat fighters), including 85 saliva and 131 serum samples. These were collected at 1 week or 1 hour pre-fight time points, and at one or more of 4 post-fight time points: immediately post-fight (15-30 min), 2-3 days, 1 week, and 3+ weeks (Table 12). Each MMA fight consisted of three rounds of 3 minutes each, unless a fighter was knocked out or forfeited by submission. Blood collection was performed on-site by a trained phlebotomist into sterile BD Vacutainer SST tubes (Becton-Dickenson), allowed to sit for 20 minutes and centrifuged per manufacturer instructions. Saliva was collected by expectoration into Oragene RNA collection vials (RE-100, DNAGenotek, Ottawa, ON) or by swab absorption using the Oragene Nucleic Acid Stabilizing Kit swab (P-157, DNAGenotek, Ottawa, ON).

The MMA subjects included 40 males and 2 females, with an average age of 26.5 yrs and mean BMI of 24.6. Two-thirds (66%) of the subjects self-reported as Caucasian, 17% African American, and 14% Hispanic. A total of 29% of the fighters also reported a prior history of concussion, without complication. Serum samples from a subset of these fighters were used to evaluate potential changes in pre- and post-fight protein biomarkers of mTBI. These samples were derived from 24 fighters (23 male), aged 18-42 (mean 24.9 yrs), with a mean BMI of 23.4. One of the subjects had a noted history of hearing loss, and 5 had a previous history of a single concussion (without complication). The majority (57%) of the fighters were Caucasian, 20% were African American, and 20% were Hispanic.

TABLE 12

Saliva and serum samples used for miRNA analysis.

| | N | 1 wk pre | 0 d pre | 0 d post | 2-3 d post | 1 wk post | 3+ wks post | Functional Data | |
|---|---|---|---|---|---|---|---|---|---|
| Saliva | 85 | 4 | 23 | 23 | 15 | 12 | 8 | 54 | 64% |
| Serum | 131 | 7 | 52 | 52 | 17 | 3 | 0 | 49 | 37% |
| Total | 216 | 11 | 75 | 75 | 32 | 15 | 8 | 103 | 48% |

Protein Biomarkers in Serum.

On a subset (n=24) of the fighters, expression of several candidate protein biomarkers of TBI based on pre-existing literature (which often focused on severe TBI cases or animal models) using an ELISA or Luminex platform was examined. The same serum aliquot was used for both assays, which was collected at the time points indicated in Table 12, and stored at −80° C. for subsequent processing.

Luminex Assay:

Using a custom 8-plex Magnetic Luminex® Screening Panel (R&D Systems, Minneapolis, Minn.; catalog #LXSAHM), serum samples were assayed for the expression level of BDNF, CCL2/MCP-1, CRP, ICAM1, IL-6, NSE2, S100B, and VCAM according to the manufacturer's protocol. The sensitivity limits for each analyte were 0.32, 9.9, 116, 140, 87.9, 1.7, 4.34, and 238 pg/mL, respectively. Sample fluorescence was read on a Bio-Rad Bioplex® 200 System and analyzed using Bioplex®Manager 6.1 software (Bio-Rad, Hercules, Calif.).

ELISA:

Serum levels of UCHL1, MBP, GFAP were detected using Mybiosource ELISA kits (MyBiosource, Inc., San Diego, Calif.) according to the manufacturer's instructions. The catalog numbers and detection limits were as follows: UCHL1 (#MBS2512760), 78.125-5000 pg/mL; MBP (#MBS261463), 1000 pg/ml-15.6 pg/ml; and GFAP (#MBS262801), 20 ng/ml-0.312 ng/ml. The optical density of the peroxidase product was measured spectrophotometrically using a Synergy 2 microplate reader (Biotek, Winooski, Vt.) at a wavelength of 450 nm.

Statistical analysis of the protein biomarker data was performed using a pairwise T test comparing the post-fight levels to the pre-fight levels for the 24 fighters, as well as linear regression to examine the relationship of the changes in post-fight levels compared to the number of hits to the head (HTH) that were observed from fight videos for each subject.

RNA Isolation.

RNA was isolated from serum and saliva using the miRNeasy Serum/Plasma Kit (Qiagen Inc) according to the manufacturer's instructions. Serum: frozen serum samples were thawed on ice, and 200 μL of serum was added to 1 mL of QIAzol lysis reagent. Following vigorous vortexing, 200 μL of chloroform was added and the samples were incubated for 5 minutes at room temperature (RT), then centrifuged at 12,000×g for 15 minutes at RT. The resultant aqueous phase was removed, mixed with 1.5 volumes of 100% ethanol, transferred to an RNeasy MinElute spin column, and centrifuged for 15 seconds. The column was washed with Buffers RWT and RPE at the manufacturer's indicated volumes, and the RNA was eluted with 30 μL of RNase-free water. Saliva: refrigerated saliva samples originally collected in an Oragene vial or swab collection kit were incubated at 50° C. for 1 hour. A 250 μL aliquot was then removed, transferred to a microcentrifuge tube, incubated at 90° C. for 15 minutes, and cooled to RT. 750 μL of QIAzol lysis reagent was added, and the sample was vortexed vigorously for 1 minute, and incubated for 5 minutes at RT. Chloroform (200 μL) was added, and the sample was vortexed for 1 minute, then centrifuged at maximum speed (>13,000×g) for 10 minutes. 450 μL of the resultant aqueous phase was transferred to a new tube, mixed with 675 μL of 100% ethanol, transferred to an RNeasy MinElute spin column, and centrifuged for 15 seconds. The column was sequentially washed with Buffers RWT and RPE at the manufacturer's indicated volumes, and the RNA was eluted with 30 μL of RNase-free water. RNA quality was assessed using the Agilent Technologies Bioanalyzer on the RNA Nanochip.

RNA Sequencing.

Stranded RNA-sequencing libraries were prepared using the TruSeq Stranded Small RNA Kit (Illumina) according to manufacturer instructions. Samples were indexed in batches of 48, with a targeted sequencing depth of 10 million reads per sample. Sequencing was performed using 36 bp single end reads on an Illumina NextSeq 500 instrument at the SUNY Molecular Analysis Core (SUNYMAC) at Upstate Medical University. FastQ files were trimmed to remove adapter sequences, and alignment performed to the mature miRbase21 database using the Shrimp2 algorithm in Partek Flow (Partek, Inc., St. Louis, Mo.).

RNA-Seq Analysis.

The aligned reads were quantified and normalized to an internal relatively invariant reference miRNA (miR-24-3p) and converted to log 2 scale. Each subject's normalized miRNA post-fight data was then contrasted with their respective pre-fight/baseline values (obtained at either 1 week or immediately prior to the fight), yielding a total of 141 sample difference values (n=62 saliva, 79 serum). Normalized miRNA difference values were screened for sphericity using principal component analysis (PCA) prior to statistical analysis and filtered to eliminate those with more than 60% missingness.

We used two different analytical workflows to identify miRNAs associated with mTBI. In the first method, the 141 samples were split into 3 groups based on the probability of mTBI occurring at or prior to the time of collection based on the number of hits to the head (HTH) that a fighter experienced. These HTH values were obtained from video recordings of each fight. The defined groups were Very Likely (10+HTH; mean=24.2), Moderately Likely (4-9 HTH; mean=6.5), and Unlikely (0-3 HTH; mean=0.3)(Table 13):

TABLE 13

Sample classificiations used in analysis separated by fluid type

| Comparison Types by TBI Risk (HTH) | | N | Fluid Type | Ave HTH |
|---|---|---|---|---|
| Low | 0-3 HTH | 50 | 24 saliva/26 serum | 0.3 |
| Moderate | 4-9 HTH | 41 | 15 saliva/26 serum | 6.5 |
| Very Likely | 10-65 HTH | 50 | 23 saliva/27 serum | 24.2 |

"HTH": hits to the head observed by video.

Subject Binning.

We initially used a two-way analysis of variance (ANOVA) examining the main effects of Sample Type and TBI Classification as well as their interaction to screen for miRNAs with a significant effect of the TBI probability rating based on the HTH scores. This was performed in all of the samples from both biofluids with a False Discovery Rate (FDR) correction<0.15. The miRNAs which passed this filter were then used in a stepwise linear regression to establish the miRNAs that best predicted the actual HTH values. A logistic regression classification analysis was then completed to assess the ability to distinguish all of the Very Likely and Unlikely TBI samples from each other (holding out the Moderate group). 100-fold Monte-Carlo Cross-Validation (MCCV) was performed to estimate empirical accuracy across biofluids. miRNAs that showed the strongest predictive utility were then subjected to functional analysis using Diana Tools miRpathv3. The correlation in differences in miRNAs showing strong discriminatory power also was assessed in relation to various functional measures using correlation analysis.

Temporal Binning.

Because the first analysis combined all the initial samples from each subject post-fight into the same TBI probability class, it was possible some miRNAs may have eluded detection if they only had acute or delayed effects. Nonetheless, such temporal-dependent responses could be as important as any derived from the subject binning. To reveal potential acute or delayed effects we used a General Linear Model to examine the effects of Time and Sample Type, and their interaction, on relative miRNA expression based on four different temporal bins. As before, the 122 samples used in this analysis were normalized to the levels of expression pre-fight (Table 12). Time 1 thus contained samples from subjects who showed up to the MMA match but did not participate in a fight, and still provided a biofluid sample (these serve as controls for non-specific effects of the event) as well as subjects that participated in a match but experienced no hits to the head (these serve as exercise controls). Collectively, these are referred to as Time 1 Controls. The remaining temporal bins were from fighters who participated in a match and received at least 2 hits to the head (HTH). These were grouped by collection time point into Time 1 HTH (within 1 hour post-fight), Time 2 HTH (2-3 days post-fight), and Time 3 HTH (7 days post-fight). The temporal profiles of all miRNAs with significant Time effects were visualized and subjected to supervised classification analysis to identify the most salient patterns. miRNAs with expression profiles of interest were then subjected to functional analysis using Diana Tools miRpathv3 and compared with the miRNAs from the Subject Binning analysis.

Functional Studies.

Assessment of MMA fighter balance and cognitive function was performed using a version of the ClearEdge™ assessment system developed by Quadrant Biosciences Inc. (Syracuse N.Y.), that measured body sway in three dimensions during 8 different stances, as well as body sway and completion times during the performance of dual motor and cognitive tasks. The dual tasks and cognitive tasks were completed by each subject using a hand-held tablet computer (Toshiba, Model: WTB-B) and stylus. The analysis of body sway (balance) was measured via the use of an inertial sensor worn by each subject around the waist that sampled motion in all three planes at a frequency of 250 Hz with the resulting data downloaded from each tablet for post-processing. Stances were held by each subject for 30 seconds, with their shoes removed, while standing either on the floor or on a foam pad and data were obtained with the eyes open or closed. During the stances, the feet were either positioned side by side with the ankles or medial aspects of the feet touching, or they were in a tandem position with the dominant foot forward and the non-dominant foot positioned directly behind and the heel of the lead foot in contact with the toes of the trailing foot. The cognitive component of the dual tasks included a digital version of the Trails A and Trails B tasks, and an auditory working memory task (Backward Digit Span) in addition to a simple dual task of merely holding the tablet steady while maintaining fixation on it. In Trails A, subjects had to quickly connect an ascending series of encircled numbers (1-2-3 etc.) with a stylus on the screen. In Trails B, subjects had to connect an ascending series of encircled numbers and letters in an alternating alpha-numeric sequence (1-A-2-B-3-C etc.). The Backward Digit Span task consisted of measuring reverse-order recall of increasingly long number sequences that were delivered to each subject via headphones. Altogether, 14 tasks were measured on the fighters. Notably, it was only possible to obtain simultaneous functional and biofluid measures on the same subjects in approximately half (48%) of the sample times.

As with the miRNA data, the functional data were converted to standardized difference measures by comparison of all post-fight timepoints with a common pre-fight timepoint within each subject. Missing datapoints for some of the Backward Digit Span task measures were filled in using a K-nearest neighbor approach. The functional data were screened for sphericity prior to statistical analysis using principal component analysis (PCA). Then, a two-way (Sample Type×TBI Classification) analysis of variance (ANOVA) was performed to screen for functional measures with a significant effect of the TBI classification assignment at the time of collection with the False Discovery Rate (FDR)<0.05. We also examined the relationships of the significantly changed functional parameters with each other using Pearson's correlation metric and an R to T test of significance. Finally, two-way ANOVA was performed in a manner similar to the miRNA measures to identify functional outcomes that were related to the likelihood of an HTH or the temporal interval since an HTH.

Combined Analysis of Temporal Patterns in Functional and miRNA Data.

After identifying miRNAs with expression profiles of interest, we examined the balance and cognitive score data along with the molecular data using principal component analysis (PCA) to detect the molecular and functional features that show the most similarity across time. For this analysis, only ASR or DSR miRNAs were used along with the functional data from all of the post-fight samples (n=39 saliva, n=31 serum). Iterative principal axis PCA was performed using a quartimax root curve extraction. Factor weights were examined to identify functional variables most similar to the miRNA variables, with line plots created for visualization purposes.

TABLE 14

Functional Outcome Measures

Standing on floor

| | |
|---|---|
| 1) | Sway during Two Legs Eyes Open (TLEO) |
| 2) | Sway during Two Legs Eyes Closed (TLEC) |
| 3) | Sway during Tandem Stance Eyes Open (TSEO) |
| 4) | Sway during Tandem Stance Eyes Closed (TSEC) |

Standing on foam pad

| | |
|---|---|
| 5) | Sway during TLEO Foam Pad (TLEOFP) |
| 6) | Sway during TLEC Foam Pad (TLECFP) |
| 7) | Sway during TSEO Foam Pad (TSEOFP) |
| 8) | Sway during TSEC Foam Pad (TSECFP) |

Dual task

| | |
|---|---|
| 9) | Sway during Holding Tablet (HT) |
| 10) | Sway during Dual Task Trails B Task (TMB_Dual_Bal) |
| 11) | Sway during Dual Task Digit Span Backwards (DSB_Bal) |
| 12) | Completion Time for Trails A Task (TMA_Cog) |
| 13) | Completion Time for Trails B Task (TMB_Cog) |
| 14) | Completion Time for Dual Task Digit Span Backwards (DSB_Cog) |

Results: Functional Changes in WA Fighters.

Figure 6:
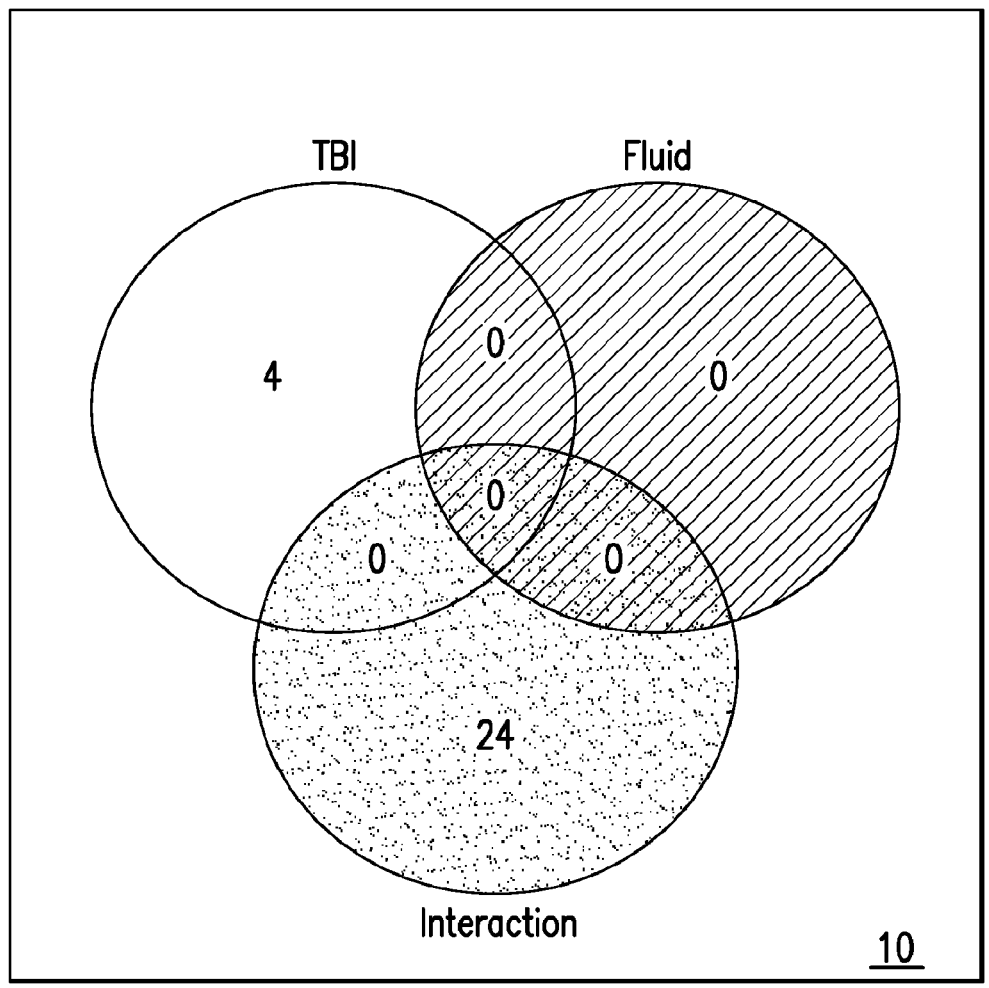
FIG. 6 shows significant effect of TBI likelihood classification on the changes in functional measures assessed following an MMA fight.
Figure 7A:
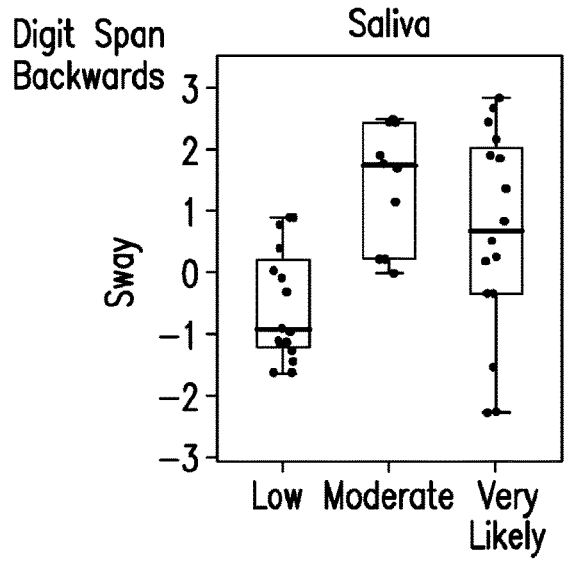
FIGS. 7A, B, C, D show Whisker box plots of consistent changes in body sway post-fight versus pre-fight seen during two different functional tests in subjects who provided saliva or serum samples and were classified into three different TBI likelihood categories (Low, Moderate, Very Likely). A and B—top plots, left to right; C and D—bottom plots, left to right. Note that one of the sway measures was obtained during a cognitive task performance (Digit Span Backwards, A-B) while the other was obtained during a balance test performed without visual guidance (Two Legs, Eyes Closed, C-D). The increase in sway is evident for both sets of measures in the Moderate and Very Likely groups compared with Low TBI likelihood groups.
Figure 7B:
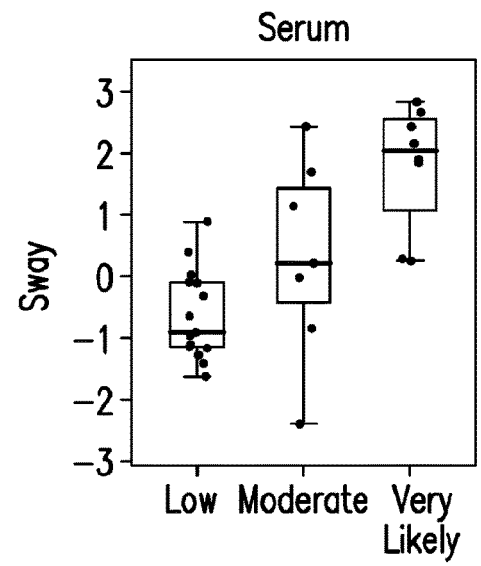
Figure 7C:
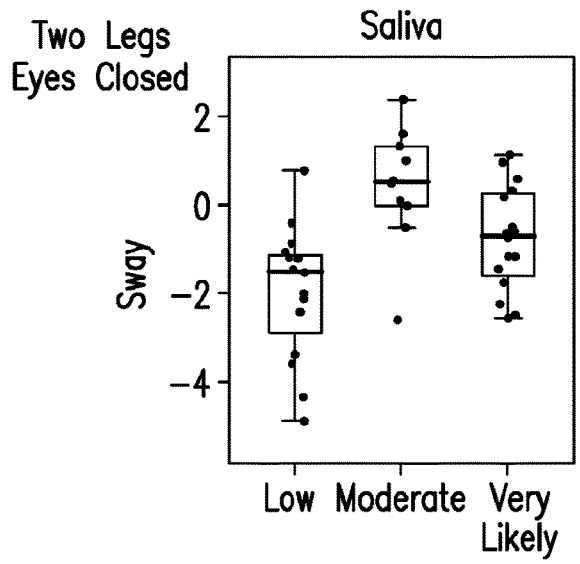
Figure 7D:
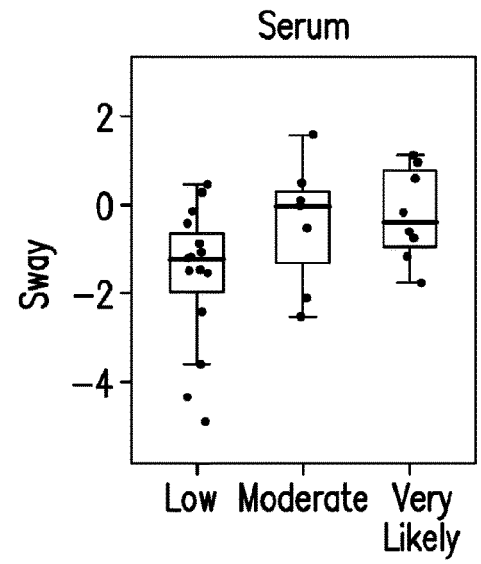
Figure 8A:
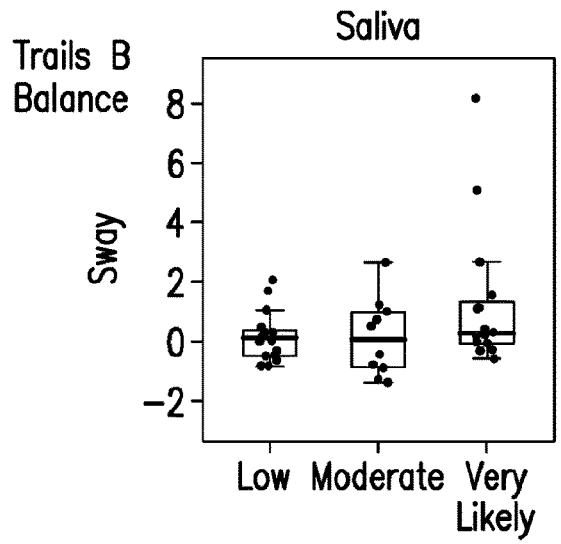
FIGS. 8A, B, C, D show less consistent changes in body sway or completion time scores post-fight versus pre-fight seen in two different functional tests, in subjects grouped by TBI likelihood. Same conventions as FIG. 7. Note slightly elevated scores in the Very Likely group of the TMB_Bal task (A-B top plots, left to right) when a serum (but not a saliva) sample was taken, and the slight elevation in the TMA_Cog score (C-D, bottom plots, left to right) in the Moderate (but not Very Likely) group.
Figure 8B:
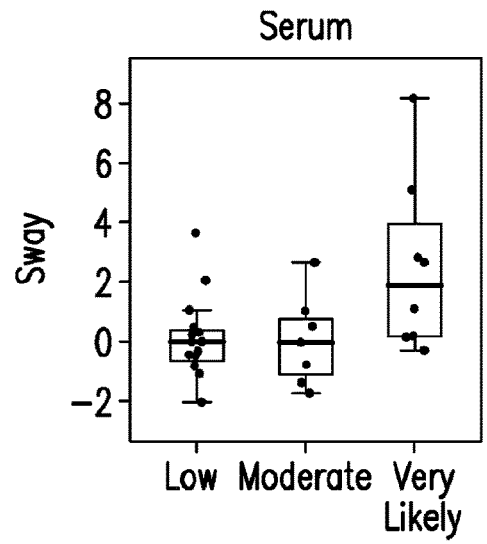
Figure 8C:
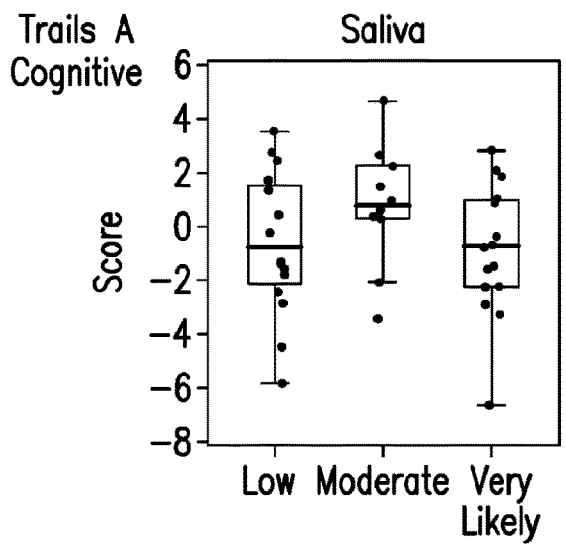
Figure 8D:
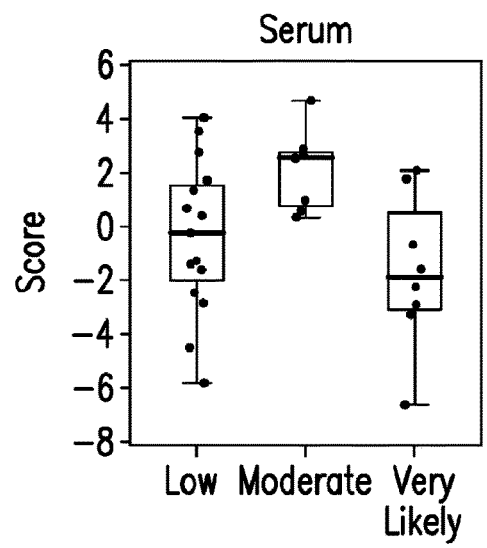

Four of the 14 functional measures showed a significant difference due to TBI likelihood classification. As expected, none of the 14 functional measures were affected by the type of biofluid that was being sampled at the time of collection and none showed any interaction effect; see Table 15 and FIG. 6. These tasks included three measures of body sway (TLEC, DSB_Bal, TMB_Bal) and one measure of cognitive function (TMA_Cog). FIG. 6 shows a significant effect of TBI likelihood classification on the changes in functional measures assessed following an MMA fight.

TABLE 15

Significant effects on functional data obtained during biofluid sampling.

| Functional Task | TBI | Fluid | Interaction |
|---|---|---|---|
| Digit Span Backwards (Sway) | 0.00004 | 0.84799 | 0.23975 |
| Two Legs Eyes Closed (Sway) | 0.00049 | 0.84799 | 0.71747 |
| Trail Making B Dual Task (Sway) | 0.02047 | 0.84799 | 0.83046 |
| Trail Making A (Cognitive) | 0.04340 | 0.84799 | 0.83046 |

Although there was no effect of biofluid type, we examined the patterns of functional changes for the sets of subjects providing saliva and serum separately, to help gauge reproducibility. Examples of the patterns of change in the body sway measures during the DSB and TLEC tasks are provided FIGS. 7A-7D. Overall, both of these functional measures increased in the Moderate and Very Likely TBI groups relative to the Low likelihood group. Notably, the patterns were not identical in both subject sample sets because different groups of subjects were assessed (with only partial overlap for the few subjects that provided both saliva and serum). FIGS. 7A-7D are whisker box plots of consistent changes in body sway post-fight versus pre-fight seen during two different functional tests in subjects who provided saliva or serum samples and were classified into three different TBI likelihood categories (Low, Moderate, Very Likely). Note that one of the sway measures was obtained during a cognitive task performance (Digit Span Backwards, upper) while the other was obtained during a balance test performed without visual guidance (Two Legs, Eyes Closed, lower). The increase in sway is evident for both sets of measures in the Moderate and Very Likely groups compared with Low TBI likelihood groups.

In addition to the two functional measures that showed clear stepwise gradients of impairment in the MMA fighters according to probability of TBI, there were two other significantly changed functional measures that did not show as clear a pattern according to TBI likelihood FIG. 8. These included the sway during the Trailmaking B task (TMB_Bal) and the difference score of the completion time for the Trailmaking A task (TMA_Cog). For the TMB_Bal task, there was a suggestion of elevated scores in the Very Likely group, particularly in subjects providing a serum sample, but it was not as evident in the subjects who provided a saliva sample FIG. 8 (A-B, top). For the TMA_Cog task, the pattern was mixed, with a potential elevation in completion time seen in the Moderate group, but no change or a slight decrease in the Very Likely group FIG. 8 (C-D, bottom). FIG. 8 shows less consistent changes in body sway or completion time scores post-fight versus pre-fight seen in two different functional tests, in subjects grouped by TBI likelihood (same conventions as FIGS. 7A-D). Note slightly elevated scores in the Very Likely group of the TMB_Bal task (upper) when a serum (but not a saliva) sample was taken, and the slight elevation in the TMA_Cog score (lower) in the Moderate (but not Very Likely) group.

The exploration of functional changes indicated that difference score measures of body sway during the TLEC task and DSB_Bal tasks were the most sensitive predictors of TBI likelihood. The correlation between these two variables was examined. Using 51 pairs of measures (excluding the missing values replaced by the K-nearest neighbor algorithm) we observed a complete absence of correlation in the two measures (Pearson's R=0.00, p=0.99). Thus, although both tasks are sensitive to differences in balance as a function of the likelihood of TBI (i.e., the hits to the head), they clearly provide different information. However, given the increased difficulty in obtaining Digit Span scores on all subjects because of the need to wear headphones, the TLEC task clearly has practical advantages.

Serum Protein Biomarkers.

The potential changes in levels of 11 serum proteins in 24 fighters immediately after their fight compared to pre-fight were examined. These proteins included UCHL1, MBP, GFAP (analyzed by ELISA) and BDNF, CCL2/MCP-1, CRP, ICAM1, IL-6, NSE2, S100B, and VCAM (analyzed by a custom Luminex assay. All of the IL-6 sample values were below the lowest standard concentration for that assay, and thus no results were available for this analyte. The majority (21/24) of the S100B values for pre-fight samples were also below the lowest standard concentration. However, 16 of the samples from the same fighters had measurable levels of S100B post-fight. In order to estimate the magnitude of changes and perform statistical comparisons for these 16 samples, the pre-fight concentration were set equal to half the lowest post-fight concentration value (22.7 pg/mL). Of the 10 proteins we obtained concentrations for, four demonstrated significant pairwise changes (all increases) in post-fight versus pre-fight serum samples. These included GFAP (p=1.4e-7, median % change=33.1%), MBP (p=0.003, median % change=65.4), NSE2 (p=0.037, median % change=50.4), and S100B (p=0.006, median % change=747%).

Figure 9:
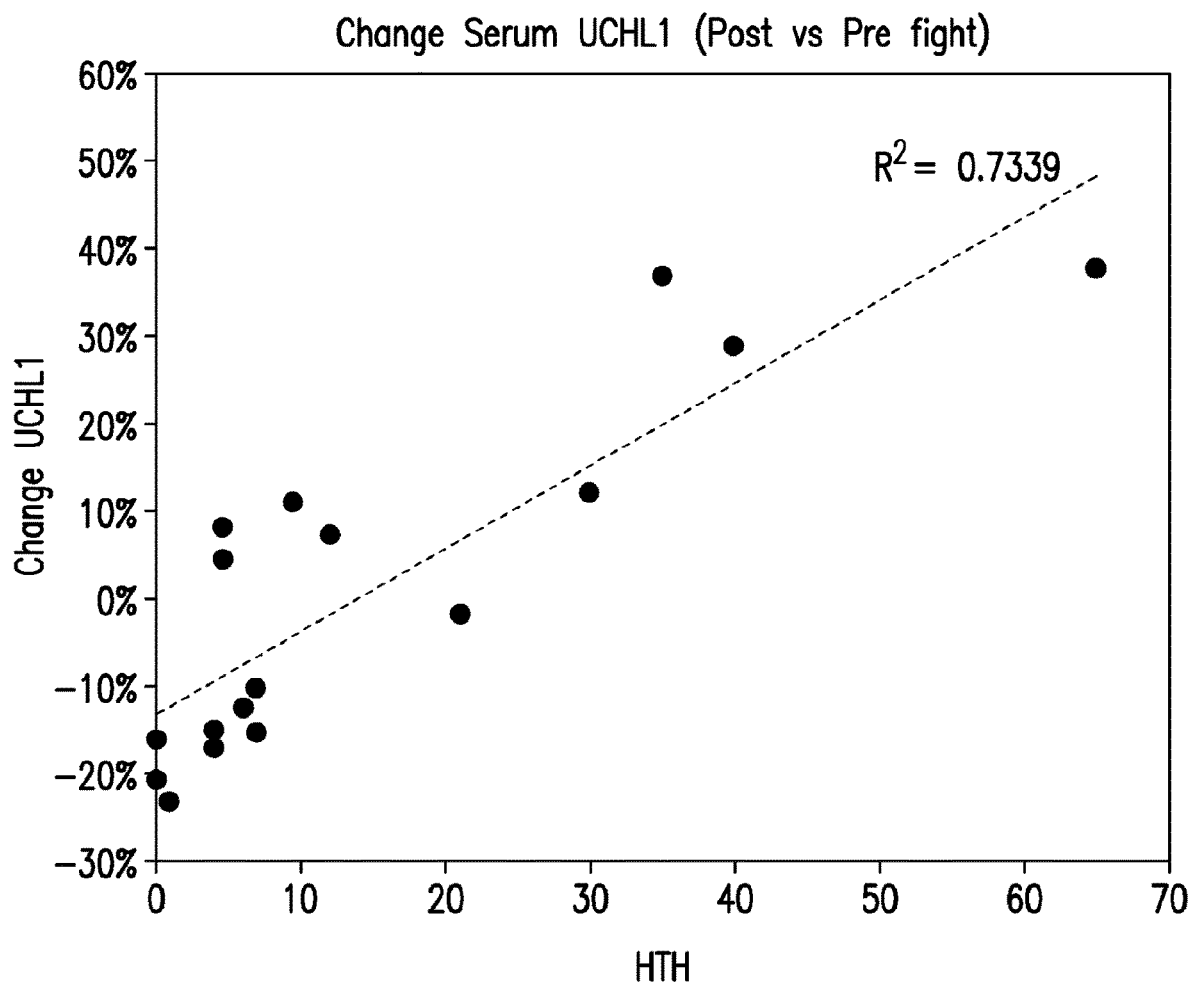
FIG. 9 shows Change in serum UCHL1 post-fight related to hits to the head (HTH). Note that this regression was largely driven by 4 fighters who received more than 30 HTH. Overall, however, there was no significant difference in the group of fighters post-fight versus pre-fight.
Figure 10A:
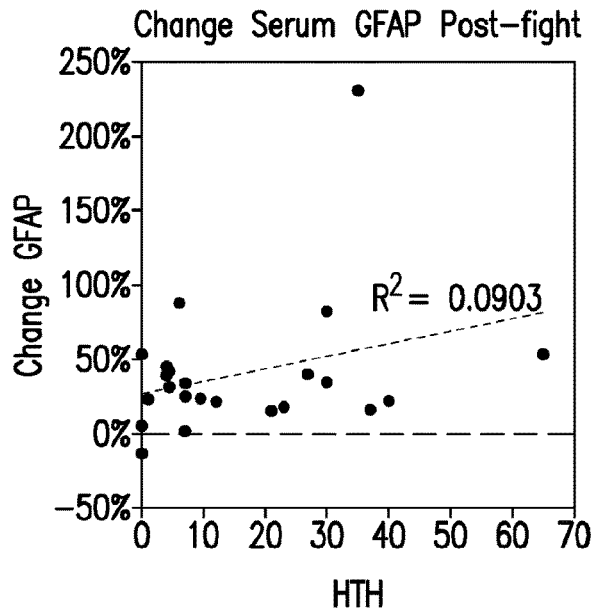
FIGS. 10A-I show Serum protein changes compared with hits to the head (HTH). For each of the 9 proteins, the change post-fight compared to pre-fight is expressed as a percentage of the pre-fight level and plotted on the Y-axis. The X-axis indicates the HTH values counted by an independent viewer of a video recording of each MMA fight. Note that none of these proteins displayed strong associations with HTH, with maximal $r^2$ values less than 0.09.
Figure 10B:
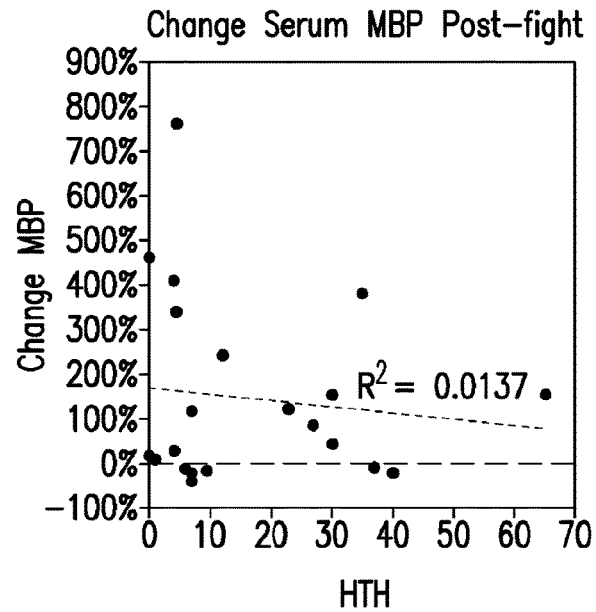
Figure 10C:
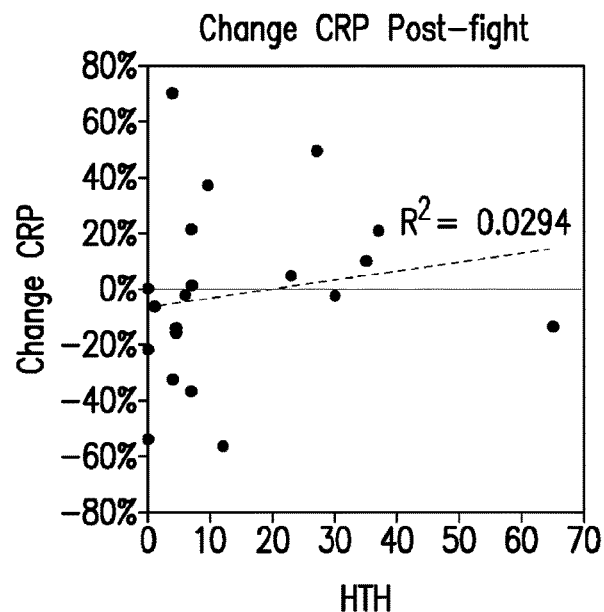
Figure 10D:
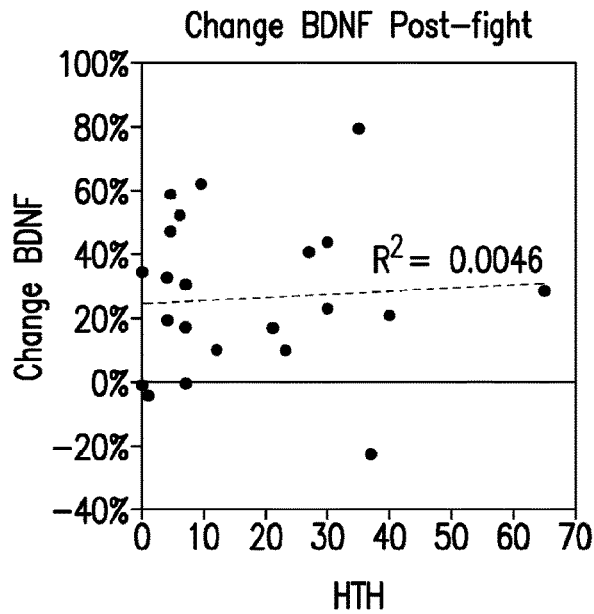
Figure 10E:
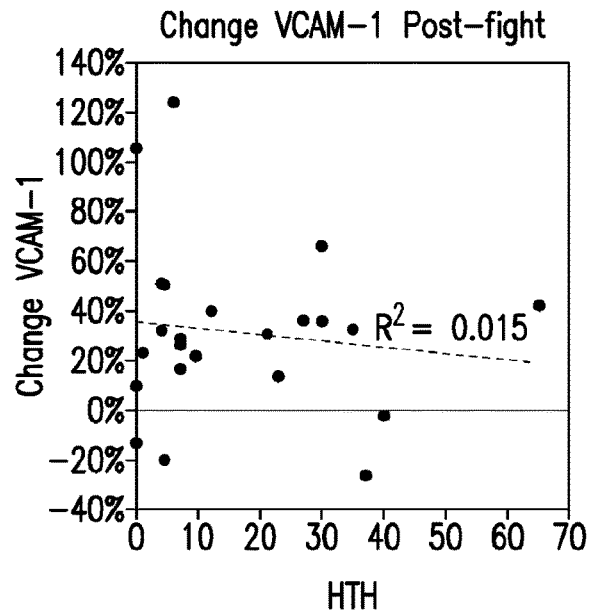
Figure 10F:
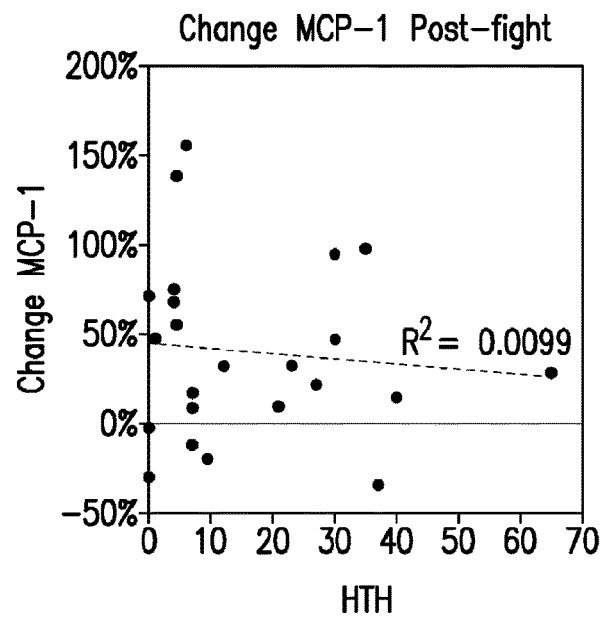
Figure 10G:
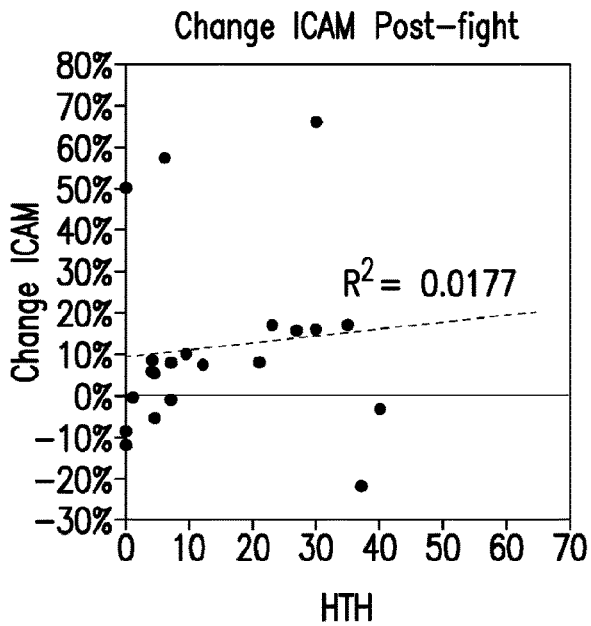
Figure 10H:
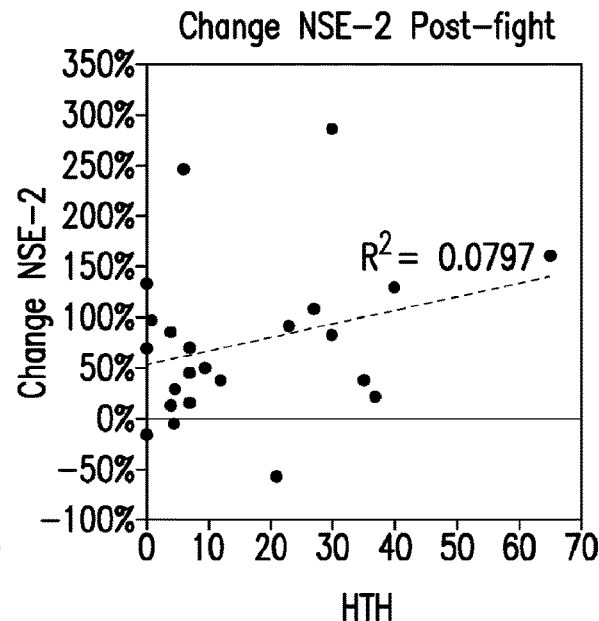
Figure 10I:
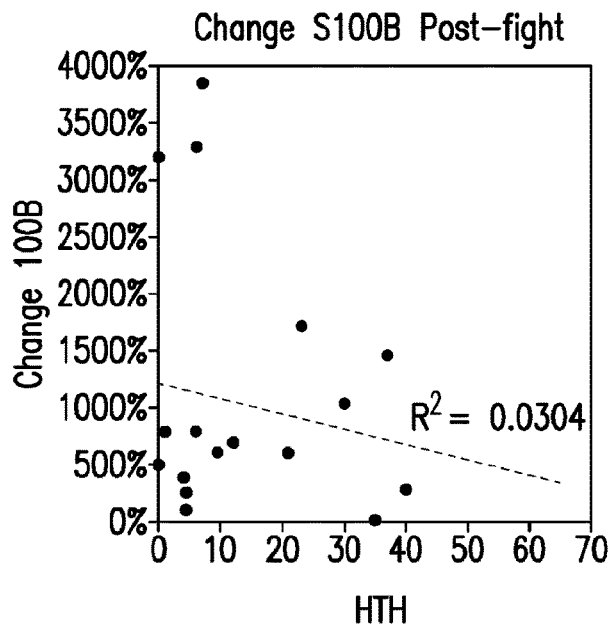

The potential relationship of changes in these 10 proteins to the number of hits to the head that each fighter received were examined. Only 1 of the biomarkers (UCHL1) demonstrated a significant regression; $r^2$=0.7339, FIG. 9. Notably, however, UCHL1 did not demonstrate a significant overall post- vs pre-effect (p=0.934, median % change=1.2). The remaining proteins demonstrated $r^2$ coefficients ranging from 0.005-0.09, FIG. 10A-10I.

miRNA Biomarkers.

Figure 11A:
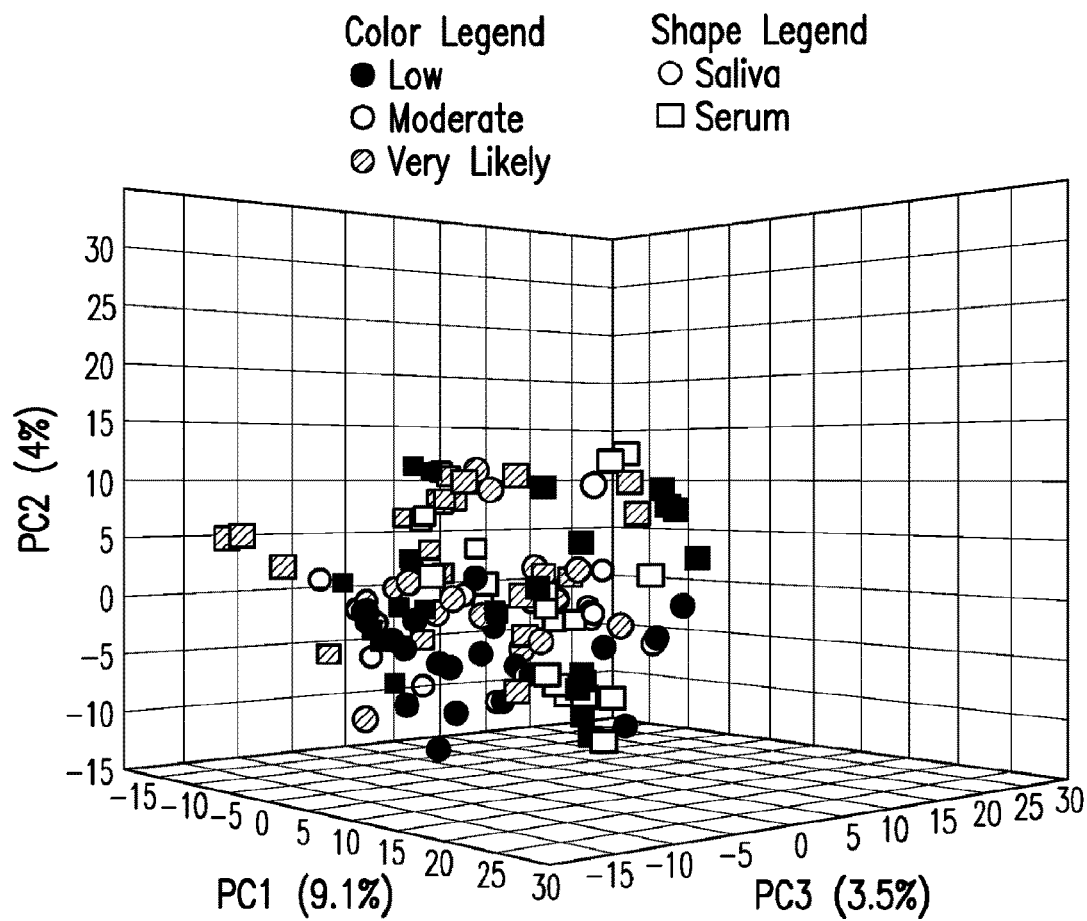
FIGS. 11A, B show Principal component analysis (PCA) demonstration of normal and highly-spherical distribution of sample types across biofluid types and TBI likelihoods prior to statistical analysis. The image (A) shows intermixing of the samples, with only a slight suggestion of separation of Very Likely serum samples (green/grayscale boxes) from the main data cloud. When all the data are collapsed, the change values are distributed in a highly normal fashion (B).
Figure 11B:
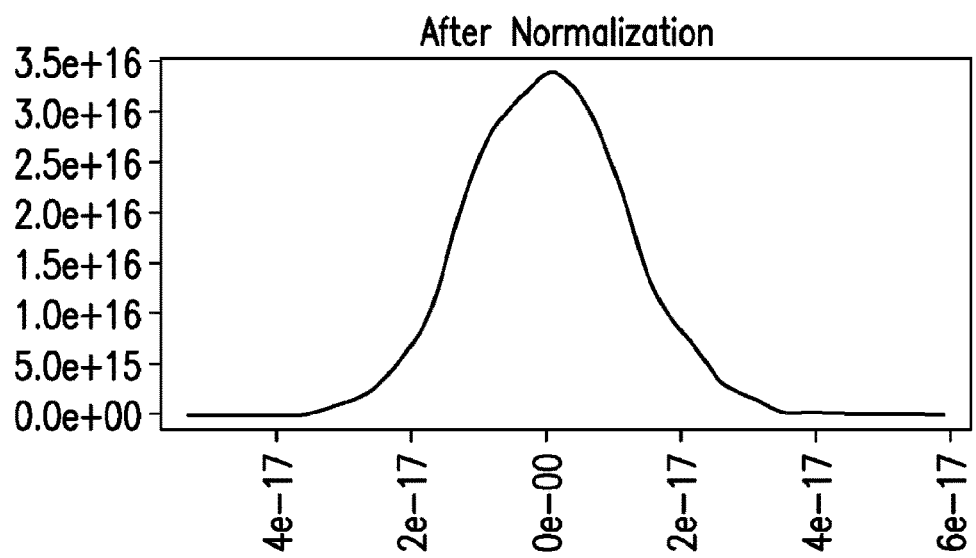

A total of 925 miRNAs were reliably quantified in the combined saliva and serum samples by RNA-Seq and subjected to downstream analysis. After normalization, the changes in miRNA values were visually screened for sphericity and normality prior to statistical analysis using principal component analysis (PCA) see FIG. 11A-11B. The results demonstrated a generally unbiased data set regardless of the biofluid type, with no obvious outliers based on the clustering and the size of the PCA axes. As shown in FIG. 11A-11B, principal component analysis (PCA) demonstration of normal and highly-spherical distribution of sample types across biofluid types and TBI likelihoods prior to statistical analysis. The image at the top (FIG. 11A) shows intermixing of the samples, with only a slight suggestion of separation of Very Likely serum samples (green/grayscale boxes) from the main data cloud. When all the data are collapsed, the change values are distributed in a highly normal fashion (11B)-lower).

Figure 44:
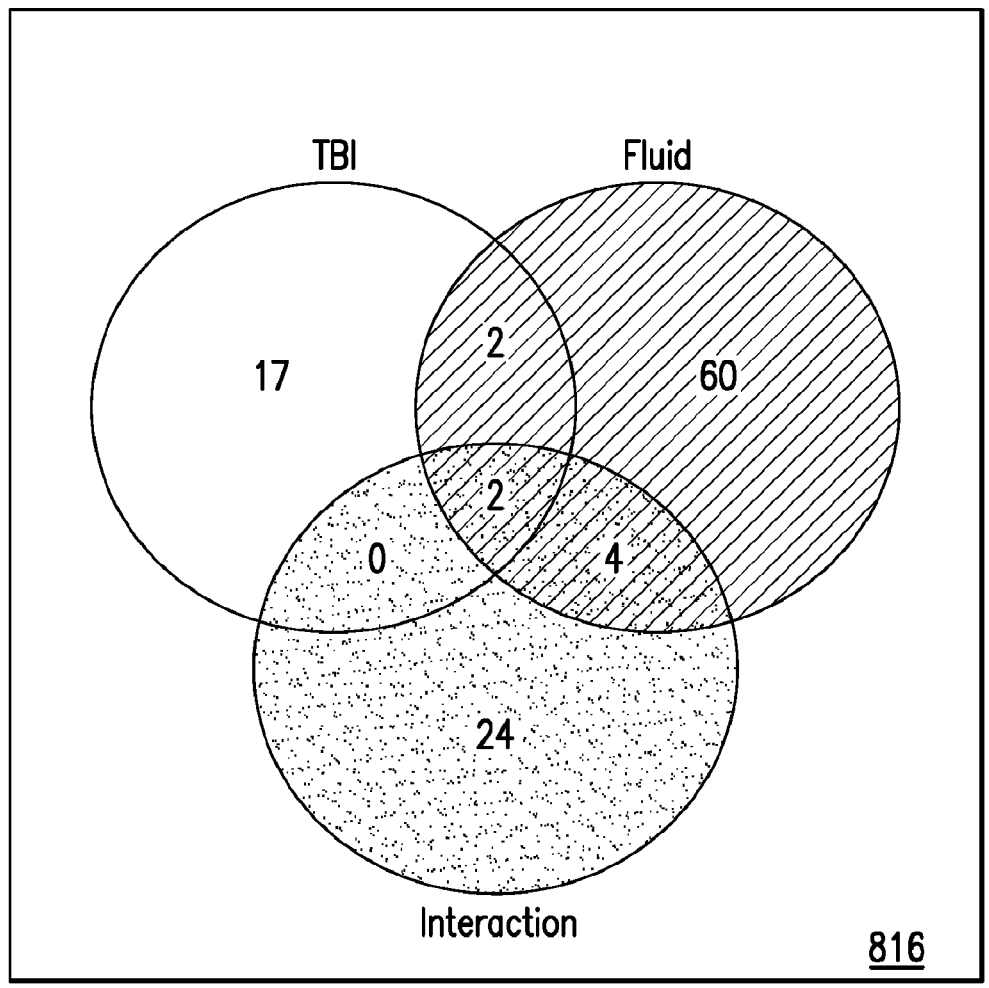
FIG. 44 shows Effects of TBI likelihood on miRNA expression changes in serum and saliva post-fight compared to pre-fight. A total of 925 miRNAs were tested, with 21 showing a significant main effect of TBI likelihood, of which two also showed a significant main effect of Fluid and two showed a significant Fluid×TBI interaction.

After correcting for multiple testing (FDR<0.15), a total of 21 miRNAs demonstrated significant changes according to the TBI likelihood classification as shown by FIG. 44 and Table 16. Of these, two also showed a significant effect of Fluid type and two showed an Interaction effect of Fluid type×TBI likelihood. FIG. 44 shows the effects of TBI likelihood on miRNA expression changes in serum and saliva post-fight compared to pre-fight. A total of 925 miRNAs were tested, with 21 showing a significant main effect of TBI likelihood, of which two also showed a significant main effect of fluid and two showed a significant Fluid×TBI interaction.

TABLE 16 miRNAs with changes related to TBI likelihood.

| miRNA | TBI | Fluid | Interaction | Chg Saliva | Chg Serum |
|---|---|---|---|---|---|
| hsa-miR-376a-5p | 0.021 | 0.535 | 0.749 | ↓ | — |
| hsa-miR-122-5p | 0.119 | 0.024 | 0.162 | — | ↑ |
| hsa-miR-4649-3p | 0.119 | 0.091 | 0.139 | ↓ | — |
| hsa-miR-10b-5p | 0.119 | 0.234 | 0.739 | ↑ | ↑ |
| hsa-miR-6809-3p | 0.119 | 0.269 | 0.668 | ↓ | ↓ |
| hsa-miR-4693-5p | 0.119 | 0.320 | 0.812 | — | ↑ |
| hsa-miR-3146 | 0.119 | 0.649 | 0.844 | ↓ | — |
| hsa-miR-92a-3p | 0.119 | 0.987 | 0.594 | ↓ | ↓ |
| hsa-miR-10a-5p | 0.136 | 0.131 | 0.417 | ↓ | ↑ |
| hsa-miR-6770-5p | 0.136 | 0.235 | 0.825 | ↓ | — |
| hsa-miR-30b-5p | 0.136 | 0.408 | 0.723 | ↑ | ↑ |
| hsa-miR-4637 | 0.136 | 0.689 | 0.516 | — | ↑ |
| hsa-miR-455-5p | 0.136 | 0.803 | 0.896 | ↓ | ↓ |
| hsa-miR-20a-5p | 0.136 | 0.987 | 0.396 | ↑ | — |
| hsa-miR-4766-5p | 0.147 | 0.015 | 0.139 | ↓ | — |
| hsa-miR-155-5p | 0.147 | 0.589 | 0.806 | — | ↑ |
| hsa-miR-5694 | 0.147 | 0.649 | 0.665 | ↓ | ↓ |
| hsa-miR-1307-3p | 0.147 | 0.720 | 0.760 | ↓ | ↑ |
| hsa-miR-128-3p | 0.147 | 0.850 | 0.803 | ↓ | ↑ |
| hsa-miR-7-1-3p | 0.147 | 0.853 | 0.417 | ↓ | — |
| hsa-miR-3678-3p | 0.147 | 0.922 | 0.821 | ↓ | ↓ |

Note:
miRNAs in bold are displayed in FIG. 13

Figure 12:
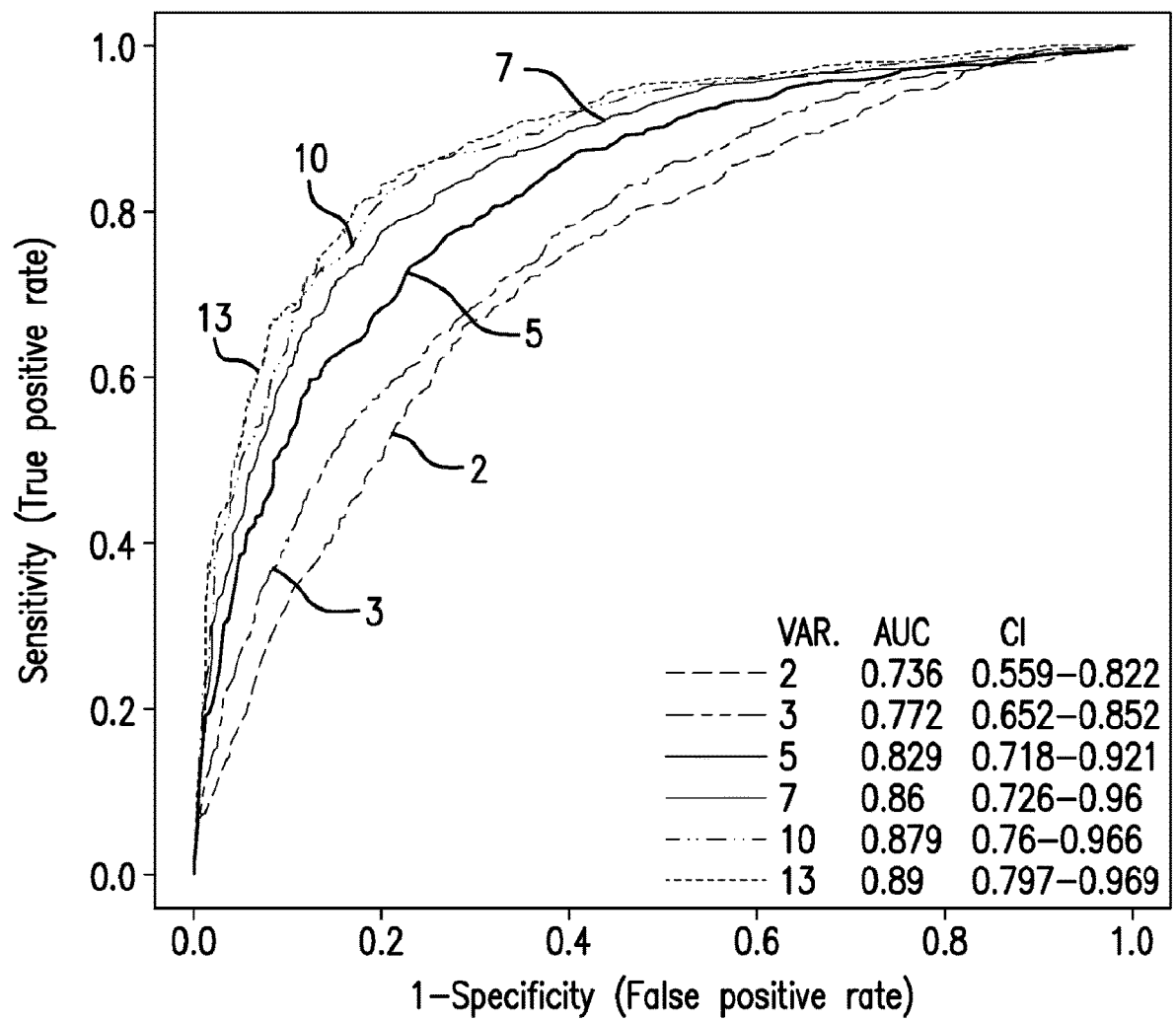
FIG. 12 shows accuracy of predicting TBI likelihood based on changes in miRNA expression from serum or saliva samples compared to baseline pre-fight.
Figure 13A:
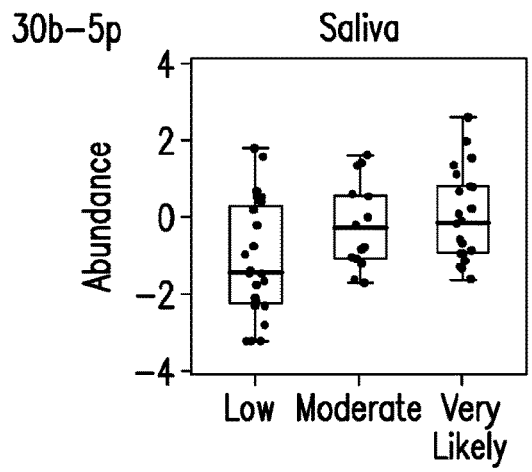
FIGS. 13A-F show Whisker box plots illustrating changes in miRNA expression levels in saliva and serum following a TBI. Each row represents a different miRNA example (three miRNAs are shown), and each dot represents the expression level of that miRNA in a particular sample. Top plots: A-B, left to right; middle plots: C-D, left to right; bottom plots: E-F, left to right.
Figure 13B:
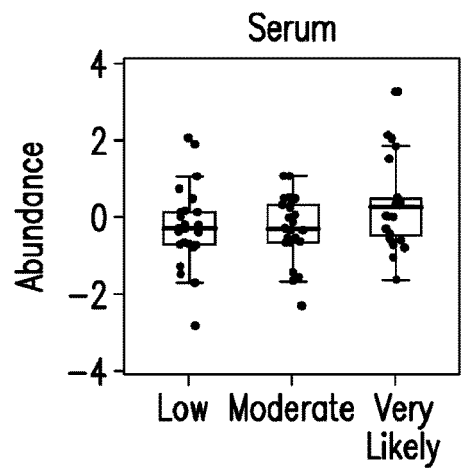
Figure 13C:
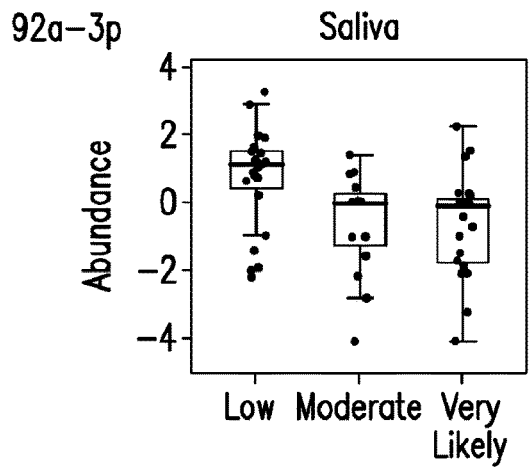
Figure 13D:
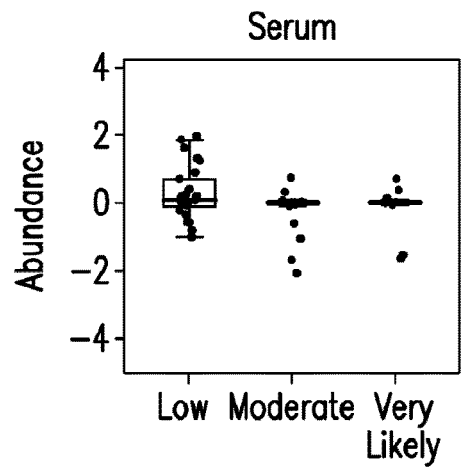
Figure 13E:
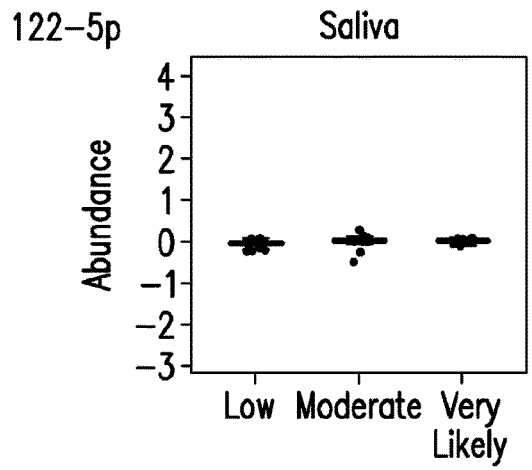
Figure 13F:
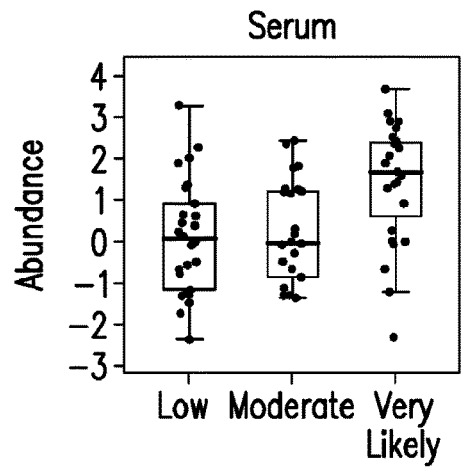

Further examination of the miRNAs was performed in attempt to identify those with the best ability to predict the likelihood of TBI, using Receiver Operating Curve (ROC) binary classification testing with feature selection and 100-fold Monte Carlo Cross Validation. In this case, the Low and the Very Likely TBI groups were compared. In addition, the selection of TBI predictors was limited to those miRNAs that specifically showed a relationship between their expression changes and the number of hits to the head in the full set of samples (as determined by a stepwise linear regression). The results from this analysis yielded a multivariate prediction model with almost 90% accuracy (AUC=0.89) for predicting TBI likelihood in a given sample, regardless of fluid type, using as few as 13 miRNAs; see FIG. 12. FIG. 12 shows the accuracy of predicting TBI likelihood based on changes in miRNA expression from serum or saliva samples compared to baseline pre-fight. For these analyses, stepwise linear regression was used to preselect an optimal number of miRNAs for prediction of Hits to the Head (HTH) values, and this set of 13 was subjected to 100-fold Monte Carlo Cross Validation (MCCV) using Random Forest, in order to estimate classification accuracy for distinguishing Very Likely from Low likelihood TBI samples.

To further establish the validity of the miRNA biomarkers that were identified, the ROC analysis was complemented with a logistic regression analysis that either combined or separated the two different sample types. The results indicated that the same 13 miRNAs achieved perfect classification when separate logistic regression models (with different beta coefficients for each biofluid) were utilized (Table 17). Thus, it was concluded that both serum and saliva contain subsets of miRNAs that can accurately classify samples according to TBI likelihood, but that the information provided by each is somewhat distinct.

TABLE 17

Logistic regression model performance for TBI classification using miRNAs.

| | Predicted Low | Predicted Very Likely | % Accuracy |
|---|---|---|---|
| Saliva Only Model | | | |
| Observed Low | 21 | 0 | 100 |
| Observed Very Likely | 0 | 21 | 100 |
| | | | 100 |
| Serum Only Model | | | |
| Observed Low | 24 | 0 | 100 |
| Observed Very Likely | 0 | 24 | 100 |
| | | | 100 |
| Combined Biofluid Model | | | |
| Observed Low | 38 | 7 | 84.4 |
| Observed Very Likely | 5 | 39 | 88.6 |
| | | | 86.5 |

Examples of some of the 21 miRNAs in serum and saliva with changes in expression post-fight are shown in FIG. 13A-13F. Interestingly, some of these miRNAs showed a pattern of increased expression in both biofluids after TBI (FIG. 13A-13B, miR-30b-5p, top), while others showed a change that was most evident in only a single biofluid type. For example, miR-92a-3p (FIG. 13C-D, middle) was decreased largely in the saliva post-TBI, while miR-122-5p (FIG. 13E-13F, bottom) was increased largely in the serum post-TBI. FIG. 13A-13F depicts whisker box plots illustrating changes in miRNA expression levels in saliva and serum following a TBI. Each row represents a different miRNA example (three miRNAs are shown), and each dot represents the expression level of that miRNA in a particular sample. Note that some miRNAs showed a pattern of increase in both biofluids after TBI (30b-5p, top), while others showed a change that was most evident in only a single biofluid type (e.g., 92a-3p and 122-5p).

Biological Mapping of Changed miRNAs. The biological relevance of the findings for the 21 significantly changed miRNAs using DIANA Tools miRpath v.3 (with FDR correction set<0.05) was further explored. This analysis was based on predicted targets and indicated a distinct set of biological pathways was overrepresented in the target genes of the top miRNAs. The top 10 pathways defined within the Kyoto Encyclopedia of Genes and Genomes (KEGG) database were displayed along with the net expression change of each associated miRNA in comparisons of the Very Likely TBI vs Low TBI shown for each biofluid (Table 18). Notably, across all the most enriched pathways, the associated miRNAs displayed mixed effects, with several increasing and several decreasing. More than half of the miRNAs (n=13) showed mixed directionality of changes in the two biofluids, with an increase or decrease in one biofluid accompanied by no change or a change in the opposite direction in the other biofluid. However, 7 miRNAs did show changes in the same direction in the two biofluids, including 2 that increased (miR-10b-5p, miR-30b-5p) and 5 that decreased (miR-3678-3p, miR-455-5p, miR-5694, miR-6809-3p, and miR-92a-3p).

TABLE 18

Biological pathways overrepresented by target genes of TBI related miRNAs.

| KEGG pathway | FDR | Genes | miRNAs | miR-70a-5p | miR-120-5p | miR-122-5p | miR-128-5p | miR-155-5p | miR-20a-5p | miR-30b-5p | miR-3746 |
|---|---|---|---|---|---|---|---|---|---|---|---|
| Proteoglycans in cancer | 1.1E−06 | 102 | 20 | ↓↑ | ↑↑ | —↑ | ↓↑ | —↑ | ↑— | ↑↑ | ↓— |
| Mucin type O-Glycan biosynthesis | 2.7E−05 | 16 | 12 | ↓↑ | ↑↑ | —↑ | ↓↑ | —↑ | ↑— | ↑↑ | |
| TGI-beta signaling pathway | 2.7E−05 | 46 | 20 | ↓↑ | ↑↑ | —↑ | ↓↑ | —↑ | ↑— | ↑↑ | ↓— |
| FoxO signaling pathway | 1.2E−05 | 75 | 17 | ↓↑ | ↑↑ | —↑ | ↓↑ | —↑ | ↑— | ↑↑ | |
| Ubiquitin medicated proteolysis | 3.2E−05 | 80 | 19 | ↓↑ | ↑↑ | —↑ | ↓↑ | —↑ | ↑— | ↑↑ | ↓— |
| Hippo signaling pathway | 3.3E−05 | 76 | 16 | ↓↑ | ↑↑ | | ↓↑ | —↑ | ↑— | ↑↑ | ↓— |
| Axon guidance | 5.8E−05 | 70 | 17 | ↓↑ | ↑↑ | —↑ | ↓↑ | —↑ | ↑— | ↑↑ | |
| Ras signaling pathway | 0.0002 | 111 | 19 | ↓↑ | ↑↑ | —↑ | ↓↑ | —↑ | ↑— | ↑↑ | ↓— |
| AMPK signaling pathway | 0.0002 | 67 | 20 | ↓↑ | ↑↑ | —↑ | ↓↑ | —↑ | ↑— | ↑↑ | ↓— |
| Glutamatergic synapse | 0.0001 | 61 | 17 | ↓↑ | ↑↑ | —↑ | ↓↑ | —↑ | ↑— | ↑↑ | ↓— |

| KEGG pathway | miR-3076-3p | miR-376a-5p | miR-405-5p | miR-4037 | miR-4049-5p | miR-1693-5p | miR-4766-5p | miR-5694 | miR-6770-5p | miR-6809-3p | miR-7-1-3p | miR-92a-3p |
|---|---|---|---|---|---|---|---|---|---|---|---|---|
| Proteoglycans in cancer | ↓↓ | ↓— | ↓↓ | —↑ | ↓— | —↑ | ↓— | ↓↓ | ↓— | ↓↓ | ↓— | ↓↓ |
| Mucin type O-Glycan biosynthesis | | | | | ↓— | | | | ↓— | ↓↓ | ↓— | ↓↓ |
| TGI-beta signaling pathway | ↓↓ | ↓— | ↓↓ | —↑ | ↓— | —↑ | ↓— | ↓↓ | ↓— | ↓↓ | ↓— | ↓↓ |
| FoxO signaling pathway | ↓↓ | ↓— | | | ↓— | —↑ | ↓— | ↓↓ | ↓— | ↓↓ | ↓— | ↓↓ |
| Ubiquitin medicated proteolysis | ↓↓ | | ↓↓ | —↑ | ↓— | —↑ | ↓— | ↓↓ | ↓— | ↓↓ | ↓— | ↓↓ |
| Hippo signaling pathway | ↓↓ | ↓— | | | ↓— | —↑ | ↓— | | ↓— | ↓↓ | ↓— | ↓↓ |
| Axon guidance | ↓↓ | ↓— | | | ↓— | —↑ | ↓— | ↓↓ | ↓— | ↓↓ | ↓— | ↓↓ |
| Ras signaling pathway | ↓↓ | ↓— | | —↑ | ↓— | —↑ | ↓— | ↓↓ | ↓— | ↓↓ | ↓— | ↓↓ |
| AMPK signaling pathway | ↓↓ | ↓— | ↓↓ | —↑ | ↓— | —↑ | ↓— | ↓↓ | ↓— | ↓↓ | ↓— | ↓↓ |
| Glutamatergic synapse | ↓↓ | ↓— | | | ↓— | —↑ | ↓— | | ↓— | ↓↓ | ↓— | ↓↓ |

Arrows and colons indicate the direction of change for salvia and serum samples in Very Likely TBI vs Low probability TBI groups, respectively (minimum change +/− 0.1).

Notably, of the top ten ranked KEGG pathways, four were of particular interest for their potential relevance to TBI. These pathways included Ubiquitin-mediated proteolysis, Transforming growth factor-beta (TGF-beta), Axon guidance, and Glutamatergic synapse. Within each of these pathways a total of 46-80 genes were targeted by a total of 20 of the miRNAs. These findings were examined further using DIANA Tools to display maps of each pathway with the genes targeted by 1 or more miRNAs indicated; see FIGS. 14, 15, 16, and 17.

Figure 14B:
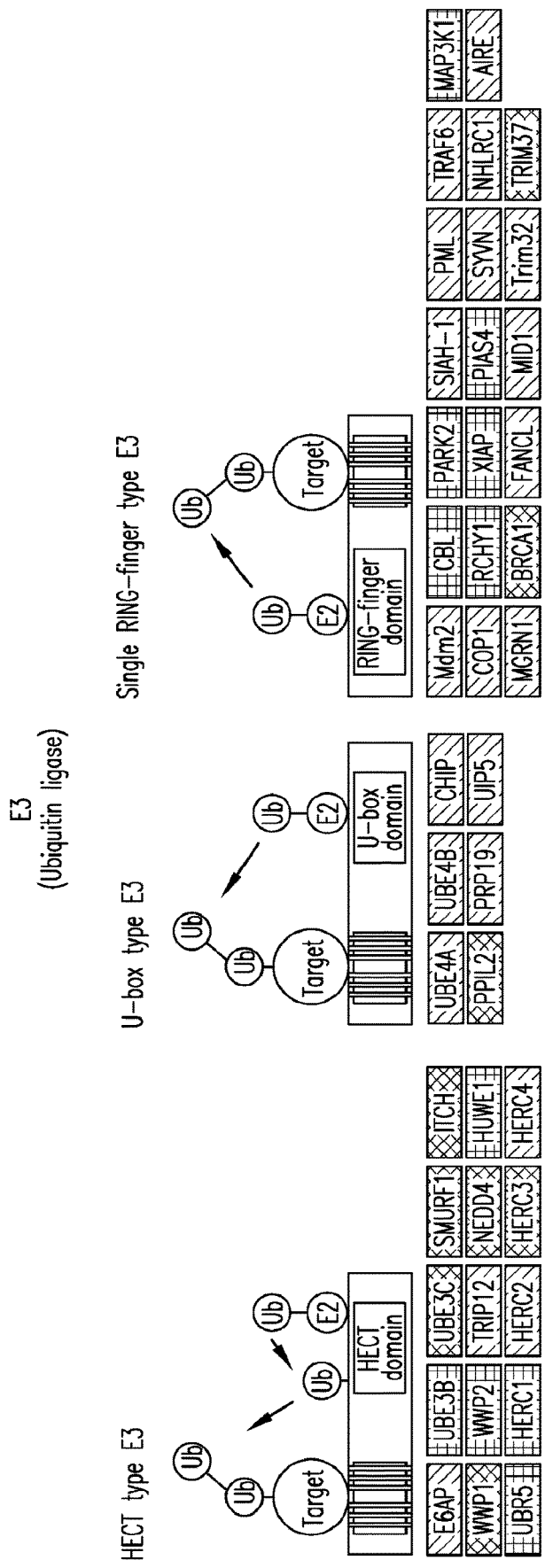
FIG. 14 shows Enrichment of changed miRNAs for target genes in the KEGG Ubiquitin-mediated proteolysis pathway.
Figure 14C:
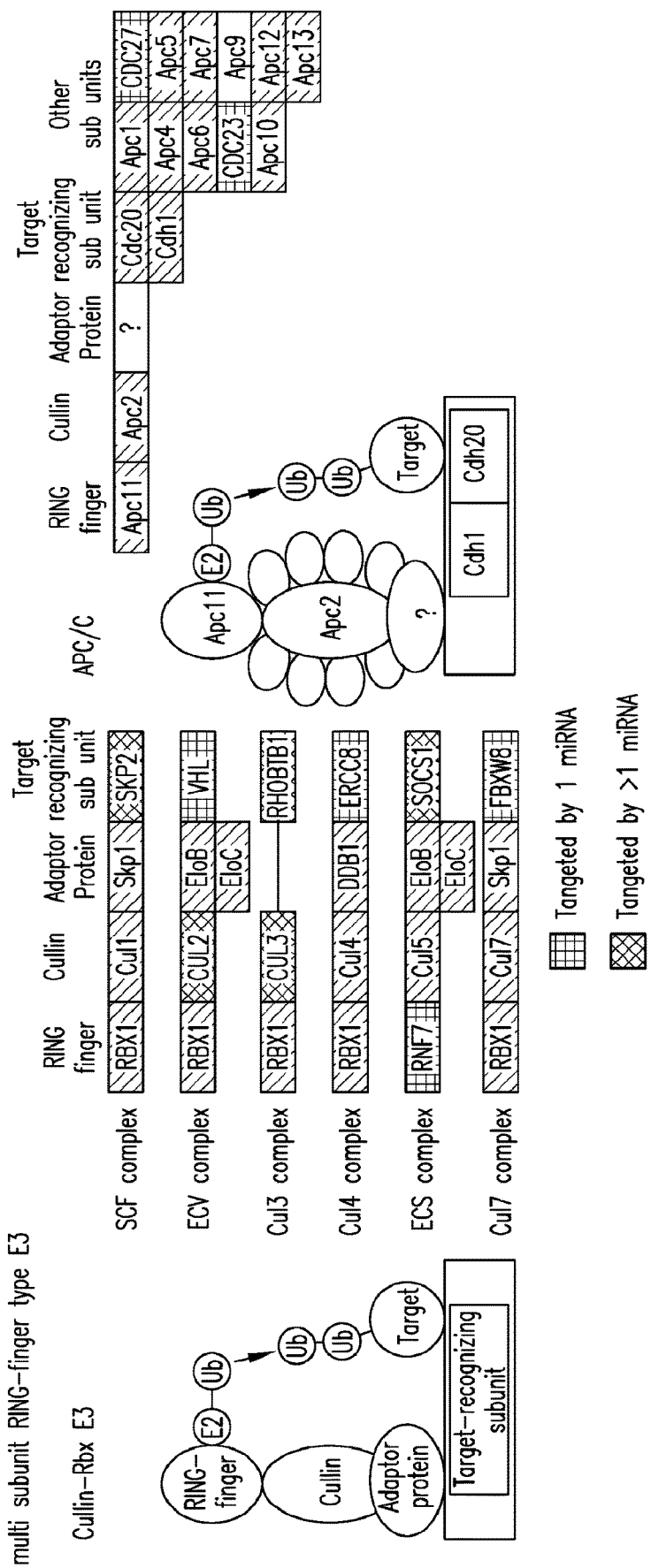
Figure 15:
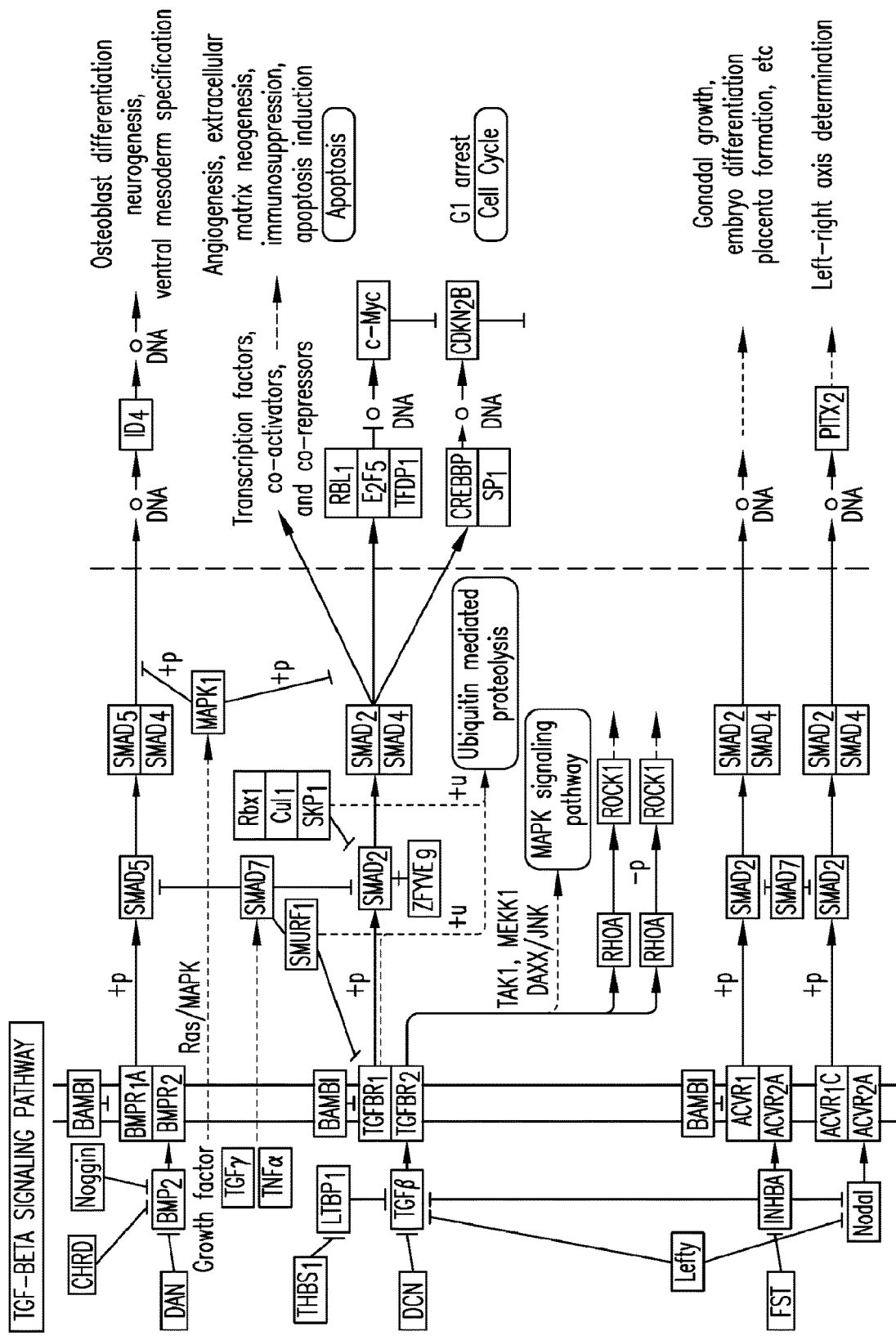
FIG. 15 shows Enrichment of changed miRNAs for target genes in the KEGG TGF-beta signaling pathway.
Figure 16:
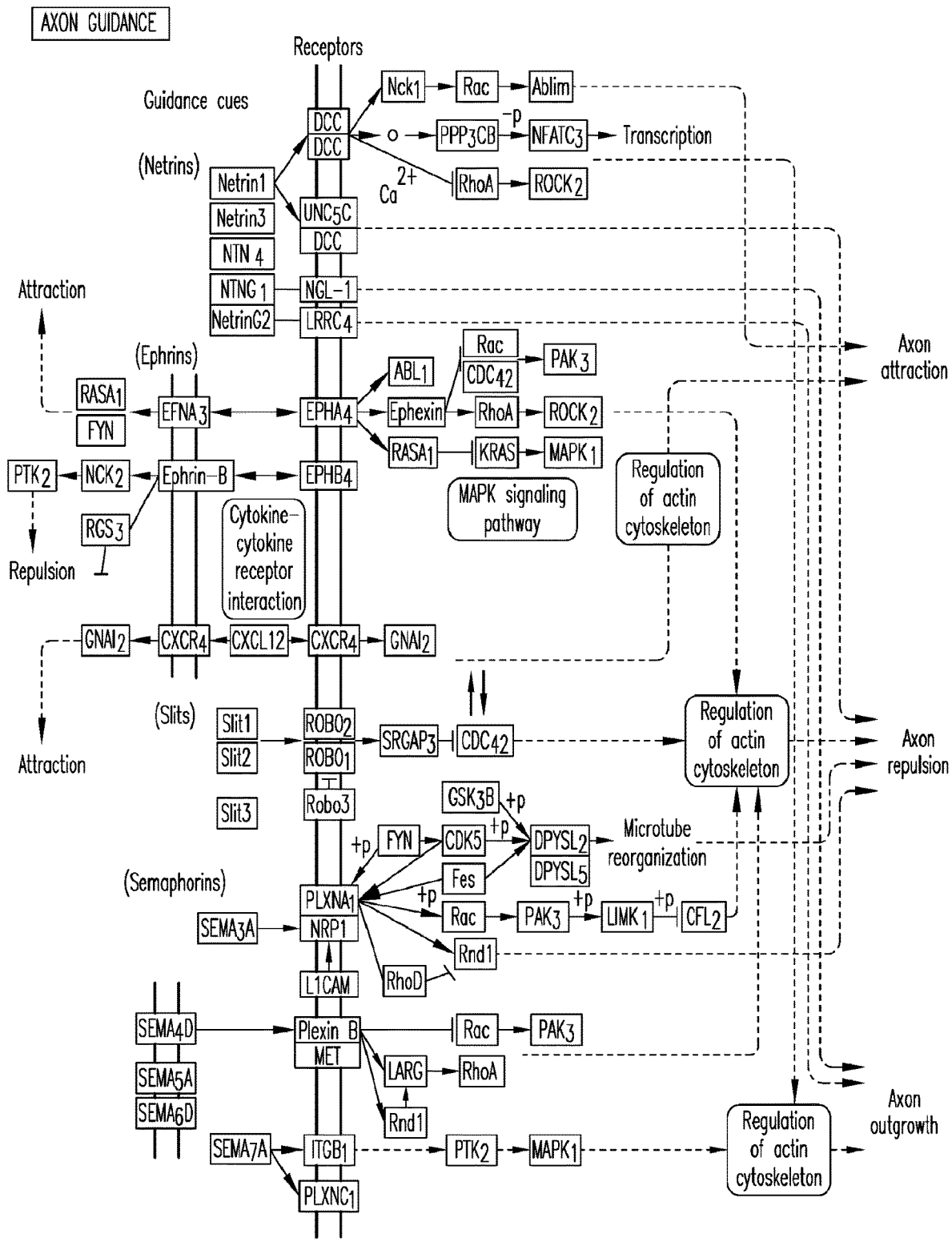
FIG. 16 shows Enrichment of changed miRNAs for target genes in the KEGG Axon guidance pathway.
Figure 17:
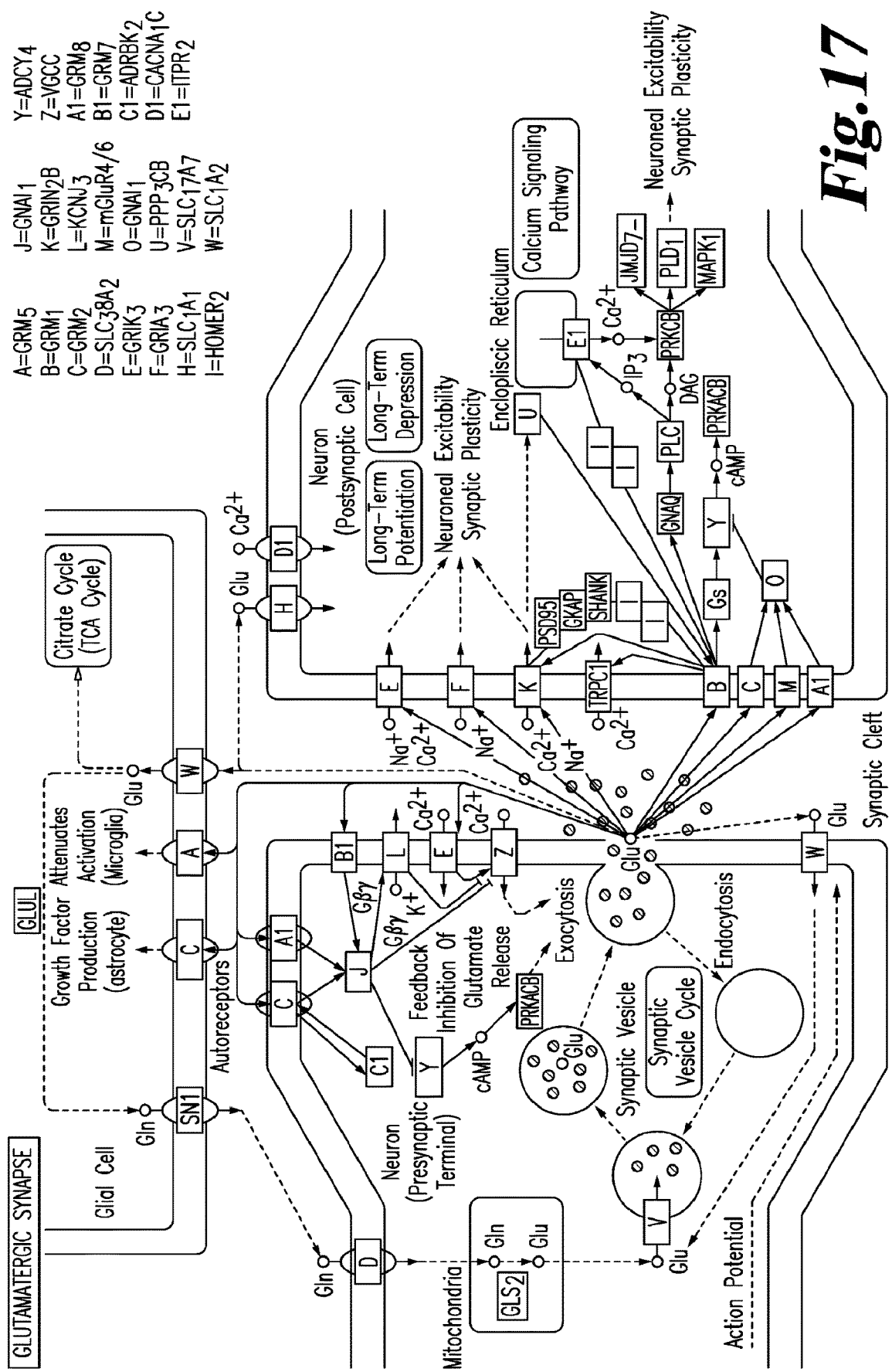
FIG. 17 shows Enrichment of changed miRNAs for target genes in the KEGG Glutamatergic synapse pathway.

FIG. 14 shows enrichment of changed miRNAs for target genes in the KEGG Ubiquitin-mediated proteolysis pathway. In this pathway, 80 genes were targeted by a total of 19 miRNAs. Genes targeted by 1 miRNA are shown in yellow, and genes targeted more than 1 miRNA are shown in orange. Genes in green have miRNAs that are predicted to target them but none of these were contained in the list of 21 changed miRNAs. Genes in white do not have predicted miRNAs that target them. FIG. 15 depicts enrichment of changed miRNAs for target genes in the KEGG TGF-beta signaling pathway (conventions same as FIG. 10). This pathway contained 46 genes that were predicted to be targeted by 20 miRNAs. FIG. 16 shows enrichment of changed miRNAs for target genes in the KEGG Axon guidance pathway (conventions same as FIG. 10). This pathway contained 70 genes that were predicted to be targeted by 17 miRNAs. FIG. 17 shows enrichment of changed miRNAs for target genes in the KEGG Glutamatergic synapse pathway (conventions same as FIG. 10). This pathway contained 61 genes that were predicted to be targeted by 20 miRNAs.

Correlation of miRNA Changes and Functional Changes.

Finally, the relationship of the 21 most significantly changed miRNAs from the two-way ANOVA and the top-changed functional measures as well as actual hits to the head values was examined. This analysis revealed a single nominally significant negative correlation between the changes in serum miR-4766-5p levels and TLEC functional measures (Table 19). Notably, this same miRNA also had a weak positive correlation between its changes in the serum and the balance score differences in the DSB_Bal test. In contrast to these nominally significant correlations with functional outcomes, several highly significant correlations with the actual HTH values that survived Bonferroni correction (n=7 in salivary miRNAs, n=3 serum miRNAs, and n=8 in the combined samples) were observed.

TABLE 19

Correlations between changes in miRNA levels (post-fight), HTH, and functional measures.

| | | Hits to the Head | | | Pearson Correlations Two Legs Eyes Closed Balance | | | Digit Span Backwards Balance | | |
|---|---|---|---|---|---|---|---|---|---|---|
| Chg | miRNA | All | Saliva | Serum | All | Saliva | Serum | All | Saliva | Serum |
| ↓↑ | hsa-miR-10a-5p | 0.013 | 0.149 | 0.031 | −0.146 | −0.029 | −0.206 | −0.006 | −0.002 | 0.036 |
| ↑↑ | hsa-miR-10b-5p | −0.583 | 0.273 | −0.610 | −0.147 | 0.078 | −0.228 | 0.020 | 0.294 | 0.012 |
| —↑ | hsa-miR-122-5p | 0.372 | 0.336 | 0.386 | −0.192 | −0.046 | −0.278 | 0.034 | −0.066 | 0.086 |
| ↓↑ | hsa-miR-128-3p | 0.280 | 0.355 | 0.268 | 0.040 | 0.076 | 0.026 | 0.079 | −0.011 | 0.157 |
| ↓↑ | hsa-miR-1307-3p | 0.237 | 0.474 | 0.185 | −0.102 | −0.018 | −0.145 | −0.061 | 0.000 | −0.070 |
| —↑ | hsa-miR-155-5p | 0.079 | 0.107 | 0.099 | −0.016 | 0.174 | −0.039 | 0.159 | 0.281 | 0.231 |
| ↑— | hsa-miR-20a-5p | −0.136 | 0.096 | −0.175 | −0.096 | −0.168 | −0.058 | −0.025 | −0.030 | 0.038 |
| ↑↑ | hsa-miR-30b-5p | 0.070 | 0.197 | −0.028 | −0.006 | −0.117 | 0.078 | 0.216 | 0.097 | 0.359 |
| ↓— | hsa-miR-3146 | 0.124 | 0.251 | −0.325 | −0.181 | −0.185 | −0.182 | −0.221 | −0.274 | −0.069 |
| ↓↓ | hsa-miR-3678-3p | 0.421 | 0.658 | −0.096 | 0.095 | 0.120 | 0.091 | 0.007 | 0.049 | 0.004 |
| ↓— | hsa-miR-376a-5p | 0.444 | 0.574 | 0.210 | −0.025 | −0.037 | 0.020 | −0.171 | −0.124 | −0.278 |
| ↓↓ | hsa-miR-455-5p | 0.254 | 0.360 | 0.118 | −0.189 | −0.187 | −0.215 | −0.195 | −0.211 | −0.176 |
| —↑ | hsa-miR-4637 | −0.210 | 0.023 | −0.250 | 0.089 | −0.009 | 0.159 | −0.019 | −0.253 | 0.298 |
| ↓— | hsa-miR-4649-3p | 0.058 | 0.055 | −0.019 | 0.001 | −0.002 | −0.005 | −0.103 | −0.098 | −0.184 |
| —↑ | hsa-miR-4693-5p | −0.006 | −0.031 | −0.008 | 0.115 | 0.090 | 0.164 | −0.015 | −0.088 | 0.324 |
| ↓— | hsa-miR-4766-5p | 0.060 | 0.488 | 0.043 | −0.063 | −0.045 | −0.385 | −0.098 | −0.121 | 0.324 |
| ↓↓ | hsa-miR-5694 | 0.055 | −0.258 | 0.094 | −0.058 | 0.027 | −0.180 | −0.037 | 0.067 | −0.204 |
| ↓— | hsa-miR-6770-5p | 0.455 | 0.524 | 0.387 | 0.104 | 0.078 | 0.156 | 0.141 | 0.130 | 0.202 |
| ↓↓ | hsa-miR-6809-3p | 0.293 | 0.439 | 0.079 | −0.012 | 0.095 | −0.132 | −0.062 | 0.074 | −0.213 |
| ↓— | hsa-miR-7-1-3p | 0.017 | 0.287 | −0.049 | −0.005 | 0.107 | −0.0.75 | −0.055 | −0.128 | 0.041 |
| ↓↓ | hsa-miR-92a-3p | 0.300 | 0.412 | −0.013 | −0.105 | −0.184 | −0.001 | −0.122 | −0.151 | 0.005 |

Pearson correlations between HTH values and changes in miRNA levels were adjusted using Bonferroni FDR < 0.05 (bold)
Correlations between TLEC, DSB_Bal and changes in miRNA levels were interpreted without FDR correction (p < 0.05)

Temporal Analysis of miRNA Changes.

In addition to probing for changes in expression based solely on TBI likelihood, the inventors sought to identify miRNAs with more complex and potentially more biologically relevant changes in expression. This was accomplished through temporal binning of samples and a General Linear Model encompassing Time and Sample Type. Using this approach, out of 1197 tested miRNAs, the inventors found 47 miRNAs with significant effects of Time, 226 with significant effects of sample type (Fluid) and 44 with significant effects of the Interaction between Time and Fluid.

Figure 37:
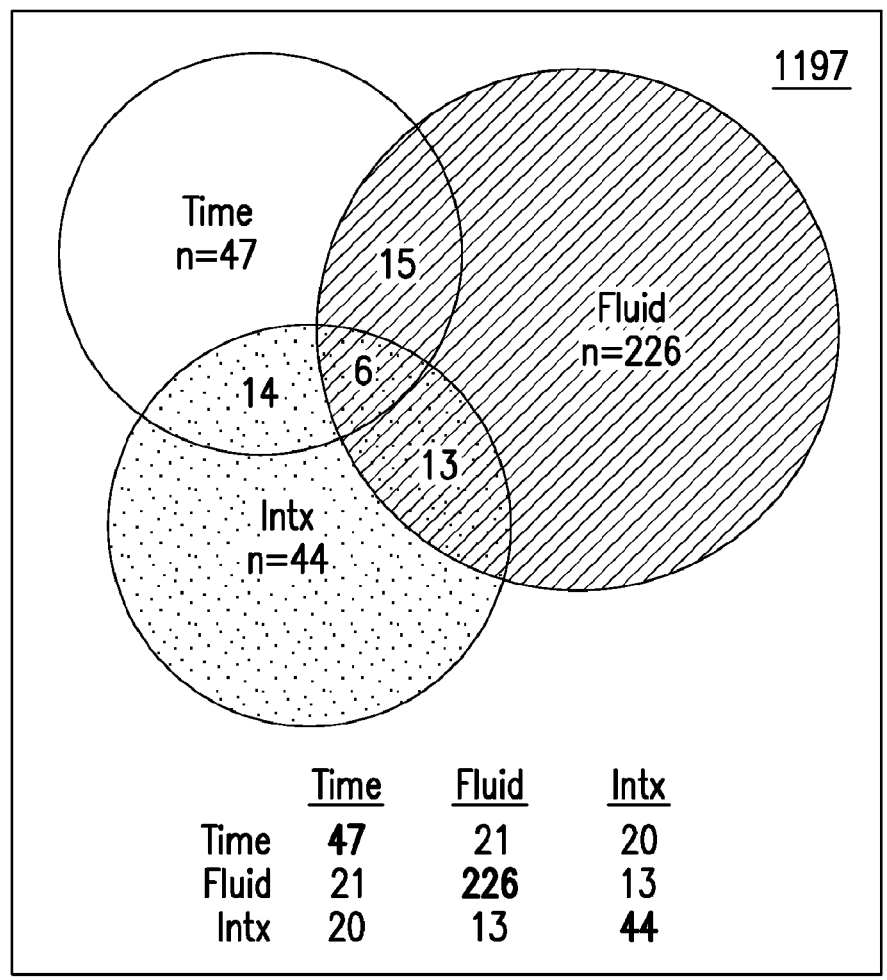
FIG. 37 shows miRNAs with changes in abundance due to Time, Fluid, and Interaction effects in serum and saliva.

FIG. 37 shows miRNAs with changes in abundance due to Time, Fluid, and Interaction effects in serum and saliva. Since a goal was to identify temporal effects that might reflect the occurrence of an mTBI event in either biofluid, the inventors focused exclusively on the 47 miRNAs with significant effects of Time (Table 20). Of these, 21 had significant effects of Fluid, and 20 had significant Interaction effects, indicating that their changes showed different temporal effects in the two biofluids. From the 47, 25 with fairly distinct patterns (Table 21) were identified.

TABLE 20

47 miRNAs with significant effect of time in relation to MMA fight in saliva and serum.

| miRNA | Time (47) | Fluid (21) | Interaction (20) | Pattern | Top Tissues |
|---|---|---|---|---|---|
| hsa-miR-4529-3p | 0.001048* | 0.000171* | 0.000260* | Delayed Serum | CNS |
| hsa-miR-4782-5p | 0.001478* | 0.771777 | 0.007645* | | PBMC, Tonsils |
| hsa-miR-4495 | 0.002438* | 0.001105* | 0.068731 | | Breast, Umbilicus |
| hsa-miR-3663-3p | 0.004628* | 0.393426 | 0.006147* | | CNS |
| hsa-miR-203a-3p | 0.005004* | 0.953766 | 0.019048* | | Skin, Head/Limb |
| hsa-miR-3170 | 0.005494* | 0.082871 | 0.001233* | Acute Saliva | Liver, Kidney |
| hsa-miR-5588-5p | 0.005613* | 0.000210* | 0.342059 | Delayed Serum | Liver, Lymphocyte |
| hsa-miR-3677-5p | 0.005844* | 0.000047* | 0.277949 | | Neurospheres |
| hsa-miR-4485-3p | 0.006945* | 0.002592* | 0.006234* | | Germ cell, Tonsil, Nose |
| hsa-miR-6755-5p | 0.007367* | 0.429112 | 0.008562* | | — |
| hsa-miR-6855-3p | 0.010420* | 0.15248 | 0.013031* | | — |
| hsa-miR-8089 | 0.013930* | 0.157337 | 0.960979 | Delayed Serum | — |
| hsa-miR-365a-5p | 0.014130* | 0.012816* | 0.125236 | | Lymphocyte, Pigmented cell |
| hsa-miR-550a-3-5p | 0.014394* | 0.000366* | 0.014623* | Delayed Serum | Nose, Adipose Tissue |
| hsa-miR-3919 | 0.015643* | 0.000245* | 0.475008 | Acute Saliva | CNS |
| hsa-miR-499a-5p | 0.016956* | 0.184234 | 0.529812 | | Heart, Kidney, Germ cell |

TABLE 20-continued 47 miRNAs with significant effect of time in relation to MMA fight in saliva and serum.

| miRNA | Time (47) | Fluid (21) | Interaction (20) | Pattern | Top Tissues |
|---|---|---|---|---|---|
| hsa-miR-433-3p | 0.017808* | 0.000472* | 0.535641 | Acute Saliva | Pharynx, CNS |
| hsa-miR-139-5p | 0.019453* | 0.000483* | 0.016949* | Delayed Serum | Bladder, Kidney, Spleen |
| hsa-miR-8082 | 0.021022* | 0.013965* | 0.027255* | | — |
| hsa-miR-2682-5p | 0.021615* | 0.000003* | 0.411552 | Acute Saliva | CNS |
| hsa-miR-548ab | 0.021980* | 0.891496 | 0.018717* | | Lymphocyte, Tonsil, CNS |
| hsa-miR-3678-3p | 0.022890* | 0.002552* | 0.24893 | Delayed Serum | Lymphocyte, Tonsil |
| hsa-miR-4632-3p | 0.024974* | 0.190454 | 0.020774* | Acute Saliva | Spleen |
| hsa-miR-5583-5p | 0.025676* | 0.012704* | 0.399673 | | Embryonic kidney |
| hsa-miR-6870-3p | 0.026225* | 0.028773* | 0.109315 | Acute Saliva | — |
| hsa-miR-1270 | 0.026246* | 0.009370* | 0.361532 | Delayed Serum | Lymphocyte, Tonsil, Thyroid |
| hsa-miR-3664-3p | 0.027180* | 0.102718 | 0.023126* | Delayed Serum | Liver, Tonsil |
| hsa-miR-421 | 0.028354* | 0.055815 | 0.014727* | Delayed Serum | Stem cell, Kidney |
| hsa-let-7b-3p | 0.028535* | 0.070946 | 0.839897 | Acute Saliva | Umbilicus, Nose |
| hsa-miR-4800-5p | 0.029069* | 0.942453 | 0.412773 | | Lymphocyte, Tonsil, Lung |
| hsa-miR-4749-5p | 0.029116* | 0.378594 | 0.885014 | | Lymphocyte, Tonsil |
| hsa-miR-30c-1-3p | 0.029679* | 0.529053 | 0.216003 | Delayed Serum | Heart, Nose |
| hsa-miR-616-5p | 0.029836* | 0.41128 | 0.177306 | | Nose, Adipose tissue |
| hsa-miR-135b-5p | 0.031594* | 0.422428 | 0.031404* | | Nose, Testes |
| hsa-miR-6840-5p | 0.037916* | 0.264125 | 0.274613 | | — |
| hsa-miR-608 | 0.038108* | 0.003982* | 0.532572 | Acute Saliva | Breast, Spleen, Thymus |
| hsa-miR-374c-5p | 0.038280* | 0.209441 | 0.412421 | | CNS |
| hsa-miR-4760-5p | 0.040453* | 0.275308 | 0.027557* | Acute Saliva | Keratinocytes, CNS |
| hsa-miR-4727-3p | 0.042900* | 0.045677* | 0.189207 | Delayed Serum | Stem Cell, Vertebral disc |
| hsa-miR-501-3p | 0.043792* | 0.113446 | 0.042896* | Delayed Serum | Nose, Adipose tissue |
| hsa-miR-3187-5p | 0.043874* | 0.579419 | 0.189533 | | PBMC, Tonsil |
| hsa-miR-3118 | 0.046986* | 0.134052 | 0.028899* | Acute Saliva | PBMC, Tonsil Plasma Cell |
| hsa-miR-766-3p | 0.047390* | 0.212496 | 0.78748 | | Pharynx, Tonsil, Nose |
| hsa-miR-6809-3p | 0.047799* | 0.000051* | 0.411403 | Delayed Serum | — |
| hsa-miR-601 | 0.049388* | 0.056646 | 0.113978 | Acute Saliva | Placenta, Cerebellar Cortex |
| hsa-miR-4660 | 0.049499* | 0.012181* | 0.210414 | Acute Saliva | Pigment cell, Tonsil |
| hsa-miR-4699-5p | 0.049827* | 0.000083* | 0.031381* | | Adipose tissue, Nose, Liver |

Bold miRNAs were changed due to TBI likelihood (Table 16). Patterned miRNAs are shown in (FIGS. 37 & 38).

TABLE 21

Temporal miRNAs, indicating biofluid & directional change

| miRNA | Acute Saliva ↑ | Delayed Serum ↑ | Delayed Serum ↓ |
|---|---|---|---|
| hsa-let-7b-3p | x | | |
| hsa-miR-30c-1-3p | | x | |
| hsa-miR-139-5p | | x | |
| hsa-miR-421 | | x | |
| hsa-miR-433-3p | x | | |
| hsa-miR-501-3p | | x | |
| hsa-miR-550a-3-5p | | x | |
| hsa-miR-601 | x | | |
| hsa-miR-608 | x | | |
| hsa-miR-1270 | | | x |
| hsa-miR-2682-5p | x | | |
| hsa-miR-3118 | x | | |
| hsa-miR-3170 | x | | |
| hsa-miR-3664-3p | | | x |
| hsa-miR-3678-3p | | | x |
| hsa-miR-3919 | x | | |
| hsa-miR-4529-3p | | | x |
| hsa-miR-4632-3p | x | | |
| hsa-miR-4660 | x | | |
| hsa-miR-4727-3p | | | x |
| hsa-miR-4760-5p | x | | |
| hsa-miR-5588-5p | | | x |
| hsa-miR-6809-3p | | | x |
| hsa-miR-6870-3p | x | | |
| hsa-miR-8089 | | | x |

Figure 38B:
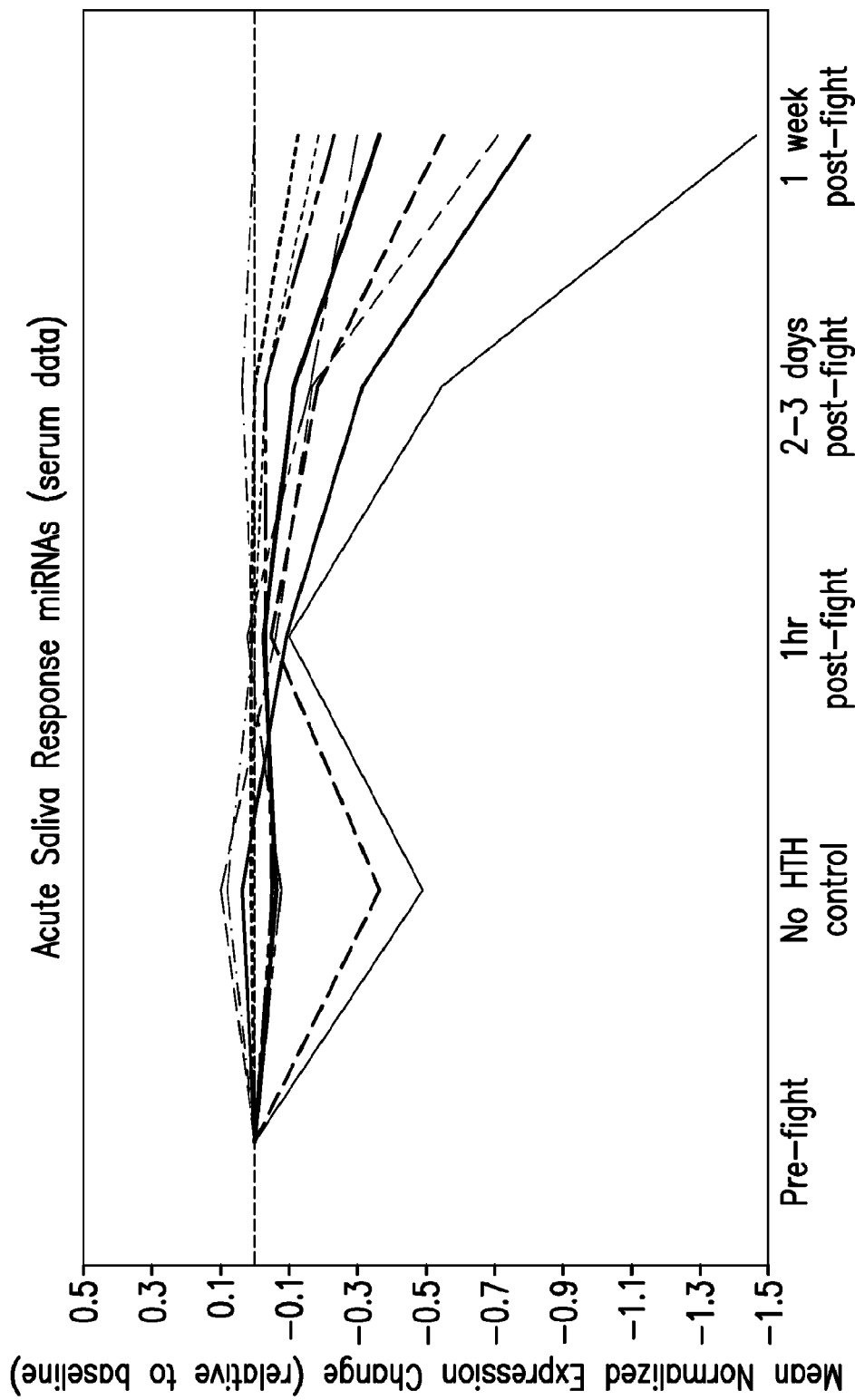

Visual inspection of the temporal patterns of significant changed miRNAs was used to identify potential biomarkers with salient patterns of either acute, delayed or sustained effects at the post-fight timepoints that exceeded the magnitude of non-specific changes seen on the day of the fight associated with the event and possibly exertion, but not hits to the head (HTH). Two criteria were used for this procedure: the magnitude of change at one or more of the post-fight time points had to exceed 1.3-fold (a log 2 change of +/−0.28) as well as the magnitude of change in the No HTH group by at least two-fold. These two simple criteria revealed two sets of miRNAs with highly distinct patterns in the biofluid samples. The first set of miRNAs showed an acute increase in saliva immediately post-fight that then returned to normal levels on days 2-3 and 1 week post-fight. This pattern was evident primarily in saliva samples and accurately described 12 of the 47 miRNAs with significant ANOVA effects (FIG. 38A). These were termed Acute Saliva Response (ASR) miRNAs. Remarkably, these same miRNAs demonstrated a distinctly different pattern of change in the serum samples. Specifically, none were increased, a small number showed no change, and several showed a delayed decrease, beginning at 2-3 days post-fight (FIG. 38B).

Figure 39A:
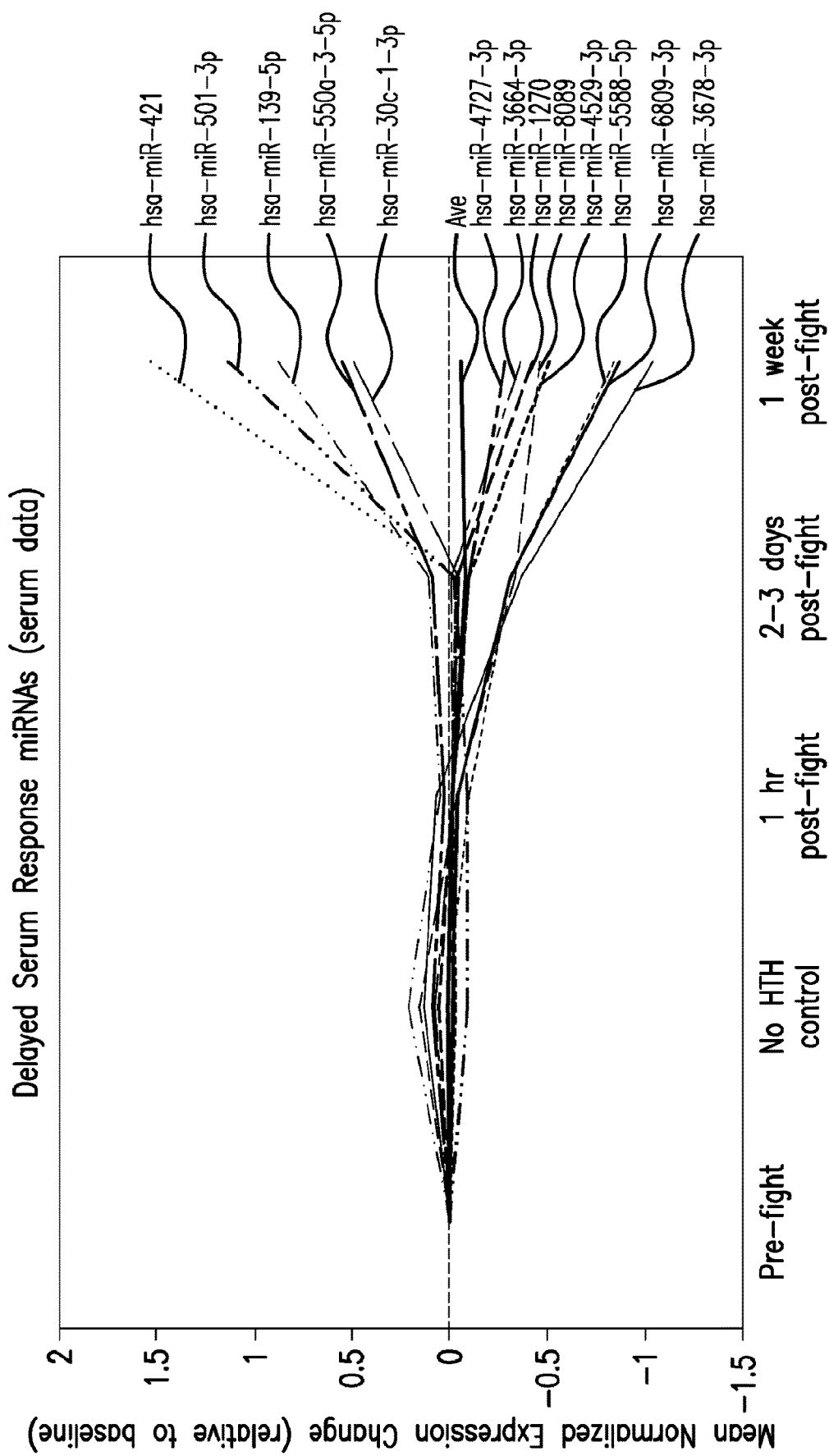
FIG. 39A-B show miRNAs identified with predominantly delayed increases (solid lines) and decreases (dashed lines) in serum at 1 week Post-fight (A-upper, blue/grayscale shaded area) that exceeded those at the non-specific exercise- or event-related timepoint (green/grayscale shaded area). Note that these miRNAs were unchanged or showed some evidence for non-specific increases in saliva (B-lower).
Figure 39B:
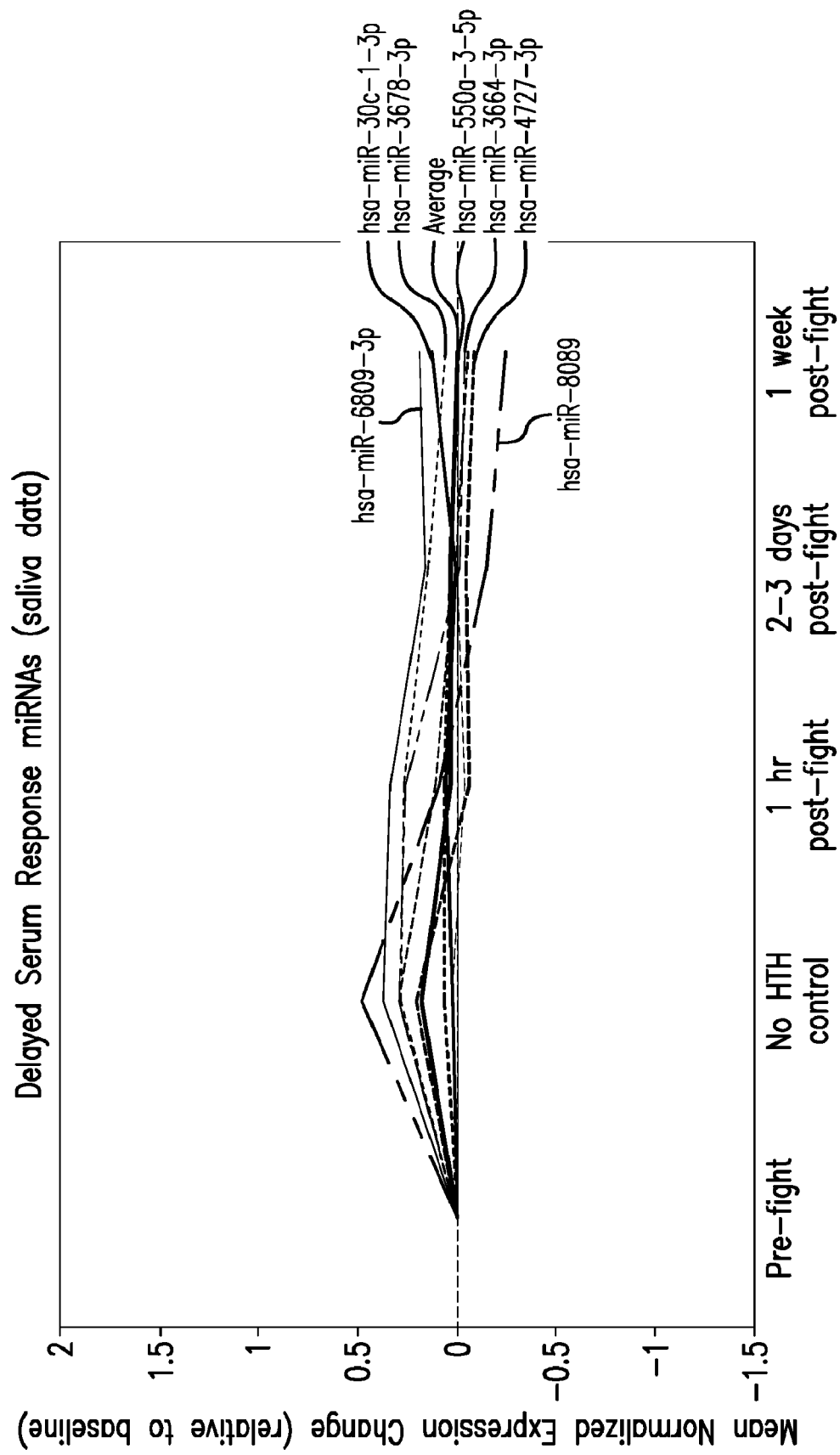

The second pattern was a delayed effect, usually a graded increase or decrease in expression on days 2-3 that reached a peak at 1 week post-fight, and was not present at the initial post-fight time point. This pattern was highly apparent in serum samples, and accurately described changes in 13 of the 47 miRNAs (FIG. 39A). These were termed Delayed Serum Response (DSR) miRNAs. Notably, these same miRNAs did not exhibit a similar pattern in the saliva samples. Rather, most were either unchanged or showed a trend for modestly increased expression at earlier time points, including potentially non-specific or exercise-related changes (FIG. 39B).

To ascertain the potential for the saliva and serum miRNAs to reflect release from central nervous system sources, the miRGator3.0 tool was used. A miRNA was considered "brain enriched" if its median expression across multiple CNS sources exceeded the median expression in any of the 31 non-neural organs and 51 non-neural tissues in the miRGator 3.0 database. Of the 11 ASR miRNAs with mapping information available, four were identified as brain enriched, suggesting possible CNS origin for the salivary miRNAs that increased within an hour post-fight (Table 20). This finding stands in contrast with the DSR miRNAs, where of the 11 serum miRNAs with mapping information available, only 1 was found to be brain enriched (Table 20).

FIGS. 38A-38B show 12 miRNAs were identified with acute temporal effects (all increases) at the 1 hr Post-fight time point (blue shaded area) in saliva samples (upper) that exceeded those at the non-specific exercise- or event-related timepoint (green shaded area). Note that most of the miRNAs returned to near baseline by 2-3 days Post-fight. The pattern for the same miRNAs was distinctly different in serum (several were unchanged and several had delayed decreases). FIGS. 39A-B depict miRNAs identified with predominantly delayed increases (solid lines) and decreases (dashed lines) in serum at 1 week Post-fight (upper, blue shaded area) that exceeded those at the non-specific exercise- or event-related timepoint (green shaded area). Note that these miRNAs were unchanged or showed some evidence for non-specific increases in saliva (lower).

Biological Mapping of miRNAs with TBI-Related Acute or Delayed Changes.

The biological relevance of the findings for the 12 miRNAs with notable increases in the saliva was further explored at the acute 1 hour post-fight time point and the 13 miRNAs identified in the serum with delayed changes (both increases and decreases) that peaked at 1 week post-fight. This analysis was performed using DIANA Tools miRpath 3.0, with the top 15 KEGG pathway enrichments identified for each set of miRNAs. Among the pathways enriched in the predicted targets of the acute saliva response miRNAs were several related to brain function, including Prion disease, Long-term depression, Glutamatergic synapse, Axon guidance, Amphetamine addiction, and Cocaine addiction (Table 22). Because these miRNAs were all increased (denoted by red upward arrows), the implication is that each of these brain-related pathways (and the others listed) were potentially being suppressed.

TABLE 22

Top biological pathways overrepresented by acute saliva response miRNAs

| KEGG pathway | FDR | Genes | miRNAs | Act-7b-3p | miR-2962-5p | miR-3118 | miR-3170 | miR-3919 | miR-433-3p | miR-3632-3p | miR-4660 | miR-4760-5p | miR-601 | miR-608 | miR-6570-3p |
|---|---|---|---|---|---|---|---|---|---|---|---|---|---|---|---|
| Prion diseases | 7.8E−11 | 7 | 5 | ↑ | ↑ | | | | ↑ | | | ↑ | ↑ | | |
| Long-term depression | 3.4E−06 | 28 | 10 | ↑ | ↑ | ↑ | ↑ | ↑ | ↑ | ↑ | ↑ | ↑ | | ↑ | |
| Hippo signaling pathway | 7.1E−06 | 46 | 11 | ↑ | ↑ | ↑ | ↑ | ↑ | ↑ | ↑ | ↑ | ↑ | ↑ | ↑ | |
| Proteoglycans in cancer | 3.2E−05 | 60 | 11 | ↑ | ↑ | ↑ | ↑ | ↑ | ↑ | | ↑ | ↑ | ↑ | ↑ | ↑ |
| Signaling pathways regulating pluripotency of stem cells | 1.5E−05 | 51 | 11 | ↑ | ↑ | ↑ | ↑ | ↑ | ↑ | | ↑ | ↑ | ↑ | ↑ | ↑ |
| Thyroid hormone signaling pathway | 1.8E−05 | 41 | 11 | ↑ | ↑ | ↑ | ↑ | ↑ | ↑ | | ↑ | ↑ | ↑ | ↑ | ↑ |
| N-Glycan biosynthesis | 0.0001 | 15 | 8 | ↑ | ↑ | ↑ | | ↑ | ↑ | | ↑ | | | ↑ | ↑ |
| Glutamatergic synapse | 0.0001 | 36 | 11 | ↑ | ↑ | ↑ | ↑ | ↑ | ↑ | | ↑ | ↑ | ↑ | ↑ | ↑ |
| Glycosaminoglycan biosynthesis - heparan sulfate/heparin | 0.0008 | 10 | 8 | | ↑ | ↑ | | ↑ | | | ↑ | ↑ | ↑ | ↑ | ↑ |
| Axon guidance | 0.0009 | 43 | 10 | ↑ | ↑ | ↑ | ↑ | ↑ | ↑ | | ↑ | ↑ | ↑ | ↑ | |
| Adherens junction | 0.00193 | 29 | 6 | ↑ | ↑ | | | ↑ | ↑ | | ↑ | ↑ | | | |
| Amphetamine addiction | 0.00193 | 21 | 10 | ↑ | ↑ | ↑ | ↑ | ↑ | ↑ | ↑ | ↑ | ↑ | ↑ | ↑ | |
| Estrogen signaling pathway | 0.00193 | 31 | 11 | ↑ | ↑ | ↑ | ↑ | ↑ | ↑ | ↑ | ↑ | ↑ | ↑ | ↑ | ↑ |

TABLE 22-continued

Top biological pathways overrepresented by acute saliva response miRNAs

| KEGG pathway | FDR | Genes | miRNAs | Act-7b-3p | miR-2962-5p | miR-3118 | miR-3170 | miR-3919 | miR-433-3p | miR-3632-3p | miR-4660 | miR-4760-5p | miR-601 | miR-608 | miR-6570-3p |
|---|---|---|---|---|---|---|---|---|---|---|---|---|---|---|---|
| Cocaine addiction | 0.00349 | 18 | 10 | ↑ | ↑ | ↑ | ↑ | ↑ | ↑ | ↑ | ↑ | ↑ | ↑ | ↑ | |
| ErbB signaling pathway | 0.00361 | 30 | 9 | ↑ | ↑ | ↑ | | | ↑ | ↑ | ↑ | ↑ | ↑ | ↑ | |

Pathways in bold were the same or highly-related to pathways enriched in the delayed serum response miRNA targets.

TABLE 23

Top biological pathways overrepresented by delayed serum response miRNAs.

| KEGG pathway | FDR | Genes | miRNAs | miR-1270 | miR-139-5p | miR-30c-3p | miR-3664-3p | miR-3678-3p | miR-421 | miR-4529-3p | miR-4727-3p | miR-501-3p | miR-550a-3-5p | miR-5538-5p | miR-6809-3p | miR-8089 |
|---|---|---|---|---|---|---|---|---|---|---|---|---|---|---|---|---|
| Mucin type O-Glycan biosynthesis | 2.9E-07 | 11 | 6 | | | | ↓ | | ↑ | | | | ↑ | ↓ | ↓ | ↓ |
| Adrenergic signaling in cardiomyocytes | 2.3E-05 | 48 | 12 | ↓ | ↑ | ↑ | ↓ | ↓ | ↑ | ↓ | | ↑ | ↑ | ↓ | ↓ | ↓ |
| ErbB signaling pathway | 0.0002 | 30 | 12 | ↓ | ↑ | ↑ | ↓ | ↓ | ↑ | ↓ | | ↑ | ↑ | ↓ | ↓ | ↓ |
| ECM-receptor interaction | 0.0004 | 20 | 8 | ↓ | | | ↓ | ↓ | ↑ | | | ↑ | ↑ | | ↓ | ↓ |
| Lysine degradation | 0.0004 | 16 | 10 | ↓ | | ↑ | ↓ | ↓ | ↑ | ↓ | | ↑ | | ↓ | ↓ | ↓ |
| Axon guidance | 0.0004 | 43 | 12 | ↓ | ↑ | ↑ | ↓ | ↓ | ↑ | | ↓ | ↑ | ↑ | ↓ | ↓ | ↓ |
| Proteoglycans in cancer | 0.0035 | 65 | 13 | ↓ | ↑ | ↑ | ↓ | ↓ | ↑ | ↓ | ↓ | ↑ | ↑ | ↓ | ↓ | ↓ |
| Estrogen signaling pathway | 0.0029 | 33 | 12 | ↓ | ↑ | ↑ | ↓ | ↓ | ↑ | ↓ | | ↑ | ↑ | ↓ | ↓ | ↓ |
| Glioma | 0.0047 | 22 | 11 | | ↑ | ↑ | ↓ | ↓ | ↑ | ↓ | | ↑ | ↑ | ↓ | ↓ | ↓ |
| Thyroid hormone synthesis | 0.0049 | 20 | 8 | | | | ↓ | ↓ | ↑ | ↓ | | ↑ | ↑ | | ↓ | ↓ |
| Oxytocin signaling pathway | 0.0077 | 51 | 13 | ↓ | ↑ | ↑ | ↓ | ↓ | ↑ | ↓ | ↓ | ↑ | ↑ | ↓ | ↓ | ↓ |
| TGF-beta signaling pathway | 0.0085 | 25 | 11 | ↓ | ↑ | ↑ | ↓ | ↓ | ↑ | ↓ | | ↑ | ↑ | | ↓ | ↓ |
| Long-term potentiation | 0.0085 | 26 | 12 | ↓ | | ↑ | ↓ | ↑ | ↓ | ↓ | ↓ | ↑ | ↑ | ↓ | ↓ | ↓ |
| Glutamatergic synapse | 0.0125 | 33 | 10 | ↓ | | ↑ | ↓ | ↓ | ↑ | ↓ | | ↑ | ↑ | | ↓ | ↓ |
| Prostate cancer | 0.0165 | 30 | 11 | | ↑ | ↑ | ↓ | ↓ | ↑ | ↓ | | ↑ | ↑ | ↓ | ↓ | ↓ |

Pathways in bold were the same or highly-related to pathways enriched in the acute saliva response miRNA targets.

Several KEGG pathways related to brain function were also among those enriched in the predicted targets of the delayed serum response miRNAs, including Axon guidance, Long-term potentiation, and Glutamatergic synapse (Table 23). Because some of these miRNAs were increased and others decreased (red arrows and green arrows, respectively), it is more difficult to interpret the consequences of these findings.

Notably, several of the pathways enriched with miRNA targets in Tables 22 and 23 were the same, or highly-related to each other (e.g., Long-term depression and Long-term potentiation). These similar enrichment findings were further examined at the gene level within selected pathways.

The first pathway that was directly compared was the Glutamatergic synapse pathway FIG. 40. It was noted that many of the same genes were targeted by miRNAs found in saliva or serum. Some exceptions to the overlapping targets included SLC1A2/EAAT2 (only targeted by acute response salivary miRNAs) and Glutaminase/GLS2 and the vesicular glutamate transporter/SLC17A7 (only targeted by the delayed response serum miRNAs).

Figure 40A:
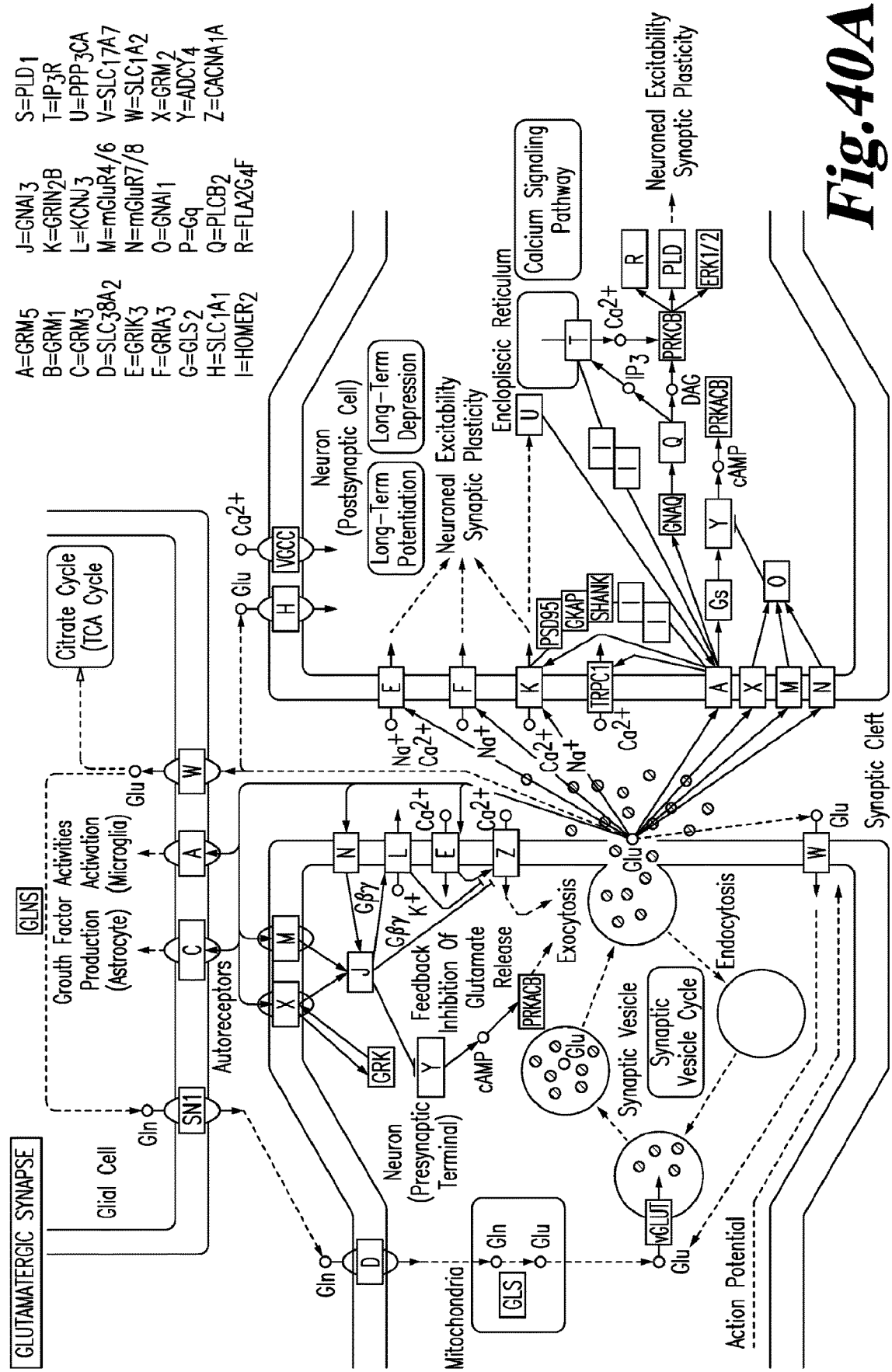
FIGS. 40A-B shows Enrichment of changed miRNAs for target genes in the KEGG Glutamatergic synapse pathway. Conventions same as FIG. 10. Note that both saliva (A) miRNAs and serum (B) miRNAs target many of the same genes in this pathway.
Figure 40B:
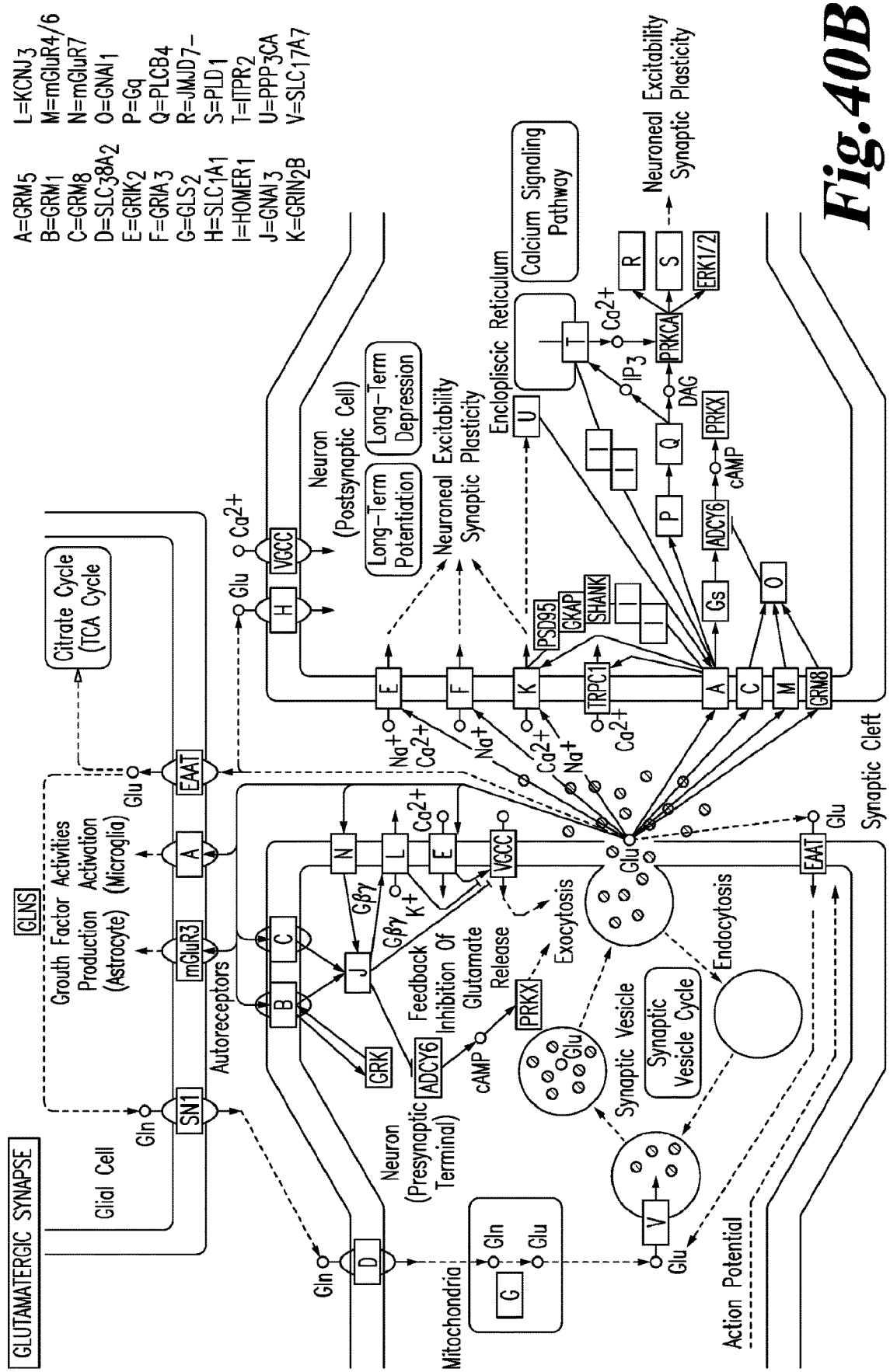
Figure 41A:
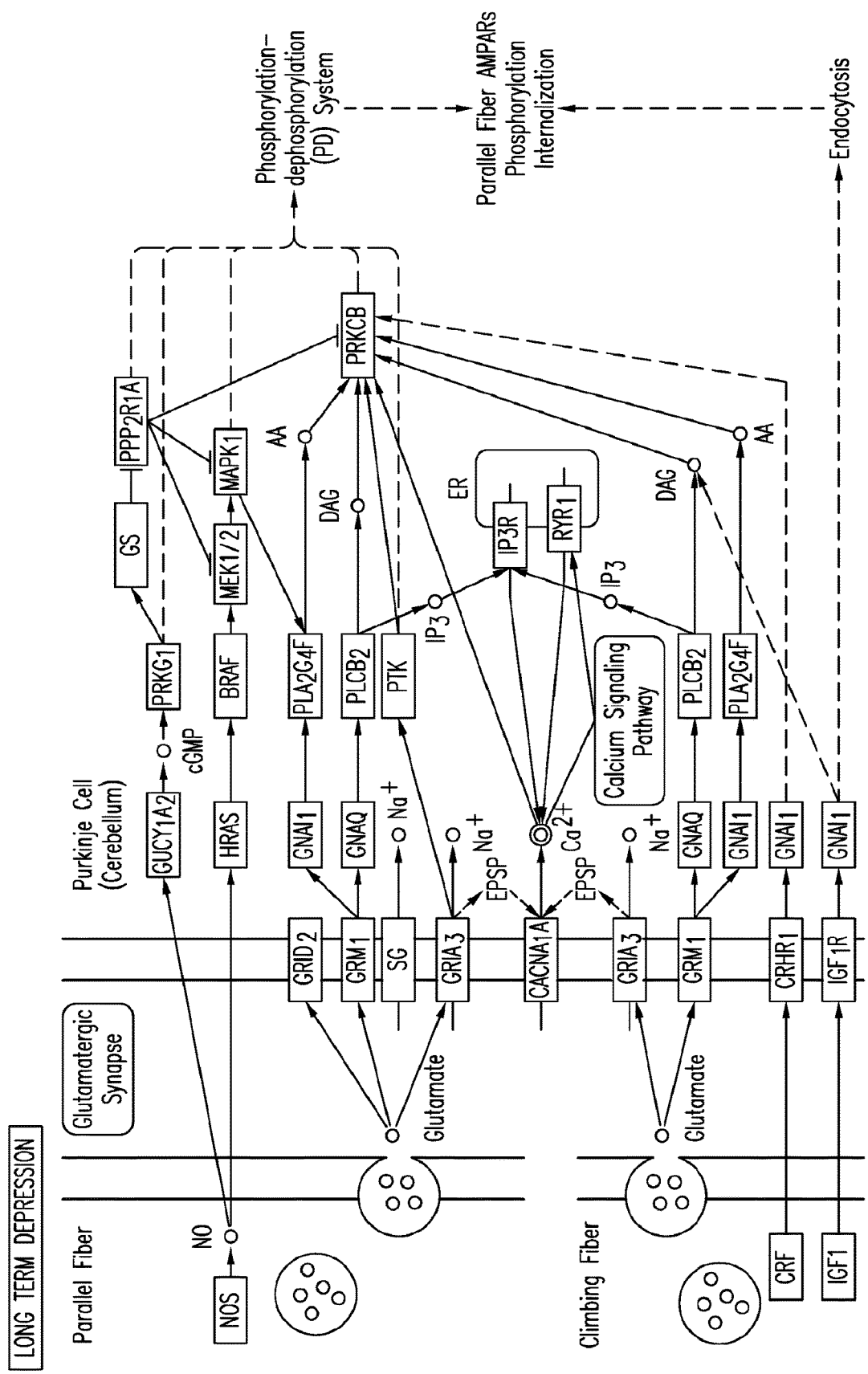
FIGS. 41A-B show Enrichment of temporally-regulated miRNAs in pathways involved in learning and memory from the saliva (Long-term depression, A), and serum (Long-term potentiation, B). Same conventions as FIG. 10.
Figure 41B:
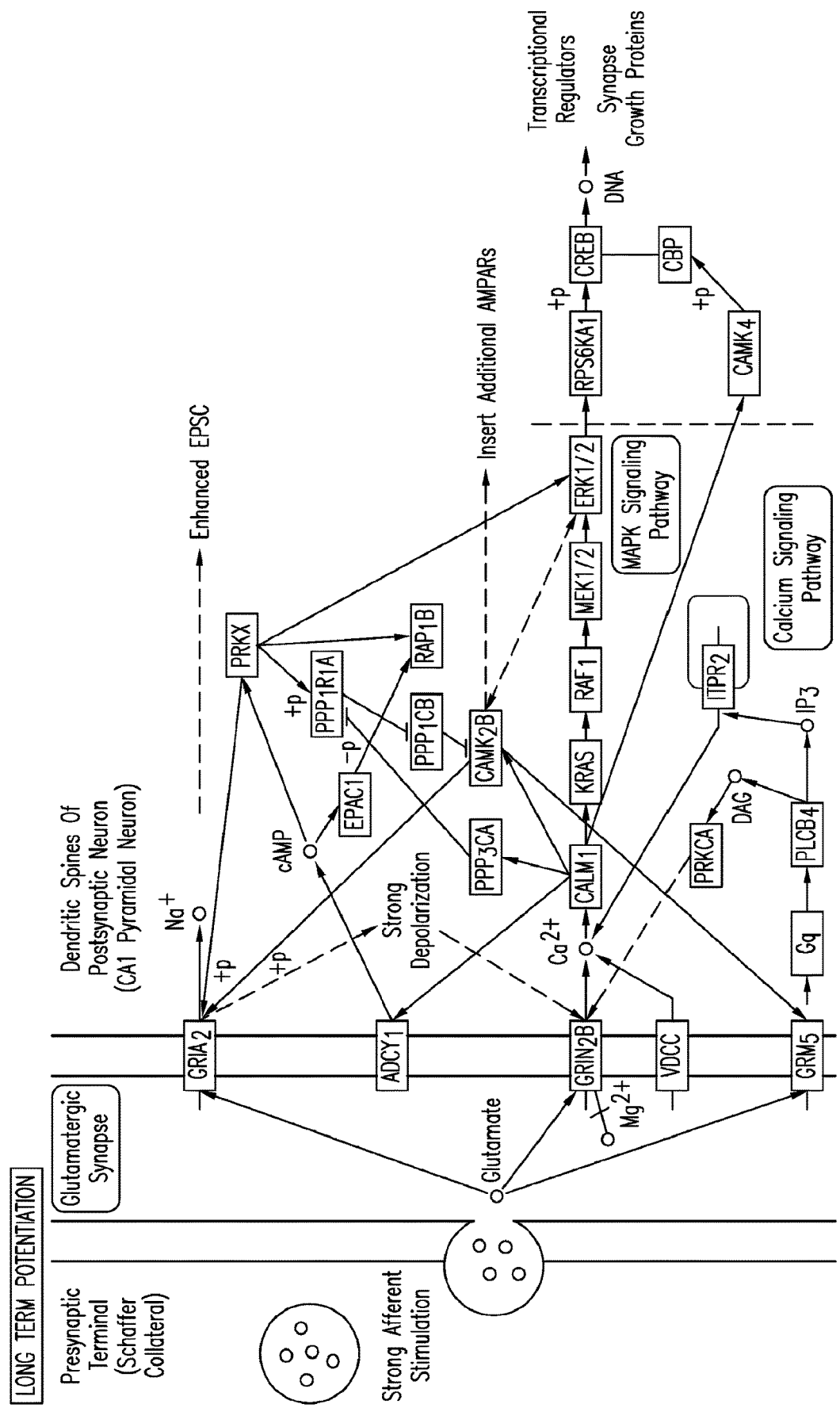

Possibly related to the Glutamatergic synapse pathway findings, it was also found evidence of potentially paradoxical actions of salivary and serum derived miRNAs on two brain-related pathways involved in learning and memory—Long-term depression (LTD; targeted by acute response salivary miRNAs) and Long-term potentiation (LTP; targeted by delayed response serum miRNAs) FIGS. 41A-41B. These two biological processes are critical for the process of synaptic plasticity, with LTP promoting the insertion of post-synaptic glutamate (AMPA) receptors and enhancing synaptic growth, while LTD functions to internalize AMPA receptors and reduce post-synaptic responses. FIGS. 40A-B shows enrichment of changed miRNAs for target genes in the KEGG Glutamatergic synapse pathway (conventions same as FIG. 10). Note that both saliva miRNAs and serum miRNAs target many of the same genes in this pathway. FIGS. 41A-41B shows enrichment of temporally-regulated miRNAs in pathways involved in learning and memory from the saliva (Long-term depression, upper), and serum (Long-term potentiation, lower) (same conventions as FIG. 10).

Figure 42:
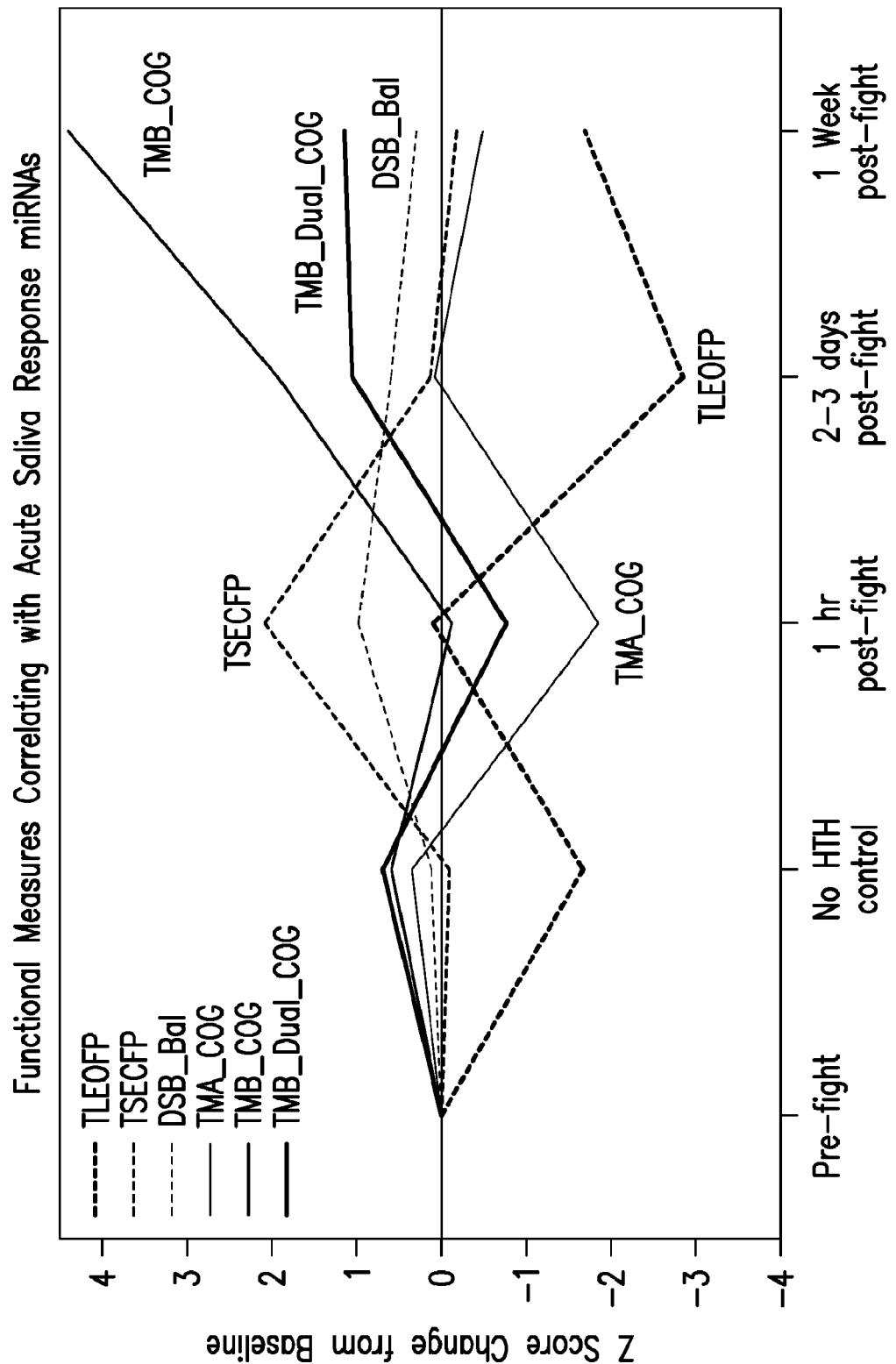
FIG. 42 shows Functional measures correlated with acute saliva response miRNAs. Solid lines show cognitive measures (higher values indicate better performance). Dashed lines show normalized body sway measures (higher values indicate worse performance).

Combined Analysis of Temporal Patterns in Functional and miRNA Data Saliva. Because the inventors were able to identify temporal changes in the saliva and serum miRNA data, the balance and cognitive score data to detect those which might show the largest changes at particular timepoints and correlate with the ASR or DSR miRNAs was also examined. This was first performed using PCA on a total of 12 ASR miRNAs and 14 functional measures in 39 post-fight saliva samples with functional data. Our results indicated that 3 factors described approximately half the variance in the combined data. Factor 1 was the maximal loading component of 9/12 miRNAs and 4 functional measures (Table 24), although some miRNAs and functional measures loaded strongly on multiple components. Notably, most Factor 1 loading saliva miRNAs showed large positive weights, along with several functional measures indicating increased body sway. In contrast, only 1 saliva miRNA showed a large negative weight on Factor 1, along with multiple functional measures indicating decreased cognitive performance (TMA_COG, TMB_Dual_COG, and TMB_COG). Graphical display of these data revealed a likely learning effect in one of the balance measures (TLEOFP), with decreased body sway evidence across time, other than the immediate post-fight time point (FIG. 42).

TABLE 24

Factor weights from PCA of ASR miRNAs and functional data.

|   | Factor 1 | Factor 2 | Factor 3 |
|---|---|---|---|
| TLEO | .101 | .305 | .063 |
| TLEC | .226 | .386 | .050 |
| TSEO | .232 | .525 | −.075 |
| TSEC | .303 | .521 | .004 |
| TLEOFP | .437 | .567 | .059 |
| TLECFP | .063 | .247 | .139 |
| TSEOFP | .404 | .128 | −.087 |
| TSECFP | .372 | .263 | −.042 |
| HT | −.021 | −.065 | .105 |
| TMB_Dual_Bal | .166 | .503 | −.016 |
| DSB_Bal | .452 | .694 | −.162 |
| TMA_COG | −.417 | −.331 | .222 |
| TMB_COG | −.242 | −.061 | −.021 |
| TMB_Dual_COG | −.494 | .267 | .160 |
| hsa-let-7b-3p | −.622 | .125 | .343 |
| hsa-miR-2682-5p | .347 | .009 | .846 |
| hsa-miR-3118 | .841 | −.322 | −.267 |
| hsa-miR-3170 | .731 | −.008 | −.221 |
| hsa-miR-3919 | .818 | −.102 | .517 |
| hsa-miR-433-3p | .683 | −.398 | .248 |
| hsa-miR-4632-3p | .900 | −.247 | −.239 |
| hsa-miR-4660 | .573 | .132 | .406 |
| hsa-miR-4760-5p | −.093 | −.279 | −.444 |
| hsa-miR-601 | .403 | −.300 | .386 |
| hsa-miR-608 | .131 | −.289 | .367 |
| hsa-miR-6870-3p | .815 | −.300 | −.346 |

FIG. 42 shows functional measures correlated with acute saliva response miRNAs. Solid lines show cognitive measures (higher values indicate better performance). Dashed lines show normalized body sway measures (higher values indicate worse performance). Note that cognitive measures showed a trend for drop in performance at the 1 hr post-fight time point, while body sway showed an increase at the same time point. Also note that two of the cognitive measures (TMB_COG and TMB_Dual_COG) showed an apparent learning effect (improved performance across time, other than the immediate post-fight time point). A learning effect was also seen in 1 of the balance measures (TLEOFP), with decreased body sway evidence across time, other than the immediate post-fight time point.

Serum.

Figure 43:
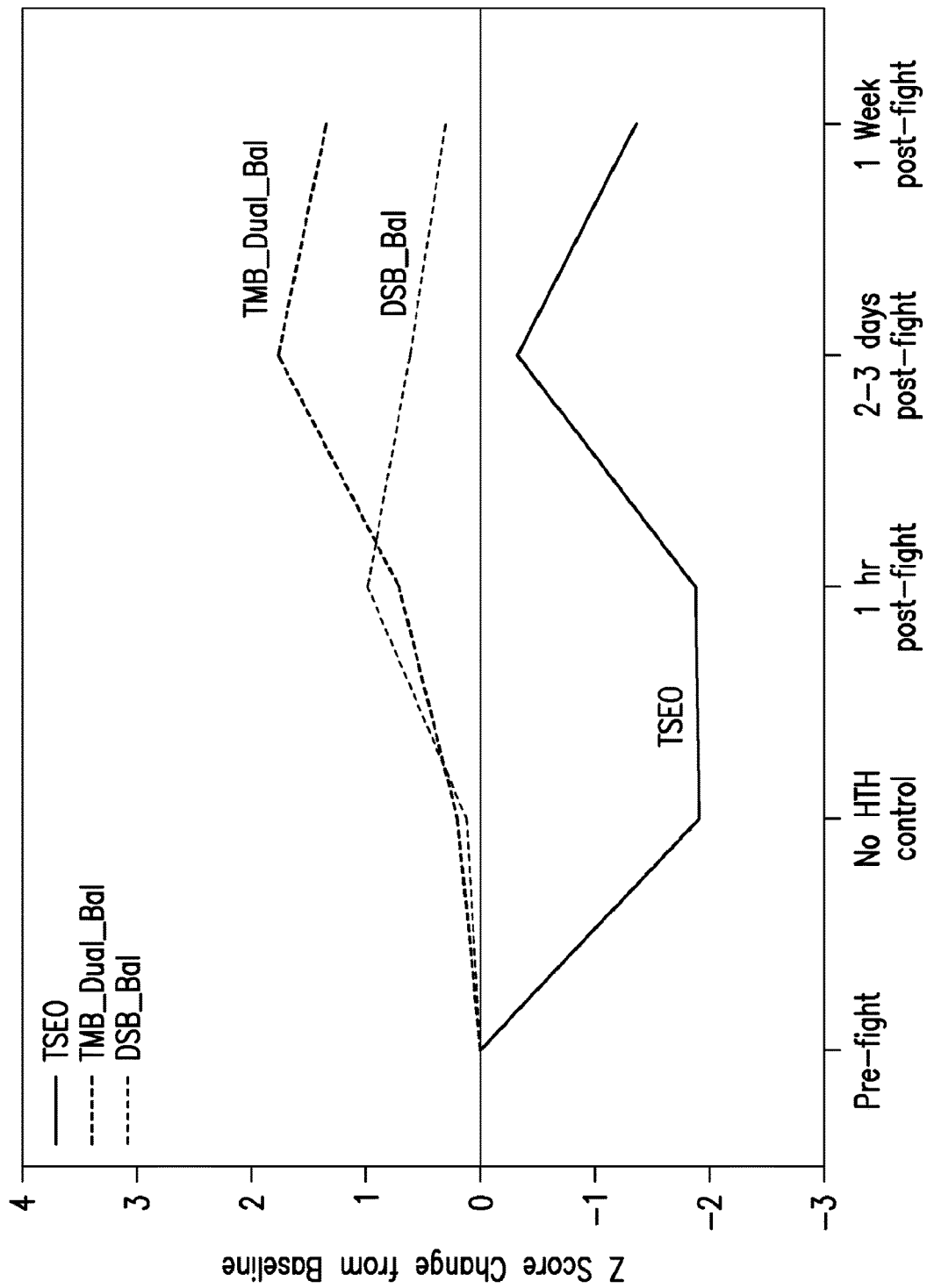
FIG. 43 shows Functional measures correlated with delayed serum response miRNAs. Solid line shows a balance measure (TSEO) with apparent learning effects (decreased sway at the No HTH control and 1 hr Post-fight time points) that subsequently showed increased sway at 2-3 days Post-fight. The dashed lines indicate two balance measures with delayed effects (TMB_Dual_Bal) or acute plus delayed effects (DSB_Bal).

The serum miRNAs that were identified with temporal effects tended to show delayed changes, with increases and decreases seen at 2-3 days and 1 week post-fight. Thus, these were examined separately from the saliva miRNAs using PCA on the combined data from 31 total samples. This revealed strong reciprocal loadings for three miRNAs that showed delayed decreases in expression (miR-139-5p, miR-30c-1-3p, miR-421) and six miRNAs (miR-6809-3p, miR-5588-5p, miR-3678-3p, miR-4529-3p, miR3664-3p, and miR-4'72'7-3p) and four functional measures (TSEO, DSB_Bal, TMB_DualBal) that showed delayed increases (Table 25; FIG. 43). Notably, one of these functional measures showed an apparent learning effect (TSEO) and one was also identified as highly-associated with acute response salivary miRNAs (DSB_Bal).

TABLE 25

Factor weights from PCA of DSR miRNAs and functional data.

|   | Factor 1 | Fader 2 | Fader 3 |
|---|---|---|---|
| TLEO | −.14235 | .15152 | −.03633 |
| TLEC | −.16705 | .12808 | −.06435 |
| TSEO | −.55827 | .10701 | .13852 |
| TSEC | −.34960 | .23822 | .17088 |
| TLEOFP | −.43068 | .43554 | −.03773 |
| TLECFP | −.07614 | .15362 | −.28359 |
| TSEOFP | −.17375 | .29220 | −.02840 |
| TSECFP | −.38810 | .42524 | −.07373 |
| HT | .19816 | .37227 | −.31037 |
| TMB_Dual_Bal | −.63915 | .01487 | .11286 |
| DSB_Bal | −.64408 | .72695 | .62334 |
| TMA_COG | .31451 | −.11814 | −.35098 |
| TMB_COG | −.20325 | −.26018 | −.11367 |
| TMB_Dual_COG | −.35048 | −.18787 | −.38892 |
| hsa-miR-1270 | .23912 | −.31624 | .31635 |
| hsa-miR-139-5p | −.44806 | −.53127 | .32092 |
| hsa-miR-30c-1-3p | −.32825 | −.31065 | .44924 |
| hsa-miR-3664-3p | .44600 | −.38881 | .11475 |
| hsa-miR-3878-3p | .55177 | .26988 | .19778 |
| hsa-miR-421 | −.58152 | −.36268 | .33586 |
| hsa-miR-4529-3p | .52331 | −.16047 | .57020 |
| hsa-miR-4727-3p | .45166 | .29143 | −.04519 |
| hsa-miR-501-3p | −.15368 | −.01707 | −.25060 |
| hsa-miR-550a-3-5p | −.12800 | .00280 | .02614 |
| hsa-miR-5588-5p | .57073 | .10670 | .42204 |
| hsa-miR-6809-3p | .79952 | .23765 | .19328 |
| hsa-miR-8089 | .35348 | .48611 | .22020 |

FIG. 43 shows functional measures correlated with delayed serum response miRNAs. Solid line shows a balance measure (TSEO) with apparent learning effects (decreased sway at the No HTH control and 1 hr Post-fight time points) that subsequently showed increased sway at 2-3 days Post-fight. The dashed lines indicate two balance measures with delayed effects (TMB_Dual_Bal) or acute plus delayed effects (DSB_Bal).

In development of the invention, the inventors investigated saliva and serum molecular measures and neurocognitive and balance measures in young adult athletes, both at baseline and various time points following an MMA event, with the goal of establishing diagnostic measures that might accurately predict the likelihood of mTBI or sports-related concussion or head impact. This was performed using four complementary approaches. First, the inventors binned subjects on mTBI probability based on the number of hits to the head that they received in an MMA bout and analyzed a set of potential serum protein biomarkers in a subset of the subjects, based on claims in the existing literature. The protein data indicated that only one of the potential biomarkers (UCHL1) showed changes that were quantitatively related to the number of hits to the head, while other biomarkers may have shown non-specific increases, potentially due to exercise effects. The inventors then examined serum and salivary miRNA data as well as neurocognitive and balance measures using two-way ANOVA and ROC curve analyses to identify other potential measures which could distinguish low-probability from high-probability concussion samples. Next, the inventors examined the miRNA data using repeated measures ANOVA and revealed molecular biomarkers with either acute or delayed temporal effects relative to the MMA bout. This was true of both saliva and serum miRNAs, although the patterns tended to differ in the two biofluids. Because it was felt that the most informative biomarkers would be those associated with changes in quantifiable functional measures, the inventors then used PCA analysis of the combined data to delineate temporal patterns in the functional measures related to acutely-responsive saliva miRNAs and delayed-responsive serum miRNAs. This confirmed strong relationships between selected saliva or serum biomarkers and distinct sets of functional measures, which also tended to show acute or delayed effects, despite the presence of practice-related improvement. Overall, these results indicate that studies of molecular and functional biomarkers in mTBI must be rigorously performed and incorporate sensitive measures that are sampled at sufficient frequency to identify potential learning effects in the data. Moreover, these data also indicate that the biomarkers which are most sensitive to mTBI may have strong biological implications.

Functional Outcome Measures.

Numerous balance measures have been used to evaluate subjects at baseline or following sports related concussion. Testing included several different types of balance, measures using a computerized accelerometer and tablet device. The inventors also added dual task assessments of balance while subjects were distracted with the requirement to complete a cognitive task, and tasks with purely cognitive demands. Our initial analysis of 14 different measures performed without regard to the timing of the assessments revealed that three measures of balance were potentially sensitive to mTBI likelihood, including the Two Legs Eyes Closed (TLEO) task and two dual tasks including the Digit Span Backwards Balance test (DSB_Bal) and Trail Making B Dual Task Balance test (TMB_Dual_Bal). The inventors also found that the Trail Making A cognitive test (TMA_Cog) was potentially sensitive to mTBI likelihood.

While there are many reports in the literature of alterations in balance or neurocognitive function in subjects with mTBI, very few have benefited from the incorporation of baseline and time-course data. In the present study, the temporal effects on the functional measures were not subjected to formal repeated measures ANOVA due to the use of mostly different sets of subjects at the different time points and the presence of potential learning effects that would, by their very nature, be subject-dependent. Nonetheless, our PCA analysis of the functional data across time confirmed the presence of significant learning effects in some of the measures, as well as differences in the time point which demonstrated the largest change. These observations suggest that some balance measures, particularly those involving high dual-task cognitive demands, such as the TMB_Dual_Bal and DSB_Bal, may reveal their maximal effects at a somewhat delayed time point rather than acutely (FIG. 43). In contrast, the acute time point assessments that were performed within an hour of the MMA fight indicated that the most sensitive and reliable measures included several simple balance measures (e.g., TSECFP) as well as cognitive measures (TMA_Cog, TMB_Dual_Cog) (FIG. 42). While other balance tests did reveal an increase in body sway post-fight relative to immediately pre-fight, they also demonstrated varying degrees of overall decreased sway across time, particularly the TLEOFP, which appears to represent a learning effect. Improvement in this task performance might not be surprising given the ability of subjects to use visual feedback signals to help adjust their postural stability. In contrast, the TSECFP task likely represents the most difficult task and subjects can only use proprioceptive cues but not visual information, and this did not demonstrate any apparent improvement across time.

The trail making A and B tests have been widely used to assess cognitive performance and recent studies have implemented computerized versions of these tests for examining performance in subjects with mTBI. Such work has observed a significant learning effect in the trail making B test, but not the A test, although it has been claimed that both tests were sensitive to TBI. While the inventors data is consistent with these findings they also indicate that there may be an optimal time point for examination of trail making performance in subjects who have had prior exposure to the test.

Molecular Outcome Measures:

Protein Biomarkers.

Numerous studies in both human subjects and rodent models have examined the potential utility of different serum proteins in the context of mTBI and more commonly severe TBI. The inventors examined a set of 11 potential biomarkers in a subset of our MMA fighter samples, obtained immediately pre- and post-fight. While some of these proteins showed elevations post-fight relative to pre-fight, this was largely true regardless of whether subjects experienced many (or any) hits to the head. The only exception to this was UCHL1, which showed an increase post-fight that was correlated with the number of hits to the head. Interestingly, although the literature on UCHL1 contains many reports of changes in different studies, this is not a uniform finding and many studies have also claimed decreases in expression or a lack of change following mTBI Our data indicate that the increased expression of UCHL1 in the serum may only be observed in the most severe cases of mTBI (i.e., MMA fighters with 30 or more hits to the head). Notably, a blood test for concussion was recently approved by the United States Food and Drug Administration involving measures of UCHL1 and GFAP [https://www.fda.gov/newsevents/newsroom/pressannouncements/ucm596531.htm].

miRNA Biomarkers.

There have been several human studies published on potential blood or other biofluid measures of mTBI using miRNAs, including recent work on TBI in teenage children. These studies have generally focused on examination of a single time point in a cross-sectional comparison of mTBI and control subjects, or on focused examination of a small number of miRNAs across multiple time points. Very few studies have utilized exercise- or non-head injury (e.g., musculoskeletal injury controls in mTBI). Other studies in laboratory animals have generally involved rodents, and often employed multiple timepoints or open TBI procedures more analogous to severe TBI. Open procedures clearly introduce conditions that are beyond the scope of what occurs in mild TBI in normal circumstances. Our study attempted to explore the issues of mTBI severity and time on the miRNA data and place the changes within the context of the functional data and previous findings in the field.

The majority of our candidate miRNA biomarkers have not been reported in the previous literature. It is likely that our use of a baseline timepoint to normalize each miRNA and functional outcome measure produced greater sensitivity for detection. However, several of our candidate mTBI biomarkers have been previously reported. These miRNA biomarkers can be specified as exact matches or highly-related matches that derive from the same miRNA gene. Among the miRNAs that we detected with changes related to the hits to the head, 12 were novel and 9 are exact matches or highly-related to those identified in previous studies of TBI. Among the miRNAs with definitive time-course changes in our data, 17 were novel and 7 were exact matches or are highly-related to those reported in previous studies of TBI (Table 26). Notably, three of the current miRNAs we identified were the same and three were highly-related to those previously reported as changed in saliva from children with mild TBI (Table 26). Moreover, several of the exact and highly-related matches were also found in studies of TBI that sampled peripheral blood in humans or rodents, as well as human CSF or rodent brain tissue.

We are highly interested in the trafficking of miRNAs between the central nervous system (CNS) and peripheral locations. Because blood brain barrier (BBB) disruption occurs in all levels of TBI severity, it is generally understood that serum biomarkers can serve as an indirect readout of pathological processes occurring in the CNS of affected individuals. What is less apparent, however, is how changes in brain function could be reflected in saliva. Two potential routes are worth noting. First, the brain stem provides a potential CNS-to-oral cavity route via the sensory (V, VII, IX) and motor (XII, X, XII) cranial nerves that innervate the salivary glands and tongue. A similar mechanism of transmission from CNS to saliva occurs in Rabies virus infection, wherein the virus travels from muscle, to brain, and eventually to the cranial nerves that innervate the salivary glands. A second route for miRNA delivery to the mouth involves slow transport via the glymphatic system, although this remains to be fully characterized.

TABLE 26 miRNAs with significant effect of HTH (Table 5) or defined temporal effects (Table 21) that have been previously reported in TBI studies.

Exact miRNA matches in previous studies:

| miRNA | Change | TBI Severity | Fluid/Tissue | Species | Ref |
|---|---|---|---|---|---|
| hsa-miR-122-5p$^{HTH}$ | ↑ | mild | serum | rat | 6 |
| hsa-miR-128-3p$^{HTH}$ | ↑ | mild | saliva | human | 5 |
|  | ↑ | mild, mild-moderate | plasma | mouse | 13 |
| hsa-miR-139-5p$^{T}$ | ↓ | mild-moderate | dentate gyrus | rat | 2 |
| hsa-miR-421$^{T}$ | ↓ | mild | serum[4], saliva[5] | mouse[4], human[5] | 4, 5 |
| hsa-miR-433-3p$^{T}$ | ↓ | moderate | hippocampus | rat | 1 |
| hsa-miR-601$^{T}$ | ↑ | severe | serum | human | 3 |
| hsa-1307-3p$^{HTH}$ | ↑ | mild | saliva | human | 5 |

HTH, changes related to hits to the head in current study; T, time-course changes in current study Related miRNA matches in previous studies:

| miRNA | Related miRNA | Change | TBI Severity | Fluid/Tissue | Species | Ref |
|---|---|---|---|---|---|---|
| hsa-let-7b-3p$^{T}$ | let-7b | ↓ | mild-moderate | hippocampus | rat | 7 |
|  | let-7b-5p | ↓ | mild | saliva | human | 5 |
| hsa-miR-20a-5p$^{HTH}$ | miR-20a | ↑ | mild, moderate, severe | serum | human | 3 |
| hsa-miR-30b-5p$^{HTH}$ | miR-30b | ↑ | moderate | hippocampus | rat | 1 |
|  | miR-30b | ↑ | severe | CSF | human | 8 |
| hsa-miR-30c-1-3p$^{T}$ | miR-30c-1 | ↓ | mild | saliva | human | 5 |
| hsa-miR-92a-3p$^{HTH}$ | miR-92a | ↑ | mild | plasma | human | 9 |
|  | miR-92a | ↓ | severe | plasma | human | 9 |
| hsa-miR-155-5p$^{HTH}$ | miR-155 | ↑ | moderate | hippocampus | rat[1], mouse[10] | 1, 10 |
| hsa-miR-376a-5p$^{HTH}$ | miR-376a | ↑ | mild | serum | mouse | 4 |
|  | miR-376a | ↓ | mild-moderate | dentate gyrus | rat | 2 |
|  | miR-376a | ↓ | moderate | hippocampus | rat | 1 |
|  | miR-376a* | ↑ | mild | parietal lobe | mouse | 11 |
| hsa-miR-455-5p$^{HTH}$ | miR-455-3p | ↓ | mild | PBMCs | human | 12 |
|  | miR-455 | ↑ | mild | serum | mouse | 4 |
| hsa-miR-501-3p$^{T}$ | miR-501 | ↓ | mild | saliva | human | 5 |

Note:

miR-155-5p was ↓ed in severe TBI as determined by microarray analysis, but failed to show differential expression in qRT-PCR validation assay; miR-455-3p was ↓ed in mild TBI as determined by microarray analysis, but failed to show differential expression in qRT-PCR validation assay.

Example 3

Predictive Utility of Salivary miRNAs for TBI and Recovery from TBI

Study Population.

The study included subjects of age 7 to 21 years with a clinical diagnosis of mTBI. The mTBI group was composed of 61 children and adolescents who presented to the Penn State Hershey Medical Center for an evaluation of mTBI within 14 days of initial head injury. This 14 day cutoff period was chosen based on previous research indicating that most clinical symptoms and biomarker profiles return to baseline within two weeks of concussion (McCarthy et al., 2015). Subjects with a GCS≤12 at the time of injury, a clinical diagnosis of sTBI, penetrating head injury, skull fracture, intracranial bleeding, or those suffering from symptoms that could be attributed to depression or anxiety were excluded. Additional exclusion criteria were: primary language other than English, wards of the state, periodontal disease, upper respiratory infection, focal neurologic deficits, history of migraine, and drug/alcohol abuse.

Data Collection.

Medical and demographic characteristics for each subject were recorded, including: age, weight, height, gender, ethnicity, medical/food allergies, psychiatric history, sensorineural deficiencies, medication history, and current oropharyngeal status (e.g. seasonal allergies, dental fillings). Concussion history was also recorded: time since the injury, mechanism of injury, immediate symptoms (amnesia, loss of consciousness, emesis, seizures, fractures, or weakness), time of last analgesic use (non-steroidal anti-inflammatory or acetaminophen), and history of previous concussion. To assess cognitive and somatic concussion symptoms, the symptom evaluation portion of the child SCAT-3 was administered to each subject and their parent at the time of enrollment Kirkwood et al., 2006). Subjects and parents were contacted via telephone four weeks after the date of initial injury for re-evaluation of symptoms with the child SCAT-3. Thirty subjects with a SCAT-3 score≥5 on either self- or parent-report at four weeks were classified has having PCS. When possible, presence of PCS at a follow-up clinical visit was confirmed through review of the electronic medical record. The remaining subjects were classified as having acute concussion symptoms (ACS). Those subjects with PCS at four weeks were contacted again at eight weeks for an additional SCAT-3 phone evaluation. Seven subjects who failed to complete a follow-up SCAT-3 interview at four weeks and lacked a follow-up clinical visit were excluded from the study.

RNA Collection, Processing, and Quantification.

Saliva was collected from each subject via expectoration at the time of enrollment in a non-fasting state after an oral-tap water rinse. Each subject expectorated into an Oragene RE-100 saliva collection kit (DNA Genotek; Ottawa, Canada. Samples were shaken by hand 5-10 times and stored at room temperature for up to ten days prior to transfer into a 4° C. refrigerator. RNA was extracted with a Norgen Circulating and Exosomal RNA Purification Kit (Norgen Biotek, Ontario, Canada) per manufacturer instructions as we have previously reported (J. Head Trauma Rehabil., 1993). RNA concentrations were quantified with a Nanodrop Spectrophotometer and stored at −80° C. prior to sequencing. RNA yield and quality were assessed with the Agilent 2100 Bioanalyzer before library construction. Sequencing of salivary RNA occurred at the Penn State Genomics Core Facility using a NEXTflex Small RNA-Seq Kit v3 (Bioo Scientific; Austin, Tex.), an Illumina HiSeq 2500 Instrument, and a targeted depth of three million reads per sample. Reads were aligned to the hg38 build of the human genome using Partek Flow software (Partek; St. Louis, Mo.) and the SHRiMP2 aligner. Total miRNA counts within each sample were quantified with miRBase microRNA v21. Three saliva samples with less than $2.5 \times 10^4$ total miRNA counts were excluded from the final analysis, resulting in 52 final mTBI samples. Only miRNAs with raw read counts greater than 10 in at least 22/52 (42%) samples were evaluated in the differential expression analysis. This criterion was based on the ratio of subjects with PCS and the possibility that a miRNA might be present in only the PCS or ACS group. Prior to statistical analysis, raw read counts were quantile-normalized, mean-centered, and divided by the standard deviation of each variable.

Statistical Analysis.

Statistical analysis was performed using Metaboanalyst online software reported (J. Head Trauma Rehabil., 1993). The salivary miRNAs with differential expression between PCS and ACS groups were identified with a non-parametric Mann Whitney test with false detection rate (FDR) correction. A two-dimensional partial least squares discriminant analysis (PLSDA) was used to investigate the prognostic potential of salivary miRNA profiles in pediatric PCS. The variable importance in projection (VIP), a weighted sum of squares of PLSDA weights that takes into account explained variance of each dimension, was determined for each miRNA. The 15 miRNAs with the largest VIP scores were reported. A multivariable logistic regression analysis was used to evaluate the PCS prediction accuracy of the 15 miRNAs from PLSDA. Concentrations of miRNAs were utilized in the regression as ratios, providing a second level of control for variation in total miRNA across samples. Accuracy was determined by measuring area under the curve (AUC) on a receiver operating characteristics plot and validated with a 100-fold Monte Carlo cross validation technique. AUC for the top performing group of miRNAs was compared against the AUC for three clinical measures: 1) total symptom score on the child-response portion of the SCAT-3; 2) total symptom score on the parent-response portion of the SCAT-3; and 3) modified PCS risk score utilizing sex, age, prior concussion history, headache, fatigue, processing difficulty, and migraine history, as previously described by Zemek and colleagues (Babcock et al., 2013). It should be noted that this last tool was limited in part by absence of a balance error score and evaluation of noise sensitivity. Associations between the 15 salivary miRNAs (measured at the time of injury) and PCS characteristics (measured four weeks post-injury) were evaluated with Pearson correlation testing. Pearson correlations were also used to examine potential confounding relationships between salivary miRNAs and medical/demographic variables. Analysis of medical and demographic data across PCS and ACS groups was accomplished with a two-tailed student's t-test, with p-values<0.05 considered to be significantly different between groups. The top 15 miRNAs were inspected for functional relevance to brain injury and repair using DIANA mirPath v3 online software (Hyper Text Transfer Protocol Secure (HTTPS)://snf-515788.vm.okeanos.grnet.gr/). Human-specific, high confidence gene targets for each miRNA were identified with DIANA's microT-CDS algorithm (employing a target cut-off score of 0.90) (Barlow et al., 2011). Gene ontology (GO) and KEGG pathway categories over-represented by the miRNA gene targets (FDR<0.05; Fisher's Exact Test) were reported.

Participants.

Fifty two participants (mean age 14 years; 42% female) were included in the analysis. There were no differences between ACS (n=22) and PCS groups (n=30) in demographic, medical, or concussion characteristics (Table 27). The majority of participants were white and over 25% had used a non-steroidal anti-inflammatory drug or acetaminophen within six hours of saliva collection. Fifteen percent of subjects were taking a stimulant or selective serotonin re-uptake inhibitor at the time of enrollment. The majority of participants were enrolled within one-week of their concussion and the most common mechanisms of injury were sport (42%) and motor vehicle collision (15%). Nearly half had suffered a previous concussion (46%). The most commonly reported symptoms at the time of injury were amnesia (48%) and loss of consciousness (27%).

TABLE 27

Participant Characteristics

| | Population mean (n = 52) | ACS (n = 22) | PCS (n = 30) | P-value |
|---|---|---|---|---|
| Demographic Characteristics | | | | |
| Sex (% female) | 42 | 32 | 50 | 0.2 |
| Age (years) | 14 | 14 | 14 | 0.5 |
| Race (% white) | 92 | 91 | 93 | 0.8 |
| Height (percentile) | 61 | 55 | 65 | 0.2 |
| Weight (percentile) | 68 | 67 | 69 | 0.8 |
| Medical Characteristics | | | | |
| NSAID use (%) | 25 | 14 | 33 | 0.09 |
| Acetaminophen use (%) | 12 | 9 | 13 | 0.6 |
| Ondansetron use (%) | 0 | 0 | 0 | 1.0 |
| Stimulant or SSRI use (%) | 15 | 18 | 13 | 0.6 |
| Concussion Characteristics | | | | |
| Days since injury (at enrollment) | 6.8 | 7.1 | 6.4 | 0.5 |
| Sport Participation (%) | 42 | 37 | 50 | 0.3 |
| MVC (%) | 15 | 17 | 14 | 0.8 |
| LOC (%) | 27 | 20 | 36 | 0.4 |
| Amnesia (%) | 48 | 53 | 41 | 0.4 |
| Bony injury (%) | 10 | 13 | 5 | 0.3 |
| Emesis (%) | 23 | 20 | 27 | 0.6 |
| Previous concussion (%) | 46 | 40 | 55 | 0.3 |
| Number of previous concussion | 1.5 | 1.6 | 1.4 | 0.9 |

Symptom Reporting

The symptom evaluation portion of the child SCAT-3 was administered to all participants and their parents at initial assessment (within two weeks of injury) and again four weeks post-injury (Table 28).

TABLE 28

Concussion Symptoms

| | Population Mean | ACS | PCS | P-value |
|---|---|---|---|---|
| At enrollment (0-14 d post injury) | | | | |
| Child symptom severity score | 23 | 19 | 26 | 0.044 |
| Child total symptoms reported (#) | 12 | 11 | 13 | 0.105 |
| I have a hard time concentrating | 1.6 | 1.2 | 1.9 | 0.030 |
| I have problems remembering what people tell me | 1.3 | 0.9 | 1.6 | 0.027 |
| I daydream too much | 1.2 | 0.8 | 1.4 | 0.047 |
| I have headaches | 2.2 | 1.7 | 2.5 | 0.005 |
| I get tired a lot | 1.7 | 1.1 | 2.1 | 0.001 |
| Parental symptom severity score | 22 | 20 | 23 | 0.297 |
| Parent total symptoms reported (#) | 12 | 11 | 13 | 0.216 |
| The child has difficulty concentrating | 1.5 | 1.1 | 1.8 | 0.018 |
| The child feels dizzy | 1.3 | 1.0 | 1.6 | 0.045 |
| 4-week follow-up (28-34 d post injury) | | | | |
| Child symptom severity score | 11 | 0.8 | 18 | 7.0E−15 |
| Child total symptoms reported (#) | 6.9 | 0.8 | 11 | 1.6E−7 |
| I get tired a lot (% positive) | 0.9 | 0 (0) | 1.6 (90) | 5.9E−6 |
| I get tired easily (% positive) | 1.0 | 0.2 (18) | 1.6 (85) | 5.9E−6 |
| Parental symptom severity score | 8.8 | 0.5 | 13 | 0.005 |
| Parent total symptoms reported (#) | 4.6 | 0.3 | 7.1 | 3.8E−4 |
| 8-week follow-up (56-62 d post injury) | | | | |
| Child symptom severity score | | | 11 | |
| Child total symptoms reported (#) | | | 10 | |
| Parental symptom severity score | | | 16 | |
| I have problems remembering what people tell me (% positive) | | | 1.3 (92) | |
| Parent total symptoms reported (#) | | | 8.4 | |

Average symptom scores on the child sports concussion assessment tool (SCAT-3) are shown. Parent and child reports of symptoms were collected at enrollment (0-14d post-injury), 4 weeks post-injury, and 8 weeks post-injury (PCS group only). At each assessment 20 concussive symptoms were rated on a 0-4 Leicher scale by both child and parent, yielding a maximum possible severity score of 80 and a maximum total of 20 symptoms reported. Of the 20 symptoms assessed at each encounter, only those with significant differences between ACS and PCS groups (0-14d post-injury), or those most commonly reported (4-weeks and 8-weeks) are shown.

At the initial assessment children who went on to develop PCS reported a higher symptom severity score (p=0.044), but no difference in the number of symptoms. Parents of children who went on to develop PCS reported no initial difference in child symptom severity or total number of symptoms. Of the twenty symptoms queried, five were different between ACS and PCS groups on child survey. Children who went on to develop PCS endorsed higher symptom scores for: "I have a hard time concentrating" (p=0.030); "I have problems remembering what people tell me" (p=0.027); "I daydream too much" (p=0.048); "I have headaches" (p=0.005); and "I get tired a lot" (p=0.002). On the initial parental survey, two out of 20 symptoms were more severe in the PCS group: "The child has difficulty concentrating" (p=0.018); and "The child feels dizzy" (p=0.045). Four weeks post-injury the PCS group had a mean severity score of 18 and endorsed an average of 11/20 concussive symptoms. "I get tired a lot" and "I get tired easily" were the most commonly endorsed symptoms by participants at four weeks post injury, occurring in 90% and 85% of participants respectively. Fifteen participants continued to have concussive symptoms (SCAT-3 score>5 and/or clinically related visit) at eight weeks post-injury. The most commonly reported symptom at that time was "I have problems remembering what people tell me" (92%). Five PCS participants had symptom resolution at 8 weeks post-injury, and ten participants were lost-to-follow-up.

MicroRNA Expression

Figure 18:
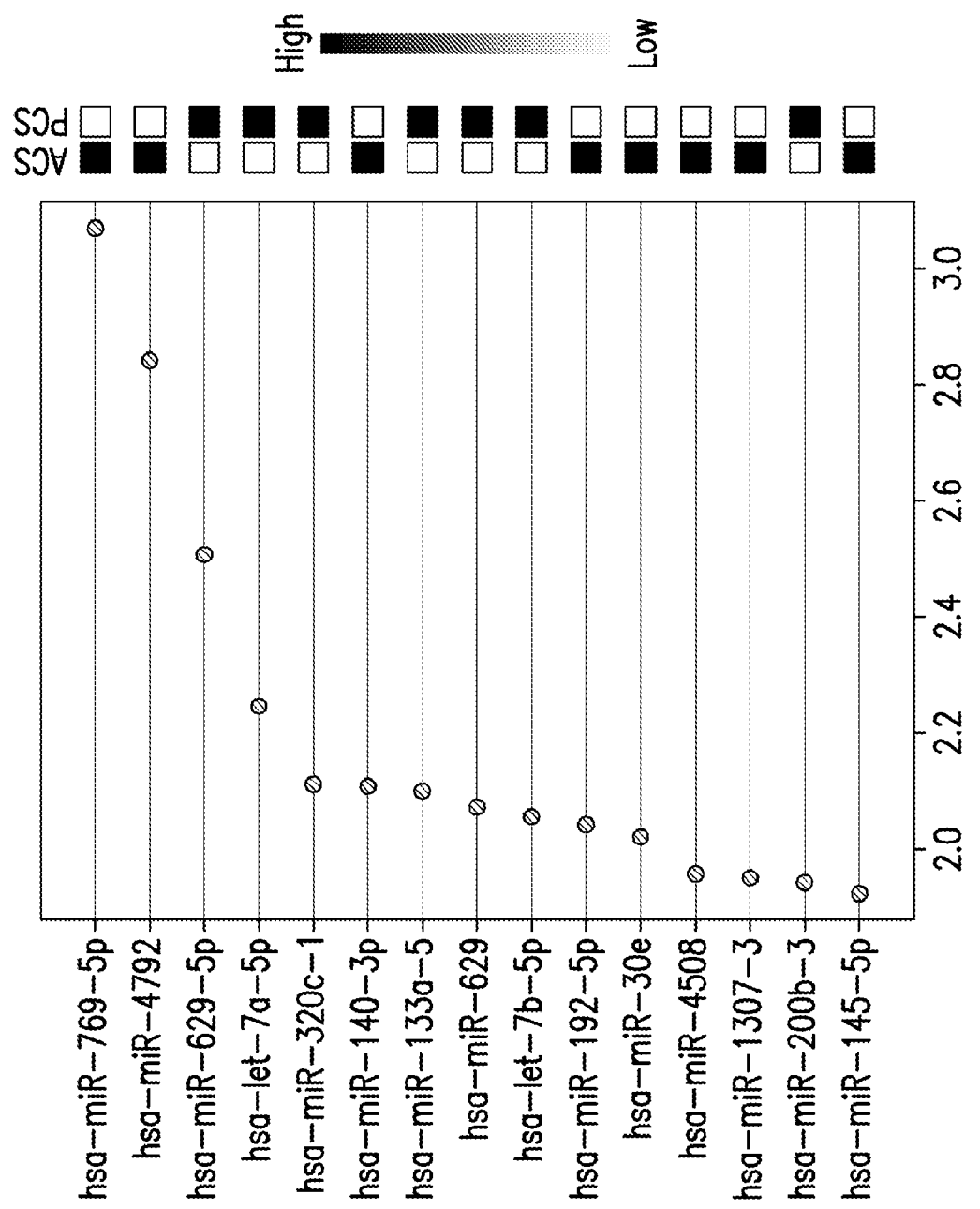
FIG. 18 shows top 15 miRNAs involved in separation. VIP scores for the 15 miRNAs most important in differentiating children with prolonged concussion symptoms (PCS) from those with acute concussion symptoms (ACS) on a partial least squared discriminant analysis.

Among the 52 Saliva Samples Analyzed, the Mean Read Count was $2.1 \times 10^5$ Reads Per sample and 437 miRNAs were detected in at least 22/30 samples. Among these 437 miRNAs, 14 demonstrated nominal differences between ACS and PCS groups on Mann-Whitney testing (Table 4B), but none survived multiple testing corrections. Of these 14 miRNAs, 3 were down-regulated in ACS subjects and 11 were up-regulated. The five miRNAs with the most significant changes between ACS and PCS groups included miR-769-5p (1.8 FC; p=0.002), miR-215-5p (2.4 FC; p=0.024), miR-769 (2.5 FC; p=0.025), miR-320c-1 (0.44 FC; p=0.028), and miR-194-2 (1.4 FC; p=0.028). A PLSDA employing miRNA expression levels for all 437 miRNAs achieved partial spatial separation of ACS and PCS groups while accounting for 21.5% of the variance in the dataset (Tables 29A-B). The 15 miRNAs most critical for separation of ACS and PCS subjects were identified by VIP score (FIG. 18). Two of these miRNAs (miR-30e and miR-320c) have been previously identified in a set of 6 salivary miRNAs as being significantly changed in the saliva following pediatric mTBI (relative to healthy controls). Certain of the 15 miRNAs have been identified in prior TBI investigations.

TABLE 29A

| Participant Characteristics | | | | | |
|---|---|---|---|---|---|
| | % Female | Age (years) | % While | Height (% ile) | Weight (% ile) |
| ACS n = 22 | 32 | 14 | 91 | 55 | 67 |
| PCS n = 30 | 50 | 14 | 93 | 65 | 69 |

*All p-values >0.05

TABLE 29B

| Concussion Characteristics | | | | | | | | |
|---|---|---|---|---|---|---|---|---|
| | Sport (%) | MVC (%) | LOC (%) | Amnesia (%) | Bony Injury (%) | Emesis (%) | Previous Concussions (%) | No. of previous concussion |
| ACS n = 22 | 37 | 17 | 20 | 53 | 13 | 20 | 40 | 1.6 |
| PCS n = 30 | 50 | 14 | 36 | 41 | 5 | 27 | 55 | 1.4 |

*All p-values > 0.05

Figure 19:
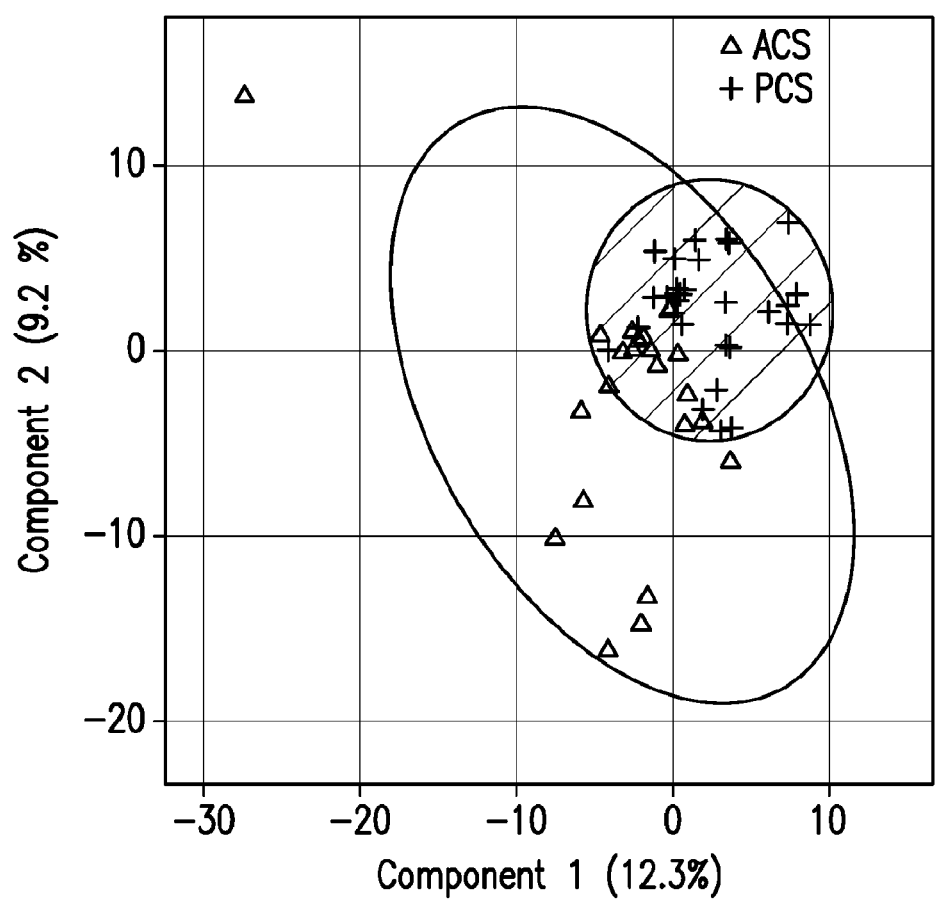
FIG. 19 shows total miRNA profiles achieve partial separation of ACS and PCS groups. PLSDA shows spatial separation of ACS and PCS groups using salivary miRNA profiles.

Total miRNA profiles achieve partial separation of ACS and PCS groups. PLSDA shows spatial separation of ACS and PCS groups using salivary miRNA profiles (FIG. 19).

MicroRNA Function.

Figure 20:
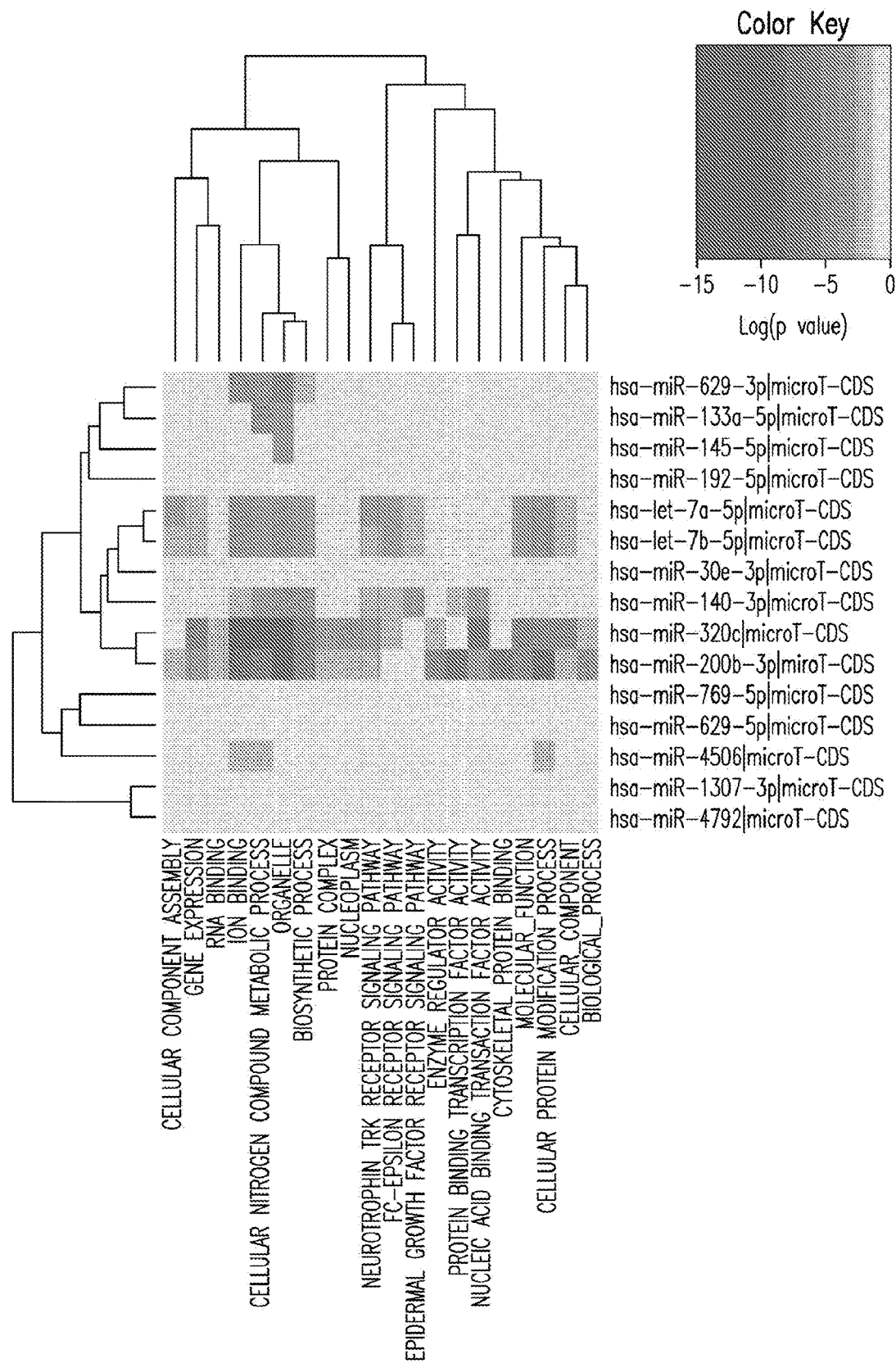
FIG. 20 shows Hierarchical clustering analysis of the 15 miRNAs demonstrated three distinct clusters of miRNAs based upon gene target function: miR-629-3p and miR-133a-5p; let-7a-5p and let-7b-5p; miR-320c and miR-200b-3p.

The fifteen miRNAs that most accurately differentiated ACS and PCS groups on PLSDA were interrogated for functional targets in DIANA miRPATH software. The 15 miRNAs targeted 2429 genes with high confidence (micro-c-tds score>0.90). These genes were implicated in 62 GO pathways and 22 KEGG pathways (Table 30). The most significantly over-represented GO pathway was organelle (p=2.77E-61; 1009 genes; 14 miRNAs) and the most over-represented KEGG pathway was extra-cellular matrix-receptor interaction (p=2.31E-13; 16 genes, 7 miRNAs). Among the targeted GO and KEGG pathways were a number of signaling cascades related to synaptic development, neuronal migration, and repair (Table 31). Targeted GO pathways included neurotrophin TRK signaling (34 genes), axon guidance (61 genes), and nervous system development (56 genes). Among the KEGG pathways of interest were glioma (14 genes), FOXO signaling (29 genes), and Wnt signaling (22 genes). Hierarchical clustering analysis of the 15 miRNAs demonstrated three distinct clusters of miRNAs based upon gene target function: miR-629-3p and miR-133a-5p; let-7a-5p and let-7b-5p; miR-320c and miR-200b-3p (FIG. 20).

TABLE 30

Fold changes and p-values between PCS and ACS groups
for all interrogated miRNAs (in order of p-values).

| KEGG pathway | FDR p-value | #genes | #miRNAs | GO Category | FDR p-value | #genes | #miRNAs |
|---|---|---|---|---|---|---|---|
| ECM-receptor interaction | 2.3E−13 | 16 | 7 | organelle | 2.8E−61 | 1009 | 14 |
| Proteoglycans in cancer | 8.2E−09 | 38 | 11 | ion binding | 6.1E−40 | 649 | 14 |
| TGF-beta signaling pathway | 3.5E−05 | 20 | 10 | cellular nitrogen compound metabolic process | 1.5E−39 | 525 | 14 |
| Focal adhesion | 3.5E−05 | 43 | 11 | biosynthetic process | 4.7E−30 | 448 | 13 |
| Renal cell carcinoma | 1.6E−04 | 18 | 7 | cellular protein modification process | 2.5E−23 | 279 | 13 |
| ErbB signaling pathway | 1.8E−04 | 21 | 9 | gene expression | 2.1E−16 | 83 | 12 |
| Signaling regulating stem cell pluripotency | 3.6E−04 | 28 | 8 | molecular_function | 1.5E−13 | 1560 | 14 |
| Glioma | 4.5E−04 | 14 | 7 | protein binding transcription factor activity | 3.1E−13 | 76 | 12 |
| PI3K-Akt signaling pathway | 4.5E−04 | 57 | 12 | cellular_component | 1.2E−10 | 1565 | 14 |
| Rap1 signaling pathway | 8.8E−04 | 36 | 10 | nucleic acid binding transcription factor activity | 3.1E−09 | 117 | 13 |
| FoxO signaling pathway | 9.7E−04 | 29 | 8 | cellular component assembly | 4.8E−09 | 145 | 13 |
| Axon guidance | 2.6E−03 | 23 | 10 | protein complex | 7.7E−09 | 371 | 14 |
| Prostate cancer | 5.1E−03 | 18 | 8 | cytoskeletal protein binding | 1.5E−08 | 97 | 13 |
| Transcriptional misregulation in cancer | 7.4E−03 | 30 | 8 | Fc-epsilon receptor signaling pathway | 1.6E−08 | 27 | 10 |
| Choline metabolism in cancer | 1.6E−02 | 19 | 7 | nucleoplasm | 5.0E−08 | 133 | 13 |
| AMPK signaling pathway | 1.6E−02 | 22 | 10 | biological_process | 7.2E−08 | 1509 | 14 |
| mTOR signaling pathway | 2.1E−02 | 14 | 7 | neurotrophin TRK receptor signaling pathway | 3.2E−07 | 34 | 9 |
| Wnt signaling pathway | 2.8E−02 | 22 | 8 | enzyme binding | 2.1E−06 | 134 | 12 |
| Dorso-ventral axis formation | 3.1E−02 | 8 | 6 | RNA binding | 8.1E−06 | 191 | 13 |
| Pathways in cancer | 3.1E−02 | 54 | 10 | cytosol | 1.1E−05 | 263 | 13 |
| Estrogen signaling pathway | 3.6E−02 | 14 | 8 | transcription initiation from RNA polymerase II promoter | 1.1E−05 | 35 | 11 |
| Ras signaling pathway | 4.4E−02 | 31 | 9 | epidermal growth factor receptor signaling pathway | 1.6E−05 | 31 | 10 |
| | | | | transcription, DNA-templated | 1.8E−05 | 257 | 13 |
| | | | | axon guidance | 3.8E−05 | 61 | 12 |
| | | | | enzyme regulator activity | 3.8E−05 | 91 | 13 |
| | | | | macromolecular complex assembly | 3.8E−05 | 92 | 13 |
| | | | | cell motility | 4.1E−05 | 69 | 12 |
| | | | | regulation of transcription from RNA polymerase II promoter in response to hypoxia | 3.3E−04 | 8 | 6 |
| | | | | symbiosis, encompassing mutualism through parasitism | 4.1E−04 | 51 | 12 |
| | | | | DNA metabolic process | 4.1E−04 | 82 | 14 |
| | | | | catabolic process | 4.1E−04 | 173 | 14 |
| | | | | anatomical structure morphogenesis | 4.8E−04 | 19 | 12 |

TABLE 30-continued

Fold changes and p-values between PCS and ACS groups for all interrogated miRNAs (in order of p-values).

| KEGG pathway | FDR p-value | #genes | #miRNAs | GO Category | FDR p-value | #genes | #miRNAs |
|---|---|---|---|---|---|---|---|
| | | | | nucleobase-containing compound catabolic process | 4.9E−04 | 88 | 14 |
| | | | | cell junction organization | 7.0E−04 | 23 | 10 |
| | | | | viral process | 7.0E−04 | 45 | 12 |
| | | | | mitotic cell cycle | 7.4E−04 | 40 | 12 |
| | | | | extracellular matrix disassembly | 9.0E−04 | 17 | 8 |
| | | | | phosphatidy linositol-mediated signaling | 9.3E−04 | 21 | 9 |
| | | | | nervous system development | 1.2E−03 | 56 | 12 |
| | | | | fibroblast growth factor receptor signaling pathway | 1.4E−03 | 26 | 9 |
| | | | | extracellular matrix organization | 1.5E−03 | 45 | 12 |
| | | | | cellular protein metabolic process | 2.4E−03 | 43 | 12 |
| | | | | cell junction assembly | 3.5E−03 | 11 | 10 |
| | | | | blood coagulation | 6.1E−03 | 43 | 10 |
| | | | | response to stress | 7.1E−03 | 197 | 14 |
| | | | | protein complex assembly | 7.1E−03 | 74 | 12 |
| | | | | cellular component disassembly involved in execution phase of apoptosis | 1.1E−02 | 8 | 7 |
| | | | | micro-ribonucleoprotein complex | 1.8E−02 | 6 | 5 |
| | | | | cell-cell junction organization | 2.2E−02 | 13 | 9 |
| | | | | post-Golgi vesicle-mediated transport | 2.2E−02 | 9 | 8 |
| | | | | RNA polymerase II core promoter proximal region sequence-specific DNA binding | 2.2E−02 | 39 | 10 |
| | | | | RNA polymerase II core promoter proximal region sequence-specific DNA binding transcription factor activity involved in positive regulation of transcription | 3.0E−02 | 36 | 9 |
| | | | | cell death | 3.4E−02 | 83 | 13 |
| | | | | post-translational protein modification | 3.8E−02 | 17 | 8 |
| | | | | cell proliferation | 3.8E−02 | 68 | 11 |
| | | | | microtubule organizing center | 3.8E−02 | 48 | 13 |
| | | | | lung development | 3.8E−02 | 27 | 11 |
| | | | | transcription compressor activity | 3.9E−02 | 33 | 12 |
| | | | | small molecule metabolic process | 4.1E−02 | 184 | 13 |
| | | | | positive regulation of protein insertion into mitochondrial membrane involved in apoptotic signaling padway | 4.2E−02 | 6 | 6 |
| | | | | collagen catabolic process | 4.4E−02 | 12 | 8 |
| | | | | protein binding, bridging | 4.8E−02 | 20 | 8 |

Symptom and miRNA Correlations

Pearson correlations were determined for symptom characteristics (four weeks post-injury) and concentrations of the 15 salivary miRNAs (at the time of initial assessment). Nominal correlations (p<0.05) were identified between 12 miRNA-symptom pairs (FIG. 21). Three of these correlations survived multiple testing corrections: miR-320c-1 was positively correlated with "I have problems remembering what people tell me" (R=0.55; FDR=0.02); miR-629 was positively correlated with "I have headaches" (R=0.47; FDR=0.04); and let-7b-5p was positively correlated with "I get tired a lot" (R=0.45; FDR=0.04). Individual miRNAs showed both positive and negative correlations with one another and the majority of individual SCAT-3 items correlated positively with one another. However, there were no correlations between individual SCAT-3 items and total SCAT-3 scores. Child and parent total SCAT-3 symptom scores correlated positively with each other, but not with individual miRNAs or individual child symptom items.

Predictive Utility.

Figure 22A:
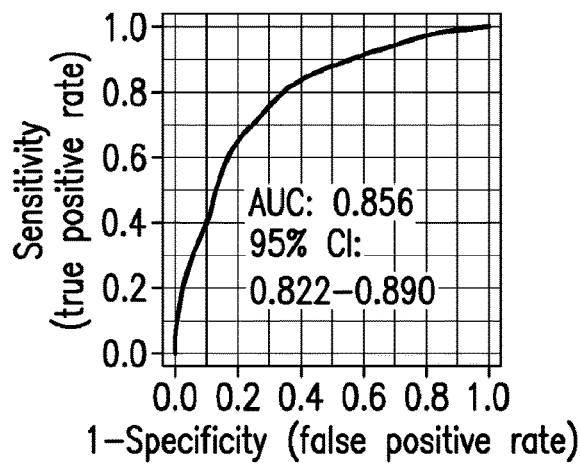
FIGS. 22A-F show receiver operating characteristic curves for a panel of 5 miRNAs (miR-320c-1, miR-133a-5p, miR-769-5p, let-7a-3p, miR-1307-3p) at differentiating PCS and ACS groups on logistic regression analysis (A), with a cross validation technique (B), with a 20% hold out technique (C). In comparison current clinical tools such as the child SCAT3 (D), parent SCAT3 (E), and a pediatric PCS clinical risk score (F) have much lower AUCs.
Figure 22B:
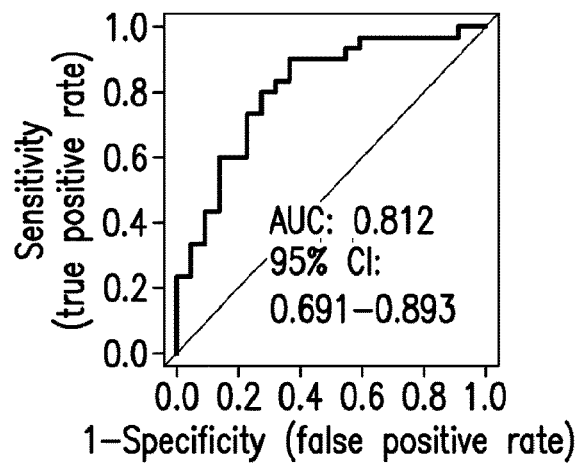
Figure 22C:
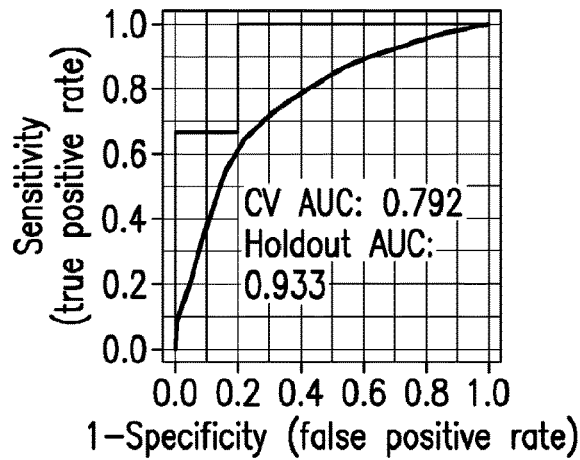
Figure 22D:
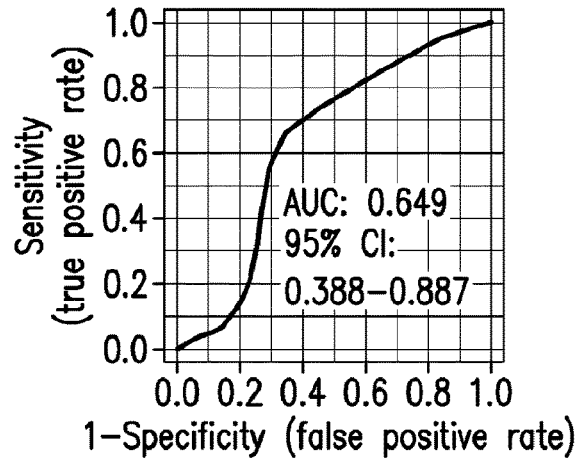
Figure 22E:
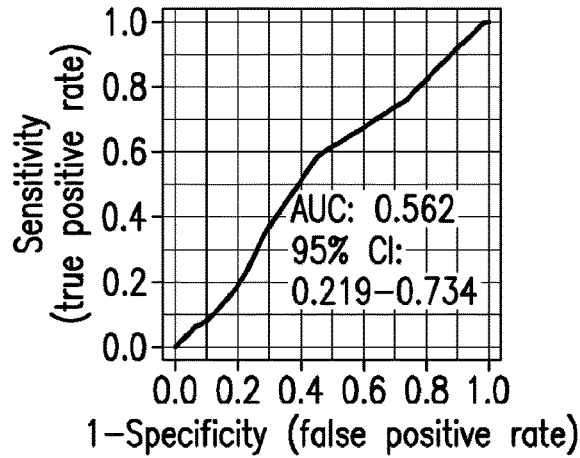
Figure 22F:
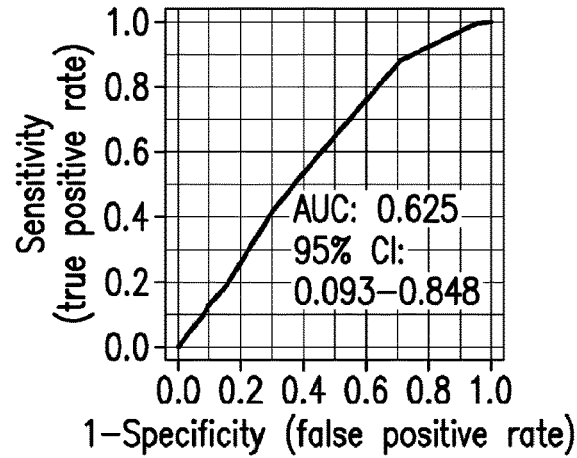
Figure 23A:
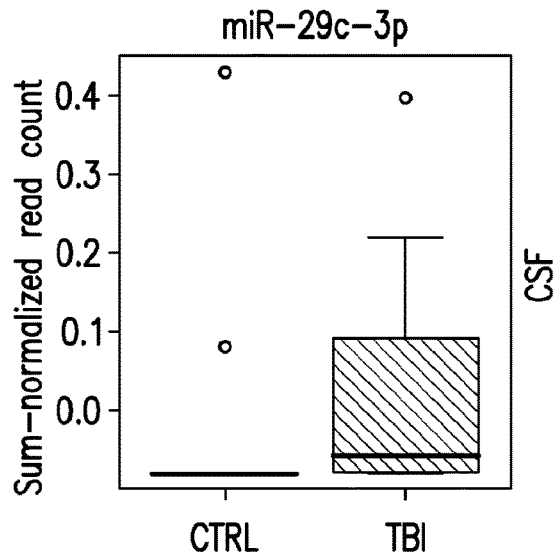
FIGS. 23A-H show miRNA overlap in Saliva-CSF after TBI.
Figure 23B:
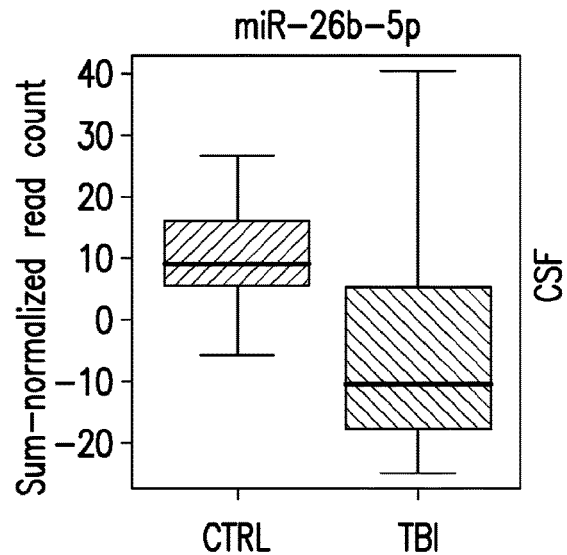
Figure 23C:
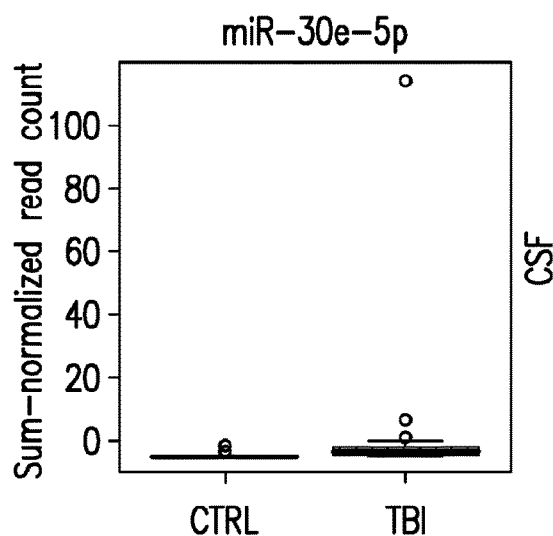
Figure 23D:
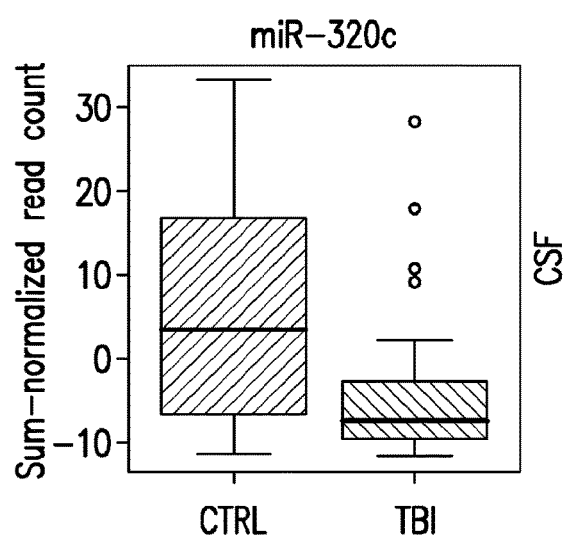
Figure 23E:
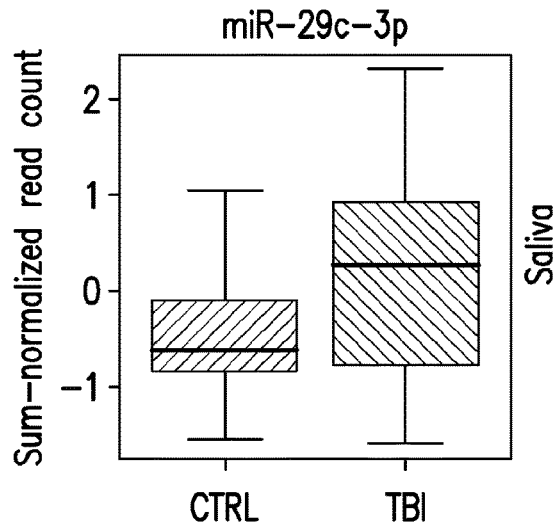
Figure 23F:
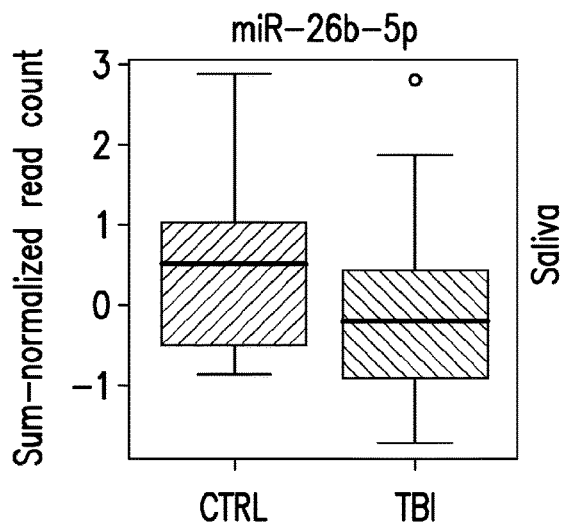
Figure 23G:
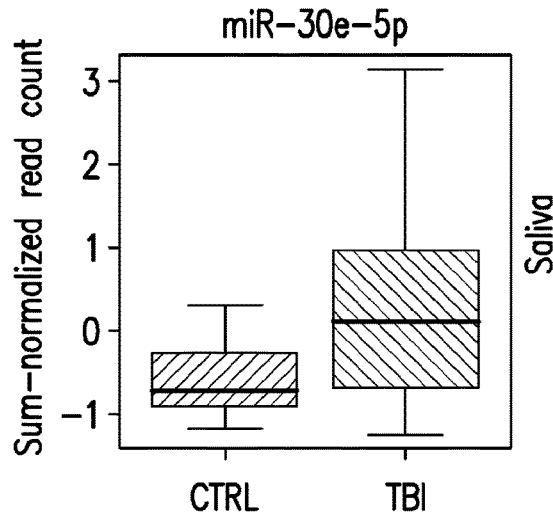
Figure 23H:
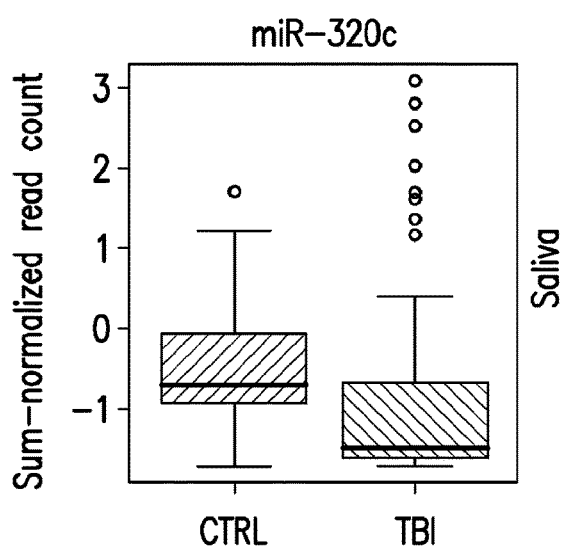

A multivariable logistic regression analysis was used to evaluate PCS prediction accuracy of the 15 miRNAs from PLSDA. A test of classification accuracy for the most predictive miRNAs was visualized with a receiver operating characteristics (ROC) curve. A model employing five miRNAs (miR-320c-1, miR-133a-5p, miR-769-5p, let-7a-3p, miR-1307-3p) demonstrated the highest classification accuracy (AUC=0.856; 95% CI: 0.822-0.890) with a sensitivity of 80% and a specificity of 75% for PCS status (FIG. 22A). To prevent over-modeling the data, two validation techniques were tested: a 10-fold cross validation technique demonstrated an AUC of 0.812; in addition, the first 20% of samples in each group were held out, producing an initial AUC of 0.792 with an AUC of 0.933 in the hold-out set (FIGS. 22B-22C). In comparison, logistic regression models using the total child SCAT-3 severity score or the total parent SCAT-3 severity score demonstrated AUCs of 0.649 and 0.562 respectively (FIGS. 22D-22E). Because several studies have shown that total SCAT-3 scores do not provide the most accurate clinical assessment for PCS risk we sought to compare the miRNA panel against a second clinical measure of PCS risk. PCS status among the 52 subjects was projected with a modified version of the PCS predictive tool developed by Zemek and colleagues. A risk score was retrospectively calculated for each subject with seven (of the nine) available risk factors (excluding balance and noise sensitivity). In our subjects this risk calculator demonstrated an AUC of 0.625 for predicting PCS status (FIG. 22F), a performance similar to that described by Zemek in colleagues in their original report. FIGS. 23A-23H show miRNA overlap in Saliva-CSF after TBI.

Further, two groups based on symptoms reports at four weeks post-injury were examined, one group was a PSC group and the second group was acute concussive symptom (ACS) group. Saliva was collected within 2 weeks of injury, miRNA was quantified with RNA sequencings, and Sport Concussion Assessment Tool (SCAT-3) at 0, 4, and 8 weeks post-injury was conducted.

The present disclosure also contemplates a kit suitable for determining whether a subject has a disease, disorder, or condition (such as a traumatic brain injury) including 2 or more miRNA probes of a probe set. Each miRNA probe may include a ribonucleotide sequence corresponding to a specific miRNA described herein. In an implementation, the kit further may include a solid support attached to the 2 or more miRNA probes. In an implementation, the kit may further include at least one of the following: (a) one randomly-generated miRNA sequence adapted to be used as a negative control; (b) at least one oligonucleotide sequence derived from a housekeeping gene, used as a standardized control for total RNA degradation; or (c) at least one randomly-generated sequence used as a positive control.

TABLE 31

Genes involved in neurodevelopmental pathways are targeted by the 15 miRNAs of interest.
Gene Targets

| Gene Ontology Category | |
|---|---|
| Neurotrophin TRK Signaling Pathway (34 genes; 9 miRNAs; p = 3.22E−07) | IRS2, SOS2, CAMK4, NRAS, CRKL, AGO3, PRKCI, AP2B1, SORT1, RAP1A, AGO2, EGFR, AGO4, RPS6KB2, TNRC6B, RICTOR, CREB1, PLCG1, CASP3, MAPK8, NDN, RIT1, SOS1, FGF9, PRKAR2A, KITLG, NGF, RPS6KA3, PIK3CA, TNRC6A, PTEN. MAPK1. ERBB4, EREG |
| Axon Guidance (61 genes; 12 miRNAs; p = 3.81E−05) | EFNB2, ACTB, NRCAM, WASL, PAX6, SOS2, CLASP2, NRAS, LMX1A, AP2B1, ROCK2, ROBO2, KCNQ3, CHL1, SRGAP1, EGFR, ITGA1, COL3A1, BDNF, ALCAM, CREB1, PTK2, ANK3, UNC5A, SLIT2, PLCG1, B3GNT1, FEZ2, NR4A3, GLI3, RELN, ITGA2, ETV1, COL4A4, SOS1, FARP2, DCX, PLXND1, TUBB3, SEMA3A, PGRMC1, RPS6KA3, VASP, PLXNA4, PLXNC1, CACNB2, NFASC, CACNA1D, EPHA4, NOG, MAPK1, TLN1, ABL2, RANBP9, NCAN, ENAH, SCN8A, EPHB1, DRAXIN, COL4A1, EFNA1 |
| Nervous System Development (56 genes; 12 miRNAs; p = 0.0012) | BDNF, BMPR1A, CHRDL1, CHRM3, CYP46A1, DBN1, DCX, DPF3, EPM2A, ERBB4, FEZ2, GMFB, GPM6B, HDAC4, HOXA1, IGF1, INHBA, LPPR1, MAP1B, MBD5, NAIP, NDN, NOG, PCDHA1, PCDHA10, PCDHA11, PCDHA2, PCDHA3, PCDHA4, PCDHA5, PCDHA6, PCDHA7, PCDHA8, PCDHAC1, PCDHAC2, PCSK2, PLXNA4, PPT1, RET, SCN2A, SCN8A, SERF1A, SERF1B, SIM1, SLC1A2, SLITRK1, SMARCA2, SMARCC1, TENM1, TFAP2A, TMOD2, TSC1, VLDLR, WDPCP, ZEB2, ZNF423 |
| KEGG Category | |
| Glioma (14 genes, 7 miRNAs; p = 0.0004) | AKT3, CDK6, E2F3, EGFR, IGF1, IGF1R, MAPK1, NRAS, PIK3CA, PLCG1, PTEN, SOS1, SOS2, TGFA |
| FOXO Signaling (29 genes; 9 miRNAs; p = 0.0009) | AKT3, ATG12, CREBBP, EGFR, FOXG1, G6PC, HOMER1, HOMER2, IGF1, IGF1R, IL10, IRS2, MAPK1, MAPK8, NRAS, PIK3CA, PLK2, RKAA1, PRKAB2, PTEN, RAG1, SETD7, SIRT1, SMAD2, SOD2, SOS1, SOS2, STK4, TGFBR1 |

TABLE 31-continued

Genes involved in neurodevelopmental pathways are targeted by the 15 miRNAs of interest.
Gene Targets

| | |
|---|---|
| Wnt Signaling (22 genes; 8 miRNAs; p = 0.0276) | APC, CREBBP, CTNNBIP1, FRAT2, FZD3, FZD4, GPC4, JUN, LEF1, LRP5, MAP3K7, MAPK5, NFATC3, PPP3CA, ROCK2, SENP2, SKP1, TBL1XR1, VANGL2, WIF1, WNT16, WNT9A |

Figures 24A, 24B:
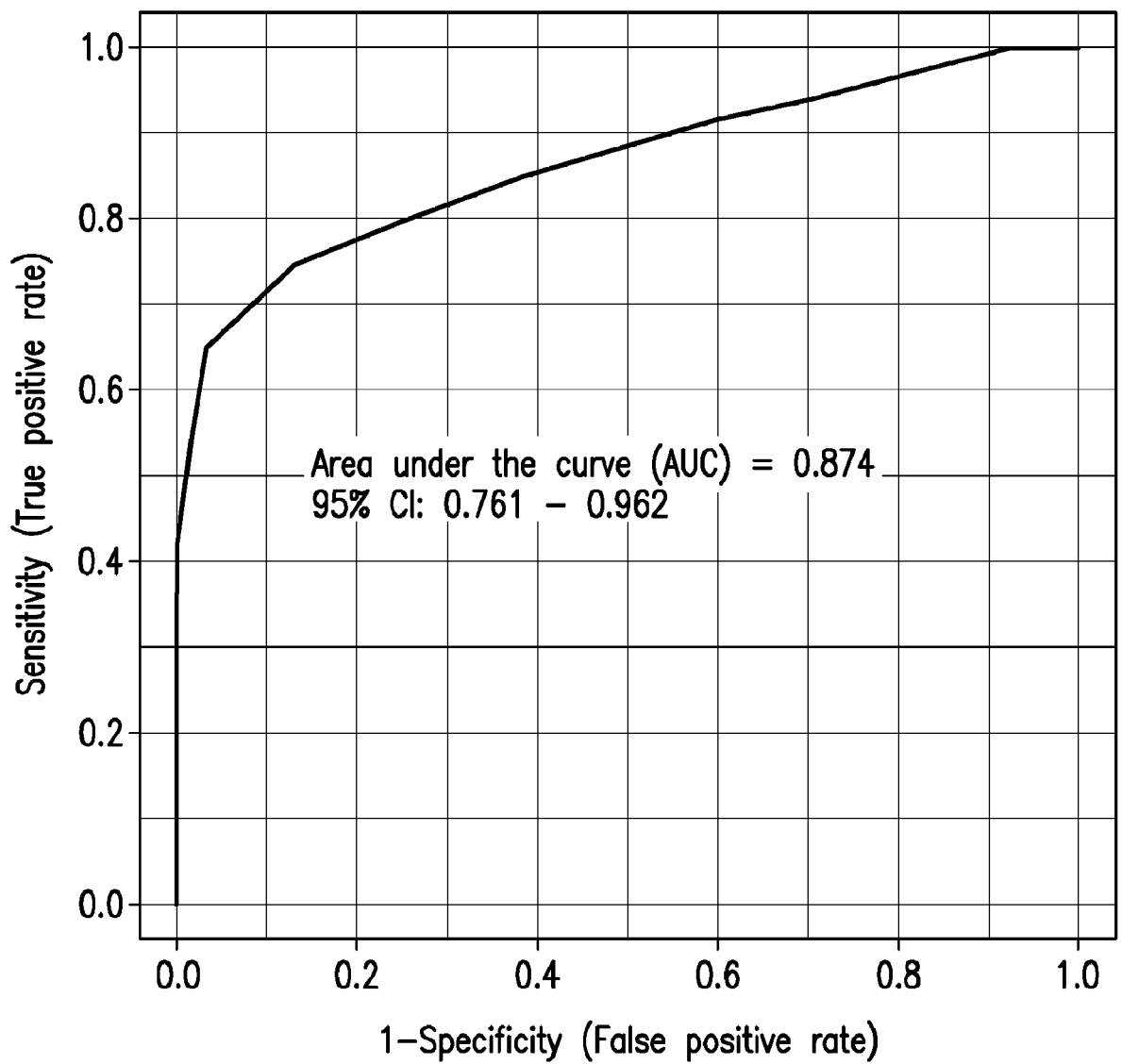
FIGS. 24A, B show Logistic Regression Analysis using miRNA (Sensitivity: 75%; Specificity: 93%; 10-Fold CV: 0.87).
Figure 25:
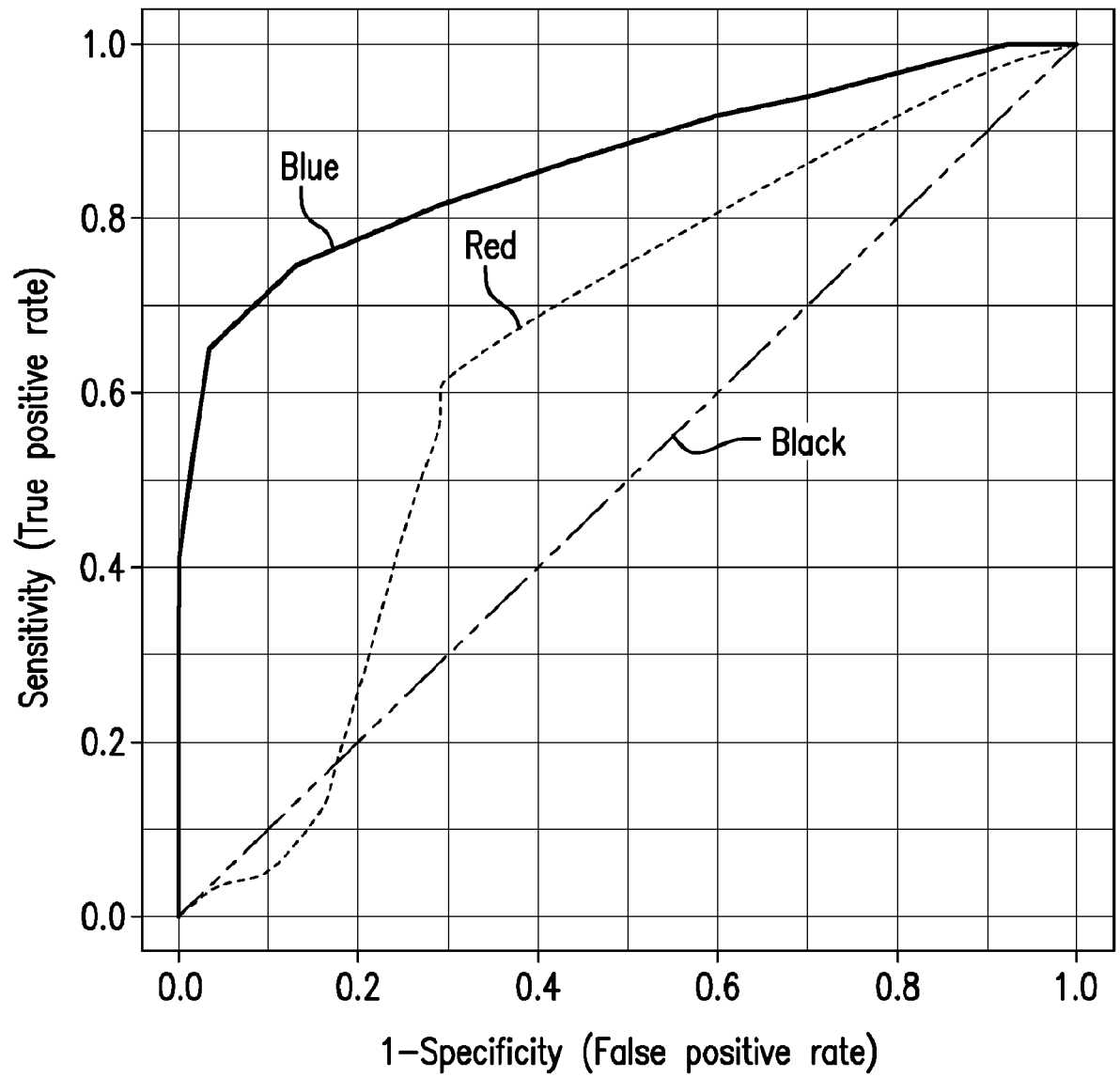
FIG. 25 shows Logistic Regression Analysis using miRNA; blue (top): miRNA AUS=0.898; child SCAT3 AUC=0.649.
Figure 26:
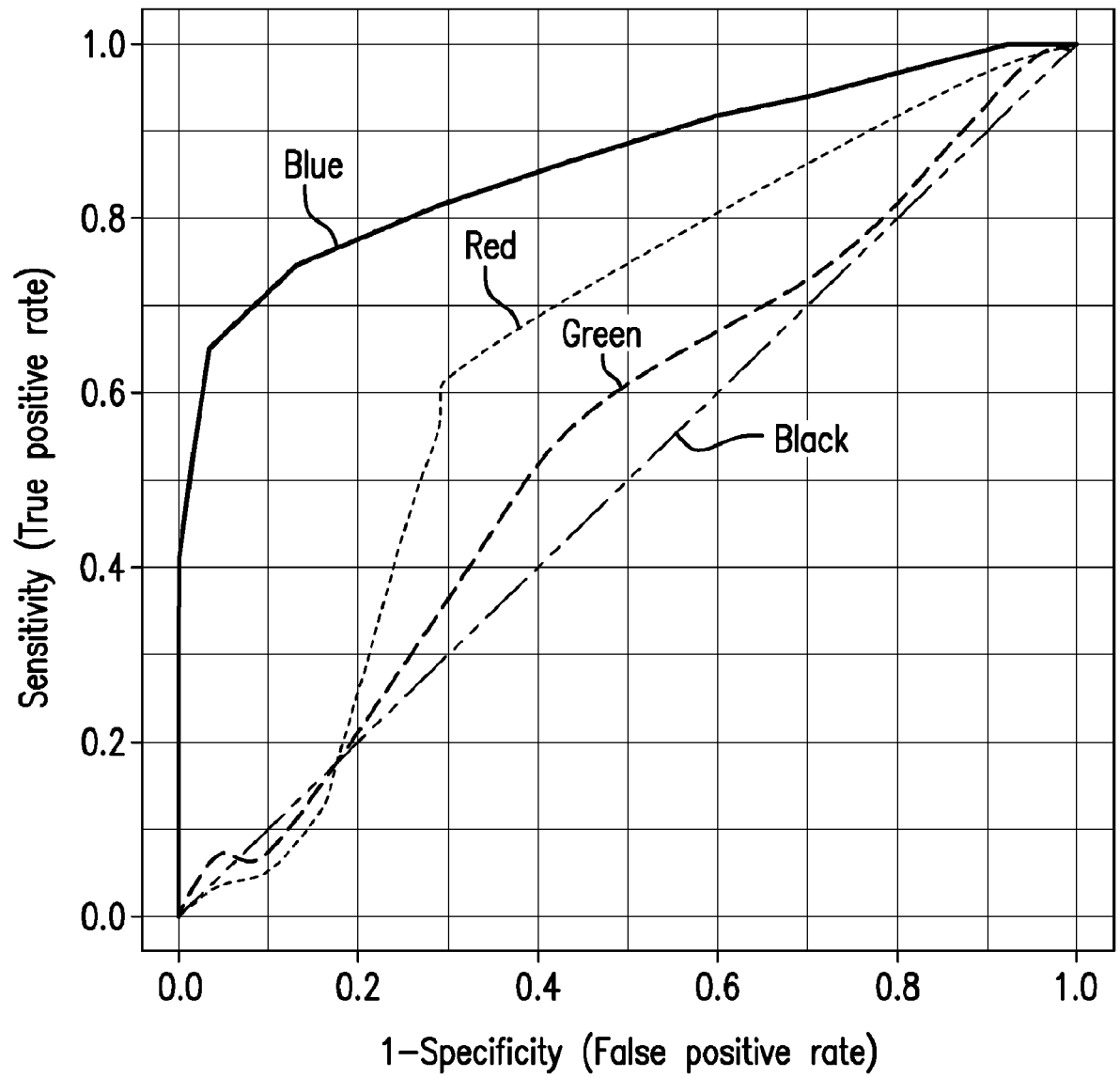
FIG. 26 shows Logistic Regression Analysis using miRNA; blue (first left): miRNA AUIS=0.898; red (second left) child SCAT3 AUS=0.649; green (third left) parent SCAT3=0.562.
Figures 27A, 27B:
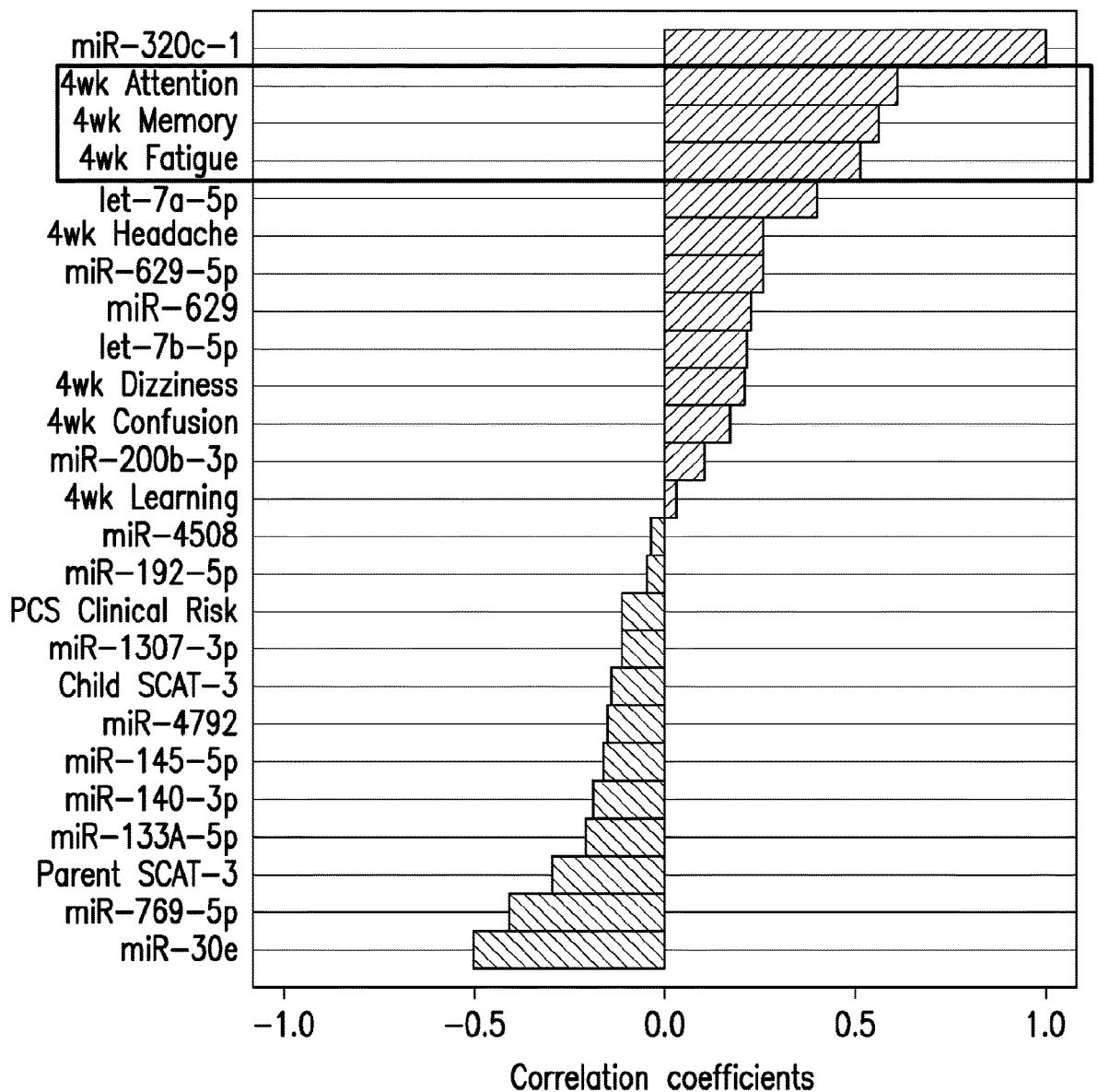
FIGS. 27A, B show miR-320c associated with specific symptoms at 4-weeks.

Logistic regression analysis using miRNA is shown in FIGS. 24-26.
Biological Plausibility
KEGG Pathways targeted by the miRNAs:
FoxO signaling (p = 0.001; 29 genes),
Axon guidance (p = 0.003; 23 genes),
Glioma (p = 0.0004; 14 genes),
PI3K-Akt signaling (p = 0.0004; 57 genes).
miRNA-320c is associated with specific symptoms at 4-weeks (FIG. 27).

As shown herein, salivary microRNAs exhibit a high-prognostic potential, are easily measured in saliva, are altered following mTBI, are functionally related or interactive with genes expressed in the grain, predict TBI symptom duration, and are associated with the character of clinical or other physical symptoms of TBI.

Figure 28:
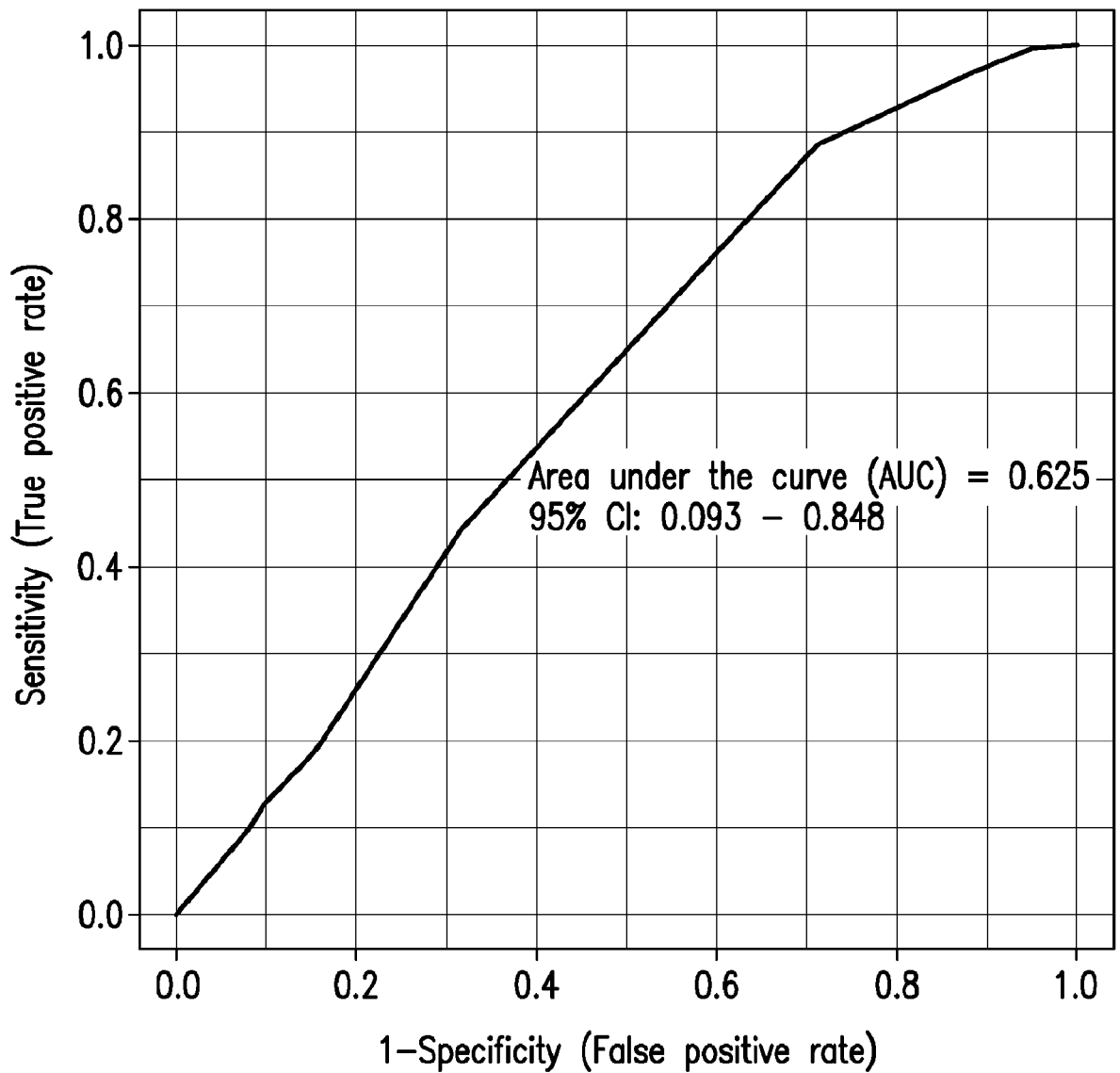
FIG. 28 shows Regression Analysis Using Modified Clinical Prediction Tool (Zemek et al. 2016).
Figure 29B:
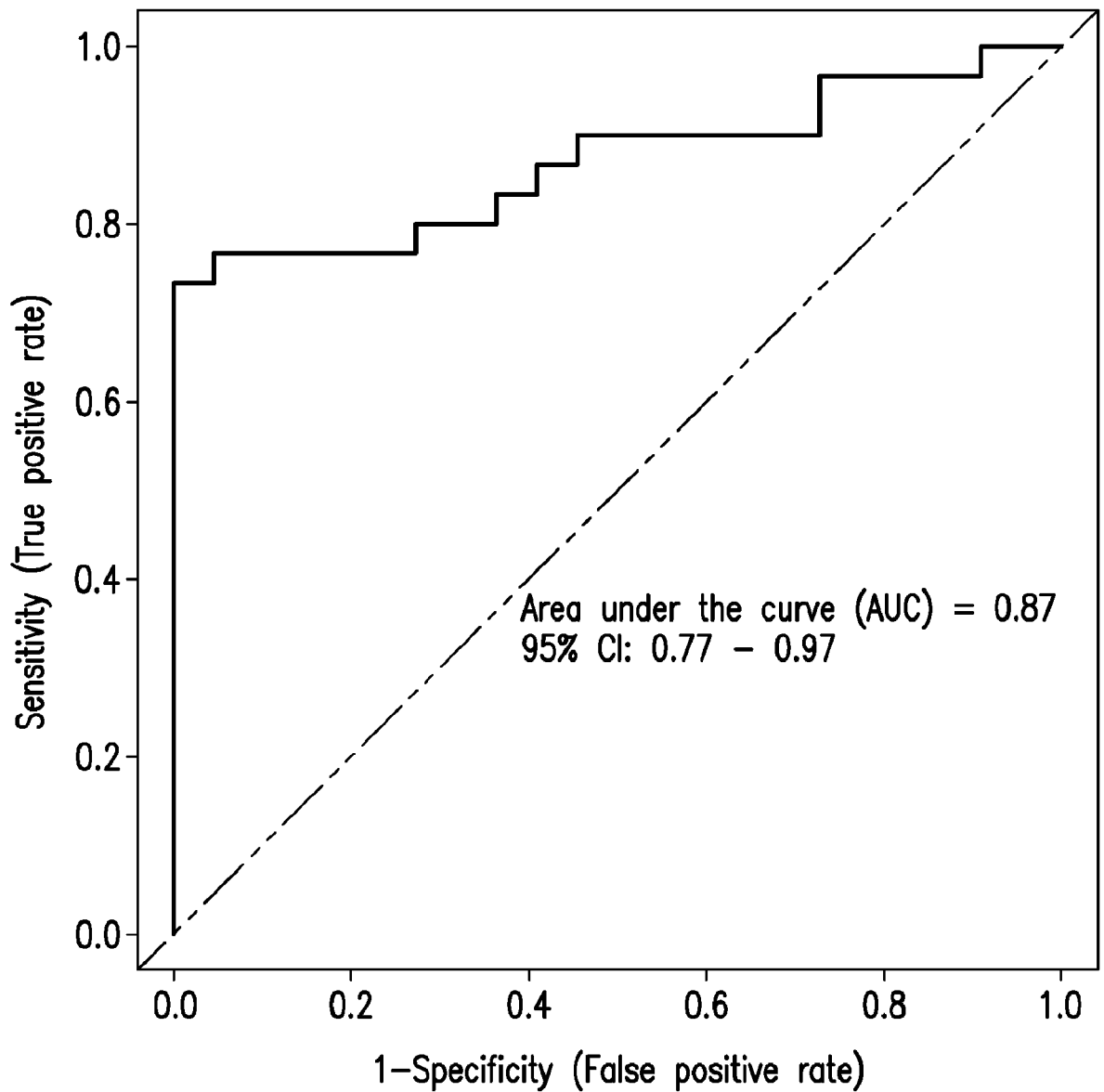
FIGS. 29A, B show a logistic regression model using a subset of those miRNAs to predict PCS status.

FIG. 28 shows Regression analysis using Modified Clinical Prediction tool (Zemek et al., 2016). Clinical risk score considers factors including sex, age, prior concussion with symptoms more than 7 days (headache, fatigue, processing difficulty). FIGS. 29A-29B present a logistic regression model using a subset of those miRNAs to predict PCS status.

TABLE 32A

Fold changes and p-values for all salivary miRNAs compared across PCS and ACS groups.

| | FC | log2(FC) | p.value | LOG10(p) |
|---|---|---|---|---|
| hsa-miR-769-5p | 1.8174 | 0.86189 | 0.00204 | 2.6904 |
| hsa-miR-215-5p | 2.3759 | 1.2485 | 0.023837 | 1.6227 |
| hsa-mir-769 | 2.4707 | 1.3049 | 0.025002 | 1.602 |
| hsa-mir-320c-1 | 0.44156 | −1.1793 | 0.02816 | 1.5504 |
| hsa-mir-194-2 | 1.4215 | 0.50741 | 0.028173 | 1.5502 |
| hsa-mir-199a-1 | 2.778 | 1.474 | 0.032367 | 1.4899 |
| hsa-mir-4792 | 1.8268 | 0.86933 | 0.033165 | 1.4793 |
| hsa-miR-140-3p | 1.8441 | 0.88288 | 0.035511 | 1.4496 |
| hsa-miR-629-5p | 0.66301 | −0.59289 | 0.036346 | 1.4395 |
| hsa-let-7f-2 | 1.3856 | 0.4705 | 0.038886 | 1.4102 |
| hsa-miR-128-3p | 2.0005 | 1.0003 | 0.039783 | 1.4003 |
| hsa-miR-192-5p | 1.4063 | 0.49191 | 0.041603 | 1.3809 |
| hsa-miR-145-5p | 1.621 | 0.69686 | 0.045449 | 1.3425 |
| hsa-let-7f-5p | 0.74675 | −0.4213 | 0.048536 | 1.3139 |
| hsa-let-7a-3 | 0.64425 | −0.6343 | 0.051941 | 1.2845 |
| hsa-mir-6763 | 0.63486 | −0.65549 | 0.052907 | 1.2765 |
| hsa-mir-1303 | 4.0212 | 2.0076 | 0.061366 | 1.2121 |
| hsa-miR-93-5p | 1.1851 | 0.245 | 0.062532 | 1.2039 |
| hsa-miR-28-3p | 3.0746 | 1.6204 | 0.063933 | 1.1943 |
| hsa-mir-128-1 | 2.135 | 1.0942 | 0.068064 | 1.1671 |
| hsa-mir-363 | 1.126 | 0.17114 | 0.073857 | 1.1316 |
| hsa-mir-505 | 2.1826 | 1.126 | 0.075334 | 1.123 |
| hsa-miR-133a-5p | 0.59031 | −0.76045 | 0.076905 | 1.114 |
| hsa-mir-93 | 1.2059 | 0.27013 | 0.081553 | 1.0886 |
| hsa-miR-4763-5p | 1.2064 | 0.27071 | 0.083287 | 1.0794 |
| hsa-mir-200c | 0.80514 | −0.31269 | 0.091606 | 1.0381 |
| hsa-miR-1307-3p | 1.4977 | 0.58273 | 0.093682 | 1.0283 |
| hsa-miR-200c-3p | 0.80993 | −0.30413 | 0.095375 | 1.0206 |
| hsa-miR-200b-3p | 0.78505 | −0.34914 | 0.09899 | 1.0044 |
| hsa-miR-199a-3p | 1.3739 | 0.45828 | 0.10116 | 0.99501 |
| hsa-miR-425-5p | 1.269 | 0.34374 | 0.10499 | 0.97886 |
| hsa-mir-4763 | 1.3111 | 0.39081 | 0.10909 | 0.96222 |
| hsa-let-7a-5p | 0.61132 | −0.70999 | 0.11289 | 0.94734 |
| hsa-miR-6763-3p | 0.51008 | −0.97119 | 0.12193 | 0.91389 |
| hsa-miR-423-5p | 0.51138 | −0.96754 | 0.12194 | 0.91386 |
| hsa-mir-4508 | 1.6478 | 0.72055 | 0.12196 | 0.91378 |
| hsa-mir-6073 | 1.7409 | 0.79987 | 0.12643 | 0.89815 |
| hsa-miR-30c-5p | 1.2674 | 0.34182 | 0.12879 | 0.89013 |
| hsa-mir-28 | 1.1798 | 0.23855 | 0.13586 | 0.8669 |
| hsa-mir-199b-3p | 1.3286 | 0.40994 | 0.13594 | 0.86666 |

TABLE 32A-continued

Fold changes and p-values for all salivary miRNAs compared across PCS and ACS groups.

| | FC | log2(FC) | p.value | LOG10(p) |
|---|---|---|---|---|
| hsa-miR-24-1-5p | 1.479 | 0.56462 | 0.14086 | 0.85122 |
| hsa-mir-146a | 0.74802 | −0.41886 | 0.14336 | 0.84358 |
| hsa-mir-133a-2 | 1.8705 | 0.90345 | 0.14339 | 0.84348 |
| hsa-mir-6840 | 0.51014 | −0.97103 | 0.14595 | 0.83579 |
| hsa-miR-505-3p | 1.3025 | 0.38131 | 0.15109 | 0.82075 |
| hsa-mir-30e | 1.5327 | 0.61607 | 0.1537 | 0.81334 |
| hsa-mir-200b | 1.9242 | 0.9443 | 0.15376 | 0.81316 |
| hsa-mir-3916-pre | 0.76985 | −0.37736 | 0.15922 | 0.79801 |
| hsa-miR-181a-5p | 1.2568 | 0.32979 | 0.16471 | 0.78327 |
| hsa-mir-215 | 1.4486 | 0.53467 | 0.16472 | 0.78325 |
| hsa-mir-140 | 1.4271 | 0.51309 | 0.16472 | 0.78325 |
| hsa-miR-146b-5p | 1.0131 | 0.018785 | 0.16475 | 0.78318 |
| hsa-mir-638 | 1.0302 | 0.042887 | 0.16478 | 0.78311 |
| hsa-mir-128-2 | 2.334 | 1.2228 | 0.16761 | 0.7757 |
| hsa-let-7b | 0.40226 | −1.3138 | 0.17047 | 0.76835 |
| hsa-mir-1307 | 1.447 | 0.53302 | 0.17049 | 0.7683 |
| hsa-miR-484 | 1.7456 | 0.80374 | 0.17336 | 0.76105 |
| hsa-miR-132-3p | 2.6713 | 1.4175 | 0.17492 | 0.75715 |
| hsa-mir-484-pre | 1.7277 | 0.78884 | 0.17931 | 0.74639 |
| hsa-miR-199b-5p | 1.3544 | 0.4377 | 0.18093 | 0.74249 |
| hsa-mir-375-pre | 0.75142 | −0.41232 | 0.18211 | 0.73966 |
| hsa-mir-1246 | 0.6865 | −0.54266 | 0.18216 | 0.73955 |
| hsa-miR-4698 | 0.42012 | −1.2511 | 0.18232 | 0.73917 |
| hsa-miR-4698-pre | 0.43666 | −1.1954 | 0.18233 | 0.73914 |
| hsa-mir-4514 | 0.56591 | −0.82136 | 0.18538 | 0.73193 |
| hsa-mir-378g-pre | 1.5662 | 0.64729 | 0.18844 | 0.72483 |
| hsa-mir-106b | 1.1686 | 0.22475 | 0.18845 | 0.72481 |
| hsa-mir-3668 | 0.87848 | −0.18692 | 0.19162 | 0.71756 |
| hsa-mir-6087 | 1.0475 | 0.066922 | 0.19479 | 0.71044 |
| hsa-miR-425 | 1.2111 | 0.27635 | 0.19785 | 0.70366 |
| hsa-mir-200a | 0.91638 | −0.12599 | 0.19791 | 0.70354 |
| hsa-mir-3667 | 0.52636 | −0.92588 | 0.19985 | 0.69929 |
| hsa-miR-375-mature | 0.79334 | −0.33398 | 0.20109 | 0.69662 |
| hsa-miR-106b-3p | 3.311 | 1.7273 | 0.20122 | 0.69633 |
| hsa-mir-30c-2 | 1.1665 | 0.22216 | 0.20761 | 0.68276 |
| hsa-mir-3182 | 1.661 | 0.73203 | 0.20784 | 0.68227 |
| hsa-mir-6773 | 2.1525 | 1.106 | 0.2112 | 0.6753 |
| hsa-mir-378i-pre | 1.2707 | 0.34566 | 0.21121 | 0.67528 |
| hsa-mir-6870 | 1.61 | 0.68707 | 0.21804 | 0.66146 |
| hsa-mir-23a | 1.0718 | 0.10007 | 0.22783 | 0.64239 |
| hsa-miR-23b-3p | 1.1316 | 0.17834 | 0.22802 | 0.64203 |
| hsa-mir-30b | 0.75613 | −0.4033 | 0.22859 | 0.64093 |
| hsa-mir-629 | 0.76788 | −0.38104 | 0.23214 | 0.63424 |
| hsa-mir-4520-1 | 1.2387 | 0.30887 | 0.23221 | 0.63411 |
| hsa-mir-195 | 0.8885 | −0.17056 | 0.2358 | 0.62745 |
| hsa-miR-194-5p | 1.3846 | 0.46947 | 0.23949 | 0.62071 |
| hsa-miR-149-5p | 19.824 | 4.3091 | 0.23952 | 0.62065 |
| hsa-mir-652 | 1.1385 | 0.1871 | 0.24319 | 0.61405 |
| hsa-miR-424-3p | 1.1809 | 0.23993 | 0.24322 | 0.61399 |
| hsa-miR-103b | 1.2223 | 0.28956 | 0.25072 | 0.6008 |
| hsa-mir-4485 | 0.92653 | −0.11009 | 0.25458 | 0.59418 |
| hsa-miR-200b-5p | 0.53123 | −0.9126 | 0.25848 | 0.58757 |
| hsa-mir-181b-1 | 1.6643 | 0.7349 | 0.25849 | 0.58756 |
| hsa-miR-186-5p | 1.6368 | 0.71087 | 0.25851 | 0.58752 |
| hsa-miR-450b-5p | 1.3462 | 0.42891 | 0.25852 | 0.58751 |

TABLE 32A-continued

Fold changes and p-values for all salivary miRNAs compared across PCS and ACS groups.

| | FC | log2(FC) | p.value | LOG10(p) |
|---|---|---|---|---|
| hsa-mir-4492 | 0.96748 | −0.0477 | 0.26238 | 0.58107 |
| hsa-mir-1273d | 1.5137 | 0.59804 | 0.2624 | 0.58103 |
| hsa-let-7c | 0.5868 | −0.76906 | 0.26638 | 0.5745 |
| hsa-mir-6752 | 0.98425 | −0.0229 | 0.26638 | 0.5745 |
| hsa-miR-223-5p | 3.2564 | 1.7033 | 0.2664 | 0.57447 |
| hsa-miR-183-5p | 0.73144 | −0.45118 | 0.26642 | 0.57444 |
| hsa-mir-132 | 1.2665 | 0.3409 | 0.27041 | 0.56797 |
| hsa-miR-532-5p | 0.57073 | −0.80912 | 0.27306 | 0.56375 |
| hsa-mir-6790 | 1.1964 | 0.25874 | 0.28266 | 0.54874 |
| hsa-miR-652-3p | 1.121 | 0.16485 | 0.28267 | 0.54873 |
| hsa-mir-7704 | 1.2297 | 0.29831 | 0.28268 | 0.54871 |
| hsa-mir-6847 | 1.459 | 0.54499 | 0.28683 | 0.54238 |
| hsa-miR-92a-3p | 1.0794 | 0.11018 | 0.2907 | 0.53656 |
| hsa-mir-4741 | 0.94548 | −0.08088 | 0.29103 | 0.53607 |
| hsa-mir-7108 | 3.0255 | 1.5972 | 0.2953 | 0.52974 |
| hsa-mir-944 | 0.81396 | −0.29696 | 0.29532 | 0.52971 |
| hsa-mir-3976 | 0.70481 | −0.50469 | 0.29957 | 0.5235 |
| hsa-let-7b-5p | 0.25104 | −1.994 | 0.30392 | 0.51724 |
| hsa-mir-183 | 0.94582 | −0.08036 | 0.30394 | 0.51721 |
| hsa-mir-4286 | 2.8837 | 1.5279 | 0.30831 | 0.51102 |
| hsa-mir-3607 | 1.5047 | 0.5895 | 0.30833 | 0.51099 |
| hsa-mir-4734 | 1.0234 | 0.033316 | 0.30833 | 0.51099 |
| hsa-mir-194-1 | 1.3497 | 0.43259 | 0.31271 | 0.50486 |
| hsa-mir-421-pre | 0.9156 | −0.12721 | 0.31276 | 0.50479 |
| hsa-mir-320a-pre | 1.1989 | 0.26172 | 0.31719 | 0.49869 |
| hsa-mir-7110 | 0.61428 | −0.70302 | 0.32165 | 0.49262 |
| hsa-mir-5580 | 0.59583 | −0.74702 | 0.32168 | 0.49258 |
| hsa-mir-450b | 1.1191 | 0.16236 | 0.3262 | 0.48652 |
| hsa-miR-744-5p | 0.66612 | −0.58614 | 0.32624 | 0.48646 |
| hsa-mir-3195 | 1.1284 | 0.17427 | 0.32625 | 0.48645 |
| hsa-mir-452 | 4.841 | 2.2753 | 0.33082 | 0.48041 |
| hsa-mir-335 | 1.0144 | 0.020684 | 0.33547 | 0.47434 |
| hsa-mir-191 | 1.3069 | 0.3861 | 0.34 | 0.46853 |
| hsa-mir-7161 | 0.8361 | −0.25825 | 0.34322 | 0.46442 |
| hsa-miR-4485-3p | 1.0981 | 0.13496 | 0.34322 | 0.46442 |
| hsa-mir-320c-2 | 0.71967 | −0.4746 | 0.34472 | 0.46254 |
| hsa-mir-199b | 1.243 | 0.31384 | 0.34476 | 0.46249 |
| hsa-mir-146b | 0.97946 | −0.02993 | 0.34476 | 0.46249 |
| hsa-miR-198 | 0.77837 | −0.36147 | 0.34958 | 0.45645 |
| hsa-miR-142-5p | 1.4053 | 0.4909 | 0.35419 | 0.45077 |
| hsa-mir-222 | 0.89917 | −0.15333 | 0.35428 | 0.45066 |
| hsa-mir-6785 | 0.38191 | −1.3887 | 0.35437 | 0.45054 |
| hsa-miR-7-5p-pre | 1.4937 | 0.57887 | 0.35438 | 0.45053 |
| hsa-mir-4701 | 1.2854 | 0.36223 | 0.3592 | 0.44466 |
| hsa-miR-582-3p | 1.2356 | 0.30521 | 0.35921 | 0.44465 |
| hsa-miR-99b-5p | 1.2336 | 0.30284 | 0.35921 | 0.44465 |
| hsa-miR-222-3p | 0.90414 | −0.14538 | 0.36398 | 0.43893 |
| hsa-miR-320c | 0.84908 | −0.23602 | 0.36399 | 0.43892 |
| hsa-mir-8072 | 0.50075 | −0.99784 | 0.36408 | 0.43881 |
| hsa-mir-149 | 6.3047 | 2.6564 | 0.37396 | 0.42717 |
| hsa-let-7c-5p | 0.53849 | −0.893 | 0.3785 | 0.42193 |
| hsa-miR-4429 | 1.9119 | 0.935 | 0.384 | 0.41567 |
| hsa-miR-145-3p | 0.89802 | −0.15518 | 0.38907 | 0.40998 |
| hsa-mir-210 | 5.0031 | 2.3228 | 0.38908 | 0.40997 |
| hsa-mir-935 | 1.0732 | 0.10194 | 0.39416 | 0.40432 |
| hsa-miR-3613-5p | 1.0725 | 0.10098 | 0.39932 | 0.39868 |
| hsa-miR-454-3p | 1.5953 | 0.67387 | 0.40453 | 0.39305 |
| hsa-mir-32 | 1.1349 | 0.1826 | 0.40457 | 0.39301 |
| hsa-mir-378a-3p | 1.3412 | 0.42349 | 0.40977 | 0.38746 |
| hsa-mir-2909 | 0.73636 | −0.44151 | 0.40979 | 0.38744 |
| hsa-miR-141-3p | 0.80225 | −0.31787 | 0.41503 | 0.38192 |
| hsa-mir-338 | 1.117 | 0.15961 | 0.41507 | 0.38188 |
| hsa-mir-191-5p | 1.2934 | 0.37113 | 0.42022 | 0.37652 |
| hsa-mir-181c | 1.2787 | 0.35471 | 0.42035 | 0.37639 |
| hsa-miR-140-5p | 1.1848 | 0.2446 | 0.42038 | 0.37636 |
| hsa-mir-598 | 3.4928 | 1.8044 | 0.43114 | 0.36538 |
| hsa-let-7a-2 | 0.87252 | −0.19673 | 0.43648 | 0.36003 |
| hsa-mir-1273g | 1.8911 | 0.91925 | 0.43652 | 0.35999 |
| hsa-mir-7-1 | 2.7772 | 1.4736 | 0.43656 | 0.35995 |
| hsa-mir-186 | 1.1116 | 0.15268 | 0.43658 | 0.35993 |
| hsa-mir-3621 | 0.79392 | −0.33294 | 0.4366 | 0.35991 |
| hsa-mir-30d | 0.97646 | −0.03437 | 0.44164 | 0.35493 |
| hsa-mir-4311 | 1.0157 | 0.022474 | 0.44209 | 0.35449 |
| hsa-miR-28-5p | 1.2476 | 0.3192 | 0.44759 | 0.34912 |
| hsa-miR-17-5p | 1.1785 | 0.23698 | 0.4476 | 0.34911 |
| hsa-mir-944-pre | 0.84209 | −0.24795 | 0.45314 | 0.34377 |
| hsa-miR-425-3p | 0.91927 | −0.12144 | 0.45875 | 0.33842 |
| hsa-mir-3160-1 | 1.0461 | 0.065061 | 0.45875 | 0.33842 |
| hsa-miR-29c-3p | 0.88126 | −0.18236 | 0.46422 | 0.33328 |
| hsa-mir-151a | 1.11 | 0.15061 | 0.46433 | 0.33317 |
| hsa-mir-185 | 1.8855 | 0.91496 | 0.46438 | 0.33313 |
| hsa-mir-4687 | 1.1087 | 0.14891 | 0.46438 | 0.33313 |
| hsa-miR-3916 | 1.0987 | 0.13579 | 0.46774 | 0.32999 |
| hsa-miR-195-5p | 1.1295 | 0.17564 | 0.46988 | 0.32801 |
| hsa-mir-1290 | 0.63283 | −0.66012 | 0.47002 | 0.32788 |
| hsa-mir-487a | 0.88751 | −0.17216 | 0.47004 | 0.32786 |
| hsa-mir-107 | 1.2207 | 0.28767 | 0.47564 | 0.32272 |
| hsa-miR-152-3p | 1.1736 | 0.231 | 0.4813 | 0.31759 |
| hsa-miR-328-3p | 1.8078 | 0.85422 | 0.4815 | 0.3174 |
| hsa-mir-4488 | 1.5239 | 0.60778 | 0.48151 | 0.31739 |
| hsa-miR-203a-3p | 0.88135 | −0.18221 | 0.48185 | 0.31709 |
| hsa-miR-598-5p | 0.70503 | −0.50424 | 0.49312 | 0.30705 |
| hsa-mir-574 | 0.55745 | −0.84308 | 0.49313 | 0.30703 |
| hsa-miR-24-3p | 0.96284 | −0.05463 | 0.49865 | 0.30221 |
| hsa-miR-4321 | 0.77925 | −0.35984 | 0.49899 | 0.30191 |
| hsa-mir-424 | 1.2383 | 0.30841 | 0.499 | 0.3019 |
| hsa-mir-15b | 1.9705 | 0.97858 | 0.50488 | 0.29681 |
| hsa-miR-29b-3p | 1.138 | 0.1865 | 0.50488 | 0.29681 |
| hsa-miR-4497 | 1.6211 | 0.69694 | 0.50489 | 0.2968 |
| hsa-miR-151a-3p | 2.8894 | 1.5308 | 0.51077 | 0.29178 |
| hsa-miR-374c-5p | 0.92192 | −0.11729 | 0.51077 | 0.29177 |
| hsa-mir-30c-1 | 0.53536 | −0.90143 | 0.5108 | 0.29175 |
| hsa-miR-181c-5p | 2.4161 | 1.2727 | 0.51081 | 0.29174 |
| hsa-mir-95 | 1.2628 | 0.33659 | 0.51082 | 0.29173 |
| hsa-miR-3135b | 1.3788 | 0.4634 | 0.51413 | 0.28893 |
| hsa-mir-182 | 1.0866 | 0.11976 | 0.51675 | 0.28672 |
| hsa-miR-92b-3p | 0.95766 | −0.06242 | 0.52262 | 0.28181 |
| hsa-miR-30e-3p | 1.1318 | 0.17868 | 0.52271 | 0.28174 |
| hsa-mir-145 | 1.7464 | 0.80437 | 0.52277 | 0.28169 |
| hsa-miR-125b-2-3p | 0.91068 | −0.13499 | 0.52279 | 0.28167 |
| hsa-mir-6127 | 1.1721 | 0.22914 | 0.5228 | 0.28167 |
| hsa-mir-130b | 0.89391 | −0.16179 | 0.52881 | 0.2767 |
| hsa-mir-142 | 1.2954 | 0.37337 | 0.54087 | 0.26691 |
| hsa-miR-148b-3p | 8.2261 | 3.0402 | 0.54101 | 0.26679 |
| hsa-mir-3656 | 1.1928 | 0.25436 | 0.54717 | 0.26188 |
| hsa-mir-25 | 1.1873 | 0.24771 | 0.55322 | 0.2571 |
| hsa-miR-361-3p | 0.89624 | −0.15804 | 0.55335 | 0.257 |
| hsa-miR-335-5p | 1.018 | 0.025707 | 0.55958 | 0.25213 |
| hsa-mir-150 | 0.94111 | −0.08756 | 0.56276 | 0.24968 |
| hsa-mir-181b-2 | 1.1308 | 0.17739 | 0.56572 | 0.2474 |
| hsa-mir-3960-pre | 1.4661 | 0.55194 | 0.56578 | 0.24735 |
| hsa-mir-342 | 2.9205 | 1.5462 | 0.56583 | 0.24731 |
| hsa-mir-92a-1 | 1.1675 | 0.22342 | 0.57189 | 0.24269 |
| hsa-mir-5096 | 1.6764 | 0.74538 | 0.5721 | 0.24253 |
| hsa-mir-1273a | 1.4635 | 0.54943 | 0.57211 | 0.24252 |
| hsa-mir-6739 | 1.3844 | 0.46923 | 0.57211 | 0.24252 |
| hsa-mir-203a | 0.90087 | −0.15061 | 0.57234 | 0.24235 |
| hsa-mir-411 | 1.1039 | 0.14263 | 0.57841 | 0.23776 |
| hsa-miR-339-3p | 1.0017 | 0.002406 | 0.57844 | 0.23774 |
| hsa-miR-16-5p | 1.0512 | 0.072086 | 0.58454 | 0.23318 |
| hsa-mir-766 | 0.88397 | −0.17793 | 0.58472 | 0.23305 |
| hsa-miR-182-5p | 1.1108 | 0.15159 | 0.58475 | 0.23303 |
| hsa-mir-328 | 2.1492 | 1.1038 | 0.58477 | 0.23302 |
| hsa-miR-22-5p | 1.4103 | 0.49604 | 0.58477 | 0.23302 |
| hsa-miR-331-3p | 1.2351 | 0.3046 | 0.58477 | 0.23302 |
| hsa-miR-1299-pre | 0.88323 | −0.17914 | 0.58478 | 0.23301 |
| hsa-mir-365b | 0.73524 | −0.4437 | 0.59114 | 0.22831 |
| hsa-mir-7703 | 1.065 | 0.09085 | 0.59114 | 0.22831 |
| hsa-mir-31 | 1.2854 | 0.36223 | 0.59754 | 0.22363 |
| hsa-miR-320b | 0.85936 | −0.21867 | 0.59754 | 0.22363 |
| hsa-miR-200a-5p | 1.5305 | 0.61403 | 0.61048 | 0.21433 |
| hsa-miR-338-5p | 1.0477 | 0.067222 | 0.61049 | 0.21432 |
| hsa-mir-5100 | 1.1218 | 0.16582 | 0.6105 | 0.21431 |
| hsa-mir-4433a | 1.577 | 0.65721 | 0.61699 | 0.20972 |
| hsa-mir-4284 | 0.974 | −0.03801 | 0.617 | 0.20972 |
| hsa-mir-4703 | 1.3688 | 0.45289 | 0.61701 | 0.20971 |
| hsa-mir-374a | 1.6261 | 0.70138 | 0.62351 | 0.20515 |
| hsa-mir-320b-2 | 0.68459 | −0.54669 | 0.62351 | 0.20515 |
| hsa-miR-7-5p | 1.1224 | 0.16653 | 0.62354 | 0.20513 |
| hsa-mir-205 | 1.1036 | 0.14217 | 0.62991 | 0.20072 |

TABLE 32A-continued

Fold changes and p-values for all salivary miRNAs compared across PCS and ACS groups.

| | FC | log2(FC) | p.value | LOG10(p) |
|---|---|---|---|---|
| hsa-mir-7641-1 | 1.4633 | 0.54924 | 0.63001 | 0.20066 |
| hsa-mir-501 | 0.49757 | −1.007 | 0.63664 | 0.19611 |
| hsa-mir-542 | 1.2051 | 0.26919 | 0.63669 | 0.19607 |
| hsa-let-7i-5p | 0.911 | −0.13448 | 0.64298 | 0.1918 |
| hsa-miR-99a-5p | 1.0168 | 0.024032 | 0.64324 | 0.19163 |
| hsa-miR-221-5p | 1.1313 | 0.17794 | 0.64329 | 0.19159 |
| hsa-miR-582-5p | 1.2217 | 0.28894 | 0.6433 | 0.19159 |
| hsa-miR-21-3p | 1.1122 | 0.15343 | 0.64331 | 0.19158 |
| hsa-miR-181b-5p | 1.5846 | 0.66408 | 0.64993 | 0.18713 |
| hsa-miR-205-5p | 1.0916 | 0.12649 | 0.65645 | 0.1828 |
| hsa-mir-374c | 0.93547 | −0.09623 | 0.65663 | 0.18268 |
| hsa-mir-17 | 0.78778 | −0.34414 | 0.65664 | 0.18267 |
| hsa-miR-210-3p | 1.0455 | 0.064255 | 0.65665 | 0.18266 |
| hsa-miR-21-5p | 1.0692 | 0.096498 | 0.65776 | 0.18193 |
| hsa-mir-6165 | 0.77696 | −0.3641 | 0.66334 | 0.17826 |
| hsa-mir-141 | 1.1418 | 0.19132 | 0.66334 | 0.17826 |
| hsa-miR-6724-5p | 1.9485 | 0.9624 | 0.66337 | 0.17825 |
| hsa-mir-92b | 0.8709 | −0.19942 | 0.67002 | 0.17391 |
| hsa-mir-744 | 0.70416 | −0.50602 | 0.6701 | 0.17386 |
| hsa-mir-21 | 1.07 | 0.097607 | 0.67147 | 0.17298 |
| hsa-mir-423 | 0.88297 | −0.17956 | 0.67653 | 0.16971 |
| hsa-miR-361-5p | 1.1197 | 0.16313 | 0.67679 | 0.16954 |
| hsa-mir-103a-1 | 1.0298 | 0.042389 | 0.67682 | 0.16952 |
| hsa-mir-3665 | 2.4904 | 1.3164 | 0.67683 | 0.16952 |
| hsa-miR-542-3p | 1.2161 | 0.28231 | 0.67686 | 0.1695 |
| hsa-mir-99a | 1.037 | 0.052426 | 0.68356 | 0.16523 |
| hsa-mir-26a-2 | 0.99372 | −0.00909 | 0.68361 | 0.16519 |
| hsa-mir-125a | 0.70635 | −0.50155 | 0.68363 | 0.16518 |
| hsa-mir-4448 | 1.0078 | 0.011214 | 0.68363 | 0.16518 |
| hsa-mir-4277 | 0.77309 | −0.37128 | 0.69044 | 0.16087 |
| hsa-mir-6883 | 0.94845 | −0.07635 | 0.7066 | 0.15083 |
| hsa-mir-1260b | 1.5897 | 0.66877 | 0.71104 | 0.14811 |
| hsa-miR-27a-5p | 1.281 | 0.35723 | 0.71104 | 0.14811 |
| hsa-miR-200a-3p | 1.2997 | 0.37817 | 0.71105 | 0.1481 |
| hsa-miR-342-3p | 0.81895 | −0.28816 | 0.71105 | 0.1481 |
| hsa-mir-3135b-pre | 2.0576 | 1.041 | 0.71105 | 0.1481 |
| hsa-miR-223-3p | 1.0672 | 0.09379 | 0.71587 | 0.14517 |
| hsa-mir-101-1 | 1.0469 | 0.066063 | 0.71791 | 0.14393 |
| hsa-miR-15a-5p | 1.0064 | 0.009233 | 0.71793 | 0.14392 |
| hsa-miR-365b-3p | 14.425 | 3.8505 | 0.71795 | 0.1439 |
| hsa-miR-365a-3p | 1.2243 | 0.29196 | 0.71795 | 0.1439 |
| hsa-miR-574-3p | 0.8845 | −0.17706 | 0.7249 | 0.13972 |
| hsa-mir-4461 | 0.60904 | −0.71538 | 0.73183 | 0.13559 |
| hsa-mir-339 | 1.2265 | 0.29451 | 0.73183 | 0.13559 |
| hsa-mir-19a-3p | 0.9735 | −0.03875 | 0.73185 | 0.13558 |
| hsa-mir-181a-2 | 1.1385 | 0.18717 | 0.73186 | 0.13557 |
| hsa-mir-223 | 1.0745 | 0.10366 | 0.73679 | 0.13266 |
| hsa-mir-4441 | 1.9115 | 0.93473 | 0.73883 | 0.13145 |
| hsa-mir-361 | 1.0148 | 0.021204 | 0.74578 | 0.12739 |
| hsa-mir-340-3p | 0.9947 | −0.00766 | 0.74581 | 0.12737 |
| hsa-mir-4522 | 1.1522 | 0.20438 | 0.74582 | 0.12736 |
| hsa-miR-3615-mature | 1.4105 | 0.49621 | 0.74583 | 0.12736 |
| hsa-mir-660 | 0.86271 | −0.21305 | 0.74583 | 0.12736 |
| hsa-let-7i | 1.0527 | 0.074041 | 0.75268 | 0.12339 |
| hsa-mir-619 | 0.069314 | −3.8507 | 0.75284 | 0.1233 |
| hsa-miR-6793-5p | 1.4948 | 0.57994 | 0.75285 | 0.12329 |
| hsa-mir-19b-1 | 0.70209 | −0.51028 | 0.75984 | 0.11928 |
| hsa-let-7d | 1.2326 | 0.30166 | 0.75985 | 0.11927 |
| hsa-miR-142-3p | 0.98301 | −0.02472 | 0.75988 | 0.11925 |
| hsa-let-7g | 1.0826 | 0.1145 | 0.75989 | 0.11925 |
| hsa-mir-4326 | 1.2274 | 0.2956 | 0.75989 | 0.11925 |
| hsa-miR-25-3p | 0.97647 | −0.03435 | 0.76686 | 0.11528 |
| hsa-miR-125a-5p | 0.72349 | −0.46695 | 0.76693 | 0.11525 |
| hsa-mir-628 | 1.1855 | 0.24556 | 0.76693 | 0.11524 |
| hsa-mir-324 | 0.95639 | −0.06433 | 0.76695 | 0.11524 |
| hsa-let-7d-3p | 1.0107 | 0.015364 | 0.76696 | 0.11523 |
| hsa-mir-224 | 1.057 | 0.079961 | 0.77403 | 0.11124 |
| hsa-miR-345-5p | 3.1566 | 1.6584 | 0.77403 | 0.11124 |
| hsa-mir-4471 | 1.0754 | 0.10482 | 0.77403 | 0.11124 |
| hsa-mir-625-3p | 1.0582 | 0.081623 | 0.77598 | 0.11015 |
| hsa-miR-101-3p | 1.0531 | 0.074664 | 0.78106 | 0.10731 |
| hsa-mir-7641-2 | 0.98833 | −0.01693 | 0.78111 | 0.10729 |
| hsa-miR-193b-3p | 1.2624 | 0.33613 | 0.78113 | 0.10728 |
| hsa-miR-23a-3p | 0.99517 | −0.00699 | 0.78813 | 0.1034 |
| hsa-miR-34a-5p | 0.99482 | −0.0075 | 0.78825 | 0.10334 |
| hsa-miR-31-5p | 2.6195 | 1.3893 | 0.78826 | 0.10333 |
| hsa-mir-7851 | 1.1171 | 0.15977 | 0.78826 | 0.10333 |
| hsa-mir-99b | 0.9514 | −0.07188 | 0.79537 | 0.099433 |
| hsa-miR-378i-mature | 1.2785 | 0.35445 | 0.79538 | 0.099428 |
| hsa-miR-429 | 2.7071 | 1.4367 | 0.79539 | 0.099421 |
| hsa-mir-1249 | 1.0917 | 0.12664 | 0.7954 | 0.099416 |
| hsa-mir-24-2 | 0.92822 | −0.10746 | 0.80249 | 0.095561 |
| hsa-miR-125b-5p | 1.0768 | 0.10673 | 0.80253 | 0.095541 |
| hsa-mir-6716 | 0.59286 | −0.75424 | 0.80253 | 0.095539 |
| hsa-miR-30d-5p | 1.0882 | 0.12193 | 0.8095 | 0.091783 |
| hsa-mir-1260a | 0.8306 | −0.26778 | 0.8097 | 0.091674 |
| hsa-miR-146a-5p | 0.9962 | −0.0055 | 0.80971 | 0.091669 |
| hsa-miR-3960 | 1.7926 | 0.84207 | 0.80972 | 0.091665 |
| hsa-let-7f-1 | 0.95905 | −0.06033 | 0.80972 | 0.091665 |
| hsa-mir-330 | 0.78368 | −0.35167 | 0.81689 | 0.087836 |
| hsa-miR-32-5p | 0.92465 | −0.11303 | 0.81689 | 0.087834 |
| hsa-miR-941 | 1.0708 | 0.098704 | 0.8169 | 0.087832 |
| hsa-mir-26b | 0.99857 | −0.00207 | 0.82379 | 0.084182 |
| hsa-miR-26a-5p | 1.0306 | 0.043513 | 0.82404 | 0.084053 |
| hsa-mir-221 | 1.1294 | 0.17554 | 0.82404 | 0.084051 |
| hsa-mir-106a | 1.1361 | 0.18405 | 0.8241 | 0.084022 |
| hsa-miR-106a-5p | 1.0108 | 0.015565 | 0.8241 | 0.084018 |
| hsa-miR-30e-5p | 1.0264 | 0.037589 | 0.83128 | 0.08025 |
| hsa-mir-125b-2 | 1.3134 | 0.39332 | 0.8313 | 0.080243 |
| hsa-mir-4419a | 0.84811 | −0.23767 | 0.83131 | 0.080235 |
| hsa-mir-331 | 0.8616 | −0.2149 | 0.83132 | 0.080232 |
| hsa-miR-26b-5p | 1.121 | 0.16474 | 0.83709 | 0.077226 |
| hsa-mir-30a | 1.2736 | 0.34888 | 0.83839 | 0.076553 |
| hsa-mir-193a | 0.96734 | −0.0479 | 0.83853 | 0.076483 |
| hsa-miR-148a-3p | 1.049 | 0.069051 | 0.83853 | 0.076481 |
| hsa-miR-340-5p | 1.073 | 0.10164 | 0.83854 | 0.076478 |
| hsa-mir-152 | 1.3047 | 0.38374 | 0.83854 | 0.076474 |
| hsa-mir-3178 | 2.0953 | 1.0671 | 0.83855 | 0.076469 |
| hsa-mir-4797 | 1.103 | 0.1414 | 0.84578 | 0.072745 |
| hsa-mir-5572 | 1.2346 | 0.304 | 0.84579 | 0.072736 |
| hsa-mir-16-2 | 1.043 | 0.060735 | 0.85276 | 0.069171 |
| hsa-mir-708 | 0.82854 | −0.27135 | 0.85304 | 0.069032 |
| hsa-miR-628-3p | 0.6812 | −0.55386 | 0.85305 | 0.069026 |
| hsa-mir-582 | 1.0208 | 0.02963 | 0.85305 | 0.069024 |
| hsa-let-7g-5p | 1.0923 | 0.12732 | 0.86031 | 0.065343 |
| hsa-mir-26a-1 | 1.033 | 0.046894 | 0.86736 | 0.061802 |
| hsa-mir-92a-2 | 0.9267 | −0.10983 | 0.86752 | 0.061719 |
| hsa-miR-15b-5p | 1.0722 | 0.10063 | 0.8676 | 0.061683 |
| hsa-miR-150-5p | 1.1127 | 0.15405 | 0.8676 | 0.061681 |
| hsa-mir-155 | 0.96454 | −0.05209 | 0.86761 | 0.061677 |
| hsa-miR-221-3p | 1.0566 | 0.079446 | 0.87485 | 0.058068 |
| hsa-miR-27a-3p | 1.0392 | 0.05542 | 0.87487 | 0.058057 |
| hsa-mir-6875 | 0.71853 | −0.47689 | 0.87601 | 0.05749 |
| hsa-miR-107-pre | 1.0552 | 0.077449 | 0.88219 | 0.054439 |
| hsa-miR-502-3p | 5.5218 | 2.4651 | 0.8822 | 0.054435 |
| hsa-miR-30b-5p | 1.0703 | 0.098031 | 0.88945 | 0.050878 |
| hsa-mir-218-2 | 0.75239 | −0.41045 | 0.88951 | 0.05085 |
| hsa-mir-4449 | 1.6297 | 0.70457 | 0.88951 | 0.050849 |
| hsa-miR-421 | 0.98956 | −0.01514 | 0.88952 | 0.050846 |
| hsa-miR-30a-5p | 1.0306 | 0.043479 | 0.89675 | 0.047328 |
| hsa-mir-3615-pre | 1.4025 | 0.48797 | 0.89684 | 0.047286 |
| hsa-mir-451a-pre | 0.23681 | −2.0782 | 0.89684 | 0.047285 |
| hsa-mir-532 | 2.614 | 1.3863 | 0.89684 | 0.047285 |
| hsa-mir-22 | 0.91631 | −0.1261 | 0.90413 | 0.043769 |
| hsa-mir-103a-2 | 1.0021 | 0.003068 | 0.90416 | 0.043755 |
| hsa-mir-101-2 | 0.97152 | −0.04168 | 0.90417 | 0.043751 |
| hsa-miR-193a-5p | 0.97247 | −0.04027 | 0.90417 | 0.043751 |
| hsa-miR-16-2-3p | 0.98454 | −0.02248 | 0.90503 | 0.043337 |
| hsa-miR-3074-5p | 1.0384 | 0.054369 | 0.91141 | 0.040285 |
| hsa-mir-193b | 1.2317 | 0.30064 | 0.91151 | 0.040239 |
| hsa-miR-22-3p | 0.89524 | −0.15966 | 0.91884 | 0.036761 |
| hsa-mir-3613 | 0.96573 | −0.0503 | 0.91884 | 0.036758 |
| hsa-miR-320a | 1.3926 | 0.47779 | 0.91885 | 0.036755 |
| hsa-mir-5481 | 2.572 | 1.3629 | 0.91885 | 0.036755 |
| hsa-mir-15a | 0.98794 | −0.01751 | 0.92618 | 0.033304 |
| hsa-let-7a-1 | 0.67814 | −0.56036 | 0.9262 | 0.033296 |
| hsa-mir-1273e | 2.1796 | 1.124 | 0.92621 | 0.033293 |
| hsa-miR-324-3p | 0.94632 | −0.0796 | 0.92621 | 0.033291 |
| hsa-miR-197-3p | 0.95731 | −0.06294 | 0.92621 | 0.03329 |
| hsa-miR-143-3p | 1.078 | 0.10837 | 0.93356 | 0.029859 |

TABLE 32A-continued

Fold changes and p-values for all salivary miRNAs compared across PCS and ACS groups.

| | FC | log2(FC) | p.value | LOG10(p) |
|---|---|---|---|---|
| hsa-mir-345 | 3.9075 | 1.9662 | 0.93357 | 0.029853 |
| hsa-mir-181a-1 | 1.1156 | 0.15784 | 0.93357 | 0.029853 |
| hsa-mir-95-3p | 1.0744 | 0.10349 | 0.93357 | 0.029852 |
| hsa-miR-451a | 0.17573 | −2.5086 | 0.93357 | 0.029851 |
| hsa-miR-103a-3p | 1.0131 | 0.018717 | 0.94093 | 0.026443 |
| hsa-mir-192 | 0.95928 | −0.05998 | 0.94094 | 0.02644 |
| hsa-mir-34a | 1.0854 | 0.11825 | 0.94094 | 0.026439 |
| hsa-mir-27a | 1.024 | 0.034213 | 0.94825 | 0.023077 |
| hsa-mir-4289 | 1.1033 | 0.14183 | 0.94829 | 0.023057 |
| hsa-mir-29a | 1.021 | 0.029917 | 0.94829 | 0.023057 |
| hsa-mir-27b | 1.1079 | 0.14785 | 0.9483 | 0.023052 |
| hsa-mir-4800 | 1.0326 | 0.046229 | 0.94831 | 0.02305 |
| hsa-mir-19a | 1.022 | 0.031412 | 0.94831 | 0.02305 |
| hsa-mir-23b | 1.0123 | 0.017668 | 0.95568 | 0.019689 |
| hsa-miR-224-5p | 1.0555 | 0.077875 | 0.95568 | 0.019687 |
| hsa-miR-29a-3p | 1.0297 | 0.042192 | 0.96306 | 0.016346 |
| hsa-mir-197 | 0.92851 | −0.10701 | 0.96306 | 0.016345 |
| hsa-mir-429-pre | 0.9929 | −0.01029 | 0.96307 | 0.016344 |
| hsa-miR-424-5p | 1.0094 | 0.01345 | 0.96307 | 0.016344 |
| hsa-miR-330-3p | 0.67984 | −0.55674 | 0.9634 | 0.016193 |
| hsa-mir-148a | 1.0845 | 0.11706 | 0.97043 | 0.013035 |
| hsa-mir-143 | 1.0899 | 0.12426 | 0.97044 | 0.013029 |
| hsa-mir-340 | 1.0565 | 0.07925 | 0.97045 | 0.013028 |
| hsa-mir-130a | 1.5112 | 0.5957 | 0.97045 | 0.013027 |
| hsa-miR-185-5p | 2.3655 | 1.2421 | 0.97045 | 0.013027 |
| hsa-mir-125b-1 | 1.2525 | 0.32478 | 0.97783 | 0.009735 |
| hsa-mir-365a | 1.1056 | 0.14479 | 0.97783 | 0.009735 |
| hsa-miR-130a-3p | 1.9792 | 0.9849 | 0.97783 | 0.009735 |
| hsa-mir-155-5p | 0.91813 | −0.12323 | 0.98522 | 0.006466 |
| hsa-mir-16-1 | 10.746 | 3.4258 | 0.99261 | 0.003221 |
| hsa-mir-184-pre | 1.6824 | 0.75051 | 0.99261 | 0.003221 |
| hsa-miR-660-5p | 1.2559 | 0.32872 | 0.99261 | 0.003221 |
| hsa-mir-4301 | 0.85446 | −0.22691 | 0.99261 | 0.003221 |
| hsa-mir-454 | 1.3792 | 0.46379 | 1 | 0 |
| hsa-mir-500a | 0.89681 | −0.15712 | 1 | 0 |
| hsa-miR-423-3p | 1.1025 | 0.14081 | 1 | 0 |
| hsa-mir-19b-3p | 0.91893 | −0.12198 | 1 | 0 |
| hsa-miR-27b-3p | 1.0531 | 0.074623 | 1 | 0 |
| hsa-mir-6884 | 0.96927 | −0.04503 | 1 | 0 |
| hsa-miR-151a-5p | 1.0287 | 0.040812 | 1 | 0 |
| hsa-mir-24-1 | 1.0144 | 0.020635 | 1 | 0 |
| hsa-mir-664a | 1.006 | 0.008638 | 1 | 0 |

Based on the data in this table, one skilled in the art may select an appropriate set or sets of miRNAs for the methods disclosed herein.

TABLE 32B nominal differences between ACS and PCS groups on Mann-Whitney testing

| | FC (in ACS) | log2(FC) | p.value | −LOG10(p) |
|---|---|---|---|---|
| hsa-miR-769-5p | 1.82 | 0.86 | 0.002 | 2.69 |
| hsa-miR-215-5p | 2.38 | 1.25 | 0.024 | 1.62 |
| hsa-mir-769 | 2.47 | 1.30 | 0.025 | 1.60 |
| hsa-mir-320c-1 | 0.44 | −1.18 | 0.028 | 1.55 |
| hsa-mir-194-2 | 1.42 | 0.51 | 0.028 | 1.55 |
| hsa-mir-199a-1 | 2.78 | 1.47 | 0.032 | 1.49 |
| hsa-mir-4792 | 1.83 | 0.87 | 0.033 | 1.48 |
| hsa-miR-140-3p | 1.84 | 0.88 | 0.036 | 1.45 |
| hsa-miR-629-5p | 0.66 | −0.59 | 0.036 | 1.44 |
| hsa-let-7f-2 | 1.39 | 0.47 | 0.039 | 1.41 |
| hsa-miR-128-3p | 2.00 | 1.00 | 0.040 | 1.40 |
| hsa-miR-192-5p | 1.41 | 0.49 | 0.042 | 1.38 |
| hsa-miR-145-5p | 1.62 | 0.70 | 0.045 | 1.34 |
| hsa-let-7f-5p | 0.75 | −0.42 | 0.049 | 1.31 |
| hsa-let-7a-3 | 0.64 | −0.63 | 0.052 | 1.28 |
| hsa-mir-6763 | 0.63 | −0.66 | 0.053 | 1.28 |
| hsa-mir-1303 | 4.02 | 2.01 | 0.061 | 1.21 |
| hsa-miR-93-5p | 1.19 | 0.25 | 0.063 | 1.20 |
| hsa-miR-28-3p | 3.07 | 1.62 | 0.064 | 1.19 |

TABLE 32B-continued nominal differences between ACS and PCS groups on Mann-Whitney testing

| | FC (in ACS) | log2(FC) | p.value | −LOG10(p) |
|---|---|---|---|---|
| hsa-mir-128-1 | 2.14 | 1.09 | 0.068 | 1.17 |
| hsa-mir-363 | 1.13 | 0.17 | 0.074 | 1.13 |
| hsa-mir-505 | 2.18 | 1.13 | 0.075 | 1.12 |
| hsa-miR-133a-5p | 0.59 | −0.76 | 0.077 | 1.11 |
| hsa-mir-93 | 1.21 | 0.27 | 0.082 | 1.09 |
| hsa-miR-4763-5p | 1.21 | 0.27 | 0.083 | 1.08 |
| hsa-mir-200c | 0.81 | −0.31 | 0.092 | 1.04 |
| hsa-miR-1307-3p | 1.50 | 0.58 | 0.094 | 1.03 |
| hsa-miR-200c-3p | 0.81 | −0.30 | 0.095 | 1.02 |
| hsa-miR-200b-3p | 0.79 | −0.35 | 0.099 | 1.00 |
| hsa-miR-199a-3p | 1.37 | 0.46 | 0.101 | 1.00 |
| hsa-miR-425-5p | 1.27 | 0.34 | 0.105 | 0.98 |
| hsa-mir-4763 | 1.31 | 0.39 | 0.109 | 0.96 |
| hsa-let-7a-5p | 0.61 | −0.71 | 0.113 | 0.95 |
| hsa-miR-6763-3p | 0.51 | −0.97 | 0.122 | 0.91 |
| hsa-miR-423-5p | 0.51 | −0.97 | 0.122 | 0.91 |
| hsa-mir-4508 | 1.65 | 0.72 | 0.122 | 0.91 |
| hsa-mir-6073 | 1.74 | 0.80 | 0.126 | 0.90 |
| hsa-miR-30c-5p | 1.27 | 0.34 | 0.129 | 0.89 |
| hsa-mir-28 | 1.18 | 0.24 | 0.136 | 0.87 |
| hsa-miR-199b-3p | 1.33 | 0.41 | 0.136 | 0.87 |
| hsa-miR-24-1-5p | 1.48 | 0.56 | 0.141 | 0.85 |
| hsa-mir-146a | 0.75 | −0.42 | 0.143 | 0.84 |
| hsa-mir-133a-2 | 1.87 | 0.90 | 0.143 | 0.84 |
| hsa-mir-6840 | 0.51 | −0.97 | 0.146 | 0.84 |
| hsa-miR-505-3p | 1.30 | 0.38 | 0.151 | 0.82 |
| hsa-mir-30e | 1.53 | 0.62 | 0.154 | 0.81 |
| hsa-mir-200b | 1.92 | 0.94 | 0.154 | 0.81 |
| hsa-mir-3916-pre | 0.77 | −0.38 | 0.159 | 0.80 |
| hsa-miR-181a-5p | 1.26 | 0.33 | 0.165 | 0.78 |
| hsa-mir-215 | 1.45 | 0.53 | 0.165 | 0.78 |
| hsa-mir-140 | 1.43 | 0.51 | 0.165 | 0.78 |
| hsa-miR-146b-5p | 1.01 | 0.02 | 0.165 | 0.78 |
| hsa-mir-638 | 1.03 | 0.04 | 0.165 | 0.78 |
| hsa-mir-128-2 | 2.33 | 1.22 | 0.168 | 0.78 |
| hsa-let-7b | 0.40 | −1.31 | 0.170 | 0.77 |
| hsa-mir-1307 | 1.45 | 0.53 | 0.170 | 0.77 |
| hsa-miR-484 | 1.75 | 0.80 | 0.173 | 0.76 |
| hsa-miR-132-3p | 2.67 | 1.42 | 0.175 | 0.76 |
| hsa-mir-484-pre | 1.73 | 0.79 | 0.179 | 0.75 |
| hsa-miR-199b-5p | 1.35 | 0.44 | 0.181 | 0.74 |
| hsa-mir-375-pre | 0.75 | −0.41 | 0.182 | 0.74 |
| hsa-mir-1246 | 0.69 | −0.54 | 0.182 | 0.74 |
| hsa-mir-4698 | 0.42 | −1.25 | 0.182 | 0.74 |
| hsa-miR-4698-pre | 0.44 | −1.20 | 0.182 | 0.74 |
| hsa-mir-4514 | 0.57 | −0.82 | 0.185 | 0.73 |
| hsa-mir-378g-pre | 1.57 | 0.65 | 0.188 | 0.72 |
| hsa-mir-106b | 1.17 | 0.22 | 0.188 | 0.72 |
| hsa-mir-3668 | 0.88 | −0.19 | 0.192 | 0.72 |
| hsa-mir-6087 | 1.05 | 0.07 | 0.195 | 0.71 |
| hsa-mir-425 | 1.21 | 0.28 | 0.198 | 0.70 |
| hsa-mir-200a | 0.92 | −0.13 | 0.198 | 0.70 |
| hsa-mir-3667 | 0.53 | −0.93 | 0.200 | 0.70 |
| hsa-miR-375-mature | 0.79 | −0.33 | 0.201 | 0.70 |
| hsa-miR-106b-3p | 3.31 | 1.73 | 0.201 | 0.70 |
| hsa-mir-30c-2 | 1.17 | 0.22 | 0.208 | 0.68 |
| hsa-mir-3182 | 1.66 | 0.73 | 0.208 | 0.68 |
| hsa-mir-6773 | 2.15 | 1.11 | 0.211 | 0.68 |
| hsa-mir-378i-pre | 1.27 | 0.35 | 0.211 | 0.68 |
| hsa-mir-6870 | 1.61 | 0.69 | 0.218 | 0.66 |
| hsa-mir-23a | 1.07 | 0.10 | 0.228 | 0.64 |
| hsa-miR-23b-3p | 1.13 | 0.18 | 0.228 | 0.64 |
| hsa-mir-30b | 0.76 | −0.40 | 0.229 | 0.64 |
| hsa-mir-629 | 0.77 | −0.38 | 0.232 | 0.63 |
| hsa-mir-4520-1 | 1.24 | 0.31 | 0.232 | 0.63 |
| hsa-mir-195 | 0.89 | −0.17 | 0.236 | 0.63 |
| hsa-miR-194-5p | 1.38 | 0.47 | 0.239 | 0.62 |
| hsa-miR-149-5p | 19.82 | 4.31 | 0.240 | 0.62 |
| hsa-mir-652 | 1.14 | 0.19 | 0.243 | 0.61 |
| hsa-miR-424-3p | 1.18 | 0.24 | 0.243 | 0.61 |
| hsa-miR-103b | 1.22 | 0.29 | 0.251 | 0.60 |
| hsa-mir-4485 | 0.93 | −0.11 | 0.255 | 0.59 |
| hsa-miR-200b-5p | 0.53 | −0.91 | 0.258 | 0.59 |
| hsa-mir-181b-1 | 1.66 | 0.73 | 0.258 | 0.59 |
| hsa-miR-186-5p | 1.64 | 0.71 | 0.259 | 0.59 |

TABLE 32B-continued nominal differences between ACS and PCS groups on Mann-Whitney testing

| | FC (in ACS) | log2(FC) | p.value | −LOG10(p) |
|---|---|---|---|---|
| hsa-miR-450b-5p | 1.35 | 0.43 | 0.259 | 0.59 |
| hsa-mir-4492 | 0.97 | −0.05 | 0.262 | 0.58 |
| hsa-mir-1273d | 1.51 | 0.60 | 0.262 | 0.58 |
| hsa-let-7c | 0.59 | −0.77 | 0.266 | 0.57 |
| hsa-mir-6752 | 0.98 | −0.02 | 0.266 | 0.57 |
| hsa-miR-223-5p | 3.26 | 1.70 | 0.266 | 0.57 |
| hsa-miR-183-5p | 0.73 | −0.45 | 0.266 | 0.57 |
| hsa-mir-132 | 1.27 | 0.34 | 0.270 | 0.57 |
| hsa-miR-532-5p | 0.57 | −0.81 | 0.273 | 0.56 |
| hsa-mir-6790 | 1.20 | 0.26 | 0.283 | 0.55 |
| hsa-miR-652-3p | 1.12 | 0.16 | 0.283 | 0.55 |
| hsa-mir-7704 | 1.23 | 0.30 | 0.283 | 0.55 |
| hsa-mir-6847 | 1.46 | 0.54 | 0.287 | 0.54 |
| hsa-miR-92a-3p | 1.08 | 0.11 | 0.291 | 0.54 |
| hsa-mir-4741 | 0.95 | −0.08 | 0.291 | 0.54 |
| hsa-mir-7108 | 3.03 | 1.60 | 0.295 | 0.53 |
| hsa-miR-944 | 0.81 | −0.30 | 0.295 | 0.53 |
| hsa-mir-3976 | 0.70 | −0.50 | 0.300 | 0.52 |
| hsa-let-7b-5p | 0.25 | −1.99 | 0.304 | 0.52 |
| hsa-mir-183 | 0.95 | −0.08 | 0.304 | 0.52 |
| hsa-mir-4286 | 2.88 | 1.53 | 0.308 | 0.51 |
| hsa-mir-3607 | 1.50 | 0.59 | 0.308 | 0.51 |
| hsa-mir-4734 | 1.02 | 0.03 | 0.308 | 0.51 |
| hsa-mir-194-1 | 1.35 | 0.43 | 0.313 | 0.50 |
| hsa-mir-421-pre | 0.92 | −0.13 | 0.313 | 0.50 |
| hsa-mir-320a-pre | 1.20 | 0.26 | 0.317 | 0.50 |
| hsa-mir-7110 | 0.61 | −0.70 | 0.322 | 0.49 |
| hsa-mir-5580 | 0.60 | −0.75 | 0.322 | 0.49 |
| hsa-mir-450b | 1.12 | 0.16 | 0.326 | 0.49 |
| hsa-miR-744-5p | 0.67 | −0.59 | 0.326 | 0.49 |
| hsa-mir-3195 | 1.13 | 0.17 | 0.326 | 0.49 |
| hsa-mir-452 | 4.84 | 2.28 | 0.331 | 0.48 |
| hsa-mir-335 | 1.01 | 0.02 | 0.335 | 0.47 |
| hsa-mir-191 | 1.31 | 0.39 | 0.340 | 0.47 |
| hsa-mir-7161 | 0.84 | −0.26 | 0.343 | 0.46 |
| hsa-miR-4485-3p | 1.10 | 0.13 | 0.343 | 0.46 |
| hsa-mir-320c-2 | 0.72 | −0.47 | 0.345 | 0.46 |
| hsa-mir-199b | 1.24 | 0.31 | 0.345 | 0.46 |
| hsa-mir-146b | 0.98 | −0.03 | 0.345 | 0.46 |
| hsa-miR-198 | 0.78 | −0.36 | 0.350 | 0.46 |
| hsa-miR-142-5p | 1.41 | 0.49 | 0.354 | 0.45 |
| hsa-mir-222 | 0.90 | −0.15 | 0.354 | 0.45 |
| hsa-mir-6785 | 0.38 | −1.39 | 0.354 | 0.45 |
| hsa-miR-7-5p-pre | 1.49 | 0.58 | 0.354 | 0.45 |
| hsa-mir-4701 | 1.29 | 0.36 | 0.359 | 0.44 |
| hsa-miR-582-3p | 1.24 | 0.31 | 0.359 | 0.44 |
| hsa-miR-99b-5p | 1.23 | 0.30 | 0.359 | 0.44 |
| hsa-miR-222-3p | 0.90 | −0.15 | 0.364 | 0.44 |
| hsa-miR-320c | 0.85 | −0.24 | 0.364 | 0.44 |
| hsa-mir-8072 | 0.50 | −1.00 | 0.364 | 0.44 |
| hsa-mir-149 | 6.30 | 2.66 | 0.374 | 0.43 |
| hsa-let-7c-5p | 0.54 | −0.89 | 0.379 | 0.42 |
| hsa-miR-4429 | 1.91 | 0.94 | 0.384 | 0.42 |
| hsa-miR-145-3p | 0.90 | −0.16 | 0.389 | 0.41 |
| hsa-mir-210 | 5.00 | 2.32 | 0.389 | 0.41 |
| hsa-mir-935 | 1.07 | 0.10 | 0.394 | 0.40 |
| hsa-miR-3613-5p | 1.07 | 0.10 | 0.399 | 0.40 |
| hsa-miR-454-3p | 1.60 | 0.67 | 0.405 | 0.39 |
| hsa-mir-32 | 1.13 | 0.18 | 0.405 | 0.39 |
| hsa-miR-378a-3p | 1.34 | 0.42 | 0.410 | 0.39 |
| hsa-mir-2909 | 0.74 | −0.44 | 0.410 | 0.39 |
| hsa-miR-141-3p | 0.80 | −0.32 | 0.415 | 0.38 |
| hsa-mir-338 | 1.12 | 0.16 | 0.415 | 0.38 |
| hsa-miR-191-5p | 1.29 | 0.37 | 0.420 | 0.38 |
| hsa-mir-181c | 1.28 | 0.35 | 0.420 | 0.38 |
| hsa-miR-140-5p | 1.18 | 0.24 | 0.420 | 0.38 |
| hsa-mir-598 | 3.49 | 1.80 | 0.431 | 0.37 |
| hsa-let-7a-2 | 0.87 | −0.20 | 0.436 | 0.36 |
| hsa-mir-1273g | 1.89 | 0.92 | 0.437 | 0.36 |
| hsa-mir-7-1 | 2.78 | 1.47 | 0.437 | 0.36 |
| hsa-mir-186 | 1.11 | 0.15 | 0.437 | 0.36 |
| hsa-mir-3621 | 0.79 | −0.33 | 0.437 | 0.36 |
| hsa-mir-30d | 0.98 | −0.03 | 0.442 | 0.35 |
| hsa-mir-4311 | 1.02 | 0.02 | 0.442 | 0.35 |
| hsa-miR-28-5p | 1.25 | 0.32 | 0.448 | 0.35 |
| hsa-miR-17-5p | 1.18 | 0.24 | 0.448 | 0.35 |
| hsa-mir-944-pre | 0.84 | −0.25 | 0.453 | 0.34 |
| hsa-mir-425-3p | 0.92 | −0.12 | 0.459 | 0.34 |
| hsa-mir-3160-1 | 1.05 | 0.07 | 0.459 | 0.34 |
| hsa-miR-29c-3p | 0.88 | −0.18 | 0.464 | 0.33 |
| hsa-mir-151a | 1.11 | 0.15 | 0.464 | 0.33 |
| hsa-mir-185 | 1.89 | 0.91 | 0.464 | 0.33 |
| hsa-mir-4687 | 1.11 | 0.15 | 0.464 | 0.33 |
| hsa-mir-3916 | 1.10 | 0.14 | 0.468 | 0.33 |
| hsa-miR-195-5p | 1.13 | 0.18 | 0.470 | 0.33 |
| hsa-mir-1290 | 0.63 | −0.66 | 0.470 | 0.33 |
| hsa-mir-487a | 0.89 | −0.17 | 0.470 | 0.33 |
| hsa-mir-107 | 1.22 | 0.29 | 0.476 | 0.32 |
| hsa-miR-152-3p | 1.17 | 0.23 | 0.481 | 0.32 |
| hsa-miR-328-3p | 1.81 | 0.85 | 0.482 | 0.32 |
| hsa-mir-4488 | 1.52 | 0.61 | 0.482 | 0.32 |
| hsa-miR-203a-3p | 0.88 | −0.18 | 0.482 | 0.32 |
| hsa-miR-598-5p | 0.71 | −0.50 | 0.493 | 0.31 |
| hsa-mir-574 | 0.56 | −0.84 | 0.493 | 0.31 |
| hsa-mir-24-3p | 0.96 | −0.05 | 0.499 | 0.30 |
| hsa-miR-4321 | 0.78 | −0.36 | 0.499 | 0.30 |
| hsa-mir-424 | 1.24 | 0.31 | 0.499 | 0.30 |
| hsa-mir-15b | 1.97 | 0.98 | 0.505 | 0.30 |
| hsa-miR-29b-3p | 1.14 | 0.19 | 0.505 | 0.30 |
| hsa-mir-4497 | 1.62 | 0.70 | 0.505 | 0.30 |
| hsa-miR-151a-3p | 2.89 | 1.53 | 0.511 | 0.29 |
| hsa-miR-374c-5p | 0.92 | −0.12 | 0.511 | 0.29 |
| hsa-mir-30c-1 | 0.54 | −0.90 | 0.511 | 0.29 |
| hsa-miR-181c-5p | 2.42 | 1.27 | 0.511 | 0.29 |
| hsa-mir-95 | 1.26 | 0.34 | 0.511 | 0.29 |
| hsa-miR-3135b | 1.38 | 0.46 | 0.514 | 0.29 |
| hsa-mir-182 | 1.09 | 0.12 | 0.517 | 0.29 |
| hsa-miR-92b-3p | 0.96 | −0.06 | 0.523 | 0.28 |
| hsa-miR-30e-3p | 1.13 | 0.18 | 0.523 | 0.28 |
| hsa-mir-145 | 1.75 | 0.80 | 0.523 | 0.28 |
| hsa-miR-125b-2-3p | 0.91 | −0.13 | 0.523 | 0.28 |
| hsa-mir-6127 | 1.17 | 0.23 | 0.523 | 0.28 |
| hsa-mir-130b | 0.89 | −0.16 | 0.529 | 0.28 |
| hsa-mir-142 | 1.30 | 0.37 | 0.541 | 0.27 |
| hsa-miR-148b-3p | 8.23 | 3.04 | 0.541 | 0.27 |
| hsa-mir-3656 | 1.19 | 0.25 | 0.547 | 0.26 |
| hsa-mir-25 | 1.19 | 0.25 | 0.553 | 0.26 |
| hsa-miR-361-3p | 0.90 | −0.16 | 0.553 | 0.26 |
| hsa-miR-335-5p | 1.02 | 0.03 | 0.560 | 0.25 |
| hsa-mir-150 | 0.94 | −0.09 | 0.563 | 0.25 |
| hsa-mir-181b-2 | 1.13 | 0.18 | 0.566 | 0.25 |
| hsa-mir-3960-pre | 1.47 | 0.55 | 0.566 | 0.25 |
| hsa-mir-342 | 2.92 | 1.55 | 0.566 | 0.25 |
| hsa-mir-92a-1 | 1.17 | 0.22 | 0.572 | 0.24 |
| hsa-mir-5096 | 1.68 | 0.75 | 0.572 | 0.24 |
| hsa-mir-1273a | 1.46 | 0.55 | 0.572 | 0.24 |
| hsa-mir-6739 | 1.38 | 0.47 | 0.572 | 0.24 |
| hsa-mir-203a | 0.90 | −0.15 | 0.572 | 0.24 |
| hsa-mir-411 | 1.10 | 0.14 | 0.578 | 0.24 |
| hsa-miR-339-3p | 1.00 | 0.00 | 0.578 | 0.24 |
| hsa-miR-16-5p | 1.05 | 0.07 | 0.585 | 0.23 |
| hsa-miR-766 | 0.88 | −0.18 | 0.585 | 0.23 |
| hsa-miR-182-5p | 1.11 | 0.15 | 0.585 | 0.23 |
| hsa-mir-328 | 2.15 | 1.10 | 0.585 | 0.23 |
| hsa-miR-22-5p | 1.41 | 0.50 | 0.585 | 0.23 |
| hsa-miR-331-3p | 1.24 | 0.30 | 0.585 | 0.23 |
| hsa-mir-1299-pre | 0.88 | −0.18 | 0.585 | 0.23 |
| hsa-mir-365b | 0.74 | −0.44 | 0.591 | 0.23 |
| hsa-mir-7703 | 1.07 | 0.09 | 0.591 | 0.23 |
| hsa-mir-31 | 1.29 | 0.36 | 0.598 | 0.22 |
| hsa-mir-320b | 0.86 | −0.22 | 0.598 | 0.22 |
| hsa-miR-200a-5p | 1.53 | 0.61 | 0.610 | 0.21 |
| hsa-miR-338-5p | 1.05 | 0.07 | 0.610 | 0.21 |
| hsa-mir-5100 | 1.12 | 0.17 | 0.611 | 0.21 |
| hsa-mir-4433a | 1.58 | 0.66 | 0.617 | 0.21 |
| hsa-mir-4284 | 0.97 | −0.04 | 0.617 | 0.21 |
| hsa-mir-4703 | 1.37 | 0.45 | 0.617 | 0.21 |
| hsa-mir-374a | 1.63 | 0.70 | 0.624 | 0.21 |
| hsa-mir-320b-2 | 0.68 | −0.55 | 0.624 | 0.21 |
| hsa-mir-7-5p | 1.12 | 0.17 | 0.624 | 0.21 |

TABLE 32B-continued nominal differences between ACS and PCS groups on Mann-Whitney testing

| | FC (in ACS) | log2(FC) | p.value | −LOG10(p) |
|---|---|---|---|---|
| hsa-mir-205 | 1.10 | 0.14 | 0.630 | 0.20 |
| hsa-mir-7641-1 | 1.46 | 0.55 | 0.630 | 0.20 |
| hsa-mir-501 | 0.50 | −1.01 | 0.637 | 0.20 |
| hsa-mir-542 | 1.21 | 0.27 | 0.637 | 0.20 |
| hsa-let-7i-5p | 0.91 | −0.13 | 0.643 | 0.19 |
| hsa-miR-99a-5p | 1.02 | 0.02 | 0.643 | 0.19 |
| hsa-miR-221-5p | 1.13 | 0.18 | 0.643 | 0.19 |
| hsa-miR-582-5p | 1.22 | 0.29 | 0.643 | 0.19 |
| hsa-miR-21-3p | 1.11 | 0.15 | 0.643 | 0.19 |
| hsa-miR-181b-5p | 1.58 | 0.66 | 0.650 | 0.19 |
| hsa-miR-205-5p | 1.09 | 0.13 | 0.656 | 0.18 |
| hsa-mir-374c | 0.94 | −0.10 | 0.657 | 0.18 |
| hsa-mir-17 | 0.79 | −0.34 | 0.657 | 0.18 |
| hsa-miR-210-3p | 1.05 | 0.06 | 0.657 | 0.18 |
| hsa-miR-21-5p | 1.07 | 0.10 | 0.658 | 0.18 |
| hsa-mir-6165 | 0.78 | −0.36 | 0.663 | 0.18 |
| hsa-mir-141 | 1.14 | 0.19 | 0.663 | 0.18 |
| hsa-miR-6724-5p | 1.95 | 0.96 | 0.663 | 0.18 |
| hsa-mir-92b | 0.87 | −0.20 | 0.670 | 0.17 |
| hsa-mir-744 | 0.70 | −0.51 | 0.670 | 0.17 |
| hsa-mir-21 | 1.07 | 0.10 | 0.671 | 0.17 |
| hsa-mir-423 | 0.88 | −0.18 | 0.677 | 0.17 |
| hsa-miR-361-5p | 1.12 | 0.16 | 0.677 | 0.17 |
| hsa-mir-103a-1 | 1.03 | 0.04 | 0.677 | 0.17 |
| hsa-mir-3665 | 2.49 | 1.32 | 0.677 | 0.17 |
| hsa-miR-542-3p | 1.22 | 0.28 | 0.677 | 0.17 |
| hsa-mir-99a | 1.04 | 0.05 | 0.684 | 0.17 |
| hsa-mir-26a-2 | 0.99 | −0.01 | 0.684 | 0.17 |
| hsa-mir-125a | 0.71 | −0.50 | 0.684 | 0.17 |
| hsa-mir-4448 | 1.01 | 0.01 | 0.684 | 0.17 |
| hsa-mir-4277 | 0.77 | −0.37 | 0.690 | 0.16 |
| hsa-mir-6883 | 0.95 | −0.08 | 0.707 | 0.15 |
| hsa-mir-1260b | 1.59 | 0.67 | 0.711 | 0.15 |
| hsa-miR-27a-5p | 1.28 | 0.36 | 0.711 | 0.15 |
| hsa-miR-200a-3p | 1.30 | 0.38 | 0.711 | 0.15 |
| hsa-miR-342-3p | 0.82 | −0.29 | 0.711 | 0.15 |
| hsa-mir-3135b-pre | 2.06 | 1.04 | 0.711 | 0.15 |
| hsa-miR-223-3p | 1.07 | 0.09 | 0.716 | 0.15 |
| hsa-mir-101-1 | 1.05 | 0.07 | 0.718 | 0.14 |
| hsa-miR-15a-5p | 1.01 | 0.01 | 0.718 | 0.14 |
| hsa-miR-365b-3p | 14.43 | 3.85 | 0.718 | 0.14 |
| hsa-miR-365a-3p | 1.22 | 0.29 | 0.718 | 0.14 |
| hsa-miR-574-3p | 0.88 | −0.18 | 0.725 | 0.14 |
| hsa-mir-4461 | 0.61 | −0.72 | 0.732 | 0.14 |
| hsa-mir-339 | 1.23 | 0.29 | 0.732 | 0.14 |
| hsa-miR-19a-3p | 0.97 | −0.04 | 0.732 | 0.14 |
| hsa-mir-181a-2 | 1.14 | 0.19 | 0.732 | 0.14 |
| hsa-mir-223 | 1.07 | 0.10 | 0.737 | 0.13 |
| hsa-mir-4441 | 1.91 | 0.93 | 0.739 | 0.13 |
| hsa-mir-361 | 1.01 | 0.02 | 0.746 | 0.13 |
| hsa-miR-340-3p | 0.99 | −0.01 | 0.746 | 0.13 |
| hsa-mir-4522 | 1.15 | 0.20 | 0.746 | 0.13 |
| hsa-miR-3615-mature | 1.41 | 0.50 | 0.746 | 0.13 |
| hsa-mir-660 | 0.86 | −0.21 | 0.746 | 0.13 |
| hsa-let-7i | 1.05 | 0.07 | 0.753 | 0.12 |
| hsa-mir-619 | 0.07 | −3.85 | 0.753 | 0.12 |
| hsa-miR-6793-5p | 1.49 | 0.58 | 0.753 | 0.12 |
| hsa-mir-19b-1 | 0.70 | −0.51 | 0.760 | 0.12 |
| hsa-let-7d | 1.23 | 0.30 | 0.760 | 0.12 |
| hsa-miR-142-3p | 0.98 | −0.02 | 0.760 | 0.12 |
| hsa-let-7g | 1.08 | 0.11 | 0.760 | 0.12 |
| hsa-mir-4326 | 1.23 | 0.30 | 0.760 | 0.12 |
| hsa-miR-25-3p | 0.98 | −0.03 | 0.767 | 0.12 |
| hsa-miR-125a-5p | 0.72 | −0.47 | 0.767 | 0.12 |
| hsa-mir-628 | 1.19 | 0.25 | 0.767 | 0.12 |
| hsa-mir-324 | 0.96 | −0.06 | 0.767 | 0.12 |
| hsa-let-7d-3p | 1.01 | 0.02 | 0.767 | 0.12 |
| hsa-mir-224 | 1.06 | 0.08 | 0.774 | 0.11 |
| hsa-miR-345-5p | 3.16 | 1.66 | 0.774 | 0.11 |
| hsa-mir-4471 | 1.08 | 0.10 | 0.774 | 0.11 |
| hsa-miR-625-3p | 1.06 | 0.08 | 0.776 | 0.11 |
| hsa-miR-101-3p | 1.05 | 0.07 | 0.781 | 0.11 |
| hsa-mir-7641-2 | 0.99 | −0.02 | 0.781 | 0.11 |
| hsa-miR-193b-3p | 1.26 | 0.34 | 0.781 | 0.11 |
| hsa-miR-23a-3p | 1.00 | −0.01 | 0.788 | 0.10 |
| hsa-miR-34a-5p | 0.99 | −0.01 | 0.788 | 0.10 |
| hsa-miR-31-5p | 2.62 | 1.39 | 0.788 | 0.10 |
| hsa-mir-7851 | 1.12 | 0.16 | 0.788 | 0.10 |
| hsa-mir-99b | 0.95 | −0.07 | 0.795 | 0.10 |
| hsa-miR-378i-mature | 1.28 | 0.35 | 0.795 | 0.10 |
| hsa-miR-429 | 2.71 | 1.44 | 0.795 | 0.10 |
| hsa-mir-1249 | 1.09 | 0.13 | 0.795 | 0.10 |
| hsa-mir-24-2 | 0.93 | −0.11 | 0.802 | 0.10 |
| hsa-miR-125b-5p | 1.08 | 0.11 | 0.803 | 0.10 |
| hsa-mir-6716 | 0.59 | −0.75 | 0.803 | 0.10 |
| hsa-miR-30d-5p | 1.09 | 0.12 | 0.810 | 0.09 |
| hsa-mir-1260a | 0.83 | −0.27 | 0.810 | 0.09 |
| hsa-miR-146a-5p | 1.00 | −0.01 | 0.810 | 0.09 |
| hsa-miR-3 960 | 1.79 | 0.84 | 0.810 | 0.09 |
| hsa-let-7f-1 | 0.96 | −0.06 | 0.810 | 0.09 |
| hsa-mir-330 | 0.78 | −0.35 | 0.817 | 0.09 |
| hsa-miR-32-5p | 0.92 | −0.11 | 0.817 | 0.09 |
| hsa-miR-941 | 1.07 | 0.10 | 0.817 | 0.09 |
| hsa-mir-26b | 1.00 | 0.00 | 0.824 | 0.08 |
| hsa-miR-26a-5p | 1.03 | 0.04 | 0.824 | 0.08 |
| hsa-mir-221 | 1.13 | 0.18 | 0.824 | 0.08 |
| hsa-mir-106a | 1.14 | 0.18 | 0.824 | 0.08 |
| hsa-miR-106a-5p | 1.01 | 0.02 | 0.824 | 0.08 |
| hsa-miR-30e-5p | 1.03 | 0.04 | 0.831 | 0.08 |
| hsa-mir-125b-2 | 1.31 | 0.39 | 0.831 | 0.08 |
| hsa-mir-4419a | 0.85 | −0.24 | 0.831 | 0.08 |
| hsa-mir-331 | 0.86 | −0.21 | 0.831 | 0.08 |
| hsa-miR-26b-5p | 1.12 | 0.16 | 0.837 | 0.08 |
| hsa-mir-30a | 1.27 | 0.35 | 0.838 | 0.08 |
| hsa-mir-193a | 0.97 | −0.05 | 0.839 | 0.08 |
| hsa-miR-148a-3p | 1.05 | 0.07 | 0.839 | 0.08 |
| hsa-miR-340-5p | 1.07 | 0.10 | 0.839 | 0.08 |
| hsa-mir-152 | 1.30 | 0.38 | 0.839 | 0.08 |
| hsa-mir-3178 | 2.10 | 1.07 | 0.839 | 0.08 |
| hsa-mir-4797 | 1.10 | 0.14 | 0.846 | 0.07 |
| hsa-mir-5572 | 1.23 | 0.30 | 0.846 | 0.07 |
| hsa-mir-16-2 | 1.04 | 0.06 | 0.853 | 0.07 |
| hsa-mir-708 | 0.83 | −0.27 | 0.853 | 0.07 |
| hsa-miR-628-3p | 0.68 | −0.55 | 0.853 | 0.07 |
| hsa-mir-582 | 1.02 | 0.03 | 0.853 | 0.07 |
| hsa-let-7g-5p | 1.09 | 0.13 | 0.860 | 0.07 |
| hsa-mir-26a-1 | 1.03 | 0.05 | 0.867 | 0.06 |
| hsa-mir-92a-2 | 0.93 | −0.11 | 0.868 | 0.06 |
| hsa-miR-15b-5p | 1.07 | 0.10 | 0.868 | 0.06 |
| hsa-miR-150-5p | 1.11 | 0.15 | 0.868 | 0.06 |
| hsa-mir-155 | 0.96 | −0.05 | 0.868 | 0.06 |
| hsa-miR-221-3p | 1.06 | 0.08 | 0.875 | 0.06 |
| hsa-miR-27a-3p | 1.04 | 0.06 | 0.875 | 0.06 |
| hsa-mir-6875 | 0.72 | −0.48 | 0.876 | 0.06 |
| hsa-miR-107-pre | 1.06 | 0.08 | 0.882 | 0.05 |
| hsa-miR-502-3p | 5.52 | 2.47 | 0.882 | 0.05 |
| hsa-miR-30b-5p | 1.07 | 0.10 | 0.889 | 0.05 |
| hsa-mir-218-2 | 0.75 | −0.41 | 0.890 | 0.05 |
| hsa-mir-4449 | 1.63 | 0.70 | 0.890 | 0.05 |
| hsa-miR-421 | 0.99 | −0.02 | 0.890 | 0.05 |
| hsa-miR-30a-5p | 1.03 | 0.04 | 0.897 | 0.05 |
| hsa-mir-3615-pre | 1.40 | 0.49 | 0.897 | 0.05 |
| hsa-mir-451a-pre | 0.24 | −2.08 | 0.897 | 0.05 |
| hsa-mir-532 | 2.61 | 1.39 | 0.897 | 0.05 |
| hsa-mir-22 | 0.92 | −0.13 | 0.904 | 0.04 |
| hsa-mir-103a-2 | 1.00 | 0.00 | 0.904 | 0.04 |
| hsa-mir-101-2 | 0.97 | −0.04 | 0.904 | 0.04 |
| hsa-miR-193a-5p | 0.97 | −0.04 | 0.904 | 0.04 |
| hsa-miR-16-2-3p | 0.98 | −0.02 | 0.905 | 0.04 |
| hsa-miR-3074-5p | 1.04 | 0.05 | 0.911 | 0.04 |
| hsa-mir-193b | 1.23 | 0.30 | 0.912 | 0.04 |
| hsa-miR-22-3p | 0.90 | −0.16 | 0.919 | 0.04 |
| hsa-mir-3613 | 0.97 | −0.05 | 0.919 | 0.04 |
| hsa-miR-320a | 1.39 | 0.48 | 0.919 | 0.04 |
| hsa-mir-5481 | 2.57 | 1.36 | 0.919 | 0.04 |
| hsa-mir-15a | 0.99 | −0.02 | 0.926 | 0.03 |
| hsa-let-7a-1 | 0.68 | −0.56 | 0.926 | 0.03 |
| hsa-mir-1273e | 2.18 | 1.12 | 0.926 | 0.03 |
| hsa-miR-324-3p | 0.95 | −0.08 | 0.926 | 0.03 |
| hsa-miR-197-3p | 0.96 | −0.06 | 0.926 | 0.03 |

TABLE 32B-continued nominal differences between ACS and
PCS groups on Mann-Whitney testing

| | FC (in ACS) | log2(FC) | p.value | −LOG10(p) |
|---|---|---|---|---|
| hsa-miR-143-3p | 1.08 | 0.11 | 0.934 | 0.03 |
| hsa-mir-345 | 3.91 | 1.97 | 0.934 | 0.03 |
| hsa-mir-181a-1 | 1.12 | 0.16 | 0.934 | 0.03 |
| hsa-miR-95-3p | 1.07 | 0.10 | 0.934 | 0.03 |
| hsa-miR-451a | 0.18 | −2.51 | 0.934 | 0.03 |
| hsa-miR-103a-3p | 1.01 | 0.02 | 0.941 | 0.03 |
| hsa-mir-192 | 0.96 | −0.06 | 0.941 | 0.03 |
| hsa-mir-34a | 1.09 | 0.12 | 0.941 | 0.03 |
| hsa-mir-27a | 1.02 | 0.03 | 0.948 | 0.02 |
| hsa-mir-4289 | 1.10 | 0.14 | 0.948 | 0.02 |
| hsa-mir-29a | 1.02 | 0.03 | 0.948 | 0.02 |
| hsa-mir-27b | 1.11 | 0.15 | 0.948 | 0.02 |
| hsa-mir-4800 | 1.03 | 0.05 | 0.948 | 0.02 |
| hsa-mir-19a | 1.02 | 0.03 | 0.948 | 0.02 |
| hsa-mir-23b | 1.01 | 0.02 | 0.956 | 0.02 |
| hsa-miR-224-5p | 1.06 | 0.08 | 0.956 | 0.02 |
| hsa-mir-29a-3p | 1.03 | 0.04 | 0.963 | 0.02 |
| hsa-mir-197 | 0.93 | −0.11 | 0.963 | 0.02 |
| hsa-mir-429-pre | 0.99 | −0.01 | 0.963 | 0.02 |
| hsa-miR-424-5p | 1.01 | 0.01 | 0.963 | 0.02 |
| hsa-miR-330-3p | 0.68 | −0.56 | 0.963 | 0.02 |
| hsa-mir-148a | 1.08 | 0.12 | 0.970 | 0.01 |
| hsa-mir-143 | 1.09 | 0.12 | 0.970 | 0.01 |
| hsa-mir-340 | 1.06 | 0.08 | 0.970 | 0.01 |
| hsa-mir-130a | 1.51 | 0.60 | 0.970 | 0.01 |
| hsa-miR-185-5p | 2.37 | 1.24 | 0.970 | 0.01 |
| hsa-mir-125b-1 | 1.25 | 0.32 | 0.978 | 0.01 |
| hsa-mir-365a | 1.11 | 0.14 | 0.978 | 0.01 |
| hsa-miR-130a-3p | 1.98 | 0.98 | 0.978 | 0.01 |
| hsa-miR-155-5p | 0.92 | −0.12 | 0.985 | 0.01 |
| hsa-mir-16-1 | 10.75 | 3.43 | 0.993 | 0.00 |
| hsa-mir-184-pre | 1.68 | 0.75 | 0.993 | 0.00 |
| hsa-miR-660-5p | 1.26 | 0.33 | 0.993 | 0.00 |
| hsa-mir-4301 | 0.85 | −0.23 | 0.993 | 0.00 |
| hsa-mir-454 | 1.38 | 0.46 | 1.000 | 0.00 |
| hsa-mir-500a | 0.90 | −0.16 | 1.000 | 0.00 |
| hsa-miR-423-3p | 1.10 | 0.14 | 1.000 | 0.00 |
| hsa-miR-19b-3p | 0.92 | −0.12 | 1.000 | 0.00 |
| hsa-miR-27b-3p | 1.05 | 0.07 | 1.000 | 0.00 |
| hsa-mir-6884 | 0.97 | −0.05 | 1.000 | 0.00 |
| hsa-miR-151a-5p | 1.03 | 0.04 | 1.000 | 0.00 |
| hsa-mir-24-1 | 1.01 | 0.02 | 1.000 | 0.00 |
| hsa-mir-664a | 1.01 | 0.01 | 1.000 | 0.00 |

Based on the data in this table, one skilled in the art may select an appropriate set or sets of miRNAs for the methods disclosed herein.

Figure 31:
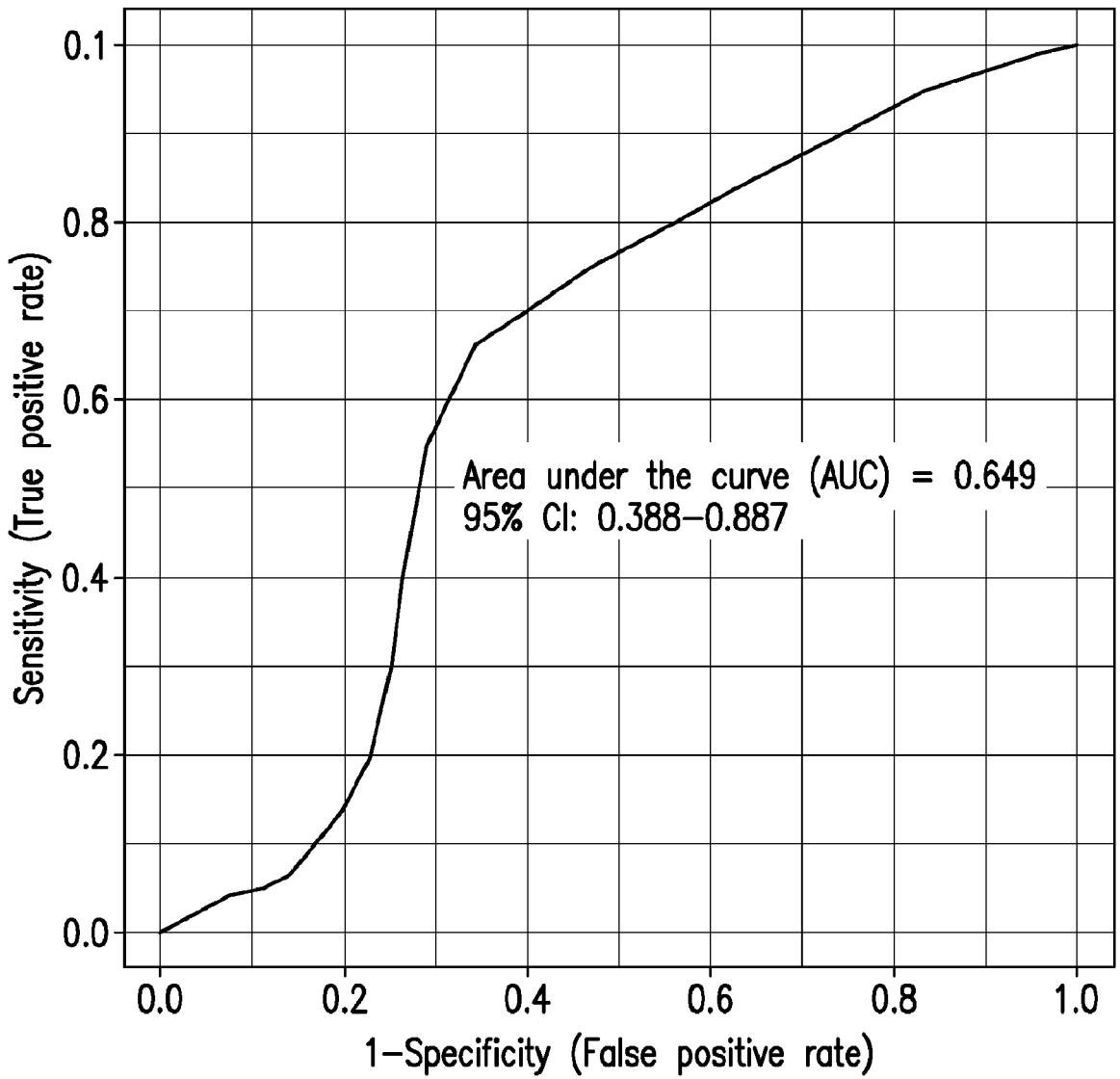
FIG. 31 shows a comparative (an under-performing) logistic regression model using child SCAT-3 scores.

FIG. 31 shows comparative (an under-performing) logistic regression model using child SCAT-3 scores.

MiRNAs that are useful for detection and prediction of PCS: miR-769, miR-769-3p, miR-769-5p, miR-320c-1, miR-320c-1-3p, miR-320c-1-5p, miR-4792, miR-4792-3p, miR-4792-5p, miR-140, miR-140-3p, miR-140-5p, miR-629, miR-629-3p, miR-629-5p, miR-192, miR-192-3p, miR-192-5p, miR-145, miR-145-3p, miR-145-5p, let-7a, let-7a-3p, let-7s-5p, miR-133a, miR-133a-3p, miR-133a-5p, miR-1307, miR-1307-3p, miR-1307-5p, miR-200b, miR-200b-3p, miR-200b-5p, let-7a, let-7a-3p, let-7a-5p, miR-4508, miR-4508-3p, miR-4508-5p, miR-30e, miR-30e-3p, miR-30e-5p, let-7b, let-7b-3p, let-7b-5p, miR-194, miR-194-3p, miR-194-5p, miR-199a, miR-199a-3p, miR-199a-5p, let-7f, let-7f-3p, let-7f-5p, miR-128, miR-128-3p, miR-128-5p, miR-215, miR-215-3p, miR-215-5p, miR-149, miR-149-3p, miR-149-5p, miR-421, miR-421-3p, and miR-421-5p.

Example 4

Longitudinal Interrogation of Salivary miRNAs

Salivary microRNA was collected from 50 children (ages 7-21) presenting to a tertiary care center with a physician-diagnosed mild traumatic brain injury at acute (0-3 days after injury), sub-acute (7-17 days after injury), and chronic (≥28 days after injury) timepoints. Injury mechanism and demographic features were recorded. Subjective symptoms were assessed with SCAT-5 survey, and functional symptoms of balance and cognition (e.g. processing speed, divided attention performance) were measured with the ClearEdge© Concussion Toolkit. Saliva microRNA levels were quantified with high throughput RNA sequencing. Spearman's rank correlations were used to identify potential relationships between microRNA levels and four continuous variables: 1) days since injury; 2) ClearEdge™ balance score; 3) ClearEdge™ cognitive score; and 4) participant age.

Initial analyses (n=35) have identified six microRNAs whose levels are associated with (R≥0.40; p<0.05) with number of days post-injury. Three of these miRNAs (50%) were identified as potential biomarkers in our previous studies (miR-574-5p, let-7b-5p, let-7f-5p). One of these microRNAs (let-7f) is negatively associated with participant age (R=−0.48; p=0.009), and may represent a unique biomarker for pediatric brain injury.

Seven salivary miRNAs were found to be associated with ClearEdge cognitive score and two of these (miR-30e-5p, R=−0.48, p=0.015; miR-320c, R=−0.43, p=0.034) were identified in previous studies. Three previously identified microRNAs were also associated with ClearEdge balance score (miR-182-5p, miR-744-5p, miR-769-5p).

This work indicates the value of assessing miRNA profiles in saliva in order to provide insight into the severity brain injury symptoms over a period of time and for estimating a degree of recovery as well as a duration of an injury. Previously the inventors have shown that salivary microRNA profiles overlap with microRNA profiles in cerebrospinal fluid after a traumatic brain injury. These profiles demonstrate utility in identifying brain injury status and predicting which patients will experience prolonged symptoms. Such information would be valuable for clinicians seeking to provide anticipatory guidance for patients and families, or to create individualized patient management plans. Further development of this tool will require a better understanding of how brain injury-related microRNAs change over time, and how microRNA levels relate to functional symptom measures.

Longitudinal interrogation of salivary miRNA biomarkers alongside measures of balance and cognition demonstrates that miRNAs show expression trends over time and are associated with objective symptoms following brain injury. A subset of microRNAs is correlated with patient age and may represent unique signatures for pediatric brain injury. These results demonstrate the utility of miRNA based diagnostic or prognostic methods as non-invasive, objective measures of brain injury and their utility for longitudinal assessment of injury as well as assessing measures of balance and cognition during recovery.

Example 5

Salivary miRNAs that Exhibit Circadian Rhythms in their Expression and Abundance As described in PCT/US 2018/023336, filed Mar. 20, 2018, which is incorporated by reference, a portion of salivary miRNAs exhibit strong circadian rhythms ("circamiRNAs"), many of which target known genes associated with circadian rhythms. Some of these miRNAs also oscillate or fluctuate in association with levels of particular microbes.

Saliva Collection at Intervals Over a Day.

Eleven human subject volunteers participated in the study and provided saliva samples at various times of day on repeated days in three different rounds of sample collection. Saliva was collected via a swab and prepared using a salivary preparation kit.

Collection 1: 8 am & 8 pm samples collected on days 1, 3, and 7.

Collection 2: 8 am, 12 pm, 4 pm, & 8 pm samples on days 1, 5, 10 & 15.

Collection 3: 12 non-repeated times throughout the day on days 1 and 2.

Identification and quantification of saliva miRNA and microbial content was performed using next generation sequencing (NGS) on a NextSeq 500 instrument at the SUNY Molecular Analysis Core (SUNYMAC) at Upstate Medical University, following the TruSeq® Small RNA Library Preparation Kit protocol (Illumina, San Diego, Calif.). Alignment of the NGS reads was performed to the miRbase21 database using the SHRRiMP2® algorithm in Partek Flow software to identify mature miRNAs. Mapping of microbiome reads was performed using Kraken software and OneCodex® software to identify only microbes that were consistently found in both. The term "reads" or "readcounts" should be understood to apply to any method for adjusting miRNA or microbiome expression data to account for variations between samples, such as using the expression levels of certain control miRNAs or metabolites that are always present at a predictable level in saliva to normalize the levels of all miRNAs in the samples so they can be compared more accurately.

In an alternative embodiment, fluorescence methods are used to determine miRNA and/or microbiome levels. In an example, separate groups of ligands targeting some or all of the target miRNA described herein are anchored in groups on a substrate. The target miRNA and microbiome sequences are tagged with a fluorescent tag (or non-fluorescent dye) either before or after it binds to the ligand. A relative intensity at each ligand group may be a measure of quantity of miRNA and/or microbiome present. This method may be implemented on a chip-type assay. Other suitable chip-type-assays may be used to determine miRNA and/or microbiome levels.

Statistical Analysis.

A two-way analysis of variance (ANOVA) was performed in the Collection 1 and 2 sample sets to identify miRNAs and microbes that varied significantly according to collection time but not the day of collection (which could have been strongly affected by daily variation in routines). A subset of these miRNAs and microbes were then used in a third sample set to assess the accuracy of prediction for the time of collection using multivariate linear regression. MiRNAs that showed the strongest circadian oscillations were termed circaMiRs and examined for being predicted regulators of a total of 139 annotated circadian genes using Ingenuity Pathway Analysis (IPA) software. CircaMiRs targeting circadian genes were then examined for evidence of association with the strongest circadian-oscillating microbes using Pearson correlation analysis. The functions of the genes targeted by circaMiRs were then examined for their specific biological functions using IPA and miRpath software.

Figure 32:
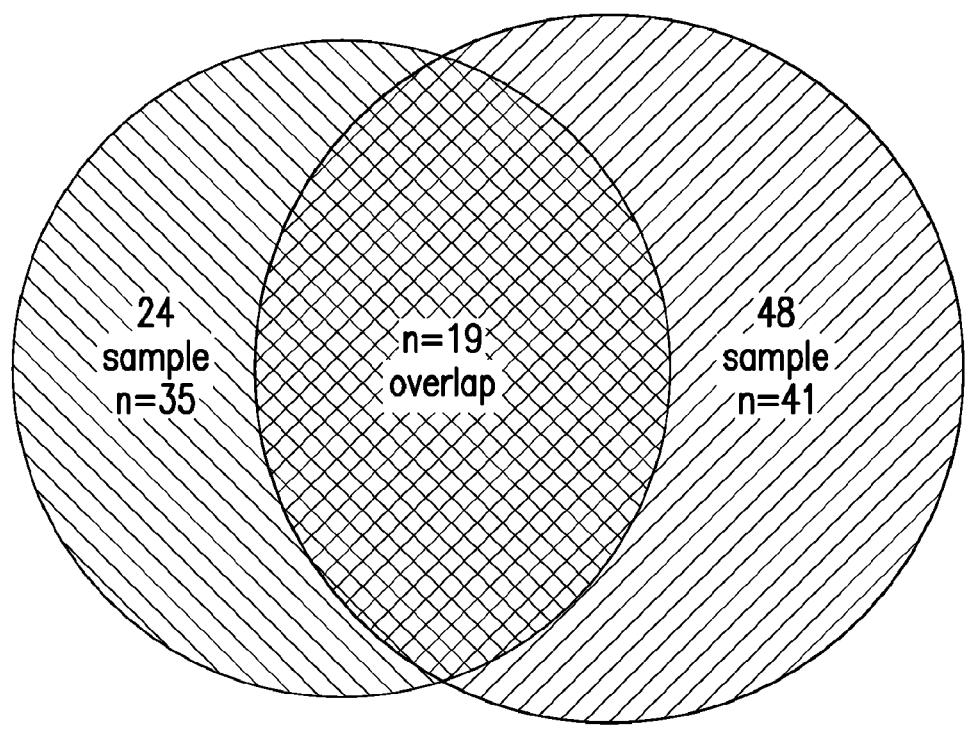
FIG. 32 shows a Venn diagram of overlapping miRNAs from analysis of 24 samples in Collection 1 and 48 samples in Collection 2.

24 sample data set: A total of 35 miRNAs showed a highly-significant effect of collection time (FDR<0.001) and no effect of day of collection;

48 sample data set: A total of 41 mi miRNAs showed a highly-significant effect of collection time (FDR<0.001) and no effect of day of collection;

19 miRNAs were commonly changed in both and examined for the ability to predict collection time in a third data set as shown in FIG. 32.

circamiRNA Time Prediction

TABLE 33

Accuracy of 19 circaMiRs to predict collection time.

| | Multiple R | P value | Margin of Error |
|---|---|---|---|
| Collection 1 | 0.990 | 0.003929 | 12.9% |
| Collection 2 | 0.878 | 0.000031 | 18.1% |
| Collection 3 | 0.875 | 0.000040 | 26.0% |
| (no 4 am) | 0.938 | $2.28e^{-10}$ | 15.7% |

Group A and Group B circa MiRs are described in Table 34.

TABLE 34

Groups A and B circaMiRNAs

| | Group A circaMiRs | Group B circaMiRs |
|---|---|---|
| 1 | hsa-miR-106b-3p | hsa-let-7a-5p |
| 2 | hsa-miR-128-3p | hsa-let-7d-3p |
| 3 | hsa-miR-130a-3p | hsa-miR-101-3p |
| 4 | hsa-miR-15a-5p | hsa-miR-10b-5p |
| 5 | hsa-miR-192-5p | hsa-miR-125b-2-3p |
| 6 | hsa-miR-199a-3p | hsa-miR-1307-5p |
| 7 | hsa-miR-199b-3p | hsa-miR-140-3p |
| 8 | hsa-miR-203a-3p | hsa-miR-142-3p |
| 9 | hsa-miR-221-3p | hsa-miR-143-3p |
| 10 | hsa-miR-26a-5p | hsa-miR-148b-3p |
| 11 | hsa-miR-26b-5p | hsa-miR-16-5p |
| 12 | hsa-miR-3074-5p | hsa-miR-181a-5p |
| 13 | hsa-miR-30e-3p | hsa-miR-181c-5p |
| 14 | hsa-miR-320a | hsa-miR-186-5p |
| 15 | hsa-miR-345-5p | hsa-miR-191-5p |
| 16 | hsa-miR-375 | hsa-miR-193a-5p |
| 17 | hsa-miR-423-3p | hsa-miR-200b-3p |
| 18 | hsa-miR-92a-3p | hsa-miR-205-5p |
| 19 | hsa-miR-93-5p | hsa-miR-215-5p |
| 20 | | hsa-miR-21-5p |
| 21 | | hsa-miR-223-3p |
| 22 | | hsa-miR-22-3p |
| 23 | | hsa-miR-23a-3p |
| 24 | | hsa-miR-23b-3p |
| 25 | | hsa-miR-24-3p |
| 26 | | hsa-miR-25-3p |
| 27 | | hsa-miR-29a-3p |
| 28 | | hsa-miR-30d-5p |
| 29 | | hsa-miR-320b |
| 30 | | hsa-miR-361-5p |
| 31 | | hsa-miR-363-3p |
| 32 | | hsa-miR-374a-3p |
| 33 | | hsa-miR-423-5p |
| 34 | | hsa-miR-425-5p |
| 35 | | hsa-miR-532-5p |
| 36 | | hsa-miR-574-3p |
| 37 | | hsa-miR-629-5p |
| 38 | | hsa-miR-98-5p |

Tables 34 lists circaMiRs that may be used to distinguish healthy subjects from subjects having a disease or disorder using the methods described herein or which may be normalized to adjust for circadian fluctuations in concentration or abundance. Other miRNAs sharing the same seed sequences as any of the miRNAs in the above tables may be used for these purposes.

Figure 33:
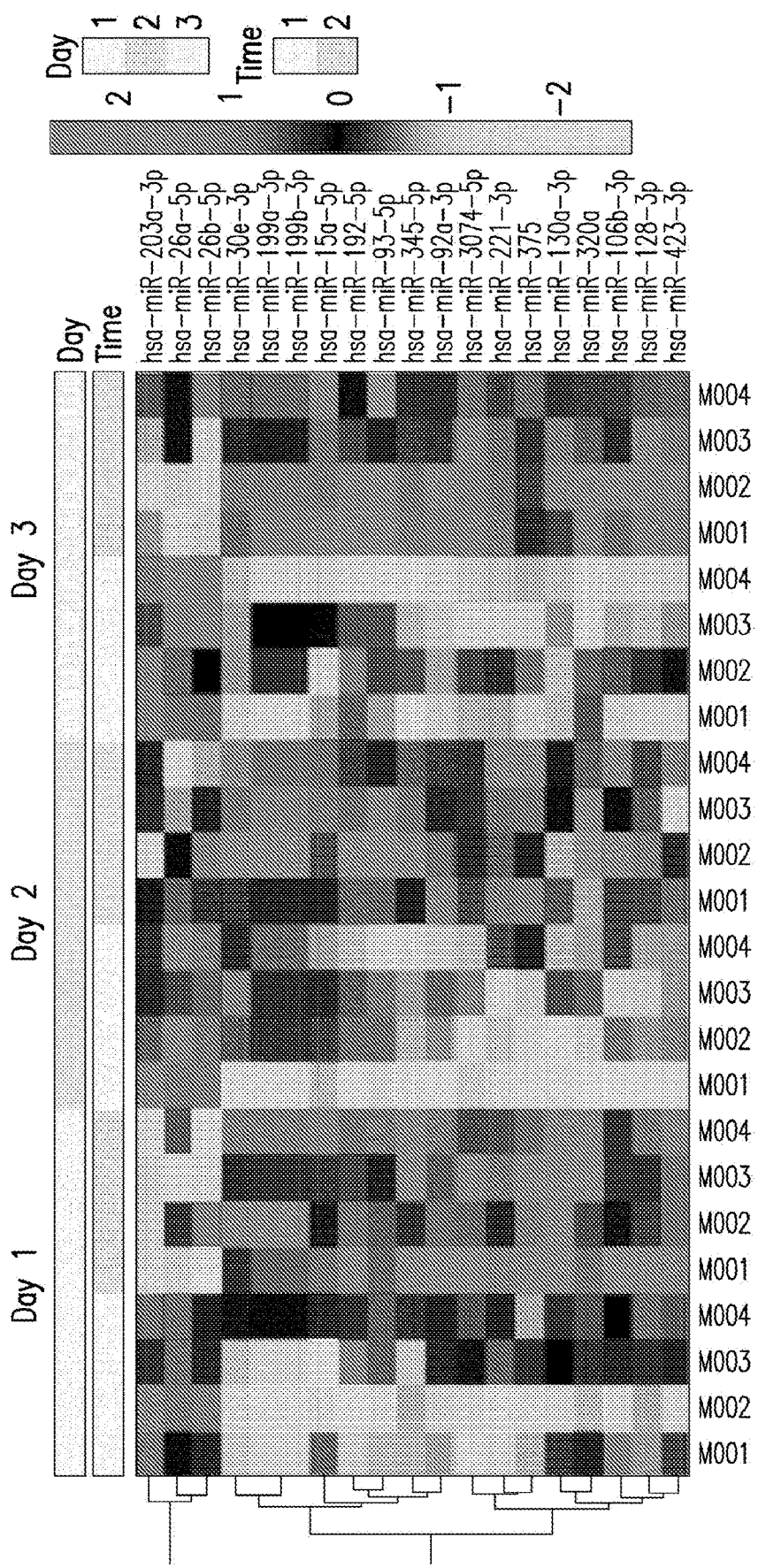
FIG. 33 shows a heat map clustering of expression data for the 19 miRNAs changed according to collection time in 24 samples from 4 subjects across 3 days of sampling (days 1, 3, 7) at a frequency of 2 times/day (8 am, 8 pm).
Figure 34:
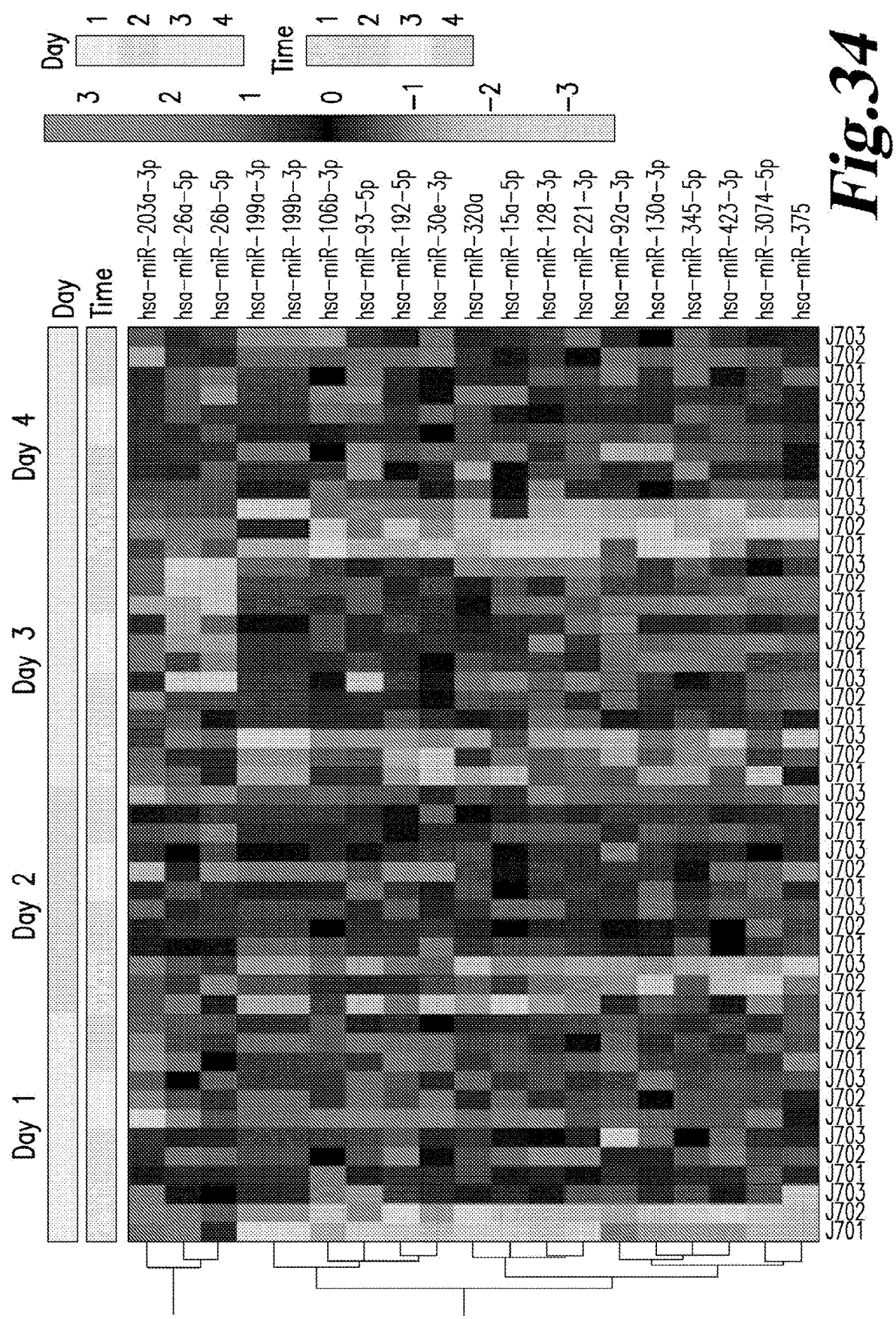
FIG. 34 shows a heat map clustering of expression data for the 19 miRNAs changed according to collection time in 48 samples from 3 subjects across 4 days of sampling (days 1, 5, 10, 15) at a frequency of 4 times/day (8 am, 12 pm, 4 pm, 8 pm).
Figure 35:
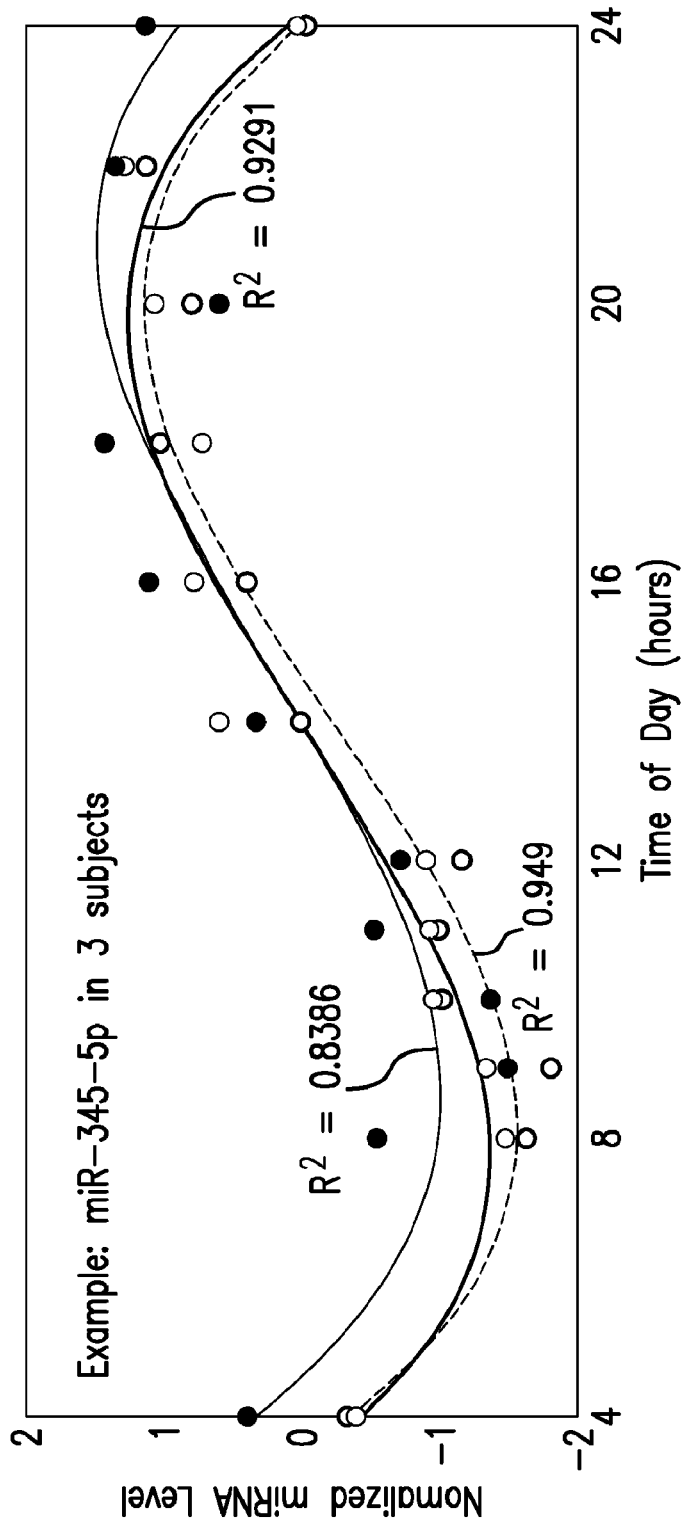
FIG. 35 shows normalized data for 1 of the top 19 miRNAs shown for 3 of the subjects in Collection 3 (collected at various times). Top (black) line: $R^2=0.8386$; middle (green/grayscale) line: $R^2=0.9291$; bottom (blue/grayscale): $R^2=0.949$.
Figure 36:
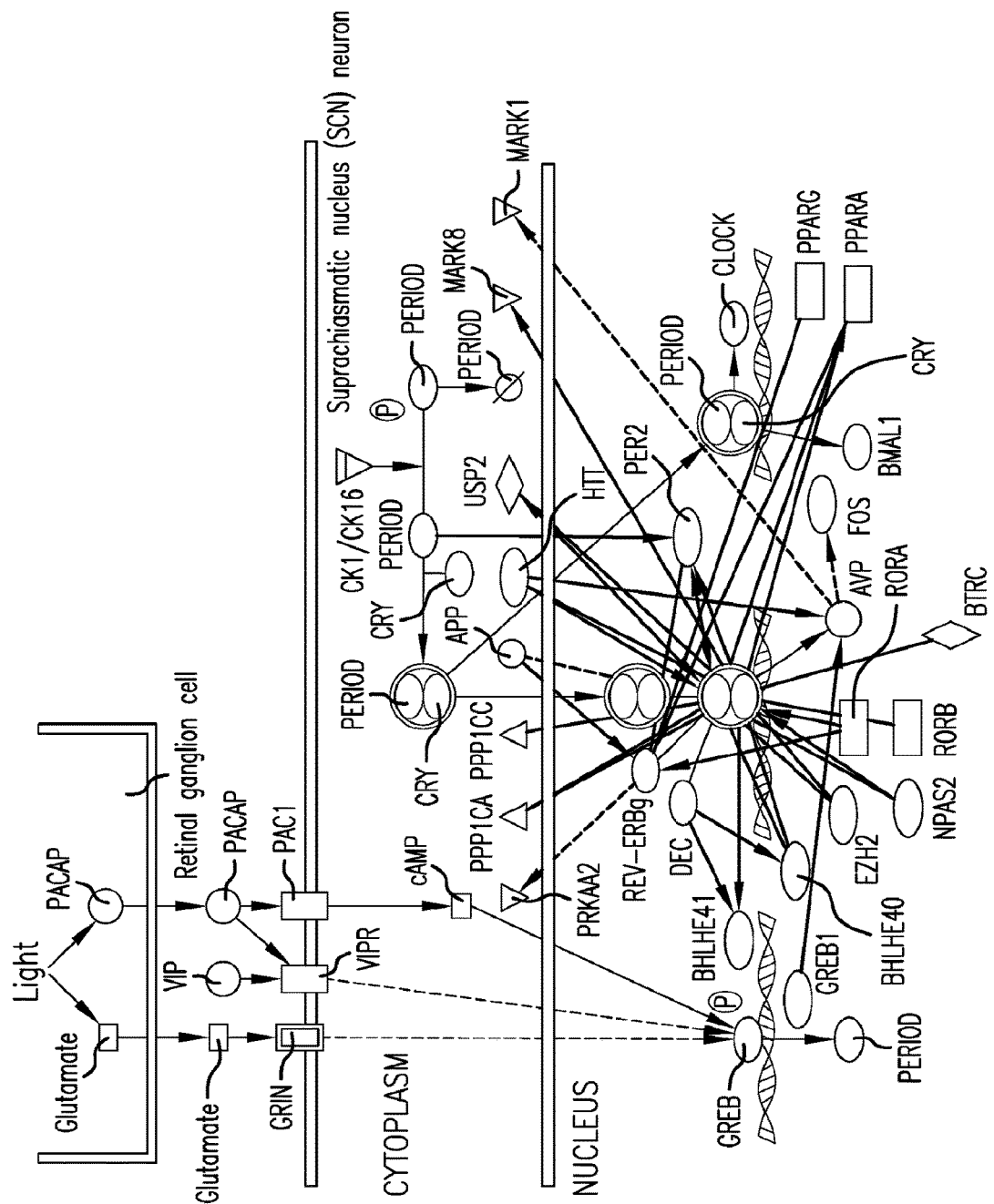
FIG. 36 shows 45 genes involved in Circadian Rhythm Signaling were identified as targets of 14 of the circaMiRs. This is almost one-third of the 139 total annotated genes involved in circadian function in IPA. In the figure, genes targeted by 1 miRNA are highlighted and gray, while genes targeted by >1 of the 14 miRNAs are highlighted and red. Untargeted genes appear as white.

A heat map clustering of expression data for the 19 miRNAs changed according to collection time in 24 samples from 4 subjects across 3 days of sampling (days 1, 3, 7) at a frequency of 2 times/day (8 am, 8 pm) is shown in FIG. 33. A heat map clustering of expression data for the 19 miRNAs changed according to collection time in 48 samples from 3 subjects across 4 days of sampling (days 1, 5, 10, 15) at a frequency of 4 times/day (8 am, 12 pm, 4 pm, 8 pm) is shown in FIG. 34. Normalized data for 1 of the top 19 miRNAs shown for 3 of the subjects in Collection 3 (collected at various times) is shown in FIG. 35. 45 genes involved in Circadian Rhythm Signaling were identified as targets of 14 of the circaMiRs (FIG. 36). This is almost one-third of the 139 total annotated genes involved in circadian function in IPA. In FIG. 36, genes targeted by 1 miRNA are highlighted and gray, while genes targeted by >1 of the 14 miRNAs are highlighted and red. Untargeted genes appear as white.

Portions of the saliva miRNA levels show strong circadian patterns. This observation has not been previously described. Most saliva circaMiRs target at least one or more circadian genes, in addition to genes involved in brain, metabolic and cancer function, for example, those described in Table 34.

TABLE 35

Biological pathways containing genes targeted by circaMiRs

| Kyoto Encyclopedia of Genes and Genomes (KEGG) Pathways | p-value | # genes | # miRNAs |
|---|---|---|---|
| Fatty acid biosynthesis | 4.6e−11 | 5 | 6 |
| Proteoglycans in cancer | 3.1e−08 | 94 | 17 |
| Prion diseases | 4.8e−07 | 10 | 9 |
| Hippo signaling pathway | 2.0e−06 | 71 | 17 |
| FoxO signaling pathway | 8.0e−06 | 70 | 16 |
| Signaling pathways regulating pluripotency of stem cells | 8.0e−06 | 68 | 17 |
| Renal cell carcinoma | 1.1e−05 | 39 | 17 |
| Glutamatergic synapse | 7.9e−05 | 52 | 17 |
| Prostate cancer | 7.9e−05 | 47 | 17 |
| Pathways in cancer | 8.0e−05 | 159 | 17 |
| Glioma | 8.7e−05 | 33 | 15 |
| Adrenergic signaling in cardiomyocytes | 8.7e−05 | 61 | 17 |
| Estrogen signaling pathway | 0.00013 | 46 | 16 |
| Thyroid hormone signaling pathway | 0.00014 | 57 | 16 |
| Rap1 signaling pathway | 0.00016 | 91 | 17 |
| Regulation of actin cytoskeleton | 0.00027 | 94 | 17 |
| PI3K-Akt signaling pathway | 0.00044 | 136 | 17 |
| Focal adhesion | 0.00044 | 91 | 17 |
| mTOR signaling pathway | 0.00055 | 34 | 15 |

Diagnostic and prognostic methods using MiRNAs that correlate or associate with particular conditions, disorders or diseases, such as TBI or concussive injuries and that also exhibit temporal or circadian fluctuations may be normalized based on known circadian fluctuations in the circaMiRs. Alternatively, diagnostic and prognostic methods may control for these circadian fluctuations by obtaining samples at a fixed time of day so as to avoid the fluctuations. In other embodiments, a diagnostic or prognostic method may use miRNAs that are exhibit constant or relatively invariant expression so as to avoid noise or error introduced by circadian or other temporal fluctuations in miRNA abundance or concentration.

Numerous modification and variations on the present invention are possible in light of the above teachings. It is therefore to be understood that within the scope of the appended claims, the invention may be practiced otherwise than as specifically described herein.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

LITERATURE

1. McCarthy, M. T., & Kosofsky, B. E. (2015). Clinical features and biomarkers of concussion and mild traumatic brain injury in pediatric patients. Annals of the New York Academy of Sciences.
2. Kirkwood, M W., Yeates K O, Wilson P E. (2006) Pediatric sport-related concussion: a review of the clinical management of an oft-neglected population. Pediatrics 117.4: 1359-1371.
3. Mild Traumatic Brain Injury Committee of the Head Injury Interdisciplinary Special Interest Group of the American Congress of Rehabilitation Medicine. Definition of mild traumatic brain injury. J Head Trauma Rehabil. 1993; 8:86-87.
4. Babcock L, Byczkowski T, Wade S L, et al. Predicting postconcussion syndrome after mild traumatic brain injury in children and adolescents who present to the emergency department. JAMA Pediatr. 2013; 167(2):156-161.6.
5. Barlow M, Schlabach D, Peiffer J, Cook C. Differences in change scores and the predictive validity of three commonly used measures following concussion in the middle school and high school aged population. Int J Sports Phys Ther. 2011; 6(3):150-157.
6. Scorza K A, Raleigh M F, O'Connor F G Current concepts in concussion: evaluation and management. Am Fam Physician. 2012; 85(2):123-132.
7. Ayr L K, Yeates K O, Taylor H G, Browne M. Dimensions of postconcussive symptoms in children with mild traumatic brain injuries. J Int Neuropsychol Soc. 2009; 15(1): 19-30.
8. Burton L J, Quinn B, Pratt-Cheney J L, Pourani M. Headache etiology in a pediatric emergency department. Pediatr Emerg Care. 1997; 13(1):1-4.
9. Yeates K O, Luria J, Bartkowski H, Rusin J, Martin L, Bigler E D. Postconcussive symptoms in children with mild closed head injuries. J Head Trauma Rehabil. 1999; 14(4):337-350.
10. Barlow K M, Crawford S, Stevenson A, Sandhu S S, Belanger F, Dewey D. Epidemiology of postconcussion syndrome in pediatric mild traumatic brain injury. Pediatrics. 2010; 126(2):e374-e381.
11. Zemek R L, Farion K J, Sampson M, McGahern C. Prognosticators of persistent symptoms following pediatric concussion. JAMA Pediatr. 2013; 167(3):259-265.
12. M R Zonfrillo, C L Master, M F Grady, F K Winston, J M Callahan, et al. Pediatric providers' self-reported knowledge, practices, and attitudes about concussion. Pediatrics 130 (6), 1120-1125, December 2012 (Epub 2012 Nov. 12).
13. Bazarian, J. J., Veenema, T., Brayer, A. F., & Lee, E. (2001). Knowledge of concussion guidelines among practitioners caring for children. Clinical pediatrics, 40(4), 207-212.
14. Scopaz K A, Hatzenbuehler J R. Risk modifiers for concussion and prolonged recovery. Sports Health. 2013; 5(6):537-541.
15. Zemek R., Barrowman N., Freedman S. B., et al. Clinical risk score for persistent postconcussion symptoms among children with acute concussion in the ED. *The Journal of the American Medical Association.* 2016; 315(10):1014-1025. doi: 10.1001/jama.2016.1203.
16. Papa, L, Ramia, M. M., Kelly, J. M., Burks, S. S., Pawlowicz, A., and Berger, R. P. (2013). Systematic review of clinical research on biomarkers for pediatric traumatic brain injury. J. Neurotrauma 30, 324-338.
17. Papa, Linda, et al. "Systematic review of clinical studies examining biomarkers of brain injury in athletes after sports-related concussion." Journal of neurotrauma 32.10 (2015): 661-673.
18. Berger, R. P., Pierce, M. C., Wisniewski, S. R., . . . & Kochanek, P. M. (2002). Neuron-specific enolase and S100B in CSF after severe traumatic brain injury in infants and children. Pediatrics 109, E31.
19. Jeter, C. B., Hergenroeder, G W., Hylin, M. J., Redell, J. B., . . . Dash, P. K. (2013). Biomarkers for the diagnosis and prognosis of mild traumatic brain injury/concussion. J Neurotrauma, 30(8), 657-670.
20. Unden, J., and Romner, B. (2009). A new objective method for CT triage after minor head injury—serum S100B. Scand. J. Clin. Lab. Invest. 69, 13-17.

21. Gazzolo, D., Michetti, F., Bruschettini, M., Marchese, & Bruschettini, P. (2003). Pediatric concentrations of S100B protein in blood: age- and sex-related changes. Clin Chem, 49(6), 967-970.
22. Kövesdi, E., Lückl, J., Bukovics, P., . . . & Büki, A. (2010). Update on protein biomarkers in traumatic brain injury with emphasis on clinical use in adults and pediatrics. Acta neurochirurgica, 152(1), 1-17.
23. Bazarian, J. J., Zemlan, F. P., Mookerjee, S., and Stigbrand, T. (2006). Serum 5-100B and cleaved-tau are poor predictors of long-term outcome after mild traumatic brain injury. Brain Inj. 20, 759-765.
24. Otto, M., Holthusen, S., Bahn, E., Söhnchen, N., Wiltfang, J., Geese, R., . . . & Reimers, C. D. (2000). Boxing and running lead to a rise in serum levels of 5-100B protein. Intntl J Sport Med, 21, 551-555.
25. Bhomia, M, Balakathiresan, N S, Wang, K K, Papa, L., & Maheshwari, R K. (2016). A Panel of Serum MiRNA Biomarkers for the Diagnosis of Severe to Mild Traumatic Brain Injury in Humans. Sci Rep, 6.
26. Ma, M., Lindsell, C. J., Rosenberry, C. M., Shaw, G J., & Zemlan, F. P. (2008). Serum cleaved tau does not predict postconcussion syndrome after mild traumatic brain injury. The American journal of emergency medicine, 26(7), 763-768.
27. Begaz, T., Kyriacou, D. N., Segal, J., & Bazarian, J. J. (2006). Serum biochemical markers for post-concussion syndrome in patients with mild traumatic brain injury. Journal of neurotrauma, 23(8), 1201-1210.
28. Nam, J. W. et al. Global analyses of the effect of different cellular contexts on microRNA targeting. Mol Cell 53, 1031-1043, doi:10.1016/j.molce1.2014.02.013 (2014).
29. Valadi H, Ekström K, Bossios A, Sjöstrand M, . . . & Lötvall, JO. (2007) Exosome-mediated transfer of mRNAs & microRNAs is a novel mechanism of genetic exchange between cells. Nat Cell Bio 9, 654-9.
30. Gilad, S., Meiri, E., Yogev, Y, Benjamin, S., Lebanony, D., Yerushalmi, N., Benjamin, H., Kushnir, M., Chajut, A. (2008). Serum microRNAs are promising novel biomarkers. PLoS One 3, e3148.
31. Pasinetti, G M., Ho, L., Dooley, C., Abbi, B., & Lange, G (2012). Select non-coding RNA in blood components provide novel clinically accessible biological surrogates for improved identification of traumatic brain injury in OEF/OIF Veterans. American J Neurodegen Dis, 1(1), 88.
32. Redell, J. B., Moore, A. N., Ward III, N. H., Hergenroeder, G W., & Dash, P. K. (2010). Human traumatic brain injury alters plasma microRNA levels. Journal of neurotrauma, 27(12), 2147-2156.
33. Di Pietro, V, Ragusa, M., Davies, D. J., Su, Z., Hazeldine, J., Lazzarino, G, & Logan, A. (2017). MicroRNAs as novel biomarkers for the diagnosis and prognosis of mild and severe traumatic brain injury. Journal of Neurotrauma, (ja).

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for detecting or diagnosing a concussion, mild traumatic brain injury (mTBI), or other traumatic brain injury (TBI) in a human subject comprising:
  (a) determining abundance or concentration level(s) of one or more micro RNAs (miRNAs) in a saliva sample taken from the human subject, and
  (b) comparing the determined abundance or concentration level(s) of the one or more miRNAs against normal level(s) of the same one or more miRNAs, wherein the normal level is that found in a subject, or an average from two of more subjects, not having a concussion or mild traumatic brain injury; or is an abundance or concentration level(s) determined in the subject prior to an event that-produces a concussion, mTBI, or other TBI, and
  (c) selecting a subject having an abnormal level of said one or more miRNAs as having a concussion, mild traumatic brain injury, or other traumatic brain injury; wherein the one or more miRNA and the abnormal level of said one or more miRNA is at least one of: miR-29c-3p which is upregulated in the human subject as compared to the normal level; miR-26b-5p which is downregulated in the human subject as compared to the normal level; miR-182-5p which is downregulated in the human subject as compared to the normal level; miR-320c which is downregulated in the human subject as compared to the normal level; or miR-221-3p which is downregulated in the human subject as compared to the normal level; and;
  (d)-further comprising treating the selected subject in (c) for a concussion, mTBI, or other TBI by administering a medication, surgery, or cognitive therapy or psychotherapy that reduces the severity of the concussion, mTBI, or other TBI.

2. The method of claim 1, wherein said miRNA expression levels are normalized to an expression level, or average expression level, of one or more housekeeping genes whose RNA expression level is substantially invariant; and/or adjusted to compensate for differences in age, sex or genetic background.

3. The method of claim 1, wherein (a) determining abundance or concentration of one or more miRNAs is done by RNA sequencing (RNA-seq), qPCR, a miRNA array, or multiplex miRNA profiling.

4. The method of claim 1, wherein the saliva sample is taken from a human subject suspected of having a mTBI and the methods comprises determining abundance or concentration levels of miR-29c-3p, miR-26b-5p, miR-182-5p, miR-320c, and miR-221-3p.

5. The method of claim 1, wherein the saliva sample is taken from a human subject suspected of having a concussion and the method comprises determining abundance or concentration levels of miR-29c-3p, miR-26b-5p, miR-182-5p, miR-320c, and miR-221-3p.

6. The method of claim 1, wherein the concentration level(s) of miRNAs in said saliva sample are compared to normal miRNA values in saliva taken at the same time of day under otherwise identical conditions.

7. The method of claim 1, wherein the saliva sample is taken from the human subject at a different time of day than the time of day at which the normal level(s) of miRNAs were determined, further comprising adjusting or normalizing the value of the miRNA level(s) determined in the saliva sample using a regression model or other statistical analysis to compensate for age, sex, or genetic background.

8. The method of claim 1, wherein the saliva sample is taken within 1 hour of waking, and before brushing, rinsing the mouth, before eating or drinking, and before exercise that elevates heart rate.

9. The method of claim 1, wherein said selecting comprises selecting a subject having abnormal levels of four or more of said miRNAs, and, calculating a Pearson correlation coefficient of said abnormal miRNA levels with at least one symptom of a concussion, mTBI, or other TBI.

10. The method of claim 1, wherein determining salivary miRNA levels is done by RNA sequencing (RNA-seq).

11. The method of claim 10, wherein the sequencing data raw read counts are quantile-normalized, mean-centered, and divided by the standard deviation of each variable; data are normalized to account for inter-sample count variations; and/or wherein data are normalized to expression of one or more invariant miRNAs to describe relative and/or absolute expression levels; and optionally further statistically analyzing the normalized data.

12. The method of claim 1, wherein (d) comprises administering a treatment that reduces at least one symptom of the concussion, mTBI, or other TBI selected from at least one of headache, dizziness, fatigue, irritability, anxiety, insomnia, loss of concentration, loss of memory, noise sensitivity, or light sensitivity.

13. The method of claim 1, wherein (d) comprises administering to the subject at least one of migraine medication, tension headache medication, an antidepressant, anxiety medication, or a depression medication.

14. The method of claim 1, wherein (d) comprises administering to the subject at least one of cognitive therapy or psychotherapy.

15. The method of claim 1, wherein (d) comprises surgical therapy for a concussion, mTBI or other TBI.

16. The method of claim 1 wherein the method comprises determining abundance or concentration levels of miR-29c-3p.

17. The method of claim 1 wherein the method comprises determining abundance or concentration levels of miR-26b-5p.

18. The method of claim 1 wherein the method comprises determining abundance or concentration levels of miR-182-5p.

19. The method of claim 1 wherein the method comprises determining abundance or concentration levels of miR-320c.

20. The method of claim 1 wherein the method comprises determining abundance or concentration levels of miR-221-3p.

* * * * *